(12) United States Patent
Ward et al.

(10) Patent No.: US 6,407,042 B1
(45) Date of Patent: Jun. 18, 2002

(54) ASSAY FOR SELECTING COMPOSITIONS PROVIDING ENHANCED EFFECTIVENESS OF EXOGENOUS CHEMICALS APPLIED TO PLANTS

(75) Inventors: Anthony J. I. Ward, Clayton; Jisheng Ge, Affton; Jane L. Gillespie, St. Louis; Joseph J. Sandbrink, Des Peres; Xiaodong C. Xu, St. Louis, all of MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/534,560

(22) Filed: Mar. 24, 2000

Related U.S. Application Data

(62) Division of application No. 08/958,149, filed on Oct. 24, 1997, now Pat. No. 6,093,681.
(60) Provisional application No. 60/029,317, filed on Oct. 25, 1996, provisional application No. 60/034,887, filed on Jan. 31, 1997, and provisional application No. 60/039,789, filed on Mar. 4, 1997.

(51) Int. Cl.$^7$ .............................. A01N 25/00; G01J 4/00; G01N 25/00

(52) U.S. Cl. ........................ 504/358; 356/365; 436/166; 514/772

(58) Field of Search ..................... 436/166; 504/358; 514/772; 356/365

(56) References Cited

U.S. PATENT DOCUMENTS 5,912,220 A * 6/1999 Sramek et al. .............. 510/284

OTHER PUBLICATIONS

Coret & Chamel (1993). Influence of some nonionic surfactants on water sorption by isolated tomato fruit cuticles in relation to cuticular penetration of glyphosate. Pesticide Science 38, 27–32.
Farag & Palta (1989). Ultrastructure and surface morphology of cranberry (*Vaccinium macrocarpon* Ait.) with reference to Ethrel penetration. Acta Horticulturae 241, 378–384.
Hess (1985). Herbicide absorption and translocation and their relationship to plant tolerances and susceptibility. In Duke, ed.: Weed Physiology, vol. 2, 191–214. Boca Raton: CRC Press.
Israelachvili et al. (1976). Theory of self–assembly of hydrocarbon amphiphiles into micelles and bilayers. Journal of the Chemical Society, Faraday Transactions II, 72, 1525–1568.
Kirkwood (1991). Pathways and mechanisms of uptake of foliage–applied herbicides with particular reference to the role of surfactants. In Kirkwood, ed.: Target Sites for Herbicide Action, 219–243. New York: Plenum Press.
Kirkwood (1993). Use and mode of action of adjuvants for herbicides: a review of some current work. Pesticide Science 38, 93–102.
Leece (1978). Foliar absorption in *Prunus domestica* L. I. Nature and development of the surface wax barrier. Australian Journal of Plant Physiology 5, 749–766.
Newton et al. (1993). Structured surfactant formulations for pesticides. Pesticide Science 37, 208–209.
Norris, R. F. and Bukovac, M.J., "Structure of the pear leaf cuticle with special reference to cuticular penetration," American Journal of Botany, vol. 55, No. 8, 1968, 975–83.
Quinn (1985). The chemico–physical properties of membrane lipids and their relevance to plant growth and protection. In St. John, ed.: Frontiers of Membrane Research in Agriculture (Beltsville Symposium 9), 55–75.
Quinn et al. (1986). An evaluation of soya lecithin in crop spray performance. Atomisation and Spray Technology 2, 235–246.
Riederer & Schönherr (1990). Effects of surfactants on water permeability of isolated plant cuticles and on the composition of their cuticular waxes. Pesticide Science 29, 85–94.
Riederer & Schreiber (1995). Waxes—the transport barriers of plant cuticles. In Hamilton, ed.: Waxes: Chemistry, Molecular Biology and Function, 131–156. Dundee: Oily Press.
Schönherr (1979). Transcuticular movement of xenobiotics. Proceedings, 4th International Congress of Pesticide Chemistry, vol. 3, 392–400.
Schönherr & Baur (1994). Modelling penetration of plant cuticles by crop protection agents and effects of adjuvants on their rates of penetration. Pesticide Science 42, 185–208.
Schönherr et al. (1991). Foliar uptake of pesticides and its activation by adjuvants: theories and methods for optimization. Proceedings, 7th International Congress of Pesticide Chemistry, vol. 1, 237–253.

(List continued on next page.)

*Primary Examiner*—S. Mark Clardy
(74) *Attorney, Agent, or Firm*—Senniger, Powers, Leavitt & Roedel; Joseph A. Schaper

(57) ABSTRACT

A composition is disclosed for application to a plant that comprises an exogenous chemical (for example, a postemergent herbicide), an aqueous diluent, and a first excipient substance that is amphiphilic. The weight/weight ratio of the first excipient substance to the exogenous chemical is between about 1:3 and about 1:100. The aqueous composition forms anisotropic aggregates on a wax layer, and the presence of the anisotropic aggregates can be detected by a test described herein. Compositions of the present invention, when applied to plants, provide enhanced biological activity per unit amount of exogenous chemical, as compared to otherwise similar compositions containing surfactants that do not form anisotropic aggregates. Without being bound by theory, it is presently believed that this enhanced biological activity results from the formation or enlargement of hydrophilic channels through the epicuticular wax of the plant.

2 Claims, No Drawings

OTHER PUBLICATIONS

Schreiber (1994). A mechanistic approach towards effects of nonionic surfactants on mobility of pesticides in reconstituted cuticular wax of barley leaves. Mededelingen Faculteit Landbouwwetenschappen Rijksuniversiteit Gent 59(3b), 1409–1414.

Souty & Guennelon (1974). The mechanisms of foliar absorption. Annales Agronomiques 25, 883–891. Abstract only.

Tan & Crabtree (1994). Cuticular penetration of 2,4–D as affected by interaction between a diethylene glycol monooleate surfactant and apple leaf cuticles. Pesticide Science 41, 35–39.

Wanamarta & Penner (1989). Foliar Absorption of herbicides. Reviews of Weed Science 4, 215–231.

Ward & Osborne (1993). Hydrotropy and penetration enhancement. In Walters & Hadgraft, ed.: Pharmaceutical Skin Penetration Enhancement, pp. 365–388. New York: Marcel Dekker.

* cited by examiner

ASSAY FOR SELECTING COMPOSITIONS PROVIDING ENHANCED EFFECTIVENESS OF EXOGENOUS CHEMICALS APPLIED TO PLANTS

This application is a division of application Ser. No. 08/958,149 filed Oct. 24, 1997, now U.S. Pat. No. 6,093,681, which claims the benefit of provisional application serial No. 60/029,317, filed Oct. 25, 1996; provisional application serial No. 60/034,887, filed Jan. 31, 1997; and provisional application serial No. 60/039,789, filed Mar. 4, 1997. Each of those provisional applications is incorporated here by reference.

BACKGROUND OF THE INVENTION

This invention relates to formulations and methods for enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like.

Exogenous chemicals, including foliar-applied herbicides, have at times been formulated with surfactants, so that when water is added, the resulting sprayable composition is more easily and effectively retained on the foliage (e.g., the leaves or other photosynthesizing organs) of plants. Surfactants can also bring other benefits, including improved contact of spray droplets with a waxy leaf surface and, in some cases, improved penetration of the accompanying exogenous chemical into the interior of leaves. Through these and perhaps other effects, surfactants have long been known to increase the biological effectiveness of herbicide compositions, or other compositions of exogenous chemicals, when added to or included in such compositions. Thus, for example, the herbicide glyphosate (N-phosphonomethylglycine) has been formulated with surfactants such as polyoxyalkylene-type surfactants including, among other surfactants, polyoxyalkylene alkylamines. Commercial formulations of glyphosate herbicide marketed under the trademark ROUNDUP® have been formulated with a surfactant composition based on such a polyoxyalkylene alkylamine, in particular a polyethoxylated tallowamine, this surfactant composition being identified as MON 0818. Surfactants have generally been combined with glyphosate or other exogenous chemicals either in a commercial concentrate (herein referred to as a "coformulation"), or in a diluted mixture that is prepared from separate compositions, one comprising an exogenous chemical (e.g. glyphosate) and another comprising surfactant, prior to use in the field (i.e., a tank mix).

Various combinations of exogenous chemicals and surfactants or other adjuvants have been tested in the past. In some instances, the addition of a particular surfactant has not produced uniformly positive or negative changes in the effect of the exogenous chemical on the plant (e.g., a surfactant that may enhance the activity of a particular herbicide on certain weeds may interfere with, or antagonize, the herbicidal efficacy on another weed species).

Some surfactants tend to degrade fairly rapidly in aqueous solutions. As a result, surfactants that exhibit this property can only be used effectively in tank mixes (i.e., mixed with the other ingredients in solution or dispersion in the tank soon before spraying is to occur), rather than being coformulated in an aqueous composition with the other ingredients in the first instance. This lack of stability, or inadequate shelf-life, has hindered the use of certain surfactants in some exogenous chemical formulations.

Other surfactants, though chemically stable, are physically incompatible with certain exogenous chemicals, particularly in concentrate coformulations. For example, most classes of nonionic surfactant including polyoxyethylene alkylether surfactants, do not tolerate solutions of high ionic strength, as for example in a concentrated aqueous solution of a salt of glyphosate. Physical incompatibility can also lead to inadequate shelf-life. Other problems that can arise from such incompatibility include the formation of aggregates large enough to interfere with commercial handling and application, for example by blocking spray nozzles.

Another problem that has been observed in the past is the effect of environmental conditions on uptake of an exogenous chemical composition into foliage of a plant. For example, conditions such as temperature, relative humidity, presence or absence of sunlight, and health of the plant to be treated, can affect the uptake of a herbicide into the plant. As a result, spraying exactly the same herbicidal composition in two different situations can result in different herbicidal control of the sprayed plants.

One consequence of the above-described variability is that often a higher rate of herbicide per unit area is applied than might actually be required in that situation, in order to be certain that adequate control of undesired plants will be achieved. For similar reasons, other foliar-applied exogenous chemicals are also typically applied at significantly higher rates than needed to give the desired biological effect in the particular situation where they are used, to allow for the natural variability that exists in efficiency of foliar uptake. A need therefore exists for compositions of exogenous chemicals that, through more efficient uptake into plant foliage, allow reduced use rates.

Many exogenous chemicals are commercially packaged as a liquid concentrate that contains a significant amount of water. The packaged concentrate is shipped to distributors or retailers. Ultimately the packaged concentrate ends up in the hands of an end user, who further dilutes the concentrate by adding water in accordance with label instructions on the package. The dilute composition thus prepared is then sprayed on plants.

A significant portion of the cost of such packaged concentrates is the cost of transporting the concentrate from the manufacturing site to the location where the end user purchases it. Any liquid concentrate formulation that contained relatively less water and thus more exogenous chemical would reduce the cost per unit amount of exogenous chemical. However, one important limit on the ability of the manufacturer to increase the loading of the exogenous chemical in the concentrate is the stability of that formulation. With some combinations of ingredients, a limit will be reached at which any further reduction of water content in the concentrate will cause it to become unstable (e.g., to separate into discrete layers), which may make it commercially unacceptable.

Accordingly, a need exists for improved formulations of exogenous chemicals, particularly herbicides, that are stable effective, less sensitive to environmental conditions, and permit the use of reduced amounts of exogenous chemical to achieve the desired biological effect in or on plants. A need also exists for stable liquid concentrate formulations of exogenous chemicals that contain less water and more exogenous chemical than prior art concentrates.

SUMMARY OF THE INVENTION

The present invention relates to novel methods and compositions wherein exogenous chemicals are applied to plants to generate a desired biological response.

One embodiment of the present invention is a method of applying an exogenous chemical to a plant, comprising the steps of (a) contacting foliage of the plant with a biologically effective amount of the exogenous chemical, and (b) contacting the same foliage with an aqueous composition that comprises a first excipient substance that is amphiphilic. The weight/weight ratio of said first excipient substance to the exogenous chemical is between about 1:3 and about 1:100. Further, the aqueous composition forms anisotropic aggregates in or on a wax layer as explained below. "Contacting" in this context means placing the substance or composition on the foliage. "Amphiphilic" means having at least one polar, water-soluble head group which is hydrophilic and at least one water-insoluble organic tail which is hydrophobic, contained within the same molecule.

In this method, step (b) can occur simultaneously with or within about 96 hours before or after step (a). In embodiments of the method in which the two steps occur simultaneously, either the exogenous chemical and the aqueous composition can be applied to the plant separately, for example by two spray nozzles directed at the same foliage, or the exogenous chemical can be contained within the aqueous composition, for example in a tank mix or coformulation.

Formation of anisotropic aggregates in or on a wax layer is determined by a test described in detail subsequently herein. In general, the test, as it applies to a composition comprising an exogenous chemical, comprises the steps of (1) providing a glass microscope slide coated with a thin, uniform layer of wax, such that the wax layer on the slide exhibits a dark field when illuminated by transmitted polarized light and examined through a microscope, (2) preparing a sample of an aqueous solution or dispersion of the composition to be tested, diluted or concentrated if necessary such that the concentration of exogenous chemical is about 15% to about 20% by weight of the composition, (3) positioning the wax-coated slide on the stage of a microscope that transmits polarized light through the slide, (4) placing a drop of the sample on the wax on the slide to form an assay slide, (5) maintaining the assay slide at approximately ambient temperature for a period of about 5 to about 20 minutes, and (6) determining, at the end of that period, whether when transmitting polarized light the locus of the drop on the slide displays birefringence. Birefringence at 5–20 minutes indicates the presence of anisotropic aggregates in or on the wax layer, while the absence of birefringence at that time indicates the absence of anisotropic aggregates as defined herein.

The test, as it applies to an aqueous composition of one or more excipient substances, not itself containing an exogenous chemical but intended for application to foliage of a plant in conjunction with an exogenous chemical, is as just described, except that in step (2) the composition is diluted or concentrated so that the concentration of the first excipient substance is approximately 5% to 7% by weight.

An "excipient substance" as that term is used in this patent is any substance other than an exogenous chemical and water that is added to the composition. "Excipient substances" include inert ingredients although an excipient substance useful in the present invention does not have to be devoid of biological activity.

Another embodiment of the present invention is a plant treatment composition comprising (a) an exogenous chemical, and (b) a first excipient substance that is amphiphilic. As described above, the weight/weight ratio of said first excipient substance to the exogenous chemical is between about 1:3 and about 1:100, and in presence of water said composition forms anisotropic aggregates in or on a wax layer. This composition can be used in a method of treating plants, in which foliage of the plant is contacted with a biologically effective amount of a composition as described above and further comprising an aqueous diluent.

A wide variety of exogenous chemicals can be used in the compositions and methods of the present invention. A preferred class is foliar-applied exogenous chemicals, i.e. exogenous chemicals that are normally applied post-emergence to foliage of plants. A preferred subclass of foliar-applied exogenous chemicals is those that are water-soluble. By "water-soluble" in this context is meant having a solubility in distilled water at 25° C. greater than about 1% by weight. Especially preferred water-soluble exogenous chemicals are salts that have an anion portion and a cation portion. In one embodiment of the invention, at least one of the anion and cation portions is biologically active and has a molecular weight of less than about 300. Particular examples of such exogenous chemicals where the cation portion is biologically active are paraquat, diquat and chlormequat. More commonly it is the anion portion that is biologically active.

Another preferred subclass of exogenous chemicals is those that exhibit systemic biological activity in the plant. Within this subclass, an especially preferred group of exogenous chemicals is N-phosphonomethylglycine and its herbicidal derivatives. N-phosphonomethylglycine, often referred to by its common name glyphosate, can be used in its acid form, but is more preferably used in the form of a salt. Any water-soluble salt of glyphosate can be used in the practice of this invention. Some preferred salts include the sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts. The ammonium, monoisopropylammonium and trimethylsulfonium salts of glyphosate are especially preferred. Mixtures of salts can also be useful in certain situations.

A composition of the present invention comprising an exogenous chemical and a first excipient substance as described above can have a number of different physical forms. For example, the composition can further comprise water in an amount effective to make the composition a dilute aqueous composition ready for application to foliage of a plant. Such a composition typically contains about 0.02 to about 2 percent by weight of the exogenous chemical, but for some purposes can contain up to about 10 percent by weight or even more of the exogenous chemical.

Alternatively, the composition can be a shelf-stable concentrate composition comprising the exogenous chemical substance in an amount of about 10 to about 90 percent by weight. By "shelf-stable" in this context it is meant that the composition does not exhibit phase separation when stored at ambient temperature for a period of time dependent on the particular circumstances. Such shelf-stable concentrates can be, for example, (1) a solid composition comprising the exogenous chemical substance in an amount of about 30 to about 90 percent by weight, such as a water-soluble or water-dispersible granular formulation, or (2) a composition that further comprises a liquid diluent, wherein the composition comprises the exogenous chemical substance in an amount of about 10 to about 60 percent by weight. In this latter embodiment, it is especially preferred for the exogenous chemical substance to be water-soluble and present in an aqueous phase of the composition in an amount of about 15 to about 45 percent by weight of the composition. In particular, such a composition can be, for example, an aqueous solution concentrate or an emulsion having an oil phase. If it is an emulsion, it can more specifically be, for example, an oil-in-water emulsion, a water-in-oil emulsion, or a water-in-oil-in-water multiple emulsion. In one particular embodiment of the invention, the solid or aqueous composition further comprises a solid inorganic particulate colloidal material.

As described above, one embodiment of the invention is a sprayable composition having the property that it forms anisotropic aggregates in or on a wax layer. This composition comprises an exogenous chemical, an aqueous diluent, and a first excipient substance which is amphiphilic. In the sprayable composition, the weight/weight ratio of the first excipient substance to the exogenous chemical is between about 1:3 and about 1:100. A sprayable composition conforms to this embodiment of the invention even if the formation of anisotropic aggregates in or on a wax layer occurs only following concentration of the composition on the wax layer by evaporation of water. The term "spray composition" is sometimes used herein to mean a sprayable composition.

In a related embodiment of the invention, a concentrate composition is provided which, upon dilution, dispersion or dissolution in water forms the sprayable composition just described. The concentrate composition contains a reduced amount of the aqueous diluent, or, in a particular embodiment, is a dry composition having less than about 5% water by weight. Typically a concentrate composition of the invention contains at least about 10% by weight of the exogenous chemical, preferably at least about 15%.

An alternative embodiment is a composition that does not itself comprise an exogenous chemical, but is intended for application to a plant in conjunction with or as a carrier for the application of an exogenous chemical. This composition comprises a first excipient substance as described above. Such a composition may be sprayable, in which case it also comprises an aqueous diluent, or it may be a concentrate, requiring dilution, dispersion or dissolution in water to provide a sprayable composition. Thus, this embodiment of the invention can be provided as a stand-alone product and applied to a plant, diluted as appropriate with water, simultaneously with the application of an exogenous chemical, or before or after the application of the exogenous chemical.

In all embodiments, it is believed that the first excipient substance forms supramolecular aggregates in aqueous solution or dispersion. In particular it is believed that aqueous compositions of the present invention form aggregates in aqueous solution or dispersion the majority of which are not simple micelles. "Majority" means that more than 50% by weight of the first excipient substance present is in the form of complex aggregates other than simple micelles, e.g. as bilayers or multilamellar structures. Preferably, more than 75% by weight is in the form of complex aggregates other than simple micelles.

Whether or not an amphiphilic substance forms such aggregates depends on its molecular architecture. The effects of molecular architecture on supramolecular self-assembly of amphiphilic molecules, as set forth for example by J. N. Israelachvili, D. J. Mitchell and B. W. Ninham in *Faraday Transactions* II, Volume 72, pp. 1525–1568 (1976) and in numerous later articles and monographs, are well known and understood. An important aspect is "critical packing parameter" (P) which is defined in the literature by the following equation:

$$P=V/lA$$

where V is the volume of the hydrophobic tail of the molecule, l is the effective length of the hydrophobic tail, and A is the area occupied by the hydrophilic headgroup. These dimensions can be calculated from physical measurements as described in the literature and have been published for numerous amphiphilic compounds.

It is believed that amphiphilic substances useful as the first excipient substance herein have a critical packing parameter greater than ⅓. The first excipient substance forms aggregates in aqueous solution or dispersion which preferably have at least one dimension that is greater than two times the molecular length of the first excipient substance.

In one embodiment of the invention, an aqueous composition comprises supramolecular aggregates of the first excipient substance which have an average diameter of at least 20 nm, preferably at least 30 nm.

These supramolecular aggregates can take a number of forms. In one preferred embodiment, the first excipient substance is a vesicle-forming amphiphilic substance, such as a vesicle-forming lipid, and when the substance is dispersed in water the majority (greater than 50% by weight, preferably greater than 75% by weight) of the first excipient substance is present as vesicles or liposomes. In another preferred embodiment the first excipient substance is present as bilayers or multilamellar structures which are not organized as vesicles or liposomes. Compositions of the present invention can also include, without limitation, colloidal systems such as emulsions (water/oil, oil/water, or multiple, e.g., water/oil/water), foams, microemulsions, and suspensions or dispersions of microparticulates, nanoparticulates, or microcapsules. Compositions of the invention can include more than one type of aggregate or colloidal system; examples include liposomes or vesicles dispersed in a microemulsion, and compositions having characteristics of both emulsions and suspensions, e.g. suspo-emulsions. The present invention also encompasses any formulation, which may or may not contain a significant amount of water, that on dilution in an aqueous medium forms such colloidal systems, and/or systems comprising vesicles, liposomes, bilayers or multilamellar structures, so long as the other requirements stipulated herein are met.

The weight ratio of the first excipient substance to the exogenous chemical is between about 1:3 and about 1:100. We have been surprised by the high level of biological effectiveness, specifically herbicidal effectiveness of a glyphosate composition, exhibited at such low ratios of excipient substance to exogenous chemical. Higher ratios can also be effective but are likely to be uneconomic in most situations and increase the risk of producing an antagonistic effect on effectiveness of the exogenous chemical.

Prior art exogenous chemical compositions that have included liposome-forming excipient substances have typically contained a higher percentage of the liposome-forming excipient substance than of the exogenous chemical. Compositions of the present invention, in contrast, contain less of the excipient substance than the exogenous chemical, and in some embodiments much less. This makes the compositions of the present invention much less expensive than the above-described prior art compositions. It is surprising that the enhancement of biological activity that has been observed when using the present invention can be achieved with the addition of relatively small amounts of such excipient substances.

In one embodiment of the invention the first excipient substance is a liposome-forming material that comprises an amphiphilic compound or mixture of such compounds having two hydrophobic moieties, each of which is a saturated alkyl or acyl chain having from about 8 to about 22 carbon atoms. The amphiphilic compound or mixture of such compounds having said two hydrophobic moieties with about 8 to about 22 carbon atoms constitutes from about 40 to 100 percent by weight of all amphiphilic compounds having two hydrophobic moieties present in the liposome-forming material. Preferably the liposome-forming material has a hydrophilic head group comprising a cationic group. More preferably, the cationic group is an amine or ammonium group.

In a preferred embodiment of the invention, the first excipient substance comprises a liposome-forming compound having a hydrophobic moiety comprising two saturated or unsaturated hydrocarbyl groups $R^1$ and $R^2$ each having about 7 to about 21 carbon atoms. A number of subclasses of such liposome-forming compounds are known.

One subclass has the formula $$N^+(CH_2R^1)(CH_2R^2)(R^3)(R^4)Z^- \quad\quad\quad I$$

wherein $R^3$ and $R^4$ are independently hydrogen, $C_{1-4}$ alkyl or $C_{1-4}$ hydroxyalkyl and Z is a suitable anion.

A second subclass has the formula $$N^+(R^5)(R^6)(R^7)CH_2CH(OCH_2R^1)CH_2(OCH_2R^2)Z^- \quad\quad II$$

wherein $R^5$, $R^6$ and $R^1$ are independently hydrogen $C_{1-4}$ alkyl or C, hydroxyalkyl and Z is a suitable anion.

A third subclass has the formula $$N^+(R^5)(R^6)(R^7)CH_2CH(OCOR^1)CH_2(OCOR^2)Z^- \quad\quad III$$

wherein $R^5$, $R^6$, $R^7$ and Z are as defined above.

A fourth subclass has the formula $$N^+(R^5)(R^6)(R^7)CH_2CH_2-PO_4^--CH_2CH(OCOR^1)CH_2(OCOR^2) \quad IV$$

wherein $R^5$, $R^6$, and $R^1$ are as defined above.

Compounds of formulas I–IV will have the indicated formulas at a pH of 4 and may have the same formulas at other pH's as well. It should be understood, however, that compositions of the present invention are not limited to use at a pH of 4.

$R^1$ and $R^2$ preferably are independently saturated straight-chain alkyl groups each having about 7 to about 21 carbon atoms. Examples of suitable agriculturally acceptable anions Z include hydroxide, chloride, bromide, iodide, sulfate, phosphate and acetate.

In all of the above subclasses of liposome-forming substances, the hydrophilic moiety comprises a cationic group. specifically an amine or ammonium group. The compound as a whole is in some cases cationic (as in I, II and III) and in some cases neutral (as in IV). Where the amine group is quaternary, it behaves as a cationic group independently of pH. Where the amine group is secondary or tertiary, it behaves as a cationic group when protonated, i.e. In an acid medium, for example at a pH of 4.

In a preferred embodiment, the first excipient substance is a phospholipid selected from the group consisting of di-$C_{8-22}$-alkanoylphosphatidylcholines and di-$C_{8-22}$-alkanoylphosphatidylethanolamines. In a particularly preferred embodiment, the first excipient substance is a dipalmitoyl or distearoyl ester of phosphatidylcholine or a mixture thereof.

Other subclasses of liposome-forming substances having two hydrophobic chains each comprising a $C_{7-21}$ hydrocarbyl group can also be used as the first excipient substance in compositions of the invention. While substances having a cationic group in the hydrophilic moiety are preferred, nonionic or anionic substances can be used if desired.

In another embodiment of the invention, the first excipient substance is an amphiphilic quaternary ammonium compound or mixture of such compounds. The hydrophobic moiety of the quaternary ammonium compound is a saturated alkyl or haloalkyl group having about 6 to about 22 carbon atoms. In this embodiment, the first excipient substance is not necessarily a liposome-forming substance, but it is believed to form aggregates in aqueous solution or dispersion as described above.

Preferred quaternary ammonium compounds (other than those which are liposome-forming and have two hydrocarbyl chains) for use as the first excipient substance in compositions of the invention have the formula $$R^8-W_a-X-Y_b-(CH_2)_n-N^+(R^9)(R^{10})(R^{11})T^- \quad\quad V$$

wherein $R^8$ represents the hydrophobic moiety and is a hydrocarbyl or haloalkyl group having from about 6 to about 22 carbon atoms, W and Y are independently O or NH, a and b are independently 0 or 1 but at least one of a and b is 1, X is CO, SO or $SO_2$, n is 2 to 4, $R^9$, $R^{10}$ and $R^{11}$ are independently $C_{1-4}$ alkyl, and T is a suitable anion. $R^8$ in one particular embodiment is hydrocarbyl having about 12 to about 18 carbon atoms. $R^8$ can also be fluorinated. In one specific embodiment, $R^8$ is perfluorinated, and preferably has about 6 to about 12 carbon atoms. Suitable anions T include hydroxide, chloride, bromide, iodide, sulfate, phosphate and acetate. In one particularly preferred embodiment, $R^8$ is saturated perfluoroalkyl having about 6 to about 12 carbon atoms, X is CO or $SO_2$, Y is NH, a is 0, b is 1, n is 3, $R^9$, $R^{10}$ and $R^{11}$ are methyl, and T is selected from the group consisting of chloride, bromide and iodide.

In a further embodiment of the invention, the first excipient substance is an alkylether surfactant or mixture of such surfactants having the formula $$R^{12}-O-(CH_2CH_2O)_n(CH(CH_3)CH_2O)_m-R^{13} \quad\quad VI$$

wherein $R^{12}$ is an alkyl or alkenyl group having about 16 to about 22 carbon atoms, n is an average number of about 10 to about 100, m is an average number of 0 to about 5 and $R^{13}$ is hydrogen or $C_{1-4}$ alkyl. Preferably $R^{12}$ is a saturated straight-chain alkyl group, $R^{13}$ is hydrogen, m is 0 and n is from about 10 to about 40, more preferably from about 20 to about 40. Most preferably the alkylether surfactant is a polyoxyethylene cetyl or stearyl ether or mixture thereof having 20–40 moles of ethylene oxide (EO). The term "alkylether" as used herein should be understood to include alkenylether surfactants.

Compositions of the present invention can optionally further comprise a second excipient substance having at least one hydrophobic moiety, wherein if the second excipient substance has one hydrophobic moiety, the hydrophobic moiety is a hydrocarbyl or haloalkyl group having about 6 to about 22 carbon atoms, and wherein if the second excipient substance has a plurality of hydrophobic moieties, each such hydrophobic moiety is a hydrocarbyl or haloalkyl group having more than 2 carbon atoms, said plurality of hydrophobic moieties having a total of about 12 to about 40 carbon atoms. The second excipient substance, if present, may or may not itself be one that forms supramolecular aggregates as described above. In a particular embodiment of the invention where the first excipient substance is a liposome-forming substance of formula I, II, III or IV above, a second excipient substance is present and is a quaternary ammonium compound or mixture of such compounds. Among preferred quaternary ammonium compounds for use as the second excipient substance in this embodiment are compounds of formula V above.

In another particular embodiment of the invention where the first excipient substance is a liposome-forming substance of formula I, II, III or IV above, a second excipient substance is present and is a compound or mixture of compounds of formula $$R^{14}\text{—CO—A—}R^{15} \qquad \text{VII}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH.

$R^{14}$ preferably has about 11 to about 21 carbon atoms, $R^{15}$ preferably has 1 to about 6 carbon atoms and A is preferably O. More preferably, the second excipient substance is a $C_{1-4}$ alkyl ester of a $C_{2-18}$ fatty acid, for example a propyl, isopropyl or butyl ester of a $C_{12-18}$ fatty acid. Butyl stearate is an especially preferred example. The aqueous composition in embodiments comprising a compound of formula VII preferably is an emulsion comprising an oil phase that comprises said second excipient substance, for example a water-in-oil-in-water multiple emulsion or an oil-in-water emulsion. Alternatively, a second excipient substance of formula VII is associated in some way with a liposome-forming first excipient substance.

In yet another particular embodiment of the invention, the first excipient substance is an alkylether surfactant of formula VI and a second excipient substance is present and is a compound or mixture of compounds of formula VII.

In any of the above particular embodiments, the exogenous chemical and/or second excipient substance can be encapsulated within or associated with aggregates (e.g., liposomes) formed by the first excipient substance, but do not necessarily have to be so encapsulated or associated. "Associated" in this context means bound to or at least partly intercalated in some fashion in a vesicle wall, as opposed to being encapsulated. In yet another embodiment of the invention where the first excipient substance forms liposomes, the exogenous chemical and/or second excipient substance is not encapsulated in or associated with the liposomes at all. Although the present invention does not exclude the possibility of so encapsulating or associating the exogenous chemical, a presently preferred dilute sprayable liposomal composition encapsulates less than 5% by weight of the exogenous chemical that is present in the overall composition. Another dilute sprayable liposomal embodiment of the present invention has no substantial amount (i.e., less than 1% by weight) of the exogenous chemical encapsulated in the liposomes. As a droplet of such a liposomal composition dries on foliage of a plant, the proportion of the exogenous chemical that is encapsulated in the liposomes may change. Compositions of the present invention that include an exogenous chemical can be applied to foliage of plants in an amount that is effective to achieve the desired biological effect of the exogenous chemical. For example, when the exogenous chemical is a post-emergence herbicide, the composition can be applied to a plant in a herbicidally effective amount.

Without being bound by theory, it is believed that that the method and compositions of the present invention create or enlarge hydrophilic channels through the epicuticular wax of the plant cuticle, these channels being capable of accommodating the mass transfer of a water-soluble exogenous chemical into the plant, and thus transporting the exogenous chemical into the plant more rapidly or more completely than an epicuticular wax layer lacking such formation or enlargement of hydrophilic channels. Of course, certain compositions of the present invention can also enter a plant through stomata, but this generally requires a very low surface tension which is not an essential feature of the present compositions. The enhanced cuticular penetration believed to be achieved by the compositions of the present invention enhances the overall delivery and effectiveness of the exogenous chemical. Whereas an exogenous chemical such as glyphosate, formulated as an aqueous solution or dispersion with surfactants which do not have the property of forming anisotropic aggregates in or on a wax layer, normally penetrates through the epicuticular wax very slowly (e.g., in 1–4 days), a substantial portion of the exogenous chemical in compositions of the present invention penetrates much more quickly (e.g., in from about 10 minutes to a few hours, preferably in less than about 30 minutes).

Thus, methods and compositions of the invention are believed to owe their superior effectiveness at least in part to accelerated uptake into plant foliage. In conventional methods of treating plants with exogenous chemicals, in particular polar exogenous chemicals, the epicuticular wax layer presents an almost continuous barrier through which such exogenous chemicals diffuse with difficulty, even in the presence of surfactants which increase diffusive mobility but do not introduce the possibility of rapid mass transfer through hydrophilic channels.

Again without being bound by theory, it is believed that the hydrophilic channels are created within the epicuticular wax layer by the self-assembly of molecules of the first excipient substance which has a hydrophobic moiety that associates with the wax and a hydrophilic moiety that attracts water to form an aqueous continuum across the epicuticular wax layer linking up with hydrophilic pathways in the cuticle proper. A polar exogenous chemical can move by mass transfer along such an aqueous continuum to enter the plant.

Again without being bound by theory, it is believed that when the composition is present on the leaf of a plant as a droplet of aqueous solution or dispersion, in an aqueous microdomain on the cuticular surface (i.e., the aqueous region at the interface between the water droplet and the epicuticular wax), the majority (i.e., more than 50% by weight) of the aggregate-forming substance is present in a form other than a monolayer, for example as a bilayer or multilamellar (liquid crystal) structure. The aggregate-forming substances employed have several preferred characteristics that are believed to contribute to the formation of transcuticular hydrophilic channels. For instance, they have a tendency to form extended self-assembled structures in the presence of water and the kinds of waxes encountered in cuticles. Generally, materials that form non-simple (i.e., not small spherical micellar structures) aggregates in solution, such as vesicles or cylindrical, discotic, or ribbon-like micellar structures are preferred. These tend to form more complex adsorbed and absorbed layers with hydrophobic substrates than those simple micellar systems that tend to produce simple adsorbed monolayers. These substances also tend to produce lyotropic mesophases such as lamellar, hexagonal or reversed hexagonal phases in the compositions established in the aqueous microdomains in or on the cuticle.

In one embodiment of the invention, a cationic headgroup on the first excipient substance is also preferred. The cationic group is believed to enhance initial adhesion to the leaf surface, since the majority of such surfaces carry an overall negative charge. The cationic group is also believed to contribute to the hydrophilicity of channels in the epicuticular wax formed or enlarged by the method and compositions of the invention. Cationic groups, in particular amine or ammonium groups, attract water molecules which further enlarge the hydrophilic channels and thereby provide an improved pathway of entry for exogenous chemicals that are polar or water-soluble.

It is further believed that the creation or enlargement of hydrophilic channels in epicuticular wax results in the wax becoming plasticized. A further embodiment of the invention is thus a method for applying an exogenous chemical to a plant having an epicuticular wax layer, comprising (a) plasticizing the epicuticular wax layer in conjunction with (b) contacting the epicuticular wax layer with the exogenous chemical. In this embodiment the step of plasticizing the epicuticular wax layer is accomplished by contacting the layer with an aqueous composition comprising a first excipient substance as defined above and optionally a second excipient substance as defined above. The weight ratio of the first excipient substance to the exogenous chemical is between about 1:3 and about 1:100.

Herbicidal compositions in accordance with the present invention are also useful in methods for enhancing the yield of a field crop. Such a method can comprise the steps of (a) planting a crop in a field, (b) substantially freeing the field of one or more weed species that would diminish the yield of the crop by applying to the weed species a herbicidally effective amount of a composition as described above, (c) allowing the crop to mature, and (d) harvesting the crop. Alternatively, the method can comprise the steps of (a) substantially freeing the field of one or more weed species that would diminish the yield of the crop by applying to the weed species a herbicidally effective amount of the composition, (b) planting the crop in the field, (c) allowing the crop to mature, and (d) harvesting the crop.

In one particular method in accordance with the present invention, a herbicidal composition as described above can be applied to a complex of weeds that are present in a single field, the weeds being, for example, velvetleaf, morningglory, and prickly sida. The composition is applied in a herbicidally effective amount, and provides herbicidal control of each of the weed species in the complex.

Another embodiment of the present invention is a herbicidal method, comprising contacting the foliage of a plant with a herbicidally effective amount of a composition as described above, whereby the herbicidal effectiveness of the composition on the plant to which it is applied is visibly better than the herbicidal effectiveness on that same species of plant, under substantially the same conditions, of a composition containing a similar amount of surfactant but that does not form anisotropic aggregates. "Visibly better" in this context means that the difference in herbicidal effect of the two compositions on the plants is readily noticeable to the eye of an experienced weed scientist.

Another embodiment of the present invention is a herbicidal method which can be used in a field that contains both weed and crop plants, where the crop plants are resistant to the effects of a particular herbicide at the rate that herbicide is used. The method comprises contacting the foliage of both the weeds and the crops in the field with a composition as described above. The composition will have a herbicidal effect on the weeds (i.e., it will partially or entirely kill the weeds) but it will not harm the crops. This herbicidal method applies to any combination of a selective post-emergence herbicide (e.g. 2,4-D) and a crop on which that herbicide can be used selectively to kill weeds (e.g., in the case of 2,4-D, wheat). This herbicidal method also applies to any combination of a normally non-selective post-emergence herbicide and a crop bred or genetically modified to be resistant to that herbicide. An example of a suitable combination of herbicide and herbicide-resistant crop is ROUNDUP® herbicide and ROUNDUP READY® crops, developed by Monsanto Company.

The compositions and methods of the present invention have a number of advantages. They provide enhanced biological activity of exogenous chemicals in or on plants in comparison with prior formulations, either in terms of greater ultimate biological effect, or obtaining an equivalent biological effect while using a reduced application rate of exogenous chemical. Certain herbicide formulations of the present invention can avoid antagonism that has been observed in some prior art herbicide formulations, and can minimize quick production of necrotic lesions on leaves that in some situations hinder overall translocation of herbicide in the plant. Certain herbicide compositions of the invention modify the spectrum of activity of the herbicide across a range of plant species. For example, certain formulations of the present invention containing glyphosate can provide good herbicidal activity against broadleaf weeds while not losing any herbicidal effectiveness on narrowleaf weeds. Others can enhance herbicidal effectiveness on narrowleaf weeds to a greater extent than on broadleaf weeds. Still others can have enhanced effectiveness which is specific to a narrow range of species or even a single species.

Another advantage of the present invention is that it employs relatively small amounts of the first and second excipient substances in relation to the amount of exogenous chemical employed. This makes the compositions and methods of the present invention relatively inexpensive, and also tends to reduce instability problems in specific compositions where one or both excipient substances are physically incompatible with the exogenous chemical (e.g., alkylether surfactants in solutions of high ionic strength, such as concentrated glyphosate salt solutions).

Even at the low concentrations of the excipient substances used in the present invention, there may be limits on the maximum concentration of exogenous chemical that can be used without causing compatibility problems (e.g., separation of the composition into discrete layers). In some preferred embodiments of the invention, composition stability at high loadings of exogenous chemical is maintained by adding other ingredients such as, for example, colloidal particulates. Some compositions of the present invention exhibit enhanced biological activity and have a higher loading of exogenous chemical than possible in prior art compositions.

Further, compositions of the present invention are less sensitive in some instances to environmental conditions such as relative humidity at the time of application to the plant.

Also, the present invention allows the use of smaller amounts of herbicides or other pesticides, while still obtaining the required degree of control of weeds or other undesired organisms.

DESCRIPTION OF SPECIFIC EMBODIMENTS

When the phrase "anisotropic aggregates in or on a wax layer" is used herein, it relates to determinations made by the following test procedure. We have found this test to predict with a high degree of reliability whether a composition comprising water and an exogenous chemical, or a composition comprising water which is to be used in conjunction with an exogenous chemical, will show enhanced biological effectiveness when applied to foliage of plants. Modifications can be made to the test; however a procedure modified in some major respect will not necessarily give the same results and will not necessarily predict enhanced effectiveness as reliably as the procedure described here.

The first stage in the procedure is to prepare a wax-coated slide. We have found a preferred wax for the purpose to be a blend of carnauba wax and beeswax in a weight/weight ratio of approximately 10:1. A clear wax mixture is prepared consisting of 5% carnauba wax and 0.5% beeswax in isopropanol, and is maintained at a temperature of approximately 82° C. The end of a glass 2.4 cm×7.2 cm microscope slide is immersed perpendicularly in the wax mixture to a depth of approximately one-third of the length of the slide. After 10 to 15 seconds, the slide is very slowly and steadily withdrawn from the wax mixture and allowed to cool, leaving a wax layer deposited on both faces of the slide.

Visual examination of the slide can give a preliminary indication of the thickness and uniformity of the wax coating. If imperfections are evident the slide is rejected. If the slide shows no obvious imperfections, the wax coating is carefully removed from one face of the slide by wiping with acetone. Further evaluation of the acceptability of the wax-coated slide for the test is done by examining the slide under a microscope. The slide is selected for use in the test if, on microscopic examination using a 4.9× objective, the wax coating is uniformly thick and there is uniform density of wax particles across the slide. Preference is for a coating that has few observable wax particles and exhibits a very dark field when examined under polarized light.

The next stage in the procedure is to conduct the test. For this purpose, samples of an exogenous chemical composition to be tested are diluted, if necessary, to 15% to 20% by weight of the exogenous chemical. In the case of glyphosate, the desired concentration in a composition sample is 15% to 20% acid equivalent (a.e.). Samples of reference compositions are also prepared; in the case of glyphosate, Formulations B and J as defined in the Examples herein are appropriate.

For a composition of a first excipient substance not containing an exogenous chemical but to be applied in conjunction with an exogenous chemical, the desired concentration is approximately 5% to 7% by weight of the first excipient substance.

The following instrumentation, or equivalent, items are required or useful:

Nikon SMZ-10A stereoscopic microscope equipped for polarized light observation, photomicrography, and video observation and recording.

3CCD MTI camera.

Diagnostic Instruments 150 IL-PS power supply.

Sony Trinitron color video monitor, model PVM-1353MD.

Mitsubishi time-lapse video cassette recorder, model HS-S5600.

Hewlett Packard Pavillion 7270 computer, with Windows 95 and Image-Pro Plus version 2.0 electronic imaging program installed.

Hewlett Packard Deskjet 870Cse printer.

A wax-coated slide, prepared and selected as described above, is positioned on the microscope stage, with the system set to provide transmitted light, both straight and polarized. A 1 $\mu$l drop of the sample to be tested is applied to the wax surface using a thoroughly cleaned 1 $\mu$l Hamilton syringe. This and subsequent operations are followed through the microscope at 4.9× objective. Duplicate or triplicate tests are done for each composition. Numerous tests can be conducted simultaneously on a single slide. Progression of change in the microscopic appearance of the sample is observed through the microscope and recorded at designated time intervals. We have found useful intervals to be 1 minute, 10 minutes, 2 hours and >24 hours after application of the drop to the wax surface. Observations can also be made at intermediate times to capture possible significant transitions occurring at such times.

The temperature of the wax layer tends to increase with prolonged exposure to the microscope light. In many cases we have found this does not significantly interfere with the results obtained. However, in some cases temperature does affect the outcome of the test and in such cases it is preferred to illuminate the sample only for the short periods necessary to make observations, so that the temperature of the wax layer remains close to ambient temperature. An example of a composition of the invention where it is believed to be important to keep temperature close to ambient is one containing a fatty acid ester such as butyl stearate.

At dark field (polarized light) the wax layer is observed for birefringence, and at light field the character of the drop surface is observed, at each time interval. The following records are made:

birefringence (yes/no);

time of initial appearance of birefringence;

character of the birefringence;

appearance of drop surface as composition "dries";

degree of spread of the drop;

effects of temperature (warming of the slide) if any;

other noticeable changes.

Optionally, images are recorded at significant times using the 3CCD MTI camera and the Image-Pro Plus program as documentation of observed changes. Tests may if desired also be recorded on video, especially during the first 15 minutes. In addition to images captured using 4.9× objective, overall-field views using 0.75× objective can be recorded to provide clear comparisons of different samples tested on the same slide.

A particularly useful parameter for predicting enhanced effectiveness is the observation of birefringence (yes/no) 5–20 minutes after deposition of the test drop on the wax-coated slide. We have found 10–15 minutes after deposition to be an especially suitable time for observation of this parameter. The following results for oil-in-water emulsion compositions comprising glyphosate IPA salt, butyl stearate and alkylether surfactants are typical of those obtained. Each of compositions WCS-1 to WCS-5 contained 15% w/w glyphosate a.e., 0.5% w/w butyl stearate and 5% w/w alkylether surfactant. Formulations B and J are commercial standard compositions of glyphosate defined in the Examples section later herein, and were diluted to 15% glyphosate a.e. for the test.

| Composition | Alkylether | Birefringence at 10 min. |
|---|---|---|
| WCS-1 | Brij 78 (steareth-20) | yes |
| WCS-2 | Plurafac A-38 (ceteareth-27) | yes |
| WCS-3 | Brij 98 (oleth-20) | yes |
| WCS-4 | Brij 35 (laureth-23) | no |
| WCS-5 | Neodol 1–9 ($C_{11}$ linear alcohol 9EO) | no |
| Formulation B | | no |
| Formulation J | | no |

It will be noted that where the hydrophobic moiety of the alkylether was a $C_{11}$ (WCS-5) or $C_{12}$ (WCS-4) hydrocarbyl group, the composition did not show anisotropic properties in the form of birefringence 10 minutes after application to the wax-coated slide. However, where the hydrophobic moiety had a carbon chain length of 16 to 18 (WCS-1 to WCS-3), birefringence was evident, indicating the presence of anisotropic aggregates in or on the wax layer. The intensity of birefringence was greatest with WCS-1 (containing steareth-20), followed by WCS-2 (containing ceteareth-27) and then WCS-3 (oleth-20).

Tests of alkylether compositions, as evidenced in Examples herein, have shown that in general those containing alkylethers of hydrophobe carbon chain length 16 or greater show greater biological effectiveness than those having a shorter hydrophobe. In general greater biological effectiveness has been obtained where the hydrophobe is saturated (as, for example, in steareth-20 and ceteareth-27) than where it is unsaturated (as, for example, in oleth-20).

The following compositions were made containing 15% glyphosate a.e. and 5% alkylether surfactant, but no butyl stearate. In WCS-10 the surfactant was steareth-10, in WCS-11 oleth-10 and in WCS-12 steareth-8 (laboratory sample from Sigma).

| Composition | Alkylether | Birefringence at 15 min. |
|---|---|---|
| WCS-10 | Brij 76 (steareth-10) | yes |
| WCS-11 | Brij 97 (oleth-10) | no |
| WCS-12 | steareth-8 | yes |

The property of forming anisotropic aggregates as determined by this test appears to require, on a $C_{16-18}$ straight-chain alcohol, a minimum of about 10 moles of ethylene oxide (EO). Where the alcohol is oleyl, an EO chain of 10 units is already too short, but where the alcohol is stearyl, even as short an EO chain as 8 units appears to suffice. It should be noted, however, that the steareth-8 used in composition WCS-12 was obtained as a laboratory sample and is likely chemically purer than the commercial surfactants used in other compositions. Commercial grade steareth-8 will not necessarily give the same result.

As further evidence of the usefulness of the present anisotropy test in predicting biological effectiveness of exogenous chemical compositions, compositions WCS-6, WCS-7 and WCS-8 were prepared. each containing 30% glyphosate a.e. by weight, and were then diluted to 15% glyphosate a.e. for the test. All contained soybean lecithin (45% phospholipid, Avanti) and were prepared by process (v) as detailed in the Examples herein. Composition WCS-6, before dilution, contained 5% lecithin, 5% Fluorad FC-754 and 0.75% Ethomeen T/25. Composition WCS-7, before dilution, contained 2% lecithin and 2% Fluorad FC-754. Composition WCS-8, before dilution, contained 2% lecithin and 0.75% Ethomeen T/25. In addition. Composition WCS-9 was prepared containing 15% glyphosate a.e. and 5% soybean lecithin (45% phospholipid, Avanti). The following results were obtained.

| Composition | Excipient ingredients | Birefringence at 10 min. |
|---|---|---|
| WCS-6 | lecithin + FC-754 + Ethomeen T/25 | yes |
| WCS-7 | lecithin + FC-754 | yes |
| WCS-8 | lecithin + Ethomeen T/25 | no |
| WCS-9 | lecithin | no |

As evidenced in the Examples herein, enhanced biological effectiveness is a feature of compositions containing lecithin as the first excipient substance and Fluorad FC-754 as the second excipient substance. In the absence of Fluorad FC-754 or like material, lecithin, either alone or together with a tertiary alkylamine surfactant such as Ethomeen T/25 or MON 0818, does not consistently generate the desired enhancement.

In a further demonstration of the usefulness of the present anisotropy test, compositions WCS-13 and WCS-14 were prepared, each containing 20% glyphosate a.e. by weight, and were then diluted to 15% glyphosate a.e. for the test. Both contained soybean lecithin (45% phospholipid, Avanti). Composition WCS-13 was made by process (x) as described in the Examples herein and, before dilution, contained 6% lecithin, 6% Ethomeen T/25 and 1.5% butyl stearate. Composition WCS-14 was identical except that it contained no butyl stearate. Particular care was taken in this study to avoid excessive warning of the wax-coated slide by prolonged illumination. The following results were obtained.

| Composition | Excipient ingredients | Birefringence at 15 min. |
|---|---|---|
| WCS-13 | lecithin + Ethomeen T/125 + butyl stearate | yes |
| WCS-14 | lecithin + Ethomeen T/25 | no |

The addition of a small quantity of butyl stearate was thus sufficient to confer, on a glyphosate+lecithin+Ethomeen T/25 composition, the property of forming anisotropic aggregates in or on a wax layer. The Examples herein illustrate the unexpected enhancement of biological effectiveness observed when an exogenous chemical is formulated with lecithin and a fatty acid ester such as butyl stearate.

Thus where, for reasons of economy, compatibility with the exogenous chemical, or other considerations it is desired to provide an exogenous chemical composition having a relatively low content of excipient substances (for example a weight ratio of each excipient substance to exogenous chemical of about 1:3 or less), the anisotropy test provided here is an in vitro assay method which can be used to identify biologically effective compositions in advance of extensive testing in vivo.

The in vitro assay method just described, together with modifications thereof that will be readily apparent to those of skill in the art, is a further embodiment of the present invention.

Examples of exogenous chemical substances that can be included in compositions of the present invention include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. In one embodiment of the invention, the exogenous chemical is polar.

A preferred group of exogenous chemicals are those that are normally applied post-emergence to the foliage of plants, i.e. foliar-applied exogenous chemicals.

Some exogenous chemicals useful in the present invention are water-soluble, for example salts that comprise biologically active ions, and also comprise counterions, which may be biologically inert or relatively inactive. A particularly preferred group of these water-soluble exogenous chemicals or their biologically active ions or moieties are systemic in plants, that is, they are to some extent translocated from the point of entry in the foliage to other parts of the plant where they can exert their desired biological effect. Especially preferred among these are herbicides, plant growth regulators and nematicides, particularly those that have a molecular weight, excluding counterions, of less than about 300. More especially preferred among these are exogenous chemical compounds having one or more functional groups selected from amine, carboxylate, phosphonate and phosphinate groups.

Among such compounds, an even more preferred group are herbicidal or plant growth regulating exogenous chemical compounds having at least one of each of amine carboxylate, and either phosphonate or phosphinate functional groups. Salts of N-phosphonomethylglycine are examples of this group of exogenous chemicals. Further examples include salts of glufosinate, for instance the ammonium salt (ammonium DL-homoalanin-4-yl (methyl) phosphinate).

Another preferred group of exogenous chemicals which can be applied by the method of the invention are nematicides such as those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

Exogenous chemicals which can usefully be applied by the method of the present invention are normally, but not exclusively, those which are expected to have a beneficial effect on the overall growth or yield of desired plants such as crops, or a deleterious or lethal effect on the growth of undesirable plants such as weeds. The method of the present invention is particularly useful for herbicides, especially those that are normally applied post-emergence to the foliage of unwanted vegetation.

Herbicides which can be applied by the method of the present invention include but are not limited to any listed in standard reference works such as the "Herbicide Handbook," *Weed Science Society of America*, 1994, 7th Edition, or the "Farm Chemicals Handbook," Meister Publishing Company, 1997 Edition. Illustratively these herbicides include acetanilides such as acetochlor, alachlor and metolachlor, aminotriazole, asulam, bentazon, bialaphos, bipyridyls such as paraquat, bromacil, cyclohexenones such as clethodim and sethoxydim, dicamba, diflufenican, dinitroanilines such as pendimethalin, diphenylethers such as acifluorfen, fomesafen and oxyfluorfen, fatty acids such as $C_{9-10}$ fatty acids, fosamine, flupoxam, glufosinate, glyphosate, hydroxybenzonitriles such as bromoxynil, imidazolinones such as imazaquin and imazethapyr, isoxaben, norflurazon, phenoxies such as 2,4-D, phenoxypropionates such as diclofop, fluazifop and quizalofop, picloram, propanil, substituted ureas such as fluometuron and isoproturon, sulfonylureas such as chlorimuron, chlorsulfuron, halosulfuron, metsulfuron, primisulfuron, sulfometuron and sulfosulfuron, thiocarbamates such as triallate, triazines such as atrazine and metribuzin, and triclopyr. Herbicidally active derivatives of any known herbicide are also within the scope of the present invention. A herbicidally active derivative is any compound which is a minor structural modification, most commonly but not restrictively a salt or ester, of a known herbicide. These compounds retain the essential activity of the parent herbicide, but may not necessarily have a potency equal to that of the parent herbicide. These compounds may convert to the parent herbicide before or after they enter the treated plant. Mixtures or coformulations of a herbicide with other ingredients, or of more than one herbicide, may likewise be employed.

An especially preferred herbicide is N-phosphonomethylglycine (glyphosate), a salt, adduct or ester thereof, or a compound which is converted to glyphosate in plant tissues or which otherwise provides glyphosate ion. Glyphosate salts that can be used according to this invention include but are not restricted to alkali metal, for example sodium and potassium, salts; ammonium salt; alkylamine, for example dimethylamine and isopropylamine, salts; alkanolamine, for example ethanolamine, salts; alkylsulfonium, for example trimethylsulfonium, salts; sulfoxonium salts; and mixtures thereof. The herbicidal compositions sold by Monsanto Company as ROUNDUP® and ACCORD® contain the monoisopropylamine (IPA) salt of N-phosphonomethylglycine. The herbicidal compositions sold by Monsanto Company as ROUNDUP® Dry and RIVAL® contain the monoammonium salt of N-phosphonomethylglycine. The herbicidal composition sold by Monsanto Company as ROUNDUP® Geoforce contains the monosodium salt of N-phosphonomethylglycine. The herbicidal composition sold by Zeneca as TOUCHDOWN® contains the trimethylsulfonium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and trisodium salts, and the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (e.g. granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinarn agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:

Annual broadleaves:
  velvetleaf (*Abutilon theophrasti*)
  pigweed (Amaranthus spp.)
  buttonweed (Borreria spp.)
  oilseed rape, canola, indian mustard, etc. (Brassica spp.)
  commelina (Commelina spp.)
  filaree (Erodium spp.)
  sunflower (Helianthus spp.)
  morningglory (Ipomoea spp.)
  kochia (*Kochia scoparia*)
  mallow (Malva spp.)
  wild buckwheat, smartweed, etc. (Polygonum spp.)
  purslane (Portulaca spp.)
  russian thistle (Salsola spp.)
  sida (Sida spp.)
  wild mustard (*Sinapis arvensis*)
  cocklebur (Xanthium spp.)
Annual narrowleaves:
  wild oat (*Avena fatua*)
  carpetgrass (Axonopus spp.)
  downy brome (*Bromus tectorum*)
  crabgrass (Digitaria spp.)
  barnyardgrass (*Echinochloa crus-galli*)
  goosegrass (*Eleusine indica*)
  annual ryegrass (*Lolium multiflorum*)
  rice (*Oryza sativa*)
  ottochloa (*Ottochloa nodosa*)
  bahiagrass (*Paspalum notatum*)
  canarygrass (Phalaris spp.)
  foxtail (Setaria spp.)
  wheat (*Triticum aestivum*)
  corn (*Zea mays*)
Perennial broadleaves:
  mugwort (Artemisia spp.)
  milkweed (Asclepias spp.)
  canada thistle (*Cirsium arvense*)
  field bindweed (*Convolvulus arvensis*)
  kudzu (Pueraria spp.)
Perennial narrowleaves:
  brachiaria (Brachiaria spp.)
  bermudagrass (*Cynodon dactylon*)
  yellow nutsedge (*Cyperus esculentus*)
  purple nutsedge (*C. rotundus*)
  quackgrass (*Elymus repens*)
  lalang (*Imperata cylindrica*)
  perennial ryegrass (*Lolium perenne*)
  guineagrass (*Panicum maximum*)
  dallisgrass (*Paspalum dilatatum*)
  reed (Phragmites spp.)
  johnsongrass (*Sorghum halepense*)
  cattail (Typha spp.)
Other perennials:
  horsetail (Equisetum spp.)
  bracken (*Pteridium aquilinum*)
  blackberry (Rubus spp.)
  gorse (*Ulex europaeus*)

Thus, the method of the present invention, as it pertains to glyphosate herbicide, can be useful on any of the above species.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

Aggregate-forming substances useful as the first excipient substance in compositions of the present invention include a wide variety of amphiphilic materials, of which three classes are preferred.

The first preferred class of aggregate-forming substances can be defined as amphiphilic liposome-forming substances. These include various lipids of synthetic, animal, or plant origin, including phospholipids, ceramides, sphingolipids, dialkyl surfactants, and polymeric surfactants. A variety of these materials are known to those skilled in the art, and are commercially available. Lecithins are particularly rich in phospholipids and can be derived from a number of plant and animal sources. Soybean lecithin is one particular example of a relatively inexpensive commercially available material that includes such substances.

Many other substances have been described which can be used to form liposomes; the present invention includes compositions comprising any such liposome-forming substances, so long as other requirements set out above are met, and use of such compositions for enhancing biological effectiveness of exogenous chemicals applied to foliage of plants. For example, U.S. Pat. No. 5,580,859, incorporated here by reference, discloses liposome-forming substances having a cationic group, including N-(2,3-di-(9-(Z)-octadecenyloxy))-prop-1-yl-N,N,N-trimethylarnmoniun chloride (DOTMA) and 1,2-bis(oleoyloxy)-3-(trimethylammonio)propane (DOTAP). Liposome-forming substances which are not themselves cationic, but do contain a cationic group as part of the hydrophilic moiety, include for example dioleoylphosphatidylcholine (DOPC) and dioleoylphosphatidylethanolamine (DOPE). Liposome-forming substances that do not contain a cationic group include dioleoylphosphatidylglycerol (DOPG). Any of these liposome-forming substances can be used with or without the addition of cholesterol.

These substances contain portions that are hydrophilic and hydrophobic within the same molecule. They have the ability to self-assemble in aqueous solution or dispersion into structures that are more complex than simple micelles. The nature of the aggregate that will be formed can be related to the critical packing parameter P by the following equation:

$$P=V/lA$$

where V is the volume of the hydrophobic tail of the molecule, l is the effective length of the hydrophobic tail, and A is the area occupied by the hydrophilic headgroup in the surface of the aggregate. The most probable self-assembled structures are spherical micelles when P is less than ⅓, rodlike micelles when P is between ⅓ and ½, lamellar when P is between 1 and ½, and inverse structures when P is greater than 1. The preferred materials in the present invention have P greater than ⅓.

Cationic liposome-forming substances having a hydrophobic moiety comprising two hydrocarbyl chains are accompanied by a counterion (anion), identified as Z in formulas I, II and III above. Any suitable anion can be used, including agriculturally acceptable anions such as hydroxide, chloride, bromide, iodide, sulfate, phosphate and acetate. In a specific embodiment where the exogenous chemical has a biologically active anion, that anion can serve as the counterion for the liposome-forming substance. For example, glyphosate can be used in its acid form together with the hydroxide of a cationic liposome-forming substance such as a compound of formula I.

Compounds of formula I known in the art to be liposome-forming include distearyldimethylammonium chloride and bromide (also known in the art as DODAC and DODAB respectively). Compounds of formula II known in the art to be liposome-forming include DOTMA referenced above and dimyristooxypropyldimethylhydroxyethylammonium bromide (DMRIE). Compounds of formula III known in the art to be liposome-forming include dioleoyloxy-3-(dimethylammonio)propane (DODAP) and DOTAP referenced above. Compounds of formula IV known in the art to be liposome-forming include DOPC and DOPE, both referenced above.

In many liposome-forming substances known in the art, the hydrophobic hydrocarbyl chains are unsaturated, having one or more double bonds. Particularly commonly used in the pharmaceutical art are dioleyl or dioleoyl compounds. A potential problem with these is that in an oxidizing environment they become oxidized at the site of the double bond. This can be inhibited by including in the formulation an antioxidant such as ascorbic acid. Alternatively the problem can be avoided by use of liposome-forming substances wherein a high proportion of the hydrophobic hydrocarbyl chains are fully saturated. Thus in a preferred embodiment of the invention, $R^1$ and $R^2$ in formulas I–IV are independently saturated straight-chain alkyl groups. Particularly preferred compositions use liposome-forming substances in which $R^1$ and $R^2$ are both palmityl (cetyl) or palmitoyl or, alternatively, are both stearyl or stearoyl groups.

Phospholipids, because of their low cost and favorable environmental properties, are particularly favored among liposome-forming substances in the method and compositions of the invention. Vegetable lecithins, such as soybean lecithin, have successfully been used in accordance with the invention. The phospholipid content of the lecithin product can range from about 10% to close to 100%. While acceptable results have been obtained with crude lecithin (10–20% phospholipid), it is generally preferred to use lecithin that is at least partially de-oiled, so that the phospholipid content is in the region of about 45% or more. Higher grades. such as 95%, provide excellent results but the much higher cost is unlikely to be justified for most applications.

The phospholipid component of lecithin, or any phospholipid composition used in the present invention, may comprise one or more phosphatides of natural or synthetic origin. Each of these phosphatides is generally a phosphoric ester that on hydrolysis yields phosphoric acid, fatty acid(s), polyhydric alcohol and, typically, a nitrogenous base. A phosphatide component may be present in a partially hydrolyzed form, e.g. as phosphatidic acid. Suitable phosphatides include, without limitation, phosphatidylcholine, hydrogenated phosphatidylcholine, phosphatidylinositol, phosphatidylserine, phosphatidic acid, phosphatidylglycerol, phosphatidylethanolamine, N-acyl phosphatidylethanolamine, and mixtures of any of these.

In vegetable lecithins a high proportion of the hydrophobic hydrocarbyl chains of the phospholipid compounds are typically unsaturated. One preferred embodiment of compositions in accordance with the present invention comprises both saturated phospholipid and unsaturated phospholipid, with the weight ratio of saturated phospholipid to unsaturated phospholipid being greater than about 1:2. In various particularly preferred embodiments, (1) at least 50% by weight of the phospholipids are di-$C_{12-22}$-saturated alkanoyl phospholipid, (2) at least 50% by weight of the phospholipids are di-$C_{16-18}$-saturated alkanoyl phospholipid, (3) at least 50% by weight of the phospholipids are distearoyl phospholipid, (4) at least 50% by weight of the phospholipids are dipalmitoyl phospholipid, or (5) at least 50% by weight of the phospholipids are distearoyl phosphatidylcholine, dipalmitoyl phosphatidylcholine, or a mixture thereof. Higher proportions of saturated alkanoyl phospholipids are generally found in lecithins of animal origin, such as for example egg yolk lecithin, than in vegetable lecithins.

Phospholipids are known to be chemically unstable, at least in acid media, where they tend to degrade to their lyso-counterparts. Thus where phospholipids rather than more stable liposome-forming substances are used, it is usually preferable to adjust the pH of the composition upward. In the case of glyphosate compositions, the pH of a composition based on a mono-salt such as the monoisopropylammonium (IPA) salt is typically around 5 or lower. When phospholipids are used as the first excipient substance in a glyphosate composition of the invention, it will therefore be preferable to raise the pH of the composition, for example to around 7. Any convenient base can be used for this purpose; it will often be most convenient to use the same base as used in the glyphosate salt, for example isopropylamine in the case of glyphosate IPA salt.

Amphiphilic compounds useful as the first excipient substance herein are not limited to those having two hydrophobic hydrocarbyl groups such as the compounds of formulas I to IV. The second preferred class of aggregate-forming substances useful in the invention are cationic surfactant compounds having formula V above. In compounds of formula V, $R^8$ unless perfluorinated preferably has from about 12 to about 18 carbon atoms. $R^8$ is preferably perfluorinated. in which case it preferably has from about 6 to about 12 carbon atoms. Preferably n is 3. $R^9$ groups are preferably methyl.

Sulfonylamino compounds of formula V are especially preferred. Suitable examples include 3-(((heptadecafluorooctyl)sulfonyl)amino)-N,N,N-trimethyl-1-propaminium iodide, available for example as Fluorad FC-135 from 3M Company, and the corresponding chloride. It is believed that Fluorad FC-754 of 3M Company is the corresponding chloride.

Fluoro-organic surfactants such as the cationic types falling within formula V belong to a functional category of surfactants known in the art as "superspreaders" or "superwetters". As a class "superspreaders" or "superwetters" are very effective in reducing surface tension of aqueous compositions containing relatively low concentrations of these surfactants. In many applications fluoro-organic surfactants can substitute for organosilicone surfactants which are likewise "superspreaders" or "superwetters". An example is found in European patent application 0 394 211 which discloses that either organosilicone or fluoro-organic surfactants can be used interchangeably in solid granular formulations of pesticides to improve dissolution rate.

Two major problems have limited interest in "superspreaders" and "superwetters" by formulators of exogenous chemicals such as pesticides. The first is high unit cost. The second is that although surfactants of this finctional category can enhance performance of an exogenous chemical on some species, for example by assisting penetration of the exogenous chemical into the interior of leaves via stomata, they can be antagonistic, sometimes severely so, to performance of the same exogenous chemical on other species.

Surprisingly, a subclass of fluoro-organic surfactants has now been found to be essentially non-antagonistic at concentrations which nevertheless provide useful adjuvant effects. This subclass comprises cationic fluoro-organic surfactants of formula V and others having a property profile in common with those of formula V. The lack of antagonism makes this subclass very different from other fluoro-organic "superspreaders" or "superwetters". Further, it has been found that these non-antagonistic fluoro-organic surfactants can be useful at concentrations low enough to be cost-effective. Data in the Examples herein for compositions comprising Fluorad FC-135 or Fluorad FC-754 illustrate the unexpected properties of this subclass.

Derivatives of Fluorad FC-754, herein described as "FC-acetate" and "FC-salicylate," have been prepared by the following procedure. (1) The solvent in a sample of Fluorad FC-754 is gently evaporated off by heating in a glass beaker at 70–80° C., to leave a solid residue. (2) The solid residue is allowed to cool to room temperature. (3) A 1 g aliquot of the residue is placed in a centrifuge tube and dissolved in 5 ml isopropanol. (4) A saturated solution of potassium hydroxide (KOH) is prepared in isopropanol. (5) This solution is added drop by drop to the solution of FC-754 residue; this results in formation of a precipitate and addition of KOH solution continues until no further precipitate forms. (6) The tube is centrifuged at 4000 rpm for 5 minutes. (7) More KOH solution is added to check if precipitation is complete; if not, the tube is centrifuged again. (8) The supernatant is decanted into another glass tube. (9) A saturated solution of acetic acid (or salicylic acid) is prepared in isopropanol. (10) This solution is added to the supernatant in an amount sufficient to lower pH to 7. (11) Isopropanol is evaporated from this neutralized solution by heating at 60° C. until completely dry. (12) The residue (either the acetate or salicylate salt) is dissolved in a suitable amount of water and is then ready for use.

The third preferred class of aggregate-forming substance useful as the first excipient substance according to the present invention is a long-chain alkylether surfactant having the formula VI above. $R^{12}$ can be branched or unbranched, saturated or unsaturated. $R^{12}$ is preferably straight chain saturated $C_{16}$ alkyl (cetyl) or straight chain saturated $C_{18}$ alkyl (stearyl). In preferred alkylethers m is 0, n is an average number from about 20 to about 40 and $R^{13}$ is preferably hydrogen. Among especially preferred alkylether surfactants are those identified in the International Cosmetic Ingredient Directory as ceteth-20, ceteareth-20, ceteareth-27, steareth-20 and steareth-30.

Of the classes of aggregate-forming substance useful as the first excipient substance, not all give rise to anisotropic aggregates in or on a wax layer, as required by the present invention, when used as the sole excipient substance in the composition at a weight ratio of 1:3 to 1:100 with the exogenous chemical. Many compounds of formulas V and VI are sufficient in the absence of a second excipient substance, but in general the liposome-forming substances of formulas I to IV require the presence of a second excipient substance to exhibit the required anisotropic behavior. However, even in the presence of a first excipient substance of formulas V or VI, there may be advantages in also including a second excipient substance as herein defined.

The second excipient substance has one or more hydrophobic moieties. If there is only one hydrophobic moiety, it is a hydrocarbyl or haloalkyl group having about 6 to about 22 carbon atoms. If there is more than one hydrophobic moiety, each such moiety is a hydrocarbyl or haloalkyl group having more than 2 carbon atoms, and the total number of carbon atoms in the hydrophobic moieties is about 12 to about 40.

One class of second excipient substance useful in the present invention is quaternary ammonium compounds. Among quaternary ammonium compounds that may be used are compounds of formula $$N^+(R^{16})(R^{17})(R^{18})(R^{19})Q^- \qquad \text{VIII}$$

where $R^{16}$, $R^{17}$, $R^{18}$ and $R^{19}$ are independently $C_{3-6}$ alkyl groups and Q is a suitable anion, such as for example hydroxide, chloride, bromide, iodide, sulfate, phosphate or acetate. In preferred compounds of formula VIII all R groups are the same. Particularly preferred compounds of formula VIII are tetrabutylammonium salts. Where the exogenous chemical comprises a biologically active anion, a salt of formula VIII where Q is that anion is an option providing both the exogenous chemical and second excipient substance. An example is the tetrabutylammonium salt of glyphosate.

Other quaternary ammonium compounds that may be useful include compounds having a single $C_{12-22}$ hydrocarbyl group and three $C_{1-4}$ alkyl groups attached to the quaternary nitrogen atom. One or more of the $C_{1-4}$ alkyl groups in such compounds can be replaced by a benzyl group. Specific examples include cetyltrimethylammonium bromide and benzalkonium chloride. Yet other quaternary ammonium compounds useful as the second excipient substance include compounds of formula I, where the first excipient substance is not of formula I.

Preferred quaternary ammonium compounds useful as the second excipient substance are compounds of formula V, where the first excipient substance is not of formula V. The same specific compounds of formula V are especially preferred whether a compound of formula V is the first or the second excipient substance. Particularly good results have been obtained where the first excipient substance is lecithin and the second excipient substance is Fluorad FC-135 or FC-754 or chemical equivalents thereof.

Another class of compound useful as the second excipient substance is an amide or ester of formula VII above.

$R^{14}$ in formula VII is preferably aliphatic and has about 7 to about 21 carbon atoms, more preferably about 13 to about 21 carbon atoms. It is especially preferred that $R^{14}$ be a saturated straight-chain alkyl group. $R^{15}$ is preferably an aliphatic group having 1–6 carbon atoms, more preferably alkyl or alkenyl having 2–4 carbon atoms. An especially preferred compound of formula VII for use as the second excipient substance is butyl stearate.

As compounds of formula VII, including butyl stearate, are generally oily liquids, aqueous compositions containing them are typically emulsions having at least one aqueous phase and at least one oil phase, with the compound of formula VII being present predominantly in the oil phase. Such emulsions may be water-in-oil, oil-in-water or water-in-oil-in-water (W/O/W) multiple emulsions.

Aqueous concentrate compositions where the first excipient substance is an alkylether of formula VI and the second excipient substance, if present, is a fatty acid ester of formula VII are limited in the degree to which an exogenous chemical such as glyphosate can be loaded. At some point, as the loading of exogenous chemical is increased, the composition will not remain suitably stable. Addition of a small amount of colloidal particulate to such compositions has surprisingly been found to greatly increase loading ability while retaining desired stability. Oxides of silicon, aluminum and titanium are preferred colloidal particulate materials. Particle size is preferably such that specific surface area is in the range from about 50 to about 400 m²/g. Where the exogenous chemical is glyphosate, the use of colloidal particulate enables loadings of at least 30% by weight for compositions containing sufficient alkylether and fatty acid ester to show enhanced herbicidal effectiveness, or at least 40% for compositions containing alkylether but no fatty acid ester, and showing herbicidal effectiveness at least equal to current commercial products loaded at about 30%.

We have found especially useful improvement in storage stability can be obtained using colloidal particulates having specific surface area between about 180 and about 400 m²/g.

Other means of improving stability of highly loaded compositions comprising an alkylether of formula VI, with or without a fatty acid ester, may also be possible and are within the scope of the present invention.

Compositions in accordance with the present invention are typically prepared by combining water, the exogenous chemical (unless it is a formulation which will not contain an exogenous chemical) and the aggregate-forming substance. Where the aggregate-forming substance is one that disperses readily in water, as is the case for example with Fluorad FC-135 or Fluorad FC-754, simple mixing with mild agitation may be sufficient. However, where the aggregate-forming substance requires high shear to disperse in water, as is the case for example with most forms of lecithin, it is presently preferred to sonicate or microfluidize the aggregate-forming substance in water. This can be done before or after a surfactant and/or the exogenous chemical is added. The sonication or microfluidization will generally produce liposomes or other aggregate structures other than simple micelles. The precise nature, including average size, of liposomes or other aggregates depends among other things on the energy input during sonication or microfluidization. Higher energy input generally results in smaller liposomes. Although it is possible to entrap or otherwise bind loosely or tightly the exogenous chemical in or on liposomes or with other supramolecular aggregates, the exogenous chemical does not need to be so entrapped or bound, and in fact the present invention is effective when the exogenous chemical is not entrapped or bound in the aggregates at all.

In a particular embodiment of the invention, the liposomes or other aggregates have an average diameter of at least 20 nm, more preferably at least 30 nm. We have determined by light scattering that certain liposomal compositions of the invention have average liposome diameters ranging from 54 to 468 nm as calculated using linear fit and from 38 to 390 nm as calculated using quadratic fit.

The concentrations of the various components will vary, in part depending on whether a concentrate is being prepared that will be further diluted before spraying onto a plant, or whether a solution or dispersion is being prepared that can be sprayed without further dilution.

In an aqueous glyphosate formulation that includes a dialkyl surfactant, for example a cationic dialkyl surfactant of formula I. suitable concentration ranges are: glyphosate 0.1–400 grams acid equivalent (a.e.)/liter, and dialkyl surfactant 0.001–10% by weight. In an aqueous glyphosate formulation using a cationic fluoro-organic surfactant and lecithin, suitable concentrations can be: glyphosate 0.1–400 g a.e./l, fluoro-organic surfactant 0.001–10% by weight, and soybean lecithin 0.001–10% by weight.

In an aqueous glyphosate formulation that includes a $C_{16-18}$ alkylether surfactant and butyl stearate, suitable concentrations can be: glyphosate 0.1–400 g a.e./l, alkylether surfactant 0.001–10% by weight, and butyl stearate 0.001–10% by weight. To achieve the higher concentrations in these ranges it is often beneficial to add other ingredients to provide acceptable storage stability, for example colloidal particulate silica or aluminum oxide at 0.5–2.5% by weight. In an aqueous glyphosate formulation that includes a $C_{16-18}$ alkylether surfactant but no butyl stearate, glyphosate concentration can suitably be increased to 500 g a.e./l or more, in the presence of a colloidal particulate at 0.5–2.5% by weight.

In solid glyphosate formulations, higher concentrations of ingredients are possible because of the elimination of most of the water.

Weight/weight ratios of ingredients may be more important than absolute concentrations. For example, in a glyphosate formulation containing lecithin and a cationic fluoro-organic surfactant, the ratio of lecithin to glyphosate a.e. is in the range from about 1:3 to about 1:100. It is generally preferred to use a ratio of lecithin to glyphosate a.e. close to as high as can be incorporated in the formulation while maintaining stability, in the presence of an amount of the fluoro-organic surfactant sufficient to give the desired enhancement of herbicidal effectiveness. For example, a lecithin/glyphosate a.e. ratio in the range from about 1:3 to about 1:10 will generally be found useful, although lower ratios, from about 1:10 to about 1:100 can have benefits on particular weed species in particular situations. The ratio of fluoro-organic surfactant, when present, to glyphosate a.e. is likewise preferably in the range from about 1:3 to about 1:100. Because fluoro-organic surfactants tend to have relatively high cost, it will generally be desirable to keep this ratio as low as possible consistent with achieving the desired herbicidal effectiveness.

The ratio of fluoro-organic surfactant where present, to lecithin is preferably in the range from about 1:10 to about 10:1, more preferably in the range from about 1:3 to about 3:1 and most preferably around 1:1. The ranges disclosed herein can be used by one of skill in the art to prepare compositions of the invention having suitable concentrations and ratios of ingredients. Preferred or optimum concentrations and ratios of ingredients for any particular use or situation can be determined by routine experimentation.

Although the combination of the components might be done in a tank mix, it is preferred in the present invention that the combination be made further in advance of the application to the plant, in order to simplify the tasks required of the person who applies the material to plants. We have found, however, that in some cases the biological effectiveness of a liposome-containing composition prepared from scratch as a dilute spray composition is superior to that of a composition having the same ingredients at the same concentrations but diluted from a previously prepared concentrate formulation.

Although various compositions of the present invention are described herein as comprising certain listed materials, in some preferred embodiments of the invention the compositions consist essentially of the indicated materials.

Optionally, other agriculturally acceptable materials can be included in the compositions. For example, more than one exogenous chemical can be included. Also, various agriculturally acceptable adjuvants can be included, whether or not their purpose is to directly contribute to the effect of the exogenous chemical on a plant. For example, when the exogenous chemical is a herbicide, liquid nitrogen fertilizer or ammonium sulfate might be included in the composition. As another example, stabilizers can be added to the composition. In some instances it might be desirable to include microencapsulated acid in the composition, to lower the pH of a spray solution on contact with a leaf. One or more surfactants can also be included. Surfactants mentioned here by trade name, and other surfactants that can be useful in the method of the invention, are indexed in standard reference works such as McCutcheon's Emulsifiers and Detergents, 1997 edition, Handbook of Industrial Surfactants, 2nd Edition, 1997, published by Gower, and International Cosmetic Ingredient Dictionary, 6th Edition, 1995.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions. Water-in-oil-in-water multiple emulsion compositions tested in the field have included:

| | | % w/w | | | | | | | |
|---|---|---|---|---|---|---|---|---|---|
| Field composition | Glyphosate g a.e./l | Fatty acid ester | Emulsifier #1 | Emulsifier #2 | % in inner aq. phase: Water | % in inner aq. phase: Glyphosate | Emulsifier #1 | Emulsifier #2 | Type of fatty acid ester |
| F-1 | 100 | 18.0 | 3.0 | 5.0 | 13.8 | 20 | Span 80 | Tween 20 | Bu stearate |
| F-2 | 100 | 7.5 | 3.0 | 5.0 | 5.6 | 20 | Span 80 | Tween 20 | Bu stearate |
| F-3 | 100 | 7.5 | 3.0 | 5.0 | 5.6 | 0 | Span 80 | Tween 20 | Bu stearate |
| F-4 | 160 | 7.5 | 3.0 | 5.0 | 5.6 | 0 | Span 80 | Tween 20 | Bu stearate |

The above compositions were prepared by process (vi) as described in the Examples.

Aqueous compositions tested in the field having an alkylether surfactant as the first excipient substance and/or containing a fatty acid ester have included:

| Field composition | Glyphosate g a.e./l | % w/w Fatty acid ester | Surfactant | Type of surfactant | Type of fatty acid ester |
|---|---|---|---|---|---|
| F-5 | 163 | 1.0 | 10.0 | oleth-20 | Bu stearate |
| F-6 | 163 | 1.0 | 10.0 | Tween 80 | Bu stearate |
| F-7 | 163 | 1.0 | 10.0 | Neodol 25-20 | Bu stearate |
| F-8 | 163 | 1.0 | 10.0 | steareth-20 | Bu stearate |
| F-9 | 163 | 1.0 | 10.0 | Neodol 25-12 | Bu stearate |
| F-10 | 105 | 7.5 | 10.0 | Tween 80 | Bu stearate |
| F-11 | 163 | 0.5 | 5.0 | oleth-20 | Bu stearate |
| F-12 | 163 | 0.3 | 5.0 | oleth-20 | Bu stearate |
| F-13 | 163 | 0.3 | 2.5 | oleth-20 | Bu stearate |
| F-14 | 163 | 1.0 | 10.0 | Neodol 25-12 | Bu stearate |
| F-15 | 163 | 0.3 | 5.0 | Genapol UD-110 | Bu stearate |
| F-16 | 163 | 0.5 | 5.0 | steareth-20 | Bu stearate |
| F-17 | 163 | 0.5 | 5.0 | ceteth-20 | Bu stearate |
| F-18 | 163 | 0.5 | 5.0 | laureth-23 | Bu stearate |
| F-19 | 163 | 0.5 | 5.0 | ceteareth-27 | Bu stearate |
| F-20 | 163 | 0.5 | 5.0 | Neodol 25-12 | Bu stearate |
| F-21 | 163 | 0.5 | 5.0 | Neodol 25-20 | Bu stearate |
| F-22 | 163 | | 5.0 | steareth-20 | |
| F-23 | 163 | | 5.0 | ceteth-20 | |
| F-24 | 163 | | 5.0 | laureth-23 | |
| F-25 | 163 | 0.3 | 5.0 | ceteareth-27 | Bu stearate |
| F-26 | 163 | 0.3 | 2.5 | ceteareth-27 | Bu stearate |
| F-27 | 163 | | 5.0 | ceteareth-27 | |
| F-28 | 163 | 0.5 | 5.0 | ceteareth-27 | Me stearate |
| F-29 | 163 | 0.5 | 5.0 | steareth-20 | Me stearate |
| F-30 | 163 | 0.5 | 5.0 | oleth-20 | |
| F-31 | 163 | 0.5 | 5.0 | Neodol 45-13 | Bu stearate |
| F-32 | 163 | | 5.0 | Neodol 45-13 | |
| F-33 | 163 | 0.5 | 5.0 | ceteareth-15 | Bu stearate |
| F-34 | 163 | | 5.0 | ceteareth-15 | |
| F-35 | 163 | 0.5 | 5.0 | steareth-30 | Bu stearate |

The above compositions were prepared by process (vii) if they contain fatty acid ester and by process (viii) if they do not. Both processes are described in the Examples.

Aqueous compositions tested in the field containing colloidal particulates have included:

| Field composition | Glyphosate g a.e./l | % w/w Fatty acid ester | Surfactant | Coll. partic. | Other | Type of surfactant | Type of colloidal particulate | Type of fatty acid ester | Other ingredients |
|---|---|---|---|---|---|---|---|---|---|
| F-36 | 360 | 1.0 | 10.0 | 1.3 | | steareth-20 | Aerosil 380 | Bu stearate | |
| F-37 | 360 | 1.0 | 10.0 | 1.3 | | oleth-20 | Aerosil 380 | Bu stearate | |
| F-38 | 360 | 1.0 | 10.0 | 1.3 | | steareth-30 | Aerosil 380 | Bu stearate | |
| F-39 | 360 | | 10.0 | 1.3 | | steareth-30 | Aerosil 380 | | |
| F-40 | 360 | | | 0.8 | | | Aerosil 90 | | |
| F-41 | 350 | | | 0.8 | | | Al oxide C | | |
| F-42 | 360 | | 3.0 | 0.8 | | Ethomeen T/25 | Al oxide C | | |
| F-43 | 360 | | 3.0 | 0.1 | | Ethomeen T/25 | Al oxide C | | |
| F-44 | 360 | | | 0.3 | | | Al oxide C | | |
| F-45 | 360 | | 3.0 | 0.3 | | Ethomeen T/25 | Al oxide C | | |
| F-46 | 360 | | 6.0 | 0.8 | | Agrimul PG-2069 | Al oxide C | | |
| F-47 | 360 | | 3.0 | 0.8 | | Tween 20 | Al oxide C | | |
| F-48 | 480 | | 1.0 | 0.4 | | Neodol 1-7 | Aerosil 90 | | |
| F-49 | 480 | | 2.0 | 0.4 | | Agrimul PG-2069 | Aerosil 90 | | |
| F-50 | 360 | 1.0 | 10.0 | 1.3 | | ceteareth-15 | Aerosil 380 | Bu stearate | |
| F-51 | 360 | 1.0 | 10.0 | 1.3 | | ceteth-20 | Aerosil 380 | Bu stearate | |
| F-52 | 360 | 1.0 | 10.0 | 1.3 | | steareth-20 | Aerosil 380 | Bu stearate | |
| F-53 | 360 | 1.0 | 10.0 | 1.3 | | oleth-20 | Aerosil 380 | Bu stearate | |
| F-54 | 360 | 1.0 | 10.0 | 1.3 | | ceteareth-27 | Aerosil 380 | Bu stearate | |
| F-55 | 360 | 1.0 | 10.0 | 1.3 | | steareth-30 | Aerosil 380 | Bu stearate | |
| F-56 | 360 | | 10.0 | 1.3 | | steareth-30 | Aerosil 380 | | |
| F-57 | 360 | | 10.0 | 1.3 | | ceteareth-27 | Aerosil 380 | | |
| F-58 | 360 | | 10.0 | 1.3 | | steareth-20 | Aerosil 380 | | |
| F-59 | 360 | | 10.0 | 1.3 | | oleth-20 | Aerosil 380 | | |
| F-60 | 360 | 1.0 | 10.0 | 1.3 | | ceteareth-27 | Aerosil 380 | Me stearate | |
| F-61 | 360 | 1.0 | 10.0 | 1.3 | | ceteareth-27 | Aerosil 380 | Me palmitate | |

-continued

| Field composition | Glyphosate g a.e./l | % w/w Fatty acid ester | Surfactant | Coll. partic. | Other | Type of surfactant | Type of colloidal particulate | Type of fatty acid ester | Other ingredients |
|---|---|---|---|---|---|---|---|---|---|
| F-62 | 300 | | 10.0 | 1.3 | | ceteareth-27 | Aerosil 380 | | |
| F-63 | 240 | | 10.0 | 1.3 | | ceteareth-27 | Aerosil 380 | | |
| F-64 | 360 | | 6.0 | 1.3 | | ceteareth-27 | Aerosil 380 | | |
| F-65 | 300 | | 6.0 | 1.3 | | ceteareth-27 | Aerosil 380 | | |
| F-66 | 240 | | 6.0 | 1.3 | | ceteareth-27 | Aerosil 380 | | |
| F-67 | 360 | | | 0.6 | | | Aerosil 90 | | |
| F-68 | 360 | | | 3.1 | | | Aerosil 90 | | |
| F-69 | 360 | | | 0.6 | | | Al oxide C | | |
| F-70 | 360 | | | 3.1 | | | Al oxide C | | |
| F-71 | 360 | | | 0.8 | | | Aerosil 90 | | |
| F-72 | 360 | | | 0.8 | | | Al oxide C | | |
| F-73 | 360 | | 3.0 | 0.8 | | Ethomeen T/25 | Aerosil 90 | | |
| F-74 | 360 | | 3.0 | 0.8 | | Ethomeen T/25 | Al oxide C | | |
| F-75 | 360 | | 3.0 | 0.3 | | Ethomeen T/25 | Al oxide C | | |
| F-76 | 360 | | 3.0 | 0.8 | | Ethomeen T/25 | Nalco 1056 | | |
| F-77 | 360 | | 3.0 | 0.8 | | Ethomeen C/25 | Nalco 1056 | | |
| F-78 | 480 | | 3.0 + 1.0 | 0.4 | | Ethomeen T/25 + Agrimul PG-2069 | Al oxide C | | |
| F-79 | 480 | | 3.0 + 3.0 | 0.4 | | Ethomeen T/25 + Agrimul PG-2069 | Al oxide C | | |
| F-80 | 360 | | 3.0 | 0.8 | | Agrimul PG-2069 | Aerosil 90 | | |
| F-81 | 360 | | 3.0 | 0.8 | | Tween 20 | Aerosil 90 | | |
| F-82 | 360 | | 3.1 + 3.1 | 0.8 | 7.1 | Ethomeen T/25 + Tween 20 | Aerosil 90 | | $(Bu)_4NOH$ |
| F-83 | 360 | | | 0.8 | 7.1 | | Aerosil 90 | | $(Bu)_4NOH$ |
| F-84 | 480 | | 3.0 | 0.8 | | steareth-20 | Aerosil 380 | | |
| F-85 | 480 | | 3.0 | 1.5 | | oleth-20 | Aerosil 380 | | |
| F-86 | 480 | | 3.0 | 1.5 | | oleth-20 | Aerosil MOX-170 | | |
| F-87 | 480 | | 3.0 | 1.5 | | oleth-20 | Aerosil OX-50 | | |
| F-88 | 480 | | 3.0 | 1.5 | | Velvetex AB-45 | Aerosil 380 | | |
| F-89 | 480 | | 3.0 | 1.5 | | steareth-20 | Aerosil blend 1 | | |
| F-90 | 480 | | 3.0 | 1.5 | | oleth-20 | Aerosil blend 2 | | |
| F-91 | 480 | | 4.5 | 1.5 | | oleth-20 | Aerosil 380 | | |
| F-92 | 480 | | 4.5 | 1.5 | | steareth-20 | Aerosil 380 | | |
| F-93 | 480 | | 3.0 | 1.5 | | steareth-20 | Aerosil blend 1 | | |
| F-94 | 480 | | 1.0 | 1.5 | | steareth-20 | Aerosil blend 1 | | |
| F-95 | 480 | | 6.0 | 1.5 | | steareth-20 | Aerosil blend 1 | | |
| F-96 | 480 | | 4.5 | 1.5 | 0.5 | steareth-20 | Aerosil blend 2 | | propylene glycol |
| F-97 | 480 | | 6.0 | 1.5 | 0.5 | steareth-20 | Aerosil blend 2 | | propylene glycol |
| F-98 | 480 | | 6.0 | 1.5 | 0.5 | oleth-20 | Aerosil blend 2 | | propylene glycol |
| F-99 | 480 | | 4.5 + 2.3 | 1.5 | 0.5 | steareth-20 + Ethomeen T/25 | Aerosil blend 2 | | propylene glycol |
| F-100 | 480 | | 6.0 | 1.5 | | steareth-20 | Al oxide C | | |
| F-101 | 480 | | 4.5 + 2.3 | 1.5 | 0.5 | steareth-20 + Ethomeen T/25 | Al oxide C | | propylene glycol |

-continued

| Field composition | Glyphosate g a.e./l | Fatty acid ester | Sur- factant | Coll. partic. | Other | Type of surfactant | Type of colloidal particulate | Type of fatty acid ester | Other ingredients |
|---|---|---|---|---|---|---|---|---|---|
| F-102 | 480 | | 4.5 + 1.0 | 1.5 | 0.5 | steareth-20 + Ethomeen T/25 | Al oxide C | | propylene glycol |
| F-103 | 480 | | 3.0 | 1.5 | | steareth-20 | Aerosil 380 | | |
| F-104 | 480 | | 4.5 | 1.5 | | steareth-20 | Al oxide C | | |
| F-105 | 480 | | 6.0 | 1.5 | | steareth-20 | Aerosil 380 | | |
| F-106 | 480 | | 4.5 + 1.0 | 1.5 | 0.5 | steareth-20 + Ethomeen T/25 | Aerosil 380 | | propylene glycol |
| F-107 | 480 | | 4.5 + 2.3 | 1.5 | 0.5 | steareth-20 + Ethomeen T/25 | Aerosil 380 | | propylene glycol |
| F-108 | 480 | | 4.5 | 1.5 | | steareth-20 | Aerosil blend 2 | | |
| F-109 | 480 | | 6.0 | 1.5 | | steareth-20 | Aerosil blend 2 | | |
| F-110 | 480 | | 4.5 + 1.0 | 1.5 | 0.5 | steareth-20 + Ethomeen T/25 | Aerosil blend 2 | | propylene glycol |
| F-111 | 480 | | 4.5 | 1.5 | | steareth-30 | Aerosil blend 2 | | |
| F-112 | 480 | | 4.5 + 1.0 | 1.5 | 0.5 | steareth-20 + Ethomeen T/25 | Aerosil blend 2 | | propylene glycol |
| F-113 | 480 | | 6.0 | 1.5 | | steareth-30 | Aerosil blend 2 | | |
| F-114 | 480 | | 4.5 + 2.3 | 1.5 | 0.5 | steareth-20 + Ethomeen T/25 | Aerosil blend 2 | | propylene glycol |
| F-115 | 480 | | 10.0 | 1.5 | | steareth-20 | Aerosil blend 2 | | |
| F-116 | 480 | | 4.5 | 1.5 | | ceteareth-27 | Aerosil 380 | | |
| F-117 | 480 | | 6.0 | 1.5 | | ceteareth-27 | Aerosil 380 | | |
| F-118 | 480 | | 4.5 | 1.5 | | ceteareth-27 | Aerosil blend 2 | | |
| F-119 | 480 | | 6.0 | 1.5 | | ceteareth-27 | Aerosil blend 2 | | |
| F-120 | 480 | | 4.5 | 1.5 | | ceteareth-27 | Al oxide C | | |
| F-121 | 480 | | 6.0 | 1.5 | | ceteareth-27 | Al oxide C | | |

Aerosil blend 1: Aerosil MOX-80 + Aerosil MOX-170 (1:1)
Aerosil blend 2: Aerosil MOX-80 + Aerosil 380 (1:2)

The above compositions were prepared by process (ix) as described in the Examples.

Aqueous compositions tested in the field having soybean lecithin (45% phospholipid, Avanti) as the first excipient substance and a cationic fluoro-organic surfactant as the second excipient substance have included:

| Field composition | Glyphosate g a.e./l | Lecithin | Fluorad FC-135 | Fluorad FC-754 | MON 0818 |
|---|---|---|---|---|---|
| F-122 | 167 | 6.0 | 8.3 | | 4.0 |
| F-123 | 168 | 6.0 | | 8.3 | 4.0 |
| F-124 | 228 | 2.0 | | 2.0 | 0.5 |
| F-125 | 347 | 3.0 | | 3.0 | 0.5 |
| F-126 | 344 | 1.0 | | 1.0 | 0.5 |
| F-127 | 111 | 8.0 | 8.0 | | 0.5 |
| F-128 | 228 | 6.0 | | 3.0 | 6.0 |
| F-129 | 228 | 6.0 | | 6.0 | 6.0 |
| F-130 | 228 | 3.3 | | 5.0 | 0.5 |
| F-131 | 228 | 5.0 | | 5.0 | 0.8 |
| F-132 | 372 | 3.0 | | 3.0 | 0.8 |
| F-133 | 372 | 3.0 | | 5.0 | 0.8 |
| F-134 | 372 | 3.0 | | 12.0 | 0.8 |

The above compositions were prepared by process (v) as described in the Examples.

Aqueous compositions tested in the field having soybean lecithin (45% phospholipid, Avanti) as the first excipient substance and fatty acid ester as the second excipient substance have included:

| Field composition | Glyphosate g a.e./l | Lecithin | MON 0818 | Fatty acid ester | Surfactant | Type of surfactant | Type of fatty acid ester |
|---|---|---|---|---|---|---|---|
| F-135 | 360 | 0.5 | 6.0 | 7.5 | 6.0 | Ethomeen T/25 | Bu stearate |
| F-136 | 360 | 6.0 | 4.5 | 1.5 | 3.0 + 4.5 | ceteareth-27 + Ethomeen T/25 | Bu stearate |
| F-137 | 228 | 6.0 | 3.0 | 1.5 | 3.0 | Ethomeen T/25 | Bu stearate |
| F-138 | 228 | 0.8 | | 3.8 | 3.0 + 3.0 | ceteareth-27 + Ethomeen T/25 | Bu stearate |
| F-139 | 228 | 1.5 | | 1.5 | 3.0 + 3.0 | ceteareth-27 + Ethomeen T/25 | Bu stearate |
| F-140 | 228 | 6.7 | 0.8 | 0.7 | 0.8 | Ethomeen T/25 | Bu stearate |
| F-141 | 228 | 6.7 | 1.7 | 0.7 | 1.7 | Ethomeen T/25 | Bu stearate |
| F-142 | 228 | 6.7 | 3.3 | 0.7 | 3.3 | Ethomeen T/25 | Bu stearate |
| F-143 | 228 | 3.3 | 0.8 | 0.7 | 0.8 | Ethomeen T/25 | Bu stearate |
| F-144 | 228 | 3.3 | 1.7 | 0.7 | 1.7 | Ethomeen T/25 | Bu stearate |
| F-145 | 228 | 3.3 | 2.5 | 0.7 | 2.5 | Ethomeen T/25 | Bu stearate |
| F-146 | 228 | 3.3 | 3.3 | 0.7 | 3.3 | Ethomeen T/25 | Bu stearate |
| F-147 | 228 | 6.7 | 2.5 | 0.7 | 2.5 | Ethomeen T/25 | Bu stearate |
| F-148 | 228 | | 3.0 | 0.5 | 3.0 | Ethomeen T/25 | Bu stearate |
| F-149 | 228 | 2.0 | 2.5 | 0.5 | 2.5 | Ethomeen T/25 | Bu stearate |
| F-150 | 228 | 4.0 | 6.0 | 0.5 | | | Bu stearate |
| F-151 | 228 | 4.0 | 6.0 | 2.0 | | | Bu stearate |
| F-152 | 228 | 4.0 | 6.0 | 1.0 | | | Bu stearate |
| F-153 | 228 | 2.0 | 2.0 | 0.5 | | | Bu stearate |
| F-154 | 228 | 2.0 | 4.0 | 0.5 | | | Bu stearate |
| F-155 | 228 | | 6.0 | 0.5 | | | Bu stearate |

The above compositions were prepared by process (x) as described in the Examples.

Dry compositions tested in the field have included:

| Field composition | Glyphosate a.e. | Lecithin | Butyl stearate | Surfactant | Coll. partic. | Other | Type of surfactant | Type of colloidal particulate | Other ingredients |
|---|---|---|---|---|---|---|---|---|---|
| F-156 | 64 | | | 25.0 | 2.0 | | steareth-20 | Aerosil blend 1 | |
| F-157 | 68 | | | 20.0 | 2.0 | | steareth-20 | Aerosil blend 1 | |
| F-158 | 72 | | | 15.0 | 2.0 | | steareth-20 | Aerosil blend 1 | |
| F-159 | 64 | | | 25.0 | 1.0 | | ceteth-20 | Aerosil 380 | |
| F-160 | 65 | | | 25.0 | 1.0 | | steareth-20 | Aerosil 380 | |
| F-161 | 65 | | | 25.0 | 1.0 | | oleth-20 | Aerosil 380 | |
| F-162 | 67 | 10.0 | | 10.0 + 1.5 | 1.0 | | Fluorad FC-754 + Ethomeen T/25 | Aerosil 380 | |
| F-163 | 73 | 7.0 | | 7.0 + 1.5 | 1.0 | | Fluorad FC-754 + Ethomeen T/25 | Aerosil 380 | |
| F-164 | 64 | 12.0 | 3.0 | 12.0 | | | MON 0818 | | |
| F-165 | 64 | 6.7 | 6.7 | 13.2 | | | MON 0818 | | |
| F-166 | 68 | | | 20.0 | 2.0 | | steareth-20 | Aerosil blend 1 | |
| F-167 | 66 | | 2.0 | 20.0 | 2.0 | | steareth-20 | Aerosil blend 1 | |
| F-168 | 68 | | | 20.0 | 2.0 | | oleth-20 | Aerosil blend 1 | |
| F-169 | 66 | | 2.0 | 20.0 | 2.0 | | oleth-20 | Aerosil blend 1 | |
| F-170 | 66 | | 2.0 | 20.0 | 2.0 | | ceteareth-27 | Aerosil blend 1 | |
| F-171 | 48 | | | 14.1 | | 36.1 | ceteareth-27 | | NH$_4$ phosphate |
| F-172 | 65 | | | 20.0 | | 5.0 | ceteareth-27 | | Na acetate |
| F-173 | 70 | | | 20.0 | | | ceteareth-27 | | |

Aerosil blend 1: Aerosil MOX-80 + Aerosil MOX-170 (1:1)

The above compositions were prepared by the process described for dry granular compositions in the Examples.

EXAMPLES

In the following Examples illustrative of the invention, greenhouse tests were conducted to evaluate relative herbicidal effectiveness of glyphosate compositions. Compositions included for comparative purposes included the following:

Formulation B: which consists of 41% by weight of glyphosate IPA salt in aqueous solution. This formulation is sold in the USA by Monsanto Company under the ACCORD® trademark.

Formulation C: which consists of 41% by weight of glyphosate IPA salt in aqueous solution with a coformulant (15% by weight) of a surfactant (MON 0818 of Monsanto Company) based on polyoxyethylene (15) tallowamine. This formulation is sold in Canada by Monsanto Company under the ROUNDUP® trademark.

Formulation J: which consists of 41% by weight of glyphosate IPA salt in aqueous solution, together with surfactant. This formulation is sold in the USA by Monsanto Company under the ROUNDUP® ULTRA trademark.

Formulation K: which consists of 75% by weight of glyphosate ammonium salt together with surfactant, as a water-soluble dry granular formulation. This formulation is sold in Australia by Monsanto Company under the ROUNDUP® DRY trademark.

Formulations B, C and J contain 356 grams of glyphosate acid equivalent per liter (g a.e./l). Formulation K contains 680 grams of glyphosate acid equivalent per kilogram (g a.e./kg).

Various proprietary excipients were used in compositions of the Examples. They may be identified as follows:

| Trade name | Manufacturer | Chemical description |
|---|---|---|
| Aerosil 90 | Degussa | amorphous silica, 90 m$^2$/g |
| Aerosil 200 | Degussa | amorphous silica, 200 m$^2$/g |
| Aerosil 380 | Degussa | amorphous silica, 380 m$^2$/g |
| Aerosil MOX-80 | Degussa | amorphous silica/aluminum oxide, 80 m$^2$/gm |
| Aerosil MOX-170 | Degussa | amorphous silica/aluminum oxide, 170 m$^2$/g |
| Aerosil OX-50 | Degussa | amorphous silica, 50 m$^2$/g |
| Aerosil R-202 | Degussa | amorphous hydrophobic silica (dimethylsiloxane surface group) |
| Aerosil R-805 | Degussa | amorphous hydrophobic silica (octyl surface group) |
| Aerosil R-812 | Degussa | amorphous hydrophobic silica (trimethylsilyl surface group) |
| Aerosol OS | Cytec | diisopropyl naphthalene sulfonate, Na salt |
| Aerosol OT | Cytec | dioctyl sulfosuccinate, Na salt |
| Agrimer AL-25 | ISP | i-ethenyl hexadecyl-2-pyrrolidinone |
| Agrimer AL-30 | ISP | i-ethenyl-2-pyrrolidinone polymer |
| Agrimul PG-2069 | Henkel | $C_{9-11}$ alkylpolyglycoside |
| Alcodet 218 | Rhone-Poulenc | isolauryl 10EO thioether |
| Aluminum oxide C | Degussa | aluminum oxide, 100 m$^2$/g |
| Amidox L-5 | Stepan | lauramide 5EO |
| Ammonyx CO | Stepan | palmitamine oxide |
| Ammonyx LO | Stepan | lauramine oxide |
| Arcosolve DPM | Arco | dipropyleneglycol monomethyl ether |
| Diacid 1550 | Westvaco | cyclocarboxypropyl oleic acid |
| Dowanol PNB | Dow | propylene glycol n-butyl ether |
| Dowanol TPNB | Dow | tripropylene glycol n-butyl ether |
| Emerest 2421 | Henkel | glyceryl oleate |
| Emerest 2661 | Henkel | PEG-12 laurate |

-continued

| Trade name | Manufacturer | Chemical description |
|---|---|---|
| Emid 6545 | Henkel | oleic diethanolamide |
| Emphos CS-121 | Witco | alkylaryl ethoxylate phosphate ester |
| Emphos CS-131 | Witco | alkylaryl ethoxylate phosphate ester |
| Emphos CS-141 | Witco | nonylphenol 10EO phosphate |
| Emphos CS-330 | Witco | alkylaryl ethoxylate phosphate ester |
| Emphos PS-21A | Witco | alcohol ethoxylate phosphate ester |
| Emphos PS-121 | Witco | linear alcohol ethoxylate phosphate ester, acid form |
| Emphos PS-400 | Witco | linear alcohol ethoxylate phosphate ester, acid form |
| Ethomeen C/12 | Akzo | cocoamine 2EO |
| Ethomeen C/25 | Akzo | cocoamine 15EO |
| Ethomeen T/12 | Akzo | tallowamine 2EO |
| Ethomeen T/25 | Akzo | tallowamine 15EO |
| Ethoquad T/20 | Akzo | methyltallowammonium chloride 10EO |
| Exxate 700 | Exxon | $C_7$ alkyl acetate |
| Exxate 1000 | Exxon | $C_{10}$ alkyl acetate |
| Exxol D-130 | Exxon | dearomatized aliphatic solvent |
| Fluorad FC-120 | 3M | $C_{9-10}$ perfluoroalkyl sulfonate, NH4 salt |
| Fluorad FC-129 | 3M | fluorinated alkyl carboxylate, K salt |
| Fluorad FC-135 | 3M | fluorinated alkyl quaternary ammonium iodide |
| Fluorad FC-170C | 3M | fluorinated alkanol EO |
| Fluorad FC-171 | 3M | fluorinated alkanol EO |
| Fluorad FC-431 | 3M | fluorinated alkyl ester |
| Fluorad FC-750 | 3M | fluorinated alkyl quaternary ammonium iodide |
| Fluorad FC-751 | 3M | fluorinated amphoteric surfactant |
| Fluorad FC-754 | 3M | fluorinated alkyl quaternary ammonium chloride |
| Fluorad FC-760 | 3M | fluorinated alkanol EO |
| Genapol UD-030 | Hoechst | $C_{11}$ oxo alcohol 3EO |
| Genapol UD-110 | Hoechst | $C_{11}$ oxo alcohol 11EO |
| Isopar V | Exxon | isoparaffinic oil |
| Kelzan | Monsanto | xanthan gum |
| LI-700 | Loveland | lecithin-based adjuvant |
| Makon 4 | Stepan | nonylphenol 4EO |
| Makon 6 | Stepan | nonylphenol 6EO |
| Makon 30 | Stepan | nonylphenol 30EO |
| Makon NF-5 | Stepan | polyalkoxylated aliphatic base |
| MON 0818 | Monsanto | tallowamine 15EO-based surfactant |
| Myrj 52 | ICI | PEG-40 stearate |
| Myrj 59 | ICI | PEG-100 stearate |
| Nalco 1056 | Nalco | silica (26%)/aluminum oxide (4%); average particle size 20 nm |
| Neodol 1-12 | Shell | $C_{11}$ linear alcohol 12EO |
| Neodol 1-7 | Shell | $C_{11}$ linear alcohol 7EO |
| Neodol 1-9 | Shell | $C_{11}$ linear alcohol 9EO |
| Neodol 25-12 | Shell | $C_{12-15}$ linear alcohol 12EO |
| Neodol 25-20 | Shell | $C_{12-15}$ linear alcohol 20EO |
| Neodol 25-3 | Shell | $C_{12-15}$ linear alcohol 3EO |
| Neodol 25-7 | Shell | $C_{12-15}$ linear alcohol 7EO |
| Neodol 25-9 | Shell | $C_{12-15}$ linear alcohol 9EO |
| Neodol 45-13 | Shell | $C_{14-15}$ linear alcohol 13EO |
| Neodol 91-2.5 | Shell | $C_{9-11}$ linear alcohol 2.5EO |
| Neodox 25-11 | Shell | $C_{12-15}$ linear alcohol ethoxycarboxylate 11EO |
| Ninate 411 | Stepan | amine dodecylbenzene sulfonate |
| Ninol 40-CO | Stepan | coco diethanolamide |
| Orchex 796 | Exxon | paraffinic oil |
| Pluronic 31-R1 | BASF | 21PO-7EO-21PO block copolymer |
| Pluronic F-108 | BASF | 128EO-54PO-128EO block copolymer |
| Pluronic F-127 | BASF | 98EO-67PO-98EO block copolymer |
| Pluronic F-68 | BASF | 75EO-30PO-75EO block copolymer |
| Pluronic L-35 | BASF | 11EO-16PO-11EO block copolymer |
| Pluronic L-43 | BASF | 7EO-21PO-7EO block copolymer |
| Pluronic L-81 | BASF | 6EO-39PO-6EO block copolymer |
| Pluronic P-84 | BASF | 27EO-39PO-27EO block copolymer |
| Polystep B-25 | Stepan | decyl sulfate, Na salt |
| Reax 88B | Westvaco | highly sulfonated lignin, Na salt |
| Sident 9 | Degussa | abrasive silica, 50 m$^2$/g |
| Silwet 800 | Witco | heptamethyltrisiloxane EO |
| Silwet L-77 | Witco | heptamethyltrisiloxane 7EO methyl ether |

-continued

| Trade name | Manufacturer | Chemical description |
|---|---|---|
| Simulsol SL-4 | Seppic | alkyl polyglucoside |
| Simulsol SL-10 | Seppic | alkyl polyglucoside |
| Simulsol SL-62 | Seppic | alkyl polyglucoside |
| Sipernat 22 | Degussa | hydrophilic precipitated silica, 190 m²/g, av. aggregate size 100 μm |
| Sipernat 22S | Degussa | hydrophilic precipitated silica, 190 m²/g, av. aggregate size <10 μm |
| Span 60 | ICI | sorbitan monostearate |
| Span 65 | ICI | sorbitan tristearate |
| Span 80 | ICI | sorbitan monooleate |
| Span 85 | ICI | sorbitan trioleate |
| Steol CS-370 | Stepan | lauryl EO sulfate, Na salt |
| Stepanol WAC | Stepan | lauryl sulfate, Na salt |
| Stepfac 8170 | Stepan | nonylphenol EO phosphate |
| Surfynol 104 | Air Products | tetramethyldecyne diol |
| Surfynol 465 | Air Products | tetramethyldecyne diol 10EO |
| Tergitol 15-S-15 | Union Carbide | $C_{15}$ branched secondary alcohol 15EO |
| Tergitol 15-S-20 | Union Carbide | $C_{15}$ branched secondary alcohol 20EO |
| Tergitol 15-S-30 | Union Carbide | $C_{15}$ branched secondary alcohol 30EO |
| Tergitol 15-S-40 | Union Carbide | $C_{15}$ branched secondary alcohol 40EO |
| Titanium dioxide P25 | Degussa | titanium dioxide, average particle size 21 nm |
| Toximul 8240 | Stepan | PEG-36 castor oil |
| Toximul 8302 | Stepan | alcohol EO blend |
| Triton RW-20 | Union Carbide | alkylamine 2EO |
| Triton RW-50 | Union Carbide | alkylamine 5EO |
| Triton RW-75 | Union Carbide | alkylamine 7.5EO |
| Triton RW-100 | Union Carbide | alkylamine 10EO |
| Triton RW-150 | Union Carbide | alkylamine 15EO |
| Tryfac 5552 | Henkel | decyl EO phosphate, free acid |
| Tween 20 | ICI | sorbitan monolaurate 20EO |
| Tween 40 | ICI | sorbitan monopalmitate 20EO |
| Tween 80 | ICI | sorbitan monooleate 20EO |
| Tween 85 | ICI | sorbitan trioleate 20EO |
| Velvetex AB-45 | Henkel | cocobetaine |
| Westvaco H-240 | Westvaco | dicarboxylate surfactant, K salt |

Fluorad FC-135, though defined only generically as above in 3M product literature and in standard directories, has been specifically identified as

in a paper by J. Linert & J. N. Chasman of 3M, titled "The effects of fluorochemical surfactants on recoatability" in the Dec. 20, 1993 issue of American Paint & Coatings Journal, and reprinted as a trade brochure by 3M. Fluorad FC-750 is believed to be based on the same surfactant. Fluorad FC-754 is believed to have the structure

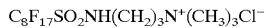

that is, identical to Fluorad FC-135 but with a chloride anion replacing iodide.

The following surfactants, identified in the Examples as "Surf H1" to "Surf H5", have hydrocarbyl groups as the hydrophobic moiety but otherwise bear some structural similarity to the above Fluorad surfactants. They were synthesized and characterized under contract to Monsanto Company.

Surf H1: 

Surf H2: 

Surf H3: 

Surf H4: 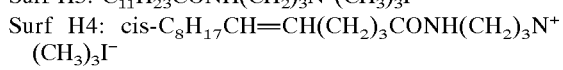

Surf H5: 

Fatty alcohol ethoxylate surfactants are referred to in the Examples by their generic names as given in the International Cosmetic Ingredient Dictionary, 6th Edition, 1995 (Cosmetic, Toiletry and Fragrance Association, Washington, DC). They were interchangeably sourced from various manufacturers, for example:

Laureth-23: Brij 35 (ICI), Trycol 5964 (Henkel).

Ceteth-10: Brij 56 (ICI).

Ceteth-20: Brij 58 (ICI).

Steareth-10: Brij 76 (ICI).

Steareth-20: Brij 78 (ICI), Emthox 5888-A (Henkel), STA-20 (Heterene).

Steareth-30: STA-30 (Heterene).

Steareth-100: Brij 700 (ICI).

Ceteareth-15: CS-15 (Heterene).

Ceteareth-20: CS-20 (Heterene).

Ceteareth-27: Plurafac A-38 (BASF).

Ceteareth-55: Plurafac A-39 (BASF).

Oleth-2: Brij 92 (ICI).

Oleth-10: Brij 97 (ICI).

Oleth-20: Brij 98 (ICI), Trycol 5971 (Henkel).

Where a proprietary excipient is a surfactant supplied as a solution in water or other solvent, the amount to be used was calculated on a true surfactant basis, not an "as is" basis. For example, Fluorad FC-135 is supplied as 50% true surfactant, together with 33% isopropanol and 17% water; thus to provide a composition containing 0.1% w/w Fluorad FC-135 as reported herein, 0.2 g of the product as supplied was included in 100 g of the composition.

Spray compositions of the Examples contained an exogenous chemical, such as glyphosate IPA salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

Except where otherwise indicated, these aqueous spray compositions were prepared by one of the following processes (i), (ii) or (iii).

(i) For compositions not containing lecithin or phospholipids, aqueous compositions were prepared by simple mixing of ingredients under mild agitation.

(ii) A weighed quantity of lecithin in powder form was dissolved in 0.4 ml chloroform in a 100 ml bottle. The resulting solution was air-dried to leave a thin film of lecithin, to which was added 30 ml deionized water. The bottle and its contents were then sonicated in a Fisher Sonic Dismembrator, Model 550, fitted with a 2.4 cm probe tip, set at output level 8, and operated continuously for 3 minutes. The resulting aqueous dispersion of lecithin was then allowed to cool to room temperature, and formed a lecithin stock which was later mixed in the required amounts with other ingredients under mild agitation. In some cases, as indicated in the Examples, certain ingredients were added to the lecithin in water before sonication, so that the lecithin and these ingredients were sonicated together. Without being bound by theory, it is believed that by sonicating a formulation ingredient together with lecithin, at least some of that ingredient becomes encapsulated within, or otherwise bound to or trapped by, vesicles or other aggregates formed by phospholipids present in the lecithin.

(iii) The procedure of process (ii) was followed except that. before sonication, the step of forming a lecithin solution in chloroform was omitted. Instead, lecithin in powder form was placed in a beaker, water was added and the beaker and its contents were then sonicated.

Except where otherwise indicated, aqueous concentrate compositions were prepared by one of the following processes (iv) to (x).

(iv) A weighed amount of lecithin powder of the type indicated was placed in a beaker and deionized water was added in no more than the amount required for the desired final composition. The beaker and its contents were then placed in a Fisher Sonic Dismembrator, Model 550, fitted with a 2.4 cm probe tip, set at output level 8, and operated for 5 minutes. The resulting lecithin dispersion formed the basis to which other ingredients were added with mild agitation to make the aqueous concentrate formulation. The order of addition of these ingredients was varied and was sometimes found to affect the physical stability of the concentrate formulation. Where a fluoro-organic surfactant such as Fluorad FC-135 or FC-754 was to be included, it was generally added first, followed by other surfactants if required and then by the exogenous chemical. Where the exogenous chemical used was glyphosate IPA salt, this was added in the form of a 62% (45% a.e.) solution by weight, at a pH of 4.4 to 4.6. A final adjustment with water took place if necessary as the last step. In some cases certain ingredients of the concentrate formulation were added before rather than after sonication, so that they were sonicated with the lecithin.

(v) A weighed amount of lecithin powder of the type indicated was placed in a beaker and deionized water was added in sufficient quantity to provide, after sonication as detailed below, a lecithin stock at a convenient concentration, normally in the range from 10% to 20% w/w and typically 15% w/w. The beaker and its contents were then placed in a Fisher Sonic Dismembrator, Model 550, fitted with a 2.4 cm probe tip with the pulse period set at 15 seconds with 1 minute intervals between pulses to allow cooling. Power output was set at level 8. After a total of 3 minutes of sonication (12 pulse periods) the resulting lecithin stock was finally adjusted to the desired concentration if necessary with deionized water. To prepare an aqueous concentrate formulation, the following ingredients were mixed in the appropriate proportions with mild agitation, normally in the order given although this was sometimes varied and was found in some cases to affect the physical stability of the concentrate formulation: (a) exogenous chemical, for example glyphosate IPA salt as a 62% w/w solution at pH 4.4–4.6; (b) lecithin stock; (c) other ingredients if required; and (d) water.

(vi) Water-in-oil-in-water (W/O/W) multiple emulsions were prepared as follows. First a water-in-oil emulsion was prepared. To do this, the required amounts of the selected oil and a first emulsifier (referred to in the Examples as "emulsifier #1") were mixed thoroughly. If it was desired to prepare the formulation with glyphosate in the inner aqueous phase, a measured amount of concentrated (62% w/w) aqueous solution of glyphosate IPA salt was added to the mixture of oil and first emulsifier with agitation to ensure homogeneity. The amount of water required in the inner aqueous phase was then added to complete the water-in-oil emulsion, which was finally subjected to high-shear mixing, typically using a Silverson L4RT-A mixer fitted with a fine emulsor screen operated for 3 minutes at 10,000 rpm. The required amount of a second emulsifier (referred to in the Examples as "emulsifier #2") was next added to the water-in-oil emulsion with agitation to ensure homogeneity. If it was desired to prepare the formulation with glyphosate in the outer aqueous phase, a measured amount of concentrated (62% w/w) aqueous solution of glyphosate IPA salt was added to the blend of the water-in-oil emulsion and the second emulsifier with further agitation. To complete the water-in-oil-in-water multiple emulsion composition, the amount of water required in the outer aqueous phase was added. The composition was finally subjected to high-shear mixing, typically using a Silverson L4RT-A mixer fitted with a medium emulsor screen, operated for 3 minutes at 7,000 rpm.

(vii) Oil-in-water (O/W) emulsions were prepared as follows. The required amount of the selected oil and surfactant (sometimes referred to in the Examples as "emulsifier #2" as it corresponds to the second emulsifier in process (vi)) were mixed thoroughly. If the surfactant selected was not free-flowing at ambient temperature, heat was applied to bring the surfactant into a flowable condition before mixing with the oil. A measured amount of concentrated (62% w/w) aqueous solution of glyphosate IPA salt was added to the surfactant-oil mixture with agitation. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(viii) Surfactant-containing aqueous solution concentrates having no oil component were prepared as follows. A concentrated (62% w/w) aqueous solution of glyphosate IPA salt was added in the desired amount to a weighed quantity of the selected surfactant(s). If the surfactant selected is not free-flowing at ambient temperature, heat was applied to bring the surfactant into a flowable condition before adding the glyphosate solution. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(ix) For compositions containing a colloidal particulate, the required amount by weight of the selected colloidal particulate was suspended in a concentrated (62% w/w) aqueous solution of glyphosate IPA salt and agitated with cooling to ensure homogeneity. To the resulting suspension was added the required amount by weight of the selected surfactant(s). For a surfactant which is not free-flowing at ambient temperature, heat was applied to bring the surfactant into a flowable condition before adding it to the suspension. In those instances where an oil, such as butyl stearate, was also to be included in the composition, the oil was first thoroughly mixed with the surfactant and the surfactant-oil mixture added to the suspension. To complete the aqueous concentrate, the required amount of water was added to bring the concentration of glyphosate and other ingredients to the desired level. The concentrate was finally subjected to high-shear mixing, typically using a Silverson L4RT-A mixer fitted with a medium emulsor screen, operated for 3 minutes at 7,000 rpm.

(x) The procedure for preparing aqueous concentrate formulations containing lecithin and butyl stearate was different from that followed for other lecithin-containing concentrates. Exogenous chemical, for example glyphosate IPA salt, was first added, with mild agitation, to deionized water in a formulation jar. The selected surfactant (other than lecithin) was then added, while continuing the agitation, to form a preliminary exogenous chemical/ surfactant mixture. Where the surfactant is not free-flowing at ambient temperature, the order of addition was not as above. Instead, the non-free-flowing surfactant was first added to water together with any other surfactant (other than lecithin) required in the composition, and was then heated to 55° C. in a shaker bath for 2 hours. The resulting mixture was allowed to cool, then exogenous chemical was added with mild agitation to form the preliminary exogenous chemical/surfactant mixture. A weighed amount of the selected lecithin was added to the preliminary exogenous chemical/surfactant mixture, with stirring to break up lumps. The mixture was left for about 1 hour to allow the lecithin to hydrate, then butyl stearate was added, with further stirring until no phase separation occurred. The mixture was then transferred to a microfluidizer (Microfluidics International Corporation, Model M-110F) and microfluidized for 3 to 5 cycles at 10,000 psi (69 MPa). In each cycle, the formulation jar was rinsed with microfluidized mixture. In the last cycle, the finished composition was collected in a clean dry beaker.

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 14-14-14 NPK slow release fertilizer at a rate of 3.6 kg/m3. The pots were placed in a greenhouse with subirrigation. About one week after emergence, seedlings were thinned as needed, including removal of any unhealthy or abnormal plants. to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated.

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as those of the Examples it is normal to apply compositions at rates which give less than 85% inhibition, as this makes it easier to discriminate among compositions having different levels of effectiveness.

Example 1

Glyphosate-containing spray compositions were prepared by tank-mixing Formulations B and C with excipients as shown in Table 1.

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 16 days after planting ECHCF, and evaluation of herbicidal inhibition was done 18 days after application. Results, averaged for all replicates of each treatment, are shown in Table 1.

TABLE 1

| Glyphosate composition | Glyphosate rate g a.e./ha | Additive | Additive rate % v/v | % Inhibition ABUTH | % Inhibition ECHCF |
|---|---|---|---|---|---|
| Formulation C | 175 | none |  | 40 | 75 |
|  | 350 |  |  | 69 | 89 |
|  | 500 |  |  | 97 | 100 |
| Formulation B | 175 | none |  | 45 | 37 |
|  | 350 |  |  | 73 | 66 |
|  | 500 |  |  | 83 | 97 |
| Formulation B | 175 | L-77 | 0.25 | 64 | 30 |
|  | 175 |  | 0.50 | 77 | 27 |
| Formulation B | 175 | FC-135 | 0.25 | 55 | 72 |
|  | 175 |  | 0.50 | 73 | 61 |
| Formulation B | 175 | FC-135 + L-77 8:1 | 0.50 | 71 | 58 |
|  | 175 | FC-135 + L-77 4:1 | 0.50 | 76 | 61 |
|  | 175 | FC-135 + L-77 2:1 | 0.50 | 63 | 56 |
|  | 175 | FC-135 + L-77 1:1 | 0.50 | 77 | 40 |
|  | 175 | FC-135 + L-77 1:2 | 0.50 | 54 | 23 |
|  | 175 | FC-135 + L-77 1:4 | 0.50 | 76 | 31 |
|  | 175 | FC-135 + L-77 1:8 | 0.50 | 53 | 29 |

TABLE 1-continued

| Glyphosate composition | Glyphosate rate g a.e./ha | Additive | Additive rate % v/v | % Inhibition ABUTH | ECHCF |
|---|---|---|---|---|---|
| Formulation B | 175 | FC-135 + L-77 8:1 | 0.25 | 51 | 48 |
| | 175 | FC-135 + L-77 4:1 | 0.25 | 37 | 47 |
| | 175 | FC-135 + L-77 2:1 | 0.25 | 45 | 37 |
| | 175 | FC-135 + L-77 1:1 | 0.25 | 65 | 27 |
| | 175 | FC-135 + L-77 1:2 | 0.25 | 45 | 29 |
| | 175 | FC-135 + L-77 1:4 | 0.25 | 60 | 17 |
| | 175 | FC-135 + L-77 1:8 | 0.25 | 52 | 15 |

Tank mixtures of Fluorad FC-135 with Formulation B gave markedly superior herbicidal effectiveness on ABUTH by comparison with Formulation C, but did not match the herbicidal effectiveness of Formulation C on ECHCF. The antagonism of glyphosate activity on ECHCF seen with the nonionic organosilicone surfactant Silwet L-77 did not occur with the cationic fluoro-organic surfactant Fluorad FC-135.

Example 2

Aqueous spray compositions were prepared containing glyphosate sodium or IPA salts and excipient ingredients as shown in Table 2a. Process (ii) was followed for all compositions, using soybean lecithin (10–20% phospholipid, Sigma Type II-S). Without adjustment, the pH of the compositions was approximately 5. For those compositions having a pH of approximately 7 as shown in Table 2a, the pH was adjusted using the same base (sodium hydroxide or IPA) that formed the glyphosate salt.

TABLE 2a

| Spray composition | Lecithin g/l | Fluorad FC-135 | L-77 | Components sonicated with lecithin | Glyphosate salt | pH |
|---|---|---|---|---|---|---|
| 2-01 | 5.0 | | | none | IPA | 5 |
| 2-02 | 5.0 | | 0.50 | none | IPA | 5 |
| 2-03 | 5.0 | | | none | Na | 7 |
| 2-04 | 5.0 | | 0.50 | none | Na | 7 |
| 2-05 | 5.0 | | | none | IPA | 7 |
| 2-06 | 5.0 | | 0.50 | none | IPA | 7 |
| 2-07 | 5.0 | | | none | Na | 5 |
| 2-08 | 5.0 | | 0.50 | none | Na | 5 |
| 2-09 | 2.5 | | | none | IPA | 5 |
| 2-10 | 2.5 | 0.50 | | none | IPA | 5 |
| 2-11 | 5.0 | 0.50 | | none | IPA | 5 |
| 2-12 | 5.0 | 0.33 | 0.17 | none | IPA | 5 |
| 2-13 | 5.0 | | 0.50 | L-77 | IPA | 5 |
| 2-14 | 5.0 | | 0.50 | L-77 | Na | 7 |
| 2-15 | 5.0 | | 0.50 | L-77 | IPA | 7 |
| 2-16 | 5.0 | | 0.50 | L-77 | Na | 5 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 17 days after application.

Formulation C, alone and tank mixed with 0.5% Silwet L-77, were applied as comparative treatments. Results, averaged for all replicates of each treatment, are shown in Table 2b.

TABLE 2b

| Spray composition | Glyphosate rate g a.e./ha | % Inhibition ABUTH | ECHCF |
|---|---|---|---|
| Formulation C | 100 | 8 | 54 |
| | 200 | 54 | 75 |
| | 300 | 77 | 90 |
| Formulation C + Silwet L-77 0.5% v/v | 100 | 62 | 10 |
| | 200 | 91 | 25 |
| | 300 | 95 | 27 |
| 2-01 | 100 | 59 | 64 |
| | 200 | 74 | 83 |
| | 300 | 82 | 99 |
| 2-02 | 100 | 66 | 44 |
| | 200 | 73 | 45 |
| | 300 | 92 | 76 |
| 2-03 | 100 | 17 | 29 |
| | 200 | 37 | 72 |
| | 300 | 70 | 89 |
| 2-04 | 100 | 48 | 24 |
| | 200 | 67 | 50 |
| | 300 | 81 | 61 |
| 2-05 | 100 | 40 | 44 |
| | 200 | 77 | 89 |
| | 300 | 79 | 95 |
| 2-06 | 100 | 76 | 43 |
| | 200 | 87 | 74 |
| | 300 | 90 | 85 |
| 2-07 | 100 | 40 | 50 |
| | 200 | 66 | 54 |
| | 300 | 84 | 83 |
| 2-08 | 100 | 69 | 34 |
| | 200 | 57 | 70 |
| | 300 | 78 | 66 |
| 2-09 | 100 | 44 | 62 |
| | 200 | 83 | 82 |
| | 300 | 90 | 91 |
| 2-10 | 100 | 84 | 83 |
| | 200 | 97 | 85 |
| | 300 | 95 | 93 |
| 2-11 | 100 | 79 | 65 |
| | 200 | 89 | 84 |
| | 300 | 98 | 98 |
| 2-12 | 100 | 74 | 63 |
| | 200 | 93 | 84 |
| | 300 | 94 | 92 |
| 2-13 | 100 | 86 | 85 |
| | 200 | 91 | 92 |
| | 300 | 97 | 97 |
| 2-14 | 100 | 56 | 17 |
| | 200 | 69 | 48 |
| | 300 | 87 | 81 |
| 2-15 | 100 | 61 | 39 |
| | 200 | 87 | 73 |
| | 300 | 83 | 78 |
| 2-16 | 100 | 42 | 32 |
| | 200 | 35 | 78 |
| | 300 | 59 | 85 |

Surprisingly strong herbicidal effectiveness was observed with compositions 2-10 and 2-11 containing lecithin and Fluorad FC-135 on both ABUTH and ECHCF, by comparison with otherwise similar compositions (2-09 and 2-01) lacking the Fluorad FC-135. Herbicidal effectiveness of composition 2-11 at the 100 g a.e./ha glyphosate rate was superior to that of Formulation C at a threefold higher rate on ABUTH and superior to that of Formulation C at a twofold higher rate on ECHCF.

Example 3

Aqueous spray compositions were prepared containing glyphosate IPA salt and excipient ingredients as shown in Table 3a. Process (ii), indicated in Table 3a as involving "high" sonication power, was followed for all compositions, except that for composition 3-06 a different sonication procedure, referred to as "low" sonication power, was used. In this procedure the lecithin in water was sonicated in a Fisher Model FS 14H ultrasonic bath for 30 minutes. Soybean lecithin (10–20% phospholipid, Sigma Type II-S) was used for all compositions. Without adjustment, the pH of the compositions was approximately 5. For those compositions having a pH of approximately 7 as shown in Table 3a, the pH was adjusted using the same base (sodium hydroxide or IPA) that formed the glyphosate salt.

TABLE 3a

| Spray composition | % w/w Lecithin g/l | Fluorad FC-135 | L-77 | Components sonicated with lecithin | pH | Sonication power |
|---|---|---|---|---|---|---|
| 3-01 | 5.0 | | | none | 5 | high |
| 3-02 | 5.0 | | 0.50 | none | 5 | high |
| 3-03 | 5.0 | | 0.50 | L-77 | 5 | high |
| 3-04 | 5.0 | | 0.50 | glyphosate | 5 | high |
| 3-05 | 5.0 | | 0.50 | L-77, glyphosate | 5 | high |
| 3-06 | 5.0 | | | none | 7 | low |
| 3-07 | 5.0 | | | none | 7 | high |
| 3-08 | 5.0 | | 0.50 | none | 7 | high |
| 3-09 | 5.0 | | 0.50 | L-77 | 7 | high |
| 3-10 | 5.0 | | 0.50 | glyphosate | 7 | high |
| 3-11 | 5.0 | | 0.50 | L-77, glyphosate | 7 | high |
| 3-12 | 5.0 | 0.50 | | none | 5 | high |
| 3-13 | 5.0 | 0.50 | | FC-135 | 5 | high |
| 3-14 | 5.0 | 0.50 | | glyphosate | 5 | high |
| 3-15 | 5.0 | 0.17 | 0.33 | FC-135, glyphosate | 5 | high |
| 3-16 | 5.0 | 0.17 | 0.33 | none | 5 | high |
| 3-17 | 5.0 | 0.17 | 0.33 | FC-135, L-77 | 5 | high |
| 3-18 | 10.0 | | | none | 5 | high |
| 3-19 | 20.0 | | | none | 5 | high |
| 3-20 | 10.0 | | 0.50 | none | 5 | high |
| 3-21 | 10.0 | | 0.50 | L-77 | 5 | high |
| 3-22 | 20.0 | | 0.50 | L-77 | 5 | high |
| 3-23 | 20.0 | | 0.50 | L-77, glyphosate | 5 | high |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 16 days after application.

Formulations B and C, alone and tank mixed with 0.5% Silwet L-77, were applied as comparative treatments. Results, averaged for all replicates of each treatment, are shown in Table 3b.

TABLE 3b

| Spray | Glyphosate rate | % Inhibition | |
|---|---|---|---|
| composition | g a.e./ha | ABUTH | ECHCF |
| Formulation B | 100 | 11 | 12 |
| | 200 | 55 | 43 |
| | 300 | 65 | 38 |
| Formulation B + Silwet L-77 0.5% v/v | 100 | 77 | 5 |
| | 200 | 95 | 10 |
| | 300 | 95 | 17 |
| Formulation C | 100 | 33 | 42 |
| | 200 | 63 | 98 |
| | 300 | 85 | 99 |
| Formulation C + Silwet L-77 0.5% v/v | 100 | 78 | 7 |
| | 200 | 95 | 19 |
| | 300 | 98 | 54 |
| 3-01 | 100 | 63 | 22 |
| | 200 | 77 | 69 |
| | 300 | 92 | 82 |
| 3-02 | 100 | 79 | 30 |
| | 200 | 96 | 67 |
| | 300 | 98 | 70 |
| 3-03 | 100 | 81 | 29 |
| | 200 | 96 | 70 |
| | 300 | 97 | 86 |
| 3-04 | 100 | 85 | 32 |
| | 200 | 94 | 60 |
| | 300 | 98 | 61 |
| 3-05 | 100 | 82 | 34 |
| | 200 | 98 | 60 |
| | 300 | 96 | 69 |
| 3-06 | 100 | 55 | 40 |
| | 200 | 91 | 69 |
| | 300 | 97 | 90 |
| 3-07 | 100 | 77 | 29 |
| | 200 | 93 | 82 |
| | 300 | 97 | 100 |
| 3-08 | 100 | 83 | 48 |
| | 200 | 95 | 67 |
| | 300 | 94 | 74 |
| 3-09 | 100 | 83 | 37 |
| | 200 | 95 | 75 |
| | 300 | 99 | 83 |
| 3-10 | 100 | 77 | 36 |
| | 200 | 99 | 75 |
| | 300 | 98 | 69 |
| 3-11 | 100 | 81 | 38 |
| | 200 | 94 | 81 |
| | 300 | 97 | 76 |
| 3-12 | 100 | 56 | 47 |
| | 200 | 91 | 90 |
| | 300 | 97 | 95 |
| 3-13 | 100 | 81 | 41 |
| | 200 | 94 | 58 |
| | 300 | 97 | 84 |
| 3-14 | 100 | 77 | 37 |
| | 200 | 94 | 70 |
| | 300 | 96 | 94 |
| 3-15 | 100 | 76 | 61 |
| | 200 | 95 | 79 |
| | 300 | 96 | 85 |
| 3-16 | 100 | 95 | 84 |
| | 200 | 94 | 56 |
| | 300 | 75 | 32 |
| 3-17 | 100 | 78 | 44 |
| | 200 | 93 | 86 |
| | 300 | 94 | 87 |
| 3-18 | 100 | 59 | 27 |
| | 200 | 94 | 84 |
| | 300 | 96 | 100 |
| 3-19 | 100 | 74 | 44 |
| | 200 | 94 | 74 |
| | 300 | 95 | 95 |
| 3-20 | 100 | 79 | 62 |
| | 200 | 89 | 78 |
| | 300 | 92 | 93 |
| 3-21 | 100 | 66 | 69 |
| | 200 | 80 | 79 |
| | 300 | 86 | 88 |

TABLE 3b-continued

| Spray composition | Glyphosate rate g a.e./ha | % Inhibition ABUTH | % Inhibition ECHCF |
|---|---|---|---|
| 3-22 | 100 | 44 | 69 |
|  | 200 | 83 | 97 |
|  | 300 | 74 | 94 |
| 3-23 | 100 | 50 | 71 |
|  | 200 | 68 | 91 |
|  | 300 | 85 | 76 |

Composition 3-12 containing lecithin and Fluorad FC-135 again showed surprisingly high herbicidal effectiveness by comparison with composition 3-01, lacking the Fluorad FC-135, and also by comparison with Formulation C. When efforts were made to encapsulate Fluorad FC-135 or glyphosate (compositions 3-13 or 3-14 respectively) in lecithin liposomes by sonication in the presence of the ingredients sought to be encapsulated, some further enhancement of herbicidal effectiveness was evident on ABUTH. but effectiveness was reduced on ECHCF. Overall, the best activity in this test was obtained without encapsulation.

Example 4

Compositions 3-01 to 3-12 of Example 3 were tested in this Example. Black nightshade (*Solanum nigrum*, SOLNI) plants were grown and treated by the standard procedures given above. Applications of spray compositions were made 26 days after planting SOLNI and evaluation of herbicidal inhibition was done 16 days after application.

Formulations B and C, alone and tank mixed with 0.5% Silwet L-77, were applied as comparative treatments. Results, averaged for all replicates of each treatment, are shown in Table 4.

TABLE 4

| Spray composition | Glyphosate rate g a.e./ha | % Inhibition SOLNI |
|---|---|---|
| Formulation B | 100 | 28 |
|  | 200 | 35 |
|  | 300 | 70 |
| Formulation B + Silwet L-77 0.5% v/v | 100 | 85 |
|  | 200 | 98 |
|  | 300 | 97 |
| Formulation C | 100 | 30 |
|  | 200 | 58 |
|  | 300 | 70 |
| Formulation C + Silwet L-77 0.5% v/v | 100 | 78 |
|  | 200 | 82 |
|  | 300 | 94 |
| 3-01 | 100 | 47 |
|  | 200 | 77 |
|  | 300 | 93 |
| 3-02 | 100 | 33 |
|  | 200 | 50 |
|  | 300 | 78 |
| 3-03 | 100 | 36 |
|  | 200 | 79 |
|  | 300 | 90 |
| 3-04 | 100 | 33 |
|  | 200 | 72 |
|  | 300 | 84 |
| 3-05 | 100 | 38 |
|  | 200 | 68 |
|  | 300 | 82 |

TABLE 4-continued

| Spray composition | Glyphosate rate g a.e./ha | % Inhibition SOLNI |
|---|---|---|
| 3-06 | 100 | 84 |
|  | 200 | 92 |
|  | 300 | 96 |
| 3-07 | 100 | 58 |
|  | 200 | 75 |
|  | 300 | 85 |
| 3-08 | 100 | 50 |
|  | 200 | 83 |
|  | 300 | 91 |
| 3-09 | 100 | 50 |
|  | 200 | 72 |
|  | 300 | 83 |
| 3-10 | 100 | 53 |
|  | 200 | 75 |
|  | 300 | 78 |
| 3-11 | 100 | 75 |
|  | 200 | 96 |
|  | 300 | 100 |
| 3-12 | 100 | 62 |
|  | 200 | 93 |
|  | 300 | 99 |

Composition 3-12 containing lecithin and Fluorad FC-135, as in the test of Example 3, showed remarkably strong herbicidal effectiveness, this time on SOLNI.

Example 5

Aqueous spray compositions were prepared containing glyphosate IPA salt and excipient ingredients as shown in Table 5a. Process (ii) was followed for all compositions, using soybean lecithin (20% phospholipid, Avanti). The pH of all compositions was approximately 5.

TABLE 5a

| Spray composition | Lecthin g/l | % w/w Fluorad FC-135 | Silwet L-77 | KCl | Components sonicated with lecithin |
|---|---|---|---|---|---|
| 5-01 | 5.0 |  |  |  | glyphosate |
| 5-02 | 5.0 |  | 0.50 |  | L-77 |
| 5-03 | 5.0 |  | 0.50 |  | L-77 |
| 5-04 | 5.0 |  | 1.00 |  | L-77 |
| 5-05 | 5.0 |  | 0.20 |  | none |
| 5-06 | 5.0 |  | 1.00 |  | none |
| 5-07 | 5.0 |  | 0.20 |  | L-77, glyphosate |
| 5-08 | 5.0 |  | 0.50 |  | L-77, glyphosate |
| 5-09 | 5.0 |  | 1.00 |  | L-77, glyphosate |
| 5-10 | 2.5 |  | 0.10 |  | L-77 |
| 5-11 | 2.5 |  | 0.25 |  | L-77 |
| 5-12 | 2.5 |  | 0.50 |  | L-77 |
| 5-13 | 2.5 |  | 0.10 |  | none |
| 5-14 | 2.5 |  | 0.25 |  | none |
| 5-15 | 2.5 |  | 0.10 |  | L-77, glyphosate |
| 5-16 | 2.5 |  | 0.25 |  | L-77, glyphosate |
| 5-17 | 2.5 |  | 0.50 |  | L-77, glyphosate |
| 5-18 | 5.0 |  | 0.50 | 0.02 | L-77 |
| 5-19 | 5.0 |  | 0.50 | 0.02 | L-77, glyphosate |
| 5-20 | 5.0 | 0.50 |  |  | none |
| 5-21 | 5.0 | 0.50 |  |  | glyphosate |
| 5-22 | 5.0 | 0.33 | 0.17 |  | none |
| 5-23 | 5.0 | 033 | 0.17 |  | glyphosate |

Velvetleaf *Abutilon theophrasti*, ABUTH) and Japanese millet *Echinochloa crus-galli*, ECHCF) plants were grown and treated by the standard procedures given above. Applications of spray compositions were made 18 days after planting ABUTH and 16 days after planting ECHCF, and evaluation of herbicidal inhibition was done 17 days after application.

Formulations B and C, alone and tank mixed with 0.5% Silwet L-77, were applied as comparative treatments. Results, averaged for all replicates of each treatment, are shown in Table 5b.

TABLE 5b

| Spray composition | Glyphosate rate g a.e./ha | % Inhibition ABUTH | % Inhibition ECHCF |
|---|---|---|---|
| Formulation B | 200 | 47 | 83 |
| | 300 | 64 | 84 |
| | 400 | 71 | 90 |
| Formulation B + Silwet L-77 0.5% v/v | 200 | 83 | 58 |
| | 300 | 94 | 76 |
| | 400 | 100 | 85 |
| Formulation C | 200 | 46 | 96 |
| | 300 | 68 | 90 |
| | 400 | 75 | 93 |
| Formulation C + Silwet L-77 0.5% v/v | 200 | 81 | 66 |
| | 300 | 93 | 68 |
| | 400 | 96 | 86 |
| 5-01 | 200 | 70 | 91 |
| | 300 | 74 | 100 |
| | 400 | 93 | 94 |
| 5-02 | 200 | 81 | 95 |
| | 300 | 68 | 100 |
| | 400 | 81 | 100 |
| 5-03 | 200 | 78 | 100 |
| | 300 | 99 | 83 |
| | 400 | 98 | 99 |
| 5-04 | 200 | 89 | 95 |
| | 300 | 93 | 95 |
| | 400 | 86 | 100 |
| 5-05 | 200 | 60 | 89 |
| | 300 | 79 | 100 |
| | 400 | 86 | 100 |
| 5-06 | 200 | 76 | 100 |
| | 300 | 84 | 100 |
| | 400 | 100 | 96 |
| 5-07 | 200 | 65 | 97 |
| | 300 | 78 | 97 |
| | 400 | 77 | 100 |
| 5-08 | 200 | 82 | 100 |
| | 300 | 95 | 100 |
| | 400 | 96 | 100 |
| 5-09 | 200 | 78 | 99 |
| | 300 | 89 | 99 |
| | 400 | 90 | 100 |
| 5-10 | 200 | 66 | 100 |
| | 300 | 79 | 98 |
| | 400 | 89 | 100 |
| 5-11 | 200 | 67 | 95 |
| | 300 | 81 | 100 |
| | 400 | 97 | 100 |
| 5-12 | 200 | 76 | 88 |
| | 300 | 79 | 100 |
| | 400 | 95 | 96 |
| 5-13 | 200 | 59 | 85 |
| | 300 | 66 | 93 |
| | 400 | 67 | 100 |
| 5-14 | 200 | 56 | 89 |
| | 300 | 67 | 100 |
| | 400 | 83 | 100 |
| 5-15 | 200 | 54 | 100 |
| | 300 | 63 | 100 |
| | 400 | 78 | 100 |
| 5-16 | 200 | 46 | 88 |
| | 300 | 73 | 100 |
| | 400 | 86 | 100 |
| 5-17 | 200 | 81 | 98 |
| | 300 | 83 | 97 |
| | 400 | 92 | 96 |
| 5-18 | 200 | 56 | 92 |
| | 300 | 64 | 100 |
| | 400 | 74 | 100 |
| 5-19 | 200 | 64 | 94 |
| | 300 | 80 | 97 |
| | 400 | 80 | 96 |
| 5-20 | 200 | 88 | 91 |
| | 300 | 96 | 100 |
| | 400 | 98 | 98 |
| 5-21 | 200 | 92 | 94 |
| | 300 | 100 | 100 |
| | 400 | 100 | 100 |
| 5-22 | 200 | 88 | 97 |
| | 300 | 93 | 95 |
| | 400 | 95 | 100 |
| 5-23 | 200 | 79 | 100 |
| | 300 | 96 | 100 |
| | 400 | 97 | 96 |

Glyphosate activity on ECHCF in this test was too high to make meaningful comparisons. However, on ABUTH, composition 5-20 containing lecithin and Fluorad FC-135 exhibited remarkably strong herbicidal effectiveness by comparison with composition 5-01 (no Fluorad FC-135) and Formulation C. As in previous testing, a slight further advantage on ABUTH was obtained by efforts to encapsulate the glyphosate in lecithin liposomes, as in composition 5-21. Compositions 5-22 and 5-23, containing both Fluorad FC-135 and Silwet L-77 in addition to lecithin, also showed remarkably good herbicidal effectiveness.

Example 6

Compositions 5-01 to 5-23 of Example 5 were tested in this Example. Morningglory (Ipomoea spp., IPOSS) plants were grown and treated by the standard procedures given above. Applications of spray compositions were made 14 days after planting IPOSS and evaluation of herbicidal inhibition was done 19 days after application.

Formulations B and C, alone and tank mixed with 0.5% Silwet L-77, were applied as comparative treatments. Results, averaged for all replicates of each treatment, are shown in Table 6.

TABLE 6

| Spray composition | Glyphosate rate g a.e./ha | % Inhibition IPOSS |
|---|---|---|
| Formulation B | 200 | 40 |
| | 400 | 66 |
| Formulation B + Silwet L-77 0.5% v/v | 200 | 68 |
| | 400 | 79 |
| Formulation C | 200 | 62 |
| | 400 | 71 |
| Formulation C + Silwet L-77 0.5% v/v | 200 | 70 |
| | 400 | 72 |
| 5-01 | 200 | 64 |
| | 400 | 77 |
| 5-02 | 200 | 68 |
| | 400 | 75 |
| 5-03 | 200 | 68 |
| | 400 | 72 |
| 5-04 | 200 | 69 |
| | 400 | 72 |
| 5-05 | 200 | 64 |
| | 400 | 78 |
| 5-06 | 200 | 80 |
| | 400 | 89 |
| 5-07 | 200 | 69 |
| | 400 | 74 |
| 5-08 | 200 | 60 |
| | 400 | 72 |
| 5-09 | 200 | 79 |
| | 400 | 84 |

TABLE 6-continued

| Spray composition | Glyphosate rate g a.e./ha | % Inhibition IPOSS |
|---|---|---|
| 5-10 | 200 | 69 |
|  | 400 | 78 |
| 5-11 | 200 | 52 |
|  | 400 | 72 |
| 5-12 | 200 | 69 |
|  | 400 | 88 |
| 5-13 | 200 | 72 |
|  | 400 | 74 |
| 5-14 | 200 | 68 |
|  | 400 | 69 |
| 5-15 | 200 | 68 |
|  | 400 | 70 |
| 5-16 | 200 | 55 |
|  | 400 | 69 |
| 5-17 | 200 | 52 |
|  | 400 | 67 |
| 5-18 | 200 | 65 |
|  | 400 | 67 |
| 5-19 | 200 | 54 |
|  | 400 | 70 |
| 5-20 | 200 | 74 |
|  | 400 | 100 |
| 5-21 | 200 | 72 |
|  | 400 | 91 |
| 5-22 | 200 | 81 |
|  | 400 | 84 |
| 5-23 | 200 | 79 |
|  | 400 | 90 |

Once again, surprisingly strong herbicidal effectiveness, this time on IPOSS, was exhibited by compositions 5-20 to 5-23, all of which contain lecithin and Fluorad FC-135.

Example 7

Aqueous spray compositions were prepared containing glyphosate IPA salt and excipient ingredients as shown in Table 7a. Process (ii) was followed for all compositions, using soybean lecithin (20% phospholipid, Avanti). The pH of all compositions was adjusted to approximately 7.

TABLE 7a

| Spray composition | Lecithin g/l | Fluorad FC-135 | Silwet L-77 | Components sonicated with lecithin |
|---|---|---|---|---|
| 7-01 | 5.0 |  | 0.50 | L-77 |
| 7-02 | 5.0 |  | 0.25 | L-77 |
| 7-03 | 5.0 |  | 0.10 | L-77 |
| 7-04 | 5.0 |  |  | none |
| 7-05 | 2.5 |  | 0.50 | L-77 |
| 7-06 | 2.5 |  | 0.25 | L-77 |
| 7-07 | 2.5 |  | 0.10 | L-77 |
| 7-08 | 1.0 |  | 0.50 | L-77 |
| 7-09 | 1.0 |  | 0.25 | L-77 |
| 7-10 | 2.5 |  | 0.10 | L-77 |
| 7-11 | 2.5 | 0.25 | 0.25 | L-77 |
| 7-12 | 2.5 | 0.17 | 0.33 | L-77 |
| 7-13 | 2.5 | 0.33 | 0.17 | L-77 |
| 7-14 | 2.5 | 0.50 |  | none |
| 7-15 | 2.5 | 0.25 |  | none |
| 7-16 | 2.5 | 0.10 |  | none |
| 7-17 | 2.5 |  | 0.25 | glyphosate |
| 7-18 | 2.5 |  | 0.10 | glyphosate |
| 7-19 | 2.5 |  | 0.50 | glyphosate |
| 7-20 | 5.0 |  | 0.50 | L-77, glyphosate |
| 7-21 | 2.5 |  | 0.25 | L-77, glyphosate |
| 7-22 | 1.0 |  | 0.25 | L-77, glyphosate |
| 7-23 | 1.0 |  | 0.10 | L-77, glyphosate |

Velvetleaf (*Abutilon theophrasti*, ABUTH), Japanese millet (*Echinochloa crus-galli*, ECHCF), and prickly sida (*Sida spinosa*, SIDSP) plants were grown and treated by the standard procedures given above. Applications of spray compositions were made 20 days after planting ABUTH and ECHCF. Planting date for SIDSP was not recorded. Evaluation of herbicidal inhibition was done 19 days after application.

Formulations B and C, alone and tank mixed with 0.5% Silwet L-77, were applied as comparative treatments. Results, averaged for all replicates of each treatment, are shown in Table 7b.

TABLE 7b

| Spray composition | Glyphosate rate g a.e./ha | % Inhibition ABUTH | ECHCF | SIDSP |
|---|---|---|---|---|
| Formulation B | 150 | 33 | 39 | 29 |
|  | 250 | 44 | 43 | 66 |
|  | 350 | 83 | 45 | 60 |
| Formulation B + Silwet L-77 0.5% v/v | 150 | 81 | 7 | 46 |
|  | 250 | 88 | 21 | 64 |
|  | 350 | 96 | 32 | 66 |
| Formuiation C | 150 | 61 | 59 | 58 |
|  | 250 | 77 | 92 | 85 |
|  | 350 | 91 | 92 | 83 |
| Formulation C + Silwet L-77 0.5% v/v | 150 | 76 | 10 | 65 |
|  | 250 | 87 | 17 | 60 |
|  | 350 | 92 | 39 | 64 |
| 7-01 | 150 | 87 | 43 | 47 |
|  | 250 | 88 | 41 | 60 |
|  | 350 | 96 | 53 | 66 |
| 7-02 | 150 | 66 | 51 | 61 |
|  | 250 | 85 | 81 | 63 |
|  | 350 | 84 | 89 | 75 |
| 7-03 | 150 | 66 | 54 | 65 |
|  | 250 | 70 | 63 | 60 |
|  | 350 | 94 | 96 | 87 |
| 7-04 | 150 | 73 | 58 | 61 |
|  | 250 | 85 | 83 | 90 |
|  | 350 | 91 | 100 | 83 |
| 7-05 | 150 | 76 | 44 | 49 |
|  | 250 | 85 | 55 | 56 |
|  | 350 | 93 | 79 | 64 |
| 7-06 | 150 | 64 | 73 | 56 |
|  | 250 | 71 | 78 | 61 |
|  | 350 | 81 | 79 | 77 |
| 7-07 | 150 | 53 | 41 | 59 |
|  | 250 | 74 | 78 | 68 |
|  | 350 | 78 | 90 | 75 |
| 7-08 | 150 | 83 | 33 | 59 |
|  | 250 | 82 | 39 | 75 |
|  | 350 | 95 | 59 | 69 |
| 7-09 | 150 | 78 | 32 | 46 |
|  | 250 | 85 | 42 | 75 |
|  | 350 | 91 | 62 | 67 |
| 7-10 | 150 | 26 | 36 | 43 |
|  | 250 | 69 | 73 | 75 |
|  | 350 | 76 | 81 | 73 |
| 7-11 | 150 | 83 | 79 | 72 |
|  | 250 | 96 | 93 | 78 |
|  | 350 | 99 | 97 | 84 |
| 7-12 | 150 | 78 | 57 | 58 |
|  | 250 | 89 | 78 | 66 |
|  | 350 | 94 | 93 | 75 |
| 7-13 | 150 | 83 | 84 | 54 |
|  | 250 | 94 | 93 | 67 |
|  | 350 | 99 | 97 | 93 |
| 7-14 | 150 | 80 | 68 | 69 |
|  | 250 | 85 | 88 | 79 |
|  | 350 | 97 | 94 | 99 |
| 7-15 | 150 | 75 | 80 | 62 |
|  | 250 | 93 | 93 | 76 |
|  | 350 | 95 | 91 | 94 |
| 7-16 | 150 | 75 | 69 | 60 |
|  | 250 | 88 | 91 | 77 |
|  | 350 | 89 | 92 | 75 |

TABLE 7b-continued

| Spray composition | Glyphosate rate g a.e./ha | % Inhibition ABUTH | ECHCF | SIDSP |
|---|---|---|---|---|
| 7-17 | 150 | 77 | 69 | 67 |
|  | 250 | 88 | 91 | 86 |
|  | 350 | 93 | 97 | 96 |
| 7-18 | 150 | 71 | 63 | 66 |
|  | 250 | 74 | 85 | 82 |
|  | 350 | 89 | 85 | 83 |
| 7-19 | 150 | 74 | 62 | 77 |
|  | 250 | 86 | 80 | 93 |
|  | 350 | 92 | 96 | 96 |
| 7-20 | 150 | 39 | 46 | 38 |
|  | 250 | 80 | 49 | 69 |
|  | 350 | 91 | 64 | 69 |
| 7-21 | 150 | 65 | 50 | 34 |
|  | 250 | 64 | 52 | 52 |
|  | 350 | 78 | 67 | 62 |
| 7-22 | 150 | 68 | 18 | 35 |
|  | 250 | 79 | 42 | 43 |
|  | 350 | 87 | 49 | 58 |
| 7-23 | 150 | 24 | 46 | 38 |
|  | 250 | 62 | 49 | 42 |
|  | 350 | 91 | 53 | 67 |

Compositions 7-14 to 7-16, containing 0.25% lecithin together with Fluorad FC-135, provided excellent herbicidal effectiveness on all three species tested. Even at the lowest concentration of Fluorad FC-135 (0.1% in composition 7-16), effectiveness was substantially maintained on ABUTH and ECHCF, although some loss of effectiveness was evident on SIDSP. Compositions 7-11 to 7-13, containing lecithin, Fluorad FC-135 and Silwet L-77, also performed well in this test, not showing the antagonism on ECHCF characteristic of compositions containing Silwet L-77 but no Fluorad FC-135.

Example 8

Aqueous spray compositions were prepared containing glyphosate IPA salt and excipient ingredients as shown in Table 8a. Process (ii) was followed for all compositions, using soybean lecithin (20% phospholipid, Avanti).

Aqueous spray compositions were prepared containing glyphosate IPA salt and excipient ingredients as shown in Table 8a. The pH of all compositions was adjusted to approximately 7.

TABLE 8a

| Spray composition | % w/w | | | |
|---|---|---|---|---|
| | Lecithin g/l | Fluorad FC-135 | Silwet L-77 | Components sonicated with lecithin |
| 8-01 | 5.0 |  | 0.50 | L-77 |
| 8-02 | 5.0 |  | 0.25 | L-77 |
| 8-03 | 5.0 |  | 0.10 | L-77 |
| 8-04 | 5.0 |  |  | none |
| 8-05 | 2.5 |  | 0.50 | L-77 |
| 8-06 | 2.5 |  | 0.25 | L-77 |
| 8-07 | 2.5 |  | 0.10 | L-77 |
| 8-08 | 1.0 |  | 0.50 | L-77 |
| 8-09 | 1.0 |  | 0.25 | L-77 |
| 8-10 | 2.5 |  | 0.10 | L-77 |
| 8-11 | 2.5 | 0.25 | 0.25 | L-77 |
| 8-12 | 2.5 | 0.17 | 0.33 | L-77 |
| 8-13 | 2.5 | 0.33 | 0.17 | L-77 |
| 8-14 | 2.5 | 0.50 |  | none |
| 8-15 | 2.5 | 0.25 |  | none |
| 8-16 | 2.5 | 0.10 |  | none |
| 8-17 | 2.5 |  | 0.25 | glyphosate |
| 8-18 | 2.5 |  | 0.10 | glyphosate |
| 8-19 | 2.5 |  | 0.50 | glyphosate |

Yellow nutsedge (*Cyperus esculentus*, CYPES) plants were grown and treated by the standard procedures given above. Applications of spray compositions were made 21 days after planting CYPES, and evaluation of herbicidal inhibition was done 27 days after application.

Formulations B and C, alone and tank mixed with 0.5% Silwet L-77, were applied as comparative treatments. Results, averaged for all replicates of each treatment, are shown in Table 8b.

TABLE 8b

| Spray composition | Glyphosate rate g a.e./ha | % Inhibition CYPES |
|---|---|---|
| Formulation B | 500 | 92 |
|  | 1000 | 95 |
|  | 5000 | 100 |
| Formulation B + Silwet L-77 0.5% v/v | 500 | 100 |
|  | 1000 | 87 |
|  | 5000 | 100 |
| Formulation C | 500 | 87 |
|  | 1000 | 96 |
|  | 5000 | 100 |
| Formulation C + Silwet L-77 0.5% v/v | 500 | 98 |
|  | 1000 | 94 |
|  | 5000 | 100 |
| 8-01 | 500 | 91 |
|  | 1000 | 100 |
|  | 1500 | 97 |
| 8-02 | 500 | 83 |
|  | 1000 | 100 |
|  | 1500 | 100 |
| 8-03 | 500 | 90 |
|  | 1000 | 88 |
|  | 1500 | 71 |
| 8-04 | 500 | 88 |
|  | 1000 | 100 |
|  | 1500 | 100 |
| 8-05 | 500 | 84 |
|  | 1000 | 99 |
|  | 1500 | 95 |
| 8-06 | 500 | 90 |
|  | 1000 | 88 |
|  | 1500 | 99 |
| 8-07 | 500 | 78 |
|  | 1000 | 94 |
|  | 1500 | 97 |
| 8-08 | 500 | 93 |
|  | 1000 | 96 |
|  | 1500 | 100 |
| 8-09 | 500 | 87 |
|  | 1000 | 88 |
|  | 1500 | 100 |
| 8-10 | 500 | 86 |
|  | 1000 | 100 |
|  | 1500 | 100 |
| 8-11 | 500 | 95 |
|  | 1000 | 94 |
|  | 1500 | 100 |
| 8-12 | 500 | 92 |
|  | 1000 | 92 |
|  | 1500 | 100 |
| 8-13 | 500 | 87 |
|  | 1000 | 97 |
|  | 1500 | 100 |

TABLE 8b-continued

| Spray composition | Glyphosate rate g a.e./ha | % Inhibition CYPES |
|---|---|---|
| 8-14 | 500 | 82 |
|  | 1000 | 100 |
|  | 1500 | 100 |
| 8-15 | 500 | 85 |
|  | 1000 | 90 |
|  | 1500 | 95 |
| 8-16 | 500 | 87 |
|  | 1000 | 91 |
|  | 1500 | 100 |
| 8-17 | 500 | 83 |
|  | 1000 | 90 |
|  | 1500 | 95 |
| 8-18 | 500 | 93 |
|  | 1000 | 100 |
|  | 1500 | 95 |
| 8-19 | 500 | 86 |
|  | 1000 | 95 |
|  | 1500 | 100 |

The commercial standard Formulation C exhibited very high herbicidal effectiveness in this test and for this reason it is not possible to discern enhancements. There is a suggestion at the lowest glyphosate rate (500 g a.e./ha), effectiveness of compositions containing lecithin and Fluorad FC-135 (8-14 to 8-16) on CYPES surprisingly improved with decreasing Fluorad FC-135 concentration.

Example 9

Aqueous spray compositions were prepared containing glyphosate IPA salt and excipient ingredients as shown in Table 9a. Process (ii) was followed for all compositions, using soybean lecithin (20% phospholipid, Avanti). The pH of all compositions was adjusted to approximately 7.

TABLE 9a

| Spray composition | % w/w | | | |
|---|---|---|---|---|
|  | Lecithin g/l | Fluorad FC-135 | Silwet L-77 | Components sonicated with lecithin |
| 9-01 | 5.0 |  |  | none |
| 9-02 | 5.0 |  | 0.50 | none |
| 9-03 | 5.0 |  | 0.50 | L-77 |
| 9-04 | 2.5 |  |  | none |
| 9-05 | 2.5 |  | 0.50 | none |
| 9-06 | 2.5 |  | 0.50 | L-77 |
| 9-07 | 1.0 |  |  | none |
| 9-08 | 1.0 |  | 0.50 | none |
| 9-09 | 1.0 |  | 0.50 | L-77 |
| 9-10 | 0.5 |  |  | none |
| 9-11 | 0.5 |  | 0.50 | none |
| 9-12 | 0.5 |  | 0.50 | L-77 |
| 9-13 | 1.0 |  | 0.25 | none |
| 9-14 | 1.0 |  | 0.25 | L-77 |
| 9-15 | 1.0 |  | 0.10 | none |
| 9-16 | 1.0 |  | 0.10 | L-77 |
| 9-17 | 1.0 | 0.50 |  | none |
| 9-18 | 1.0 | 0.20 |  | none |
| 9-19 | 1.0 | 0.10 |  | none |
| 9-20 | 0.5 | 0.50 |  | none |
| 9-21 | 0.5 | 0.20 |  | none |

Velvetleaf (*Abutilon theophrasti*, ABUTH) and Japanese millet (*Echinochloa crus-galli*, ECHCF) plants were grown and treated by the standard procedures given above. There was no record of the dates of planting. Evaluation of herbicidal inhibition was done 16 days after application.

In addition to compositions 9-01 to 9-21, spray compositions were prepared by tank mixing Formulations B and C with 0.5% Fluorad FC-135. Formulations B and C, alone and tank mixed with 0.5% Silwet L-77, were applied as comparative treatments. Results, averaged for all replicates of each treatment, are shown in Table 9b.

TABLE 9b

| Spray composition | Glyphosate rate g a.e./ha | % Inhibition | |
|---|---|---|---|
|  |  | ABUTH | ECHCF |
| Formulation B | 150 | 64 | 77 |
|  | 250 | 81 | 80 |
|  | 350 | 88 | 97 |
| Formulation B + L-77 0.5% v/v | 150 | 42 | 38 |
|  | 250 | 56 | 49 |
|  | 350 | 67 | 64 |
| Formulation C | 150 | 61 | 89 |
|  | 250 | 75 | 91 |
|  | 350 | 92 | 99 |
| Formulation C + Silwet L-77 0.5% v/v | 150 | 92 | 40 |
|  | 250 | 95 | 40 |
|  | 350 | 94 | 74 |
| Formulation B + Fluorad FC-135 0.5% w/v | 150 | 87 | 34 |
|  | 250 | 90 | 44 |
|  | 350 | 97 | 47 |
| Formulation C + Fluorad FC-135 0.5% w/v | 150 | 79 | 85 |
|  | 250 | 77 | 86 |
|  | 350 | 92 | 91 |
| 9-01 | 150 | 75 | 69 |
|  | 250 | 84 | 89 |
|  | 350 | 98 | 98 |
| 9-02 | 150 | 86 | 54 |
|  | 250 | 96 | 74 |
|  | 350 | 99 | 86 |
| 9-03 | 150 | 86 | 66 |
|  | 250 | 91 | 77 |
|  | 350 | 96 | 86 |
| 9-04 | 150 | 68 | 73 |
|  | 250 | 97 | 85 |
|  | 350 | 94 | 92 |
| 9-05 | 150 | 90 | 55 |
|  | 250 | 96 | 69 |
|  | 350 | 91 | 82 |
| 9-06 | 150 | 87 | 43 |
|  | 250 | 91 | 68 |
|  | 350 | 97 | 83 |
| 9-07 | 150 | 56 | 76 |
|  | 250 | 81 | 88 |
|  | 350 | 89 | 96 |
| 9-08 | 150 | 85 | 35 |
|  | 250 | 93 | 51 |
|  | 350 | 98 | 66 |
| 9-09 | 150 | 94 | 45 |
|  | 250 | 97 | 47 |
|  | 350 | 98 | 52 |
| 9-10 | 150 | 62 | 60 |
|  | 250 | 85 | 78 |
|  | 350 | 93 | 88 |
| 9-11 | 150 | 90 | 32 |
|  | 250 | 92 | 42 |
|  | 350 | 98 | 59 |
| 9-12 | 150 | 93 | 38 |
|  | 250 | 93 | 56 |
|  | 350 | 95 | 72 |
| 9-13 | 150 | 85 | 39 |
|  | 250 | 89 | 66 |
|  | 350 | 94 | 79 |
| 9-14 | 150 | 83 | 70 |
|  | 250 | 93 | 45 |
|  | 350 | 93 | 70 |
| 9-15 | 150 | 65 | 54 |
|  | 250 | 85 | 79 |
|  | 350 | 91 | 89 |
| 9-16 | 150 | 75 | 65 |
|  | 250 | 83 | 79 |
|  | 350 | 90 | 84 |
| 9-17 | 150 | 81 | 94 |
|  | 250 | 88 | 97 |
|  | 350 | 100 | 99 |

TABLE 9b-continued

| Spray composition | Glyphosate rate g a.e./ha | % Inhibition ABUTH | ECHCF |
|---|---|---|---|
| 9-18 | 150 | 79 | 89 |
|  | 250 | 95 | 91 |
|  | 350 | 98 | 98 |
| 9-19 | 150 | 77 | 85 |
|  | 250 | 91 | 96 |
|  | 350 | 95 | 97 |
| 9-20 | 150 | 77 | 71 |
|  | 250 | 86 | 92 |
|  | 350 | 100 | 93 |
| 9-21 | 150 | 75 | 91 |
|  | 250 | 84 | 97 |
|  | 350 | 96 | 95 |

Compositions of this Example (9-17 to 9-21) containing very low concentrations of lecithin and Fluorad FC-135 exhibited remarkably high herbicidal effectiveness. Even a composition (9-19) with just 0.1% lecithin and 0.1% Fluorad FC-135 was much more effective on ABUTH than commercial standard Formulation C, and equally as effective on ECHCF as Formulation C. The apparently strong antagonism on ECHCF seen when Formulation B was tank mixed with 0.5% Fluorad FC-135 in this test is uncharacteristic and has not been seen in other tests (see, for example, Example 12 herein); indeed the data for this set of treatments is so out of line that it is believed they may be due to an error in application.

Example 10

Aqueous spray compositions were prepared containing glyphosate IPA salt and excipient ingredients as shown in Table 10a. Process (iii) was followed for all compositions, using soybean lecithin (20% phospholipid, Avanti). The pH of all compositions was adjusted to approximately 7.

TABLE 10a

| Spray composition | Lecithin g/l | Fluorad FC-135 | Silwet L-77 | Methyl caprate | Sodium cholate | Components sonicated with lecithin |
|---|---|---|---|---|---|---|
| 10-01 | 5.0 |  |  |  |  | none |
| 10-02 | 5.0 |  | 0.50 |  |  | none |
| 10-03 | 5.0 |  | 0.50 |  |  | L-77 |
| 10-04 | 2.5 |  |  |  |  | none |
| 10-05 | 0.5 |  |  |  |  | none |
| 10-06 | 2.5 |  | 0.50 |  |  | none |
| 10-07 | 2.5 |  | 0.50 |  |  | L-77 |
| 10-08 | 0.5 |  | 0.50 |  |  | none |
| 10-09 | 0.5 |  | 0.50 |  |  | L-77 |
| 10-10 | 2.5 | 0.25 |  |  |  | none |
| 10-11 | 2.5 | 0.10 |  |  |  | none |
| 10-12 | 2.5 | 0.05 |  |  |  | none |
| 10-13 | 0.5 | 0.25 |  |  |  | none |
| 10-14 | 0.5 | 0.10 |  |  |  | none |
| 10-15 | 0.5 | 0.05 |  |  |  | none |
| 10-16 | 2.5 |  |  | 0.10 |  | Me caprate |
| 10-17 | 2.5 |  |  |  | 0.10 | Na cholate |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 21 days after planting ECHCF, and evaluation of herbicidal inhibition was done 18 days after application.

In addition to compositions 10-01 to 10-17, spray compositions were prepared by tank mixing Formulations B and C with Fluorad FC-135 at various concentrations. Formulations B and C, alone and tank mixed with 0.5% Silwet L-77, were applied as comparative treatments. Results, averaged for all replicates of each treatment, are shown in Table 101b.

TABLE 10b

| Spray composition | Glyphosate rate g a.e./ha | % Inhibition ABUTH | ECHCF |
|---|---|---|---|
| Formulation B | 200 | 53 | 69 |
|  | 300 | 76 | 85 |
|  | 400 | 77 | 81 |
| Formulation B + Silwet L-77 0.5% v/v | 200 | 100 | 28 |
|  | 300 | 100 | 35 |
|  | 400 | 100 | 47 |
| Formulation C | 200 | 57 | 81 |
|  | 300 | 73 | 90 |
|  | 400 | 98 | 94 |
| Formulation C + Silwet L-77 0.5% v/v | 200 | 99 | 28 |
|  | 300 | 98 | 53 |
|  | 400 | 99 | 56 |
| Formulation B + Fluorad FC-135 0.25% w/v | 200 | 76 | 85 |
|  | 300 | 95 | 81 |
|  | 400 | 100 | 100 |
| Formulation B + Fluorad FC-135 0.1% w/v | 200 | 77 | 70 |
|  | 300 | 94 | 81 |
|  | 400 | 98 | 87 |
| Formulation B + Fluorad FC-135 0.05% w/v | 200 | 65 | 73 |
|  | 300 | 84 | 94 |
|  | 400 | 88 | 96 |
| Formulation C + Fluorad FC-135 0.25% w/v | 200 | 83 | 78 |
|  | 300 | 98 | 94 |
|  | 400 | 97 | 95 |
| Formulation C + Fluorad FC-135 0.1% w/v | 200 | 65 | 66 |
|  | 300 | 89 | 86 |
|  | 400 | 97 | 89 |
| Formulation C + Fluorad FC-135 0.05% w/v | 200 | 70 | 78 |
|  | 300 | 79 | 84 |
|  | 400 | 96 | 98 |
| 10-01 | 200 | 93 | 71 |
|  | 300 | 91 | 89 |
|  | 400 | 97 | 97 |
| 10-02 | 200 | 95 | 59 |
|  | 300 | 97 | 68 |
|  | 400 | 99 | 79 |
| 10-03 | 200 | 97 | 55 |
|  | 300 | 98 | 62 |
|  | 400 | 100 | 76 |
| 10-04 | 200 | 83 | 72 |
|  | 300 | 87 | 84 |
|  | 400 | 95 | 100 |
| 10-05 | 200 | 69 | 78 |
|  | 300 | 92 | 93 |
|  | 400 | 98 | 97 |
| 10-06 | 200 | 94 | 61 |
|  | 300 | 99 | 67 |
|  | 400 | 100 | 76 |
| 10-07 | 200 | 99 | 52 |
|  | 300 | 99 | 63 |
|  | 400 | 100 | 80 |
| 10-08 | 200 | 96 | 47 |
|  | 300 | 99 | 57 |
|  | 400 | 99 | 55 |
| 10-09 | 200 | 99 | 23 |
|  | 300 | 98 | 58 |
|  | 400 | 100 | 53 |
| 10-10 | 200 | 89 | 91 |
|  | 300 | 91 | 99 |
|  | 400 | 98 | 100 |
| 10-11 | 200 | 81 | 91 |
|  | 300 | 91 | 99 |
|  | 400 | 92 | 100 |
| 10-12 | 200 | 66 | 96 |
|  | 300 | 86 | 100 |
|  | 400 | 94 | 99 |

TABLE 10b-continued

| Spray composition | Glyphosate rate g a.e./ha | % Inhibition ABUTH | % Inhibition ECHCF |
|---|---|---|---|
| 10-13 | 200 | 80 | 97 |
|  | 300 | 98 | 98 |
|  | 400 | 99 | 100 |
| 10-14 | 200 | 68 | 92 |
|  | 300 | 89 | 100 |
|  | 400 | 99 | 98 |
| 10-15 | 200 | 84 | 95 |
|  | 300 | 94 | 100 |
|  | 400 | 97 | 100 |
| 10-16 | 200 | 73 | 94 |
|  | 300 | 89 | 100 |
|  | 400 | 99 | 100 |
| 10-17 | 200 | 58 | 94 |
|  | 300 | 77 | 96 |
|  | 400 | 90 | 90 |

Tank mixture of Fluorad FC-135 at concentrations as low as 0.05% with Formulation B resulted in remarkably strong herbicidal efficacy in this test. The antagonism on ECHCF seen with the nonionic organosilicone surfactant Silwet L-77 did not occur with the cationic fluoro-organic surfactant Fluorad FC-135. Noteworthy was the outstanding herbicidal effectiveness provided by a composition (10-15) containing just 0.05% lecithin and 0.05% Fluorad FC-135. In this test addition of 0.1% methyl caprate to 0.25% lecithin, the methyl caprate being sonicated together with the lecithin, enhanced performance on ECHCF but not on ABUTH (compare compositions 10-16 and 10-04).

Example 11

Compositions 10-01 to 10-17 of Example 10, and tank mixtures of Formulations B and C with Fluorad FC-135, were tested in this Example. Prickly sida (*Sida spinosa*, SIDSP) plants were grown and treated by the standard procedures given above. Applications of spray compositions were made 22 days after planting SIDSP, and evaluation of herbicidal inhibition was done 19 days after application.

Formulations B and C, alone and tank mixed with 0.5% Silwet L-77, were applied as comparative treatments. Results, averaged for all replicates of each treatment, are shown in Table 11.

TABLE 11

| Spray composition | Glyphosate rate g a.e./ha | % Inhibition SIDSP |
|---|---|---|
| Formulation B | 200 | 46 |
|  | 300 | 75 |
|  | 400 | 80 |
| Formulation B + Silwet L-77 0.5% v/v | 200 | 96 |
|  | 300 | 89 |
|  | 400 | 87 |
| Formulation C | 200 | 80 |
|  | 300 | 98 |
|  | 400 | 98 |
| Formulation C + Silwet L-77 0.5% v/v | 200 | 75 |
|  | 300 | 91 |
|  | 400 | 94 |
| Formulation B + Fluorad FC-135 0.25% w/v | 200 | 82 |
|  | 300 | 94 |
|  | 400 | 98 |
| Formulation B + Fluorad FC-135 0.1% w/v | 200 | 70 |
|  | 300 | 93 |
|  | 400 | 88 |
| Formulation B + Fluorad FC-135 0.05% w/v | 200 | 79 |
|  | 300 | 92 |
|  | 400 | 99 |
| Formulation C + Fluorad FC-135 0.25% w/v | 200 | 79 |
|  | 300 | 97 |
|  | 400 | 97 |
| Formulation C + Fluorad FC-135 0.1% w/v | 200 | 90 |
|  | 300 | 96 |
|  | 400 | 97 |
| Formulation C + Fluorad FC-135 0.05% w/v | 200 | 80 |
|  | 300 | 96 |
|  | 400 | 99 |
| 10-01 | 200 | 93 |
|  | 300 | 97 |
|  | 400 | 98 |
| 10-02 | 200 | 71 |
|  | 300 | 89 |
|  | 400 | 89 |
| 10-03 | 200 | 71 |
|  | 300 | 87 |
|  | 400 | 98 |
| 10-04 | 200 | 76 |
|  | 300 | 100 |
|  | 400 | 100 |
| 10-05 | 200 | 91 |
|  | 300 | 99 |
|  | 400 | 97 |
| 10-06 | 200 | 57 |
|  | 300 | 95 |
|  | 400 | 88 |
| 10-07 | 200 | 64 |
|  | 300 | 68 |
|  | 400 | 94 |
| 10-08 | 200 | 89 |
|  | 300 | 96 |
|  | 400 | 99 |
| 10-09 | 200 | 80 |
|  | 300 | 77 |
|  | 400 | 94 |
| 10-10 | 200 | 90 |
|  | 300 | 94 |
|  | 400 | 98 |
| 10-11 | 200 | 81 |
|  | 300 | 100 |
|  | 400 | 96 |
| 10-12 | 200 | 86 |
|  | 300 | 92 |
|  | 400 | 95 |
| 10-13 | 200 | 86 |
|  | 300 | 99 |
|  | 400 | 100 |
| 10-14 | 200 | 97 |
|  | 300 | 100 |
|  | 400 | 100 |
| 10-15 | 200 | 99 |
|  | 300 | 100 |
|  | 400 | 100 |
| 10-16 | 200 | 92 |
|  | 300 | 100 |
|  | 400 | 100 |
| 10-17 | 200 | 92 |
|  | 300 | 99 |
|  | 400 | 100 |

Herbicidal effectiveness of Formulation C was very high on SIDSP in this test and accordingly enhancements are difficult to discern. However, remarkably strong performance was again seen with composition 10-15, containing just 0.05% lecithin and 0.05% Fluorad FC-135.

Example 12

Aqueous spray compositions were prepared containing glyphosate IPA salt and excipient ingredients as shown in Table 12a. Process (iii) was followed for all compositions, using soybean lecithin (20% phospholipid, Avanti). The pH of all compositions was adjusted to approximately 7.

TABLE 12a

| Spray comp. | % w/w | | | | (*) Other ingredient | Components sonicated with lecithin |
|---|---|---|---|---|---|---|
| | Lecithin g/l | Fluorad FC-135 | Silwet L-77 | Other (*) | | |
| 12-01 | 5.0 | | | | | none |
| 12-02 | 5.0 | | 0.50 | | | L-77 |
| 12-03 | 2.5 | | | | | none |
| 12-04 | 2.5 | 0.50 | | | | none |
| 12-05 | 2.5 | 0.20 | | | | none |
| 12-06 | 2.5 | 0.10 | | | | none |
| 12-07 | 5.0 | | | 0.50 | Diacid 1550 | Diacid |
| 12-08 | 5.0 | | | 0.10 | Diacid 1550 | Diacid |
| 12-09 | 2.5 | | | 0.25 | Diacid 1550 | Diacid |
| 12-10 | 2.5 | 0.25 | | 0.05 | Diacid 1550 | Diacid |
| 12-11 | 5.0 | 0.10 | | 0.50 | Genapol UD-030 | Genapol |
| 12-12 | 5.0 | 0.05 | | 0.20 | Genapol UD-030 | Genapol |
| 12-13 | 5.0 | 0.25 | | 0.50 | Neodol 25-3 | Neodol |
| 12-14 | 5.0 | 0.10 | | 0.20 | Neodol 25-3 | Neodol |

Velvetleaf (*Abutilon theophrasti*, ABUTH), Japanese millet (*Echinochloa crus-galli*, ECHCF) and morningglory (*Ipomoea* spp., IPOSS) plants were grown and treated by the standard procedures given above. Applications of spray compositions were made 16 days after planting ABUTH, 18 days after planting ECHCF and 9 days after planting IPOSS. Evaluation of herbicidal inhibition was done 15 days after application.

In addition to compositions 12-01 to 12-14, spray compositions were prepared by tank mixing Formulations B and C with Fluorad FC-135 at various concentrations. Formulations B and C, alone and tank mixed with 0.5% Silwet L-77, were applied as comparative treatments. Results, averaged for all replicates of each treatment, are shown in Table 12b.

TABLE 12b

| Spray composition | Glyphosate rate g a.e/ha | % Inhibition | | |
|---|---|---|---|---|
| | | ABUTH | ECHCF | IPOSS |
| Formulation B | 200 | 24 | 53 | 33 |
| | 300 | 47 | 37 | 37 |
| | 400 | 64 | 46 | 64 |
| Formulation B + Silwet L-77 0.5% v/v | 200 | 85 | 3 | 66 |
| | 300 | 97 | 19 | 77 |
| | 400 | 98 | 18 | 82 |
| Formulation C | 200 | 39 | 69 | 38 |
| | 300 | 71 | 90 | 67 |
| | 400 | 87 | 100 | 76 |
| Formulation C + Silwet L-77 0.5% v/v | 200 | 90 | 8 | 72 |
| | 300 | 95 | 50 | 79 |
| | 400 | 100 | 90 | 73 |
| Formulation B + Fluorad FC-135 0.5% w/v | 200 | 75 | 71 | 65 |
| | 300 | 94 | 92 | 79 |
| | 400 | 98 | 100 | 77 |
| Formulation B + Fluorad FC-135 0.25% w/v | 200 | 75 | 67 | 67 |
| | 300 | 85 | 73 | 71 |
| | 400 | 96 | 97 | 75 |
| Formulation B + Fluorad FC-135 0.1% w/v | 200 | 61 | 53 | 48 |
| | 300 | 82 | 98 | 72 |
| | 400 | 95 | 86 | 70 |
| Formulation C + Fluorad FC-135 0.5% w/v | 200 | 81 | 61 | 69 |
| | 300 | 75 | 75 | 71 |
| | 400 | 84 | 84 | 77 |
| Formulation C + Fluorad FC-135 0.25% w/v | 200 | 35 | 58 | 67 |
| | 300 | 68 | 97 | 64 |
| | 400 | 92 | 96 | 73 |
| Formulation C + Fluorad FC-135 0.1% w/v | 200 | 40 | 84 | 51 |
| | 300 | 79 | 94 | 58 |
| | 400 | 99 | 86 | 74 |
| 12-01 | 200 | 69 | 69 | 62 |
| | 300 | 82 | 82 | 73 |
| | 400 | 88 | 84 | 77 |
| 12-02 | 200 | 81 | 75 | 67 |
| | 300 | 83 | 74 | 72 |
| | 400 | 95 | 93 | 75 |
| 12-03 | 200 | 48 | 69 | 70 |
| | 300 | 82 | 93 | 71 |
| | 400 | 94 | 100 | 72 |
| 12-04 | 200 | 68 | 78 | 64 |
| | 300 | 90 | 94 | 76 |
| | 400 | 96 | 99 | 79 |
| 12-05 | 200 | 75 | 86 | 68 |
| | 300 | 86 | 95 | 72 |
| | 400 | 96 | 89 | 80 |
| 12-06 | 200 | 80 | 95 | 57 |
| | 300 | 85 | 82 | 60 |
| | 400 | 96 | 91 | 73 |
| 12-07 | 200 | 41 | 72 | 64 |
| | 300 | 76 | 82 | 68 |
| | 400 | 80 | 98 | 77 |
| 12-08 | 200 | 40 | 71 | 70 |
| | 300 | 51 | 91 | 76 |
| | 400 | 77 | 98 | 72 |
| 12-09 | 200 | 43 | 74 | 64 |
| | 300 | 58 | 95 | 76 |
| | 400 | 73 | 100 | 77 |
| 12-10 | 200 | 43 | 85 | 65 |
| | 300 | 74 | 75 | 65 |
| | 400 | 83 | 99 | 76 |
| 12-11 | 200 | 39 | 71 | 66 |
| | 300 | 61 | 88 | 71 |
| | 400 | 89 | 99 | 73 |
| 12-12 | 200 | 54 | 57 | 59 |
| | 300 | 79 | 77 | 75 |
| | 400 | 89 | 84 | 71 |
| 12-13 | 200 | 69 | 72 | 69 |
| | 300 | 59 | 66 | 69 |
| | 400 | 86 | 81 | 76 |
| 12-14 | 200 | 54 | 62 | 65 |
| | 300 | 65 | 77 | 69 |
| | 400 | 84 | 81 | 74 |

Tank mixtures of Formulation B with Fluorad FC-135 gave greater herbicidal effectiveness than Formulation C alone, without the attendant antagonism on ECHCF so characteristic of Silwet L-77. Addition of Fluorad FC-135 to glyphosate compositions containing 0.25% lecithin enhanced herbicidal effectiveness on ABUTH and ECHCF, but not, in this test, on IPOSS (compare compositions 12-04 to 12-06 with composition 12-03).

Example 13

Compositions 12-01 to 12-14 of Example 12, and tank mixtures of Formulations B and C with Fluorad FC-135, were tested in this Example. Prickly sida (*Sida spinosa*, SIDSP) plants were grown and treated by the standard procedures given above. Application of spray composition were made 23 days after planting SIDSP, and evaluation of herbicidal inhibition was done 19 days after application.

Formulation B and C, alone and tank mixed with 0.5% Silwet L-77, were applied as comparative treatments.

Results, averaged for all replicates of each treatment, are shown in Table 13.

TABLE 13

| Spray composition | Glyphosate rate g a.e./ha | % Inhibition SIDSP |
|---|---|---|
| Formulation B | 200 | 37 |
|  | 300 | 47 |
|  | 400 | 50 |
| Formulation B + Silwet L-77 0.5% v/v | 200 | 93 |
|  | 300 | 100 |
|  | 400 | 99 |
| Formulation C | 200 | 47 |
|  | 300 | 63 |
|  | 400 | 86 |
| Formulation C + Silwet L-77 0.5% v/v | 200 | 88 |
|  | 300 | 92 |
|  | 400 | 99 |
| Formulation B + Fluorad FC-135 0.5% w/v | 200 | 51 |
|  | 300 | 79 |
|  | 400 | 84 |
| Formulation B + Fluorad FC-135 0.25% w/v | 200 | 49 |
|  | 300 | 53 |
|  | 400 | 85 |
| Formulation B + Fluorad FC-135 0.1% w/v | 200 | 44 |
|  | 300 | 58 |
|  | 400 | 70 |
| Formulation C + Fluorad FC-135 0.5% w/v | 200 | 74 |
|  | 300 | 89 |
|  | 400 | 97 |
| Formulation C + Fluorad FC-135 0.25% w/v | 200 | 52 |
|  | 300 | 70 |
|  | 400 | 75 |
| Formulation C + Fluorad FC-135 0.1% w/v | 200 | 45 |
|  | 300 | 74 |
|  | 400 | 87 |
| 12-01 | 200 | 62 |
|  | 300 | 76 |
|  | 400 | 89 |
| 12-02 | 200 | 59 |
|  | 300 | 54 |
|  | 400 | 73 |
| 12-03 | 200 | 56 |
|  | 300 | 89 |
|  | 400 | 80 |
| 12-04 | 200 | 72 |
|  | 300 | 89 |
|  | 400 | 96 |
| 12-05 | 200 | 66 |
|  | 300 | 87 |
|  | 400 | 84 |
| 12-06 | 200 | 60 |
|  | 300 | 74 |
|  | 400 | 86 |
| 12-07 | 200 | 57 |
|  | 300 | 78 |
|  | 400 | 89 |
| 12-08 | 200 | 59 |
|  | 300 | 67 |
|  | 400 | 70 |
| 12-09 | 200 | 57 |
|  | 300 | 65 |
|  | 400 | 74 |
| 12-10 | 200 | 53 |
|  | 300 | 77 |
|  | 400 | 77 |
| 12-11 | 200 | 58 |
|  | 300 | 71 |
|  | 400 | 87 |
| 12-12 | 200 | 54 |
|  | 300 | 70 |
|  | 400 | 82 |
| 12-13 | 200 | 65 |
|  | 300 | 75 |
|  | 400 | 82 |
| 12-14 | 200 | 61 |
|  | 300 | 77 |
|  | 400 | 81 |

On SIDSP in this test, tank mix addition of Fluorad FC-135 to Formulation B enhanced herbicidal effectiveness over that obtained with Formulation C alone, only at the 0.5% concentration of Fluorad FC-135. Likewise, when added to a glyphosate composition containing 0.25% lecithin, Fluorad FC-135 enhanced herbicidal effectiveness most significantly at the 0.5% concentration (composition 12-04).

Example 14

Aqueous spray compositions were prepared containing glyphosate IPA salt and excipient ingredients as shown in Table 14a. Process (iii) was followed for all compositions, using soybean lecithin (20% phospholipid, Avanti). The following compositions had a pH of approximately 5: 14-01, 14-03, 14-07, 14-08, 14-10 and 14-12 to 14-17. All others were adjusted to a pH of approximately 7.

TABLE 14A

| Spray composition | Lecithin g/l | % w/w Fluorad FC-135 | Silwet L-77 | Diacid 1550 | Components sonicated with lecithin |
|---|---|---|---|---|---|
| 14-01 | 5.0 |  |  |  | none |
| 14-02 | 5.0 |  |  |  | none |
| 14-03 | 2.5 |  |  |  | none |
| 14-04 | 2.5 |  |  |  | none |
| 14-05 | 5.0 |  |  |  | glyphosate |
| 14-06 | 5.0 |  | 0.50 |  | L-77 |
| 14-07 | 5.0 |  | 0.50 |  | L-77 |
| 14-08 | 2.5 |  | 0.50 |  | L-77 |
| 14-09 | 2.5 |  | 0.50 |  | L-77 |
| 14-10 | 2.5 |  | 0.25 |  | glyphosate |
| 14-11 | 2.5 |  | 0.25 |  | glyphosate |
| 14-12 | 2.5 | 0.25 |  |  | none |
| 14-13 | 2.5 | 0.25 |  |  | glyphosate |
| 14-14 | 2.5 | 0.10 |  |  | none |
| 14-15 | 2.5 | 0.10 |  |  | glyphosate |
| 14-16 | 2.5 |  | 0.25 | 0.25 | L-77, Diacid |
| 14-17 | 2.5 |  | 0.10 | 0.05 | L-77, Diacid |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 20 days after planting ECHCF, and evaluation of herbicidal inhibition was done 20 days after application.

In addition to compositions 14-01 to 14-17, spray compositions were prepared by tank mixing Formulations B and C with Fluorad FC-135 at two concentrations. Formulations B and C, alone and tank mixed with 0.5% and 0.25% Silwet L-77, were applied as comparative treatments. Results, averaged for all replicates of each treatment, are shown in Table 14b.

TABLE 14b

| Spray composition | Glyphosate rate g a.e./ha | % Inhibition ABUTH | ECHCF |
|---|---|---|---|
| Formulation B | 200 | 53 | 43 |
|  | 300 | 73 | 50 |
|  | 400 | 91 | 74 |
| Formulation B + Silwet L-77 0.5% v/v | 200 | 86 | 24 |
|  | 300 | 88 | 15 |
|  | 400 | 94 | 58 |
| Formulation B + | 200 | 80 | 22 |

TABLE 14b-continued

| Spray composition | Glyphosate rate g a.e./ha | % Inhibition ABUTH | % Inhibition ECHCF |
|---|---|---|---|
| Silwet L-77 0.25% w/v | 300 | 93 | 38 |
|  | 400 | 87 | 38 |
| Formulation C | 200 | 56 | 88 |
|  | 300 | 86 | 98 |
|  | 400 | 94 | 98 |
| Formulation C + Silwet L-77 0.5% v/v | 200 | 87 | 23 |
|  | 300 | 93 | 52 |
|  | 400 | 91 | 60 |
| Formulation C + Silwet L-77 0.25% v/v | 200 | 79 | 42 |
|  | 300 | 83 | 73 |
|  | 400 | 87 | 95 |
| Formulation B + Fluorad FC-135 0.25% w/v | 200 | 79 | 49 |
|  | 300 | 89 | 77 |
|  | 400 | 94 | 85 |
| Formulation B + Fluorad FC-135 0.1% w/v | 200 | 73 | 64 |
|  | 300 | 89 | 68 |
|  | 400 | 92 | 75 |
| Formulation C + Fluorad FC-135 0.25% w/v | 200 | 73 | 86 |
|  | 300 | 75 | 90 |
|  | 400 | 90 | 95 |
| Formulation C + Fluorad FC-135 0.1% w/v | 200 | 53 | 97 |
|  | 300 | 89 | 96 |
|  | 400 | 91 | 99 |
| 14-01 | 200 | 71 | 66 |
|  | 300 | 89 | 62 |
|  | 400 | 97 | 85 |
| 14-02 | 200 | 83 | 52 |
|  | 300 | 89 | 72 |
|  | 400 | 82 | 93 |
| 14-03 | 200 | 54 | 53 |
|  | 300 | 89 | 84 |
|  | 400 | 93 | 77 |
| 14-04 | 200 | 81 | 38 |
|  | 300 | 94 | 76 |
|  | 400 | 98 | 88 |
| 14-05 | 200 | 85 | 53 |
|  | 300 | 95 | 80 |
|  | 400 | 94 | 91 |
| 14-06 | 200 | 80 | 0 |
|  | 300 | 95 | 100 |
|  | 400 | 98 | 94 |
| 14-07 | 200 | 72 | 50 |
|  | 300 | 95 | 84 |
|  | 400 | 98 | 92 |
| 14-08 | 200 | 81 | 69 |
|  | 300 | 99 | 83 |
|  | 400 | 100 | 80 |
| 14-09 | 200 | 86 | 38 |
|  | 300 | 94 | 80 |
|  | 400 | 96 | 90 |
| 14-10 | 200 | 58 | 67 |
|  | 300 | 82 | 85 |
|  | 400 | 92 | 90 |
| 14-11 | 200 | 83 | 64 |
|  | 300 | 88 | 74 |
|  | 400 | 90 | 88 |
| 14-12 | 200 | 89 | 90 |
|  | 300 | 100 | 88 |
|  | 400 | 100 | 98 |
| 14-13 | 200 | 95 | 91 |
|  | 300 | 93 | 97 |
|  | 400 | 100 | 98 |
| 14-14 | 200 | 88 | 93 |
|  | 300 | 93 | 85 |
|  | 400 | 98 | 90 |
| 14-15 | 200 | 85 | 87 |
|  | 300 | 98 | 98 |
|  | 400 | 96 | 100 |
| 14-16 | 200 | 76 | 72 |
|  | 300 | 83 | 87 |
|  | 400 | 89 | 97 |
| 14-17 | 200 | 53 | 67 |
|  | 300 | 48 | 62 |
|  | 400 | 82 | 85 |

Compositions 14-12 to 14-15, containing 0.25% lecithin together with Fluorad FC-135, exhibited much greater herbicidal effectiveness on both ABUTH and ECHCF than composition 14-03, containing 0.25% lecithin but no Fluorad FC-135, or even composition 14-01, containing 0.5% lecithin but no Fluorad FC-135. No great or consistent difference was seen between compositions where glyphosate had been sonicated together with the lecithin (14-13 and 14-15) than where the lecithin had been sonicated alone (14-12 and 14-14).

Example 15

Compositions 14-01 to 14-17 of Example 14, and tank mixtures of Formulations B and C with Fluorad FC-135, were tested in this Example. Prickly sida (*Sida spinosa*, SIDSP) plants were grown and treated by the standard procedures given above. Applications of spray compositions were made 22 days after planting SIDSP, and evaluation of herbicidal inhibition was done 19 days after application.

Formulations B and C, alone and tank mixed with 0.5% and 0.25% Silwet L-77, were applied as comparative treatments. Results, averaged for all replicates of each treatment, are shown in Table 15.

TABLE 15

| Spray composition | Glyphosate rate g a.e./ha | % Inhibition SIDSP |
|---|---|---|
| Formulation B | 200 | 23 |
|  | 300 | 37 |
|  | 400 | 32 |
| Formulation B + Silwet L-77 0.5% v/v | 200 | 30 |
|  | 300 | 39 |
|  | 400 | 45 |
| Formulation B + Silwet L-77 0.25% w/v | 200 | 28 |
|  | 300 | 49 |
|  | 400 | 28 |
| Formulation C | 200 | 41 |
|  | 300 | 54 |
|  | 400 | 84 |
| Formulation C + Silwet L-77 0.5% v/v | 200 | 43 |
|  | 300 | 66 |
|  | 400 | 86 |
| Formulation C + Silwet L-77 0.25% v/v | 200 | 17 |
|  | 300 | 35 |
|  | 400 | 58 |
| Formulation B + Fluorad FC-135 0.25% w/v | 200 | 48 |
|  | 300 | 60 |
|  | 400 | 62 |
| Formulation B + Fluorad FC-135 0.1% w/v | 200 | 31 |
|  | 300 | 47 |
|  | 400 | 75 |
| Formulation C + Fluorad FC-135 0.25% w/v | 200 | 43 |
|  | 300 | 57 |
|  | 400 | 71 |
| Formulation C + Fluorad FC-135 0.1% w/v | 200 | 32 |
|  | 300 | 71 |
|  | 400 | 63 |
| 14-01 | 200 | 51 |
|  | 300 | 55 |
|  | 400 | 76 |
| 14-02 | 200 | 51 |
|  | 300 | 68 |
|  | 400 | 84 |
| 14-03 | 200 | 55 |
|  | 300 | 51 |
|  | 400 | 72 |
| 14-04 | 200 | 50 |
|  | 300 | 64 |
|  | 400 | 75 |
| 14-05 | 200 | 46 |
|  | 300 | 53 |
|  | 400 | 61 |

TABLE 15-continued

| Spray composition | Glyphosate rate g a.e./ha | % Inhibition SIDSP |
|---|---|---|
| 14-06 | 200 | 40 |
| | 300 | 44 |
| | 400 | 73 |
| 14-07 | 200 | 23 |
| | 300 | 32 |
| | 400 | 39 |
| 14-08 | 200 | 18 |
| | 300 | 44 |
| | 400 | 57 |
| 14-09 | 200 | 25 |
| | 300 | 30 |
| | 400 | 43 |
| 14-10 | 200 | 19 |
| | 300 | 36 |
| | 400 | 38 |
| 14-11 | 200 | 35 |
| | 300 | 48 |
| | 400 | 57 |
| 14-12 | 200 | 65 |
| | 300 | 80 |
| | 400 | 88 |
| 14-13 | 200 | 68 |
| | 300 | 75 |
| | 400 | 87 |
| 14-14 | 200 | 76 |
| | 300 | 76 |
| | 400 | 72 |
| 14-15 | 200 | 54 |
| | 300 | 73 |
| | 400 | 84 |
| 14-16 | 200 | 44 |
| | 300 | 51 |
| | 400 | 63 |
| 14-17 | 200 | 23 |
| | 300 | 45 |
| | 400 | 57 |

Compositions 14-12 to 14-15, containing 0.25% lecithin together with Fluorad FC-135, exhibited greater herbicidal effectiveness on SIDSP than composition 14-03, containing 0.25% lecithin but no Fluorad FC-135, or even composition 14-01, containing 0.5% lecithin but no Fluorad FC-135. No great or consistent difference was seen between compositions where glyphosate had been sonicated together with the lecithin (14-13 and 14-15) than where the lecithin had been sonicated alone (14-12 and 14-14).

Example 16

Aqueous spray compositions were prepared containing glyphosate IPA salt and excipient ingredients as shown in Table 16a. Process (iii) was followed for all compositions, using soybean lecithin (20% phospholipid, Avanti). The pH of all compositions was adjusted to approximately 7.

TABLE 16a

| | % w/w | | | Components | |
|---|---|---|---|---|---|
| Spray comp. | Lecithin g/l | Fluorad FC-135 | Other (*) | (*) Other ingredient | sonicated with lecithin |
| 16-01 | 2.5 | | | | none |
| 16-02 | 2.5 | | | | glyphosate |
| 16-03 | 2.5 | 0.25 | | | none |
| 16-04 | 2.5 | 0.25 | | | glyphosate |
| 16-05 | 2.5 | | 0.25 | Silwet 800 | none |
| 16-06 | 2.5 | | 0.25 | Silwet 800 | Silwet 800 |
| 16-07 | 2.5 | | 0.25 | Silwet 800 | Silwet, glyphosate |

TABLE 16a-continued

| | % w/w | | | Components | |
|---|---|---|---|---|---|
| Spray comp. | Lecithin g/l | Fluorad FC-135 | Other (*) | (*) Other ingredient | sonicated with lecithin |
| 16-08 | 0.5 | | | | none |
| 16-09 | 0.5 | | | | glyphosate |
| 16-10 | 0.5 | 0.05 | | | none |
| 16-11 | 0.5 | 0.05 | | | glyphosate |
| 16-12 | 0.5 | 0.03 | 0.02 | Silwet L-77 | Silwet L-77 |
| 16-13 | 0.5 | | 0.05 | methyl caprate | Me caprate |
| 16-14 | 0.5 | 0.05 | 0.05 | methyl caprate | Me caprate |
| 16-15 | 0.5 | 0.05 | 0.05 | methyl caprate | Me caprate, glyphosate |
| 16-16 | 0.5 | | 0.01 | PVA | none |
| 16-17 | 0.5 | | 0.01 | PVA | glyphosate |
| 16-18 | 0.5 | 0.05 | 0.01 | PVA | glyphosate |
| 16-19 | 0.5 | | 0.05 + 0.01 | L-77 + PVA | Silwet L-77 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 17 days after application.

In addition to compositions 16-01 to 16-19, spray compositions were prepared by tank mixing Formulations B and C with Fluorad FC-135 at two concentrations. Formulations B and C, alone and tank mixed with 0.5% Silwet 800, were applied as comparative treatments. Results, averaged for all replicates of each treatment, are shown in Table 16b.

TABLE 16b

| | Glyphosate rate | % Inhibition | |
|---|---|---|---|
| Spray composition | g a.e./ha | ABUTH | ECHCF |
| Formulation B | 150 | 13 | 28 |
| | 250 | 37 | 51 |
| | 350 | 56 | 38 |
| Formulation B + Silwet 800 0.25% v/v | 150 | 81 | 15 |
| | 250 | 89 | 17 |
| | 350 | 91 | 20 |
| Formulation C | 150 | 32 | 65 |
| | 250 | 59 | 91 |
| | 350 | 85 | 89 |
| Formulation C + Silwet 800 0.25% v/v | 150 | 91 | 17 |
| | 250 | 91 | 23 |
| | 350 | 95 | 48 |
| Formulation B + Fluorad FC-135 0.25% w/v | 150 | 31 | 58 |
| | 250 | 53 | 68 |
| | 350 | 71 | 84 |
| Formulation B + Fluorad FC-135 0.05% w/v | 150 | 31 | 29 |
| | 250 | 44 | 69 |
| | 350 | 95 | 79 |
| Formulation C + Fluorad FC-135 0.25% w/v | 150 | 46 | 45 |
| | 250 | 69 | 79 |
| | 350 | 86 | 77 |
| Formulation C + Fluorad FC-135 0.05% w/v | 150 | 44 | 57 |
| | 250 | 60 | 87 |
| | 350 | 86 | 88 |
| 16-01 | 150 | 55 | 50 |
| | 250 | 87 | 81 |
| | 350 | 89 | 88 |
| 16-02 | 150 | 56 | 54 |
| | 250 | 89 | 69 |
| | 350 | 87 | 98 |
| 16-03 | 150 | 89 | 68 |
| | 250 | 89 | 84 |
| | 350 | 91 | 90 |

TABLE 16b-continued

| Spray composition | Glyphosate rate g a.e./ha | % Inhibition ABUTH | ECHCF |
|---|---|---|---|
| 16-04 | 150 | 63 | 68 |
|  | 250 | 89 | 86 |
|  | 350 | 99 | 89 |
| 16-05 | 150 | 81 | 51 |
|  | 250 | 87 | 84 |
|  | 350 | 94 | 26 |
| 16-06 | 150 | 67 | 0 |
|  | 250 | 93 | 62 |
|  | 350 | 94 | 81 |
| 16-07 | 150 | 81 | 35 |
|  | 250 | 84 | 51 |
|  | 350 | 95 | 62 |
| 16-08 | 150 | 59 | 51 |
|  | 250 | 84 | 69 |
|  | 350 | 98 | 90 |
| 16-09 | 150 | 64 | 59 |
|  | 250 | 85 | 61 |
|  | 350 | 94 | 96 |
| 16-10 | 150 | 73 | 74 |
|  | 250 | 87 | 83 |
|  | 350 | 98 | 96 |
| 16-11 | 150 | 76 | 64 |
|  | 250 | 88 | 79 |
|  | 350 | 94 | 81 |
| 16-12 | 150 | 59 | 46 |
|  | 250 | 82 | 88 |
|  | 350 | 92 | 82 |
| 16-13 | 150 | 61 | 45 |
|  | 250 | 90 | 69 |
|  | 350 | 93 | 90 |
| 16-14 | 150 | 76 | 50 |
|  | 250 | 95 | 73 |
|  | 350 | 99 | 91 |
| 16-15 | 150 | 78 | 67 |
|  | 250 | 95 | 80 |
|  | 350 | 99 | 85 |
| 16-16 | 150 | 48 | 42 |
|  | 250 | 77 | 87 |
|  | 350 | 87 | 75 |
| 16-17 | 150 | 47 | 63 |
|  | 250 | 85 | 67 |
|  | 350 | 90 | 78 |
| 16-18 | 150 | 55 | 46 |
|  | 250 | 82 | 77 |
|  | 350 | 90 | 87 |
| 16-19 | 150 | 32 | 23 |
|  | 250 | 43 | 31 |
|  | 350 | 76 | 65 |

As in Example 10, glyphosate composition (16-10 and 16-11) containing just 0.05% lecithin and 0.05% Fluorad FC-135 exhibited surprisingly great herbicidal efficacy in this test. Sonicating the lecithin in the presence of glyphosate in an effort to encapsulate some of the glyphosate (composition 16-11) did not give an advantage in performance over sonicating the lecithin alone (composition 16-10); indeed on ECHCF herbicidal efficacy was slightly better without such efforts to encapsulate the glyphosate. Addition of methyl caprate to compositions containing lecithin with or without Fluorad FC-135 (16-13 to 16-15) improved herbicidal effectiveness on ABUTH but had little effect on ECHCF.

Example 17

Aqueous spray compositions were prepared containing glyphosate IPA salt and excipient ingredients as shown in Table 17a. Process (iii) was followed for all compositions, using soybean lecithin (20% phospholipid, Avanti). The pH of all compositions was adjusted to approximately 7.

TABLE 17a

| Spray composition | Lecithin g/l | Fluorad FC-135 % w/w | Other (*) % w/w | (*) Other ingredient | Components sonicated with lecithin |
|---|---|---|---|---|---|
| 17-01 | 2.5 |  |  |  | none |
| 17-02 | 2.5 | 0.25 |  |  | none |
| 17-03 | 2.5 | 0.25 |  |  | glyphosate |
| 17-04 | 2.5 | 0.25 | 0.025 | PVA | none |
| 17-05 | 1.0 |  |  |  | none |
| 17-06 | 1.0 |  |  |  | glyphosate |
| 17-07 | 1.0 | 0.10 |  |  | none |
| 17-08 | 1.0 | 0.10 |  |  | glyphosate |
| 17-09 | 1.0 | 0.05 |  |  | none |
| 17-10 | 1.0 | 0.05 |  |  | glyphosate |
| 17-11 | 1.0 |  | 0.100 | PVA | none |
| 17-12 | 1.0 |  | 0.025 | PVA | none |
| 17-13 | 1.0 | 0.05 | 0.025 | PVA | none |
| 17-14 | 1.0 |  | 0.100 | sodium cholate | Na cholate |
| 17-15 | 1.0 |  | 0.020 | sodium cholate | Na cholate |
| 17-16 | 1.0 | 0.05 | 0.020 | sodium cholate | Na cholate |
| 17-17 | 0.5 |  |  |  | none |
| 17-18 | 0.5 | 0.05 |  |  | glyphosate |
| 17-19 | 0.5 | 0.05 | 0.020 | sodium cholate | Na cholate |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 16 days after application.

In addition to compositions 17-01 to 17-19, spray compositions were prepared by tank mixing Formulations B and C with Fluorad FC-135 at various concentrations. Formulations B and C alone were applied as comparative treatments. Results, averaged for all replicates of each treatment, are shown in Table 17b.

TABLE 17b

| Spray composition | Glyphosate rate g a.e./ha | % Inhibition ABUTH | ECHCF |
|---|---|---|---|
| Formulation B | 200 | 32 | 25 |
|  | 300 | 50 | 34 |
|  | 400 | 54 | 35 |
| Formulation C | 200 | 59 | 92 |
|  | 300 | 76 | 100 |
|  | 400 | 93 | 97 |
| Formulation B + Fluorad FC-135 0.25% w/v | 200 | 43 | 48 |
|  | 300 | 64 | 52 |
|  | 400 | 84 | 71 |
| Formulation B + Fluorad FC-135 0.1% w/v | 200 | 61 | 78 |
|  | 300 | 65 | 59 |
|  | 400 | 100 | 86 |
| Formulation B + Fluorad FC-135 0.05% w/v | 200 | 58 | 30 |
|  | 300 | 82 | 55 |
|  | 400 | 88 | 77 |
| Formulation C + Fluorad FC-135 0.25% w/v | 200 | 53 | 55 |
|  | 300 | 76 | 68 |
|  | 400 | 88 | 93 |
| Formulation C + Fluorad FC-135 0.1% w/v | 200 | 59 | 70 |
|  | 300 | 89 | 85 |
|  | 400 | 93 | 83 |
| Formulation C + Fluorad FC-135 0.05% w/v | 200 | 60 | 72 |
|  | 300 | 82 | 100 |
|  | 400 | 94 | 94 |

TABLE 17b-continued

| Spray composition | Glyphosate rate g a.e./ha | % Inhibition ABUTH | ECHCF |
|---|---|---|---|
| 17-01 | 200 | 73 | 52 |
|  | 300 | 88 | 80 |
|  | 400 | 94 | 90 |
| 17-02 | 200 | 83 | 80 |
|  | 300 | 96 | 83 |
|  | 400 | 97 | 95 |
| 17-03 | 200 | 86 | 73 |
|  | 300 | 95 | 79 |
|  | 400 | 98 | 94 |
| 17-04 | 200 | 73 | 72 |
|  | 300 | 94 | 86 |
|  | 400 | 96 | 93 |
| 17-05 | 200 | 67 | 68 |
|  | 300 | 94 | 74 |
|  | 400 | 96 | 91 |
| 17-06 | 200 | 65 | 61 |
|  | 300 | 79 | 82 |
|  | 400 | 91 | 81 |
| 17-07 | 200 | 75 | 65 |
|  | 300 | 92 | 84 |
|  | 400 | 98 | 91 |
| 17-08 | 200 | 66 | 70 |
|  | 300 | 87 | 96 |
|  | 400 | 97 | 97 |
| 17-09 | 200 | 83 | 73 |
|  | 300 | 91 | 83 |
|  | 400 | 97 | 89 |
| 17-10 | 200 | 89 | 70 |
|  | 300 | 92 | 79 |
|  | 400 | 91 | 74 |
| 17-11 | 200 | 65 | 58 |
|  | 300 | 86 | 86 |
|  | 400 | 97 | 100 |
| 17-12 | 200 | 75 | 64 |
|  | 300 | 79 | 85 |
|  | 400 | 91 | 87 |
| 17-13 | 200 | 79 | 53 |
|  | 300 | 81 | 83 |
|  | 400 | 96 | 88 |
| 17-14 | 200 | 56 | 69 |
|  | 300 | 80 | 95 |
|  | 400 | 92 | 93 |
| 17-15 | 200 | 57 | 77 |
|  | 300 | 67 | 91 |
|  | 400 | 88 | 90 |
| 17-16 | 200 | 88 | 82 |
|  | 300 | 85 | 87 |
|  | 400 | 76 | 72 |
| 17-17 | 200 | 53 | 66 |
|  | 300 | 71 | 72 |
|  | 400 | 87 | 83 |
| 17-18 | 200 | 89 | 85 |
|  | 300 | 79 | 72 |
|  | 400 | 65 | 60 |
| 17-19 | 200 | 77 | 65 |
|  | 300 | 87 | 85 |
|  | 400 | 92 | 94 |

In glyphosate compositions containing lecithin and Fluorad FC-135, no consistent difference in herbicidal effectiveness was observed between those where lecithin was sonicated alone (17-02, 17-07, 17-09) and those where glyphosate and lecithin were sonicated together (17-03, 17-08, 17-10). The anomalous inversion of the apparent rate response to glyphosate seen with composition 17-18 is believed to be the result of an error in application or recording and the data for this composition should be ignored in this Example.

Example 18

Aqueous spray compositions were prepared containing glyphosate IPA salt and excipient ingredients as shown in Table 18a. Process (iii) was followed for all compositions, using soybean lecithin (20% phospholipid, Avanti). The pH of all compositions was adjusted to approximately 7.

TABLE 18a

| Spray composition | Lecithin g/l | % w/w Fluorad FC-135 | PVA | Components sonicated with lecithin |
|---|---|---|---|---|
| 18-01 | 2.5 |  |  | none |
| 18-02 | 1.0 |  |  | none |
| 18-03 | 0.5 |  |  | none |
| 18-04 | 0.2 |  |  | none |
| 18-05 | 1.0 | 0.25 |  | none |
| 18-06 | 1.0 | 0.25 |  | glyphosate |
| 18-07 | 1.0 | 0.10 |  | none |
| 18-08 | 1.0 | 0.10 |  | glyphosate |
| 18-09 | 0.5 | 0.05 |  | none |
| 18-10 | 0.5 | 0.05 |  | glyphosate |
| 18-11 | 2.5 |  | 0.10 | none |

Hemp sesbania (*Sesbania exaltata*, SEBEX) plants were grown and treated by the standard procedures given above. Applications of spray compositions were made 22 days after planting SEBEX, and evaluation of herbicidal inhibition was done 21 days after application.

In addition to compositions 18-01 to 18-11, spray compositions were prepared by tank mixing Formulations B and C with Fluorad FC-135 at various concentrations. Formulations B and C alone, and Formulation B tank mixed with 0.1% PVA (polyvinyl alcohol), were applied as comparative treatments. Results, averaged for all replicates of each treatment, are shown in Table 18b.

TABLE 18b

| Spray composition | Glyphosate rate g a.e./ha | % Inhibition SEBEX |
|---|---|---|
| Formulation B | 500 | 43 |
|  | 1000 | 54 |
|  | 1500 | 44 |
| Formulation B + PVA 0.1% w/v | 500 | 53 |
|  | 1000 | 45 |
|  | 1500 | 44 |
| Formulation C | 500 | 56 |
|  | 1000 | 62 |
|  | 1500 | 63 |
| Formulation B + Fluorad FC-135 0.25% w/v | 500 | 40 |
|  | 1000 | 45 |
|  | 1500 | 60 |
| Formulation B + Fluorad FC-135 0.1% w/v | 500 | 33 |
|  | 1000 | 51 |
|  | 1500 | 53 |
| Formulation B + Fluorad FC-135 0.05% w/v | 500 | 21 |
|  | 1000 | 18 |
|  | 1500 | 29 |
| Formulation C + Fluorad FC-135 0.25% w/v | 500 | 34 |
|  | 1000 | 41 |
|  | 1500 | 58 |
| Formulation C + Fluorad FC-135 0.1% w/v | 500 | 50 |
|  | 1000 | 43 |
|  | 1500 | 52 |
| Formulation C + Fluorad FC-135 0.05% w/v | 500 | 48 |
|  | 1000 | 49 |
|  | 1500 | 46 |
| 18-01 | 500 | 22 |
|  | 1000 | 33 |
|  | 1500 | 37 |
| 18-02 | 500 | 16 |
|  | 1000 | 24 |
|  | 1500 | 28 |

TABLE 18b-continued

| Spray composition | Glyphosate rate g a.e./ha | % Inhibition SEBEX |
|---|---|---|
| 18-03 | 500 | 15 |
|  | 1000 | 24 |
|  | 1500 | 27 |
| 18-04 | 500 | 17 |
|  | 1000 | 13 |
|  | 1500 | 31 |
| 18-05 | 500 | 28 |
|  | 1000 | 64 |
|  | 1500 | 68 |
| 18-06 | 500 | 64 |
|  | 1000 | 51 |
|  | 1500 | 61 |
| 18-07 | 500 | 65 |
|  | 1000 | 51 |
|  | 1500 | 63 |
| 18-08 | 500 | 50 |
|  | 1000 | 56 |
|  | 1500 | 30 |
| 18-09 | 500 | 40 |
|  | 1000 | 59 |
|  | 1500 | 66 |
| 18-10 | 500 | 31 |
|  | 1000 | 23 |
|  | 1500 | 49 |
| 18-11 | 500 | 43 |
|  | 1000 | 39 |
|  | 1500 | 74 |

Glyphosate activity on SEBEX was extremely weak in this test and no firm conclusions can be drawn.

Example 19

Aqueous spray compositions were prepared containing glyphosate IPA salt and excipient ingredients as shown in Table 19a. Process (iii) was followed for all compositions, using soybean lecithin (20% phospholipid, Avanti). The pH of all compositions was adjusted to approximately 7.

TABLE 19a

| Spray composition | Lecithin g/l | % w/w Fluorad FC-135 | Components sonicated with lecithin |
|---|---|---|---|
| 19-01 | 2.5 |  | none |
| 19-02 | 1.0 |  | none |
| 19-03 | 0.5 |  | none |
| 19-04 | 0.2 |  | none |
| 19-05 | 1.0 | 0.25 | none |
| 19-06 | 1.0 | 0.25 | glyphosate |

Sicklepod (*Cassia obtusifolia*, CASOB) plants were grown and treated by the standard procedures given above. Applications of spray compositions were made 22 days after planting CASOB, and evaluation of herbicidal inhibition was done 21 days after application.

In addition to composition 19-01 to 19-06, spray compositions were prepared by tank mixing Formulations B and C with Fluorad FC-135 at two concentrations. Formulations B and C alone were applied as comparative treatments. Results, averaged for all replicates of each treatment, are shown in Table 19b.

TABLE 19b

| Spray composition | Glyphosate rate g a.e./ha | % Inhibition CASOB |
|---|---|---|
| Formulation B | 500 | 35 |
| | 800 | 37 |
| | 1200 | 34 |
| Formulation C | 500 | 49 |
| | 800 | 49 |
| | 1200 | 66 |
| Formulation B + Fluorad FC-135 0.25% w/v | 500 | 45 |
| | 800 | 50 |
| | 1200 | 71 |
| Formulation B + Fluorad FC-135 0.1% w/v | 500 | 49 |
| | 800 | 49 |
| | 1200 | 78 |
| Formulation C + Fluorad FC-135 0.25% w/v | 500 | 60 |
| | 800 | 75 |
| | 1200 | 68 |
| Formulation C + Fluorad FC-135 0.1% w/v | 500 | 47 |
| | 800 | 85 |
| | 1200 | 74 |
| 19-01 | 500 | 54 |
| | 800 | 51 |
| | 1200 | 43 |
| 19-02 | 500 | 37 |
| | 800 | 69 |
| | 1200 | 52 |
| 19-03 | 500 | 35 |
| | 800 | 51 |
| | 1200 | 43 |
| 19-04 | 500 | 71 |
| | 800 | 69 |
| | 1200 | 57 |
| 19-05 | 500 | 47 |
| | 800 | 73 |
| | 1200 | 89 |
| 19-06 | 500 | 49 |
| | 800 | 51 |
| | 1200 | 73 |

On CASOB, the addition of Fluorad FC-135 to a glyphosate composition containing lecithin significantly enhanced herbicidal effectiveness (compare compositions 19-05 and 19-02). However, where glyphosate was sonicated together with the lecithin (composition 19-06), herbicidal effectiveness was reduced.

Example 20

Aqueous spray compositions were prepared containing glyphosate IPA salt and excipient ingredients as shown in Table 20a. Process (iii) was followed for all compositions, using soybean lecithin (20% phospholipid, Avanti). The pH of all compositions was adjusted to approximately 7.

TABLE 20a

| Spray composition | Lecithin g/l | % w/w Fluorad FC-135 | % w/w Diacid 1550 | Components sonicated with lecithin |
|---|---|---|---|---|
| 20-01 | 2.5 | | | none |
| 20-02 | 0.5 | | | none |
| 20-03 | 0.2 | | | none |
| 20-04 | 2.5 | 0.05 | | none |
| 20-05 | 0.5 | 0.05 | | none |
| 20-06 | 0.2 | 0.05 | | none |
| 20-07 | 0.5 | | 0.05 | Diacid |

Common lambsquarter (*Chenopodium album*, CHEAL) plants were grown and treated by the standard procedures given above. Applications of spray compositions were made 31 days after planting CHEAL, and evaluation of herbicidal inhibition was done 18 days after application.

In addition to compositions 20-01 to 20-07, spray compositions were prepared by tank mixing Formulations B and C with 0.5% Fluorad FC-135. Formulations B and C alone were applied as comparative treatments. Results averaged for all replicates of each treatment, are shown in Table 20b.

TABLE 20b

| Spray composition | Glyphosate rate g a.e./ha | % Inhibition CHEAL |
|---|---|---|
| Formulation B | 150 | 0 |
|  | 250 | 0 |
|  | 350 | 3 |
| Formulation C | 150 | 18 |
|  | 250 | 68 |
|  | 350 | 98 |
| Formulation B + Fluorad FC-135 0.05% w/v | 150 | 0 |
|  | 250 | 10 |
|  | 350 | 5 |
| Formulation C + Fluorad FC-135 0.05% w/v | 150 | 3 |
|  | 250 | 50 |
|  | 350 | 60 |
| 20-01 | 150 | 0 |
|  | 250 | 27 |
|  | 350 | 60 |
| 20-02 | 150 | 0 |
|  | 250 | 5 |
|  | 350 | 8 |
| 20-03 | 150 | 5 |
|  | 250 | 0 |
|  | 350 | 8 |
| 20-04 | 150 | 18 |
|  | 250 | 29 |
|  | 350 | 63 |
| 20-05 | 150 | 17 |
|  | 250 | 14 |
|  | 350 | 87 |
| 20-06 | 150 | 44 |
|  | 250 | 40 |
|  | 350 | 38 |
| 20-07 | 150 | 10 |
|  | 250 | 35 |
|  | 350 | 73 |

Glyphosate activity on CHEAL was very weak in this test and no definitive conclusions can be drawn. However, none of the compositions of the invention performed as well as the commercial standard Formulation C in this test. Fluorad FC-135 at the extremely low concentration of 0.05% was ineffective as a tank-mix additive, but addition of 0.05% Fluorad FC-135 did enhance the performance of compositions containing lecithin (compare compositions 20-04 to 20-06 with 20-01 to 20-03).

Example 21

Aqueous spray compositions were prepared containing glyphosate IPA salt and excipient ingredients as shown in Table 21a. Process (iii) was followed for all compositions, using soybean lecithin (20% phospholipid, Avanti). The pH of all compositions was adjusted to approximately 7.

TABLE 21a

| Spray composition | Lecithin g/l | Fluorad FC-135 | Aerosol OT | Methyl caprate | Components sonicated with lecithin |
|---|---|---|---|---|---|
| 21-01 | 2.5 |  |  |  | none |
| 21-02 | 2.5 |  |  |  | glyphosate |
| 21-03 | 1.0 |  |  |  | none |
| 21-04 | 1.0 |  |  |  | glyphosate |
| 21-05 | 0.5 |  |  |  | none |
| 21-06 | 0.5 |  |  |  | glyphosate |
| 21-07 | 0.2 |  |  |  | none |
| 21-08 | 0.2 |  |  |  | glyphosate |
| 21-09 | 0.5 |  | 0.05 |  | none |
| 21-10 | 0.5 |  | 0.05 |  | AOT, glyphosate |
| 21-11 | 0.5 |  | 0.05 |  | AOT |
| 21-12 | 2.5 | 0.25 |  |  | none |
| 21-13 | 0.5 | 0.05 |  |  | none |
| 21-14 | 0.5 | 0.05 |  |  | glyphosate |
| 21-15 | 0.5 |  |  | 0.05 | Me caprate |
| 21-16 | 0.5 | 0.05 |  | 0.05 | Me caprate |
| 21-17 | 0.2 | 0.02 |  |  | none |
| 21-18 | 0.2 | 0.02 |  |  | glyphosate |
| 21-19 | 0.2 |  |  | 0.02 | Me caprate |

Velvetleaf (*Abutilon theophrasti*, ABUTH), Japanese millet (*Echinochloa crus-galli*, ECHCF), and prickly sida (*Sida spinosa*, SIDSP) plants were grown and treated by the standard procedures given above. Applications of spray compositions were made 19 days after planting ABUTH and 22 days after planting ECHCF. No record was found for the planting date for SIDSP. Evaluation of herbicidal inhibition was done 20 days after application.

In addition to compositions 21-01 to 21-19. spray compositions were prepared by tank mixing Formulations B and C with Fluorad FC-135 at various concentrations. Formulations B and C alone were applied as comparative treatments. Results, averaged for all replicates of each treatment, are shown in Table 21b.

TABLE 21b

| Spray composition | Glyphosate rate g a.e./ha | % Inhibition ABUTH | ECHCF | SIDSP |
|---|---|---|---|---|
| Formulation B | 150 | 16 | 23 | 30 |
|  | 250 | 17 | 33 | 57 |
|  | 350 | 24 | 43 | 65 |
| Formulation C | 150 | 18 | 58 | 53 |
|  | 250 | 30 | 71 | 79 |
|  | 350 | 49 | 83 | 94 |
| Formulation B + Fluorad FC-135 0.25% w/v | 150 | 27 | 59 | 56 |
|  | 250 | 45 | 84 | 81 |
|  | 350 | 55 | 82 | 91 |
| Formulation B + Fluorad FC-135 0.1% w/v | 150 | 17 | 43 | 56 |
|  | 250 | 21 | 56 | 75 |
|  | 350 | 64 | 80 | 90 |
| Formulation B + Fluorad FC-135 0.02% w/v | 150 | 22 | 27 | 38 |
|  | 250 | 37 | 49 | 69 |
|  | 350 | 48 | 68 | 94 |
| Formulation C + Fluorad FC-135 0.25% w/v | 150 | 41 | 41 | 59 |
|  | 250 | 57 | 53 | 85 |
|  | 350 | 67 | 67 | 94 |
| Formulation C + Fluorad FC-135 0.05% w/v | 150 | 26 | 39 | 67 |
|  | 250 | 46 | 66 | 88 |
|  | 350 | 75 | 73 | 93 |
| Formulation C + Fluorad FC-135 0.02% w/v | 150 | 30 | 52 | 66 |
|  | 250 | 67 | 50 | 89 |
|  | 350 | 61 | 88 | 92 |
| 21-01 | 150 | 35 | 62 | 64 |
|  | 250 | 63 | 77 | 90 |
|  | 350 | 71 | 83 | 85 |
| 21-02 | 150 | 35 | 44 | 67 |
|  | 250 | 53 | 79 | 86 |
|  | 350 | 58 | 92 | 90 |

TABLE 21b-continued

| Spray composition | Glyphosate rate g a.e./ha | % Inhibition ABUTH | ECHCF | SIDSP |
|---|---|---|---|---|
| 21-03 | 150 | 37 | 50 | 71 |
| | 250 | 53 | 76 | 90 |
| | 350 | 73 | 63 | 97 |
| 21-04 | 150 | 29 | 46 | 61 |
| | 250 | 43 | 77 | 85 |
| | 350 | 70 | 85 | 96 |
| 21-05 | 150 | 12 | 36 | 59 |
| | 250 | 43 | 55 | 83 |
| | 350 | 53 | 77 | 87 |
| 21-06 | 150 | 19 | 69 | 67 |
| | 250 | 62 | 47 | 84 |
| | 350 | 58 | 60 | 95 |
| 21-07 | 150 | 14 | 59 | 59 |
| | 250 | 39 | 63 | 75 |
| | 350 | 46 | 77 | 91 |
| 21-08 | 150 | 36 | 37 | 64 |
| | 250 | 38 | 68 | 82 |
| | 350 | 47 | 80 | 79 |
| 21-09 | 150 | 8 | 35 | 27 |
| | 250 | 9 | 51 | 56 |
| | 350 | 36 | 58 | 67 |
| 21-10 | 150 | 5 | 33 | 24 |
| | 250 | 15 | 73 | 47 |
| | 350 | 30 | 66 | 67 |
| 21-11 | 150 | 38 | 49 | 73 |
| | 250 | 62 | 75 | 89 |
| | 350 | 71 | 75 | 98 |
| 21-12 | 150 | 7 | 41 | 21 |
| | 250 | 18 | 67 | 38 |
| | 350 | 30 | 64 | 61 |
| 21-13 | 150 | 39 | 72 | 65 |
| | 250 | 65 | 55 | 76 |
| | 350 | 70 | 68 | 90 |
| 21-14 | 150 | 51 | 53 | 66 |
| | 250 | 60 | 82 | 85 |
| | 350 | 65 | 83 | 95 |
| 21-15 | 150 | 15 | 59 | 61 |
| | 250 | 31 | 54 | 83 |
| | 350 | 57 | 67 | 84 |
| 21-16 | 150 | 36 | 79 | 66 |
| | 250 | 50 | 60 | 95 |
| | 350 | 71 | 95 | 95 |
| 21-17 | 150 | 30 | 52 | 75 |
| | 250 | 54 | 60 | 84 |
| | 350 | 48 | 84 | 93 |
| 21-18 | 150 | 43 | 75 | 69 |
| | 250 | 47 | 78 | 88 |
| | 350 | missing | missing | 90 |
| 21-19 | 150 | 13 | 42 | 61 |
| | 250 | 29 | 51 | 79 |
| | 350 | 42 | 69 | 90 |

In this test the concentration of Fluorad FC-135 which had to be added in tank-mix to Formulation B to bring its herbicidal performance up to that of Formulation C was approximately 0.25% for ECHCF, 0.1% for SIDSP and 0.02% for ABUTH. The herbicidal effectiveness of composition 21-12 (0.25% lecithin, 0.25% Fluorad FC-135) was uncharacteristically weak in this test. However, composition 21-13 (0.05% lecithin, 0.05% Fluorad FC-135) performed well as in previous tests, exceeding the herbicidal effectiveness of Formulation C on ABUTH, at least equalling it on SIDSP and not quite equalling it on ECHCF. Contrary to results obtained in other tests, improved effectiveness on ECHCF and SIDSP was obtained by sonicating the glyphosate with the lecithin (composition 21-14 versus 21-13). The inclusion of methyl caprate (compositions 21-15 and 21-16) also improved efficacy on these species. Surprisingly high herbicidal effectiveness was seen in this test with compositions containing ultra-low concentrations of lecithin and Fluorad FC-135 (0.02% of each, 21-17 and 21-18).

Example 22

Aqueous concentrate compositions were prepared containing glyphosate IPA salt and excipient ingredients as shown in Table 22a. Process (iv) was followed for all compositions, using soybean lecithin (20% phospholipid, Avanti). The pH of these compositions was not recorded.

TABLE 22a

| Concentrate composition | Glyphosate a.e. | Lecithin | MON 0818 | Fluorad FC-135 |
|---|---|---|---|---|
| 22-01 | 10 | | | 5.0 |
| 22-02 | 10 | | | 10.0 |
| 22-03 | 10 | | | 12.5 |
| 22-04 | 10 | | | 15.0 |
| 22-05 | 10 | | | 20.0 |
| 22-06 | 10 | | | 30.0 |
| 22-07 | 15 | 4.0 | 1.0 | |
| 22-08 | 20 | 5.0 | 0.5 | |
| 22-09 | 20 | 5.0 | 1.0 | |
| 22-10 | 20 | 5.0 | 2.0 | |
| 22-11 | 20 | 4.0 | 1.0 | |
| 22-12 | 25 | 5.0 | 0.5 | |
| 22-13 | 25 | 5.0 | 1.0 | |
| 22-14 | 25 | 5.0 | 2.0 | |
| 22-15 | 25 | 4.0 | 1.0 | |
| 22-16 | 25 | 5.0 | 5.0 | |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 16 days after planting ECHCF, and evaluation of herbicidal inhibition was done 14 days after application.

Formulation C was applied as a comparative treatment. Results, averaged for all replicates of each treatment, are shown in Table 22b.

TABLE 22b

| Concentrate composition | Glyphosate rate g a.e./ha | % Inhibition ABUTH | ECHCF |
|---|---|---|---|
| Formulation C | 56 | 13 | 45 |
| | 112 | 43 | 75 |
| | 224 | 64 | 94 |
| | 448 | 88 | 97 |
| 22-01 | 112 | 38 | 61 |
| | 224 | 56 | 80 |
| | 448 | 76 | 97 |
| 22-02 | 112 | 50 | 51 |
| | 224 | 69 | 91 |
| | 448 | 81 | 97 |
| 22-03 | 112 | 51 | 63 |
| | 224 | 64 | 83 |
| | 448 | 81 | 96 |
| 22-04 | 112 | 53 | 61 |
| | 224 | 71 | 91 |
| | 448 | 78 | 95 |
| 22-05 | 112 | 41 | 56 |
| | 224 | 70 | 85 |
| | 448 | 75 | 97 |
| 22-06 | 112 | 38 | 53 |
| | 224 | 63 | 89 |
| | 448 | 75 | 94 |
| 22-07 | 112 | 48 | 53 |
| | 224 | 49 | 84 |
| | 448 | 75 | 90 |

TABLE 22b-continued

| Concentrate composition | Glyphosate rate g a.e./ha | % Inhibition ABUTH | % Inhibition ECHCF |
|---|---|---|---|
| 22-08 | 112 | 31 | 60 |
|  | 224 | 53 | 84 |
|  | 448 | 66 | 90 |
| 22-09 | 112 | 26 | 56 |
|  | 224 | 53 | 85 |
|  | 448 | 78 | 96 |
| 22-10 | 112 | 36 | 60 |
|  | 224 | 53 | 85 |
|  | 448 | 79 | 98 |
| 22-11 | 112 | 41 | 59 |
|  | 224 | 49 | 73 |
|  | 448 | 76 | 95 |
| 22-12 | 112 | 30 | 56 |
|  | 224 | 50 | 74 |
|  | 448 | 65 | 89 |
| 22-13 | 112 | 34 | 55 |
|  | 224 | 44 | 80 |
|  | 448 | 73 | 95 |
| 22-14 | 112 | 39 | 61 |
|  | 224 | 56 | 85 |
|  | 448 | 69 | 91 |
| 22-15 | 112 | 31 | 55 |
|  | 224 | 56 | 69 |
|  | 448 | 79 | 95 |
| 22-16 | 112 | 29 | 64 |
|  | 224 | 58 | 86 |
|  | 448 | 78 | 91 |

None of the concentrate compositions of this Example containing 10% glyphosate a.e. and varying amounts of Fluorad FC-135 (22-01 to 22-06) exhibited greater herbicidal effectiveness than the commercial standard Formulation C. It should be noted that the amounts of Fluorad FC-135 used in this Example were extremely high, the weight/weight ratio of Fluorad FC-135 to glyphosate a.e. ranging from 1:2 to 3:1.

Example 23

Aqueous concentrate compositions were prepared containing glyphosate IPA salt and excipient ingredients as shown in Table 23a. Process (iv) was followed for all compositions, using soybean lecithin (20% phospholipid, Avanti). The pH of all compositions was approximately 5.

TABLE 23a

| Concentrate composition | Glyphoaste a.e. | Lecithin | MON 0818 | Fluorad FC-135 | Components sonicated with lecithin |
|---|---|---|---|---|---|
| 23-01 | 20 | 5.0 | 2.0 |  | none |
| 23-02 | 20 | 4.0 | 1.0 |  | none |
| 23-03 | 20 | 5.0 | 2.0 |  | glyphosate |
| 23-04 | 20 | 4.0 | 1.0 |  | glyphosate |
| 23-05 | 20 | 5.0 | 2.0 | 5.0 | none |

Velvetleaf (*Abutilon theophrasti*, ABUTH) and Japanese millet (*Echinochloa crus-galli*, ECHCF) plants were grows and treated by the standard procedures given above. Applications of spray compositions were made 16 days after planting ABUTH and 18 days after planting ECHCF, and evaluation of herbicidal inhibition was done 14 days after application.

Formulations B and C were applied as comparative treatments. Results, averaged for all replicates of each treatment, are shown in Table 23b.

TABLE 23b

| Concentrate composition | Glyphosate rate g a.e./ha | % Inhibition ABUTH | % Inhibition ECHCF |
|---|---|---|---|
| Formulation B | 112 | 33 | 53 |
|  | 224 | 58 | 78 |
|  | 336 | 80 | 89 |
|  | 448 | 79 | 88 |
| Formulation C | 112 | 49 | 79 |
|  | 224 | 59 | 94 |
|  | 336 | 84 | 100 |
|  | 448 | 95 | 100 |
| 23-01 | 112 | 39 | 66 |
|  | 224 | 63 | 93 |
|  | 336 | 81 | 98 |
|  | 448 | 86 | 100 |
| 23-02 | 112 | 29 | 46 |
|  | 224 | 55 | 83 |
|  | 336 | 79 | 91 |
|  | 448 | 85 | 95 |
| 23-03 | 112 | 30 | 59 |
|  | 224 | 60 | 98 |
|  | 336 | 80 | 100 |
|  | 448 | 81 | 100 |
| 23-04 | 112 | 26 | 51 |
|  | 224 | 53 | 83 |
|  | 336 | 76 | 86 |
|  | 448 | 86 | 99 |
| 23-05 | 112 | 46 | 51 |
|  | 224 | 59 | 89 |
|  | 336 | 79 | 96 |
|  | 448 | 89 | 98 |

Concentrate composition 23-05 (5% lecithin. 2% MON 0818, 5% Fluorad FC-135) did not exhibit greater herbicidal effectiveness in this test than composition 23-01 lacking the Fluorad FC-135.

Example 24

Aqueous spray compositions were prepared containing glyphosate IPA salt and excipient ingredients as shown in Table 24a. Process (iii) was followed for all compositions, using soybean lecithin (20% phospholipid, Avanti). The pH of these compositions was not recorded.

TABLE 24a

| Spray composition | Lecithin g/l | % w/w Fluorad FC-135 | Components sonicated with lecithin |
|---|---|---|---|
| 24-01 | 2.5 |  | none |
| 24-02 | 1.0 |  | none |
| 24-03 | 0.5 |  | none |

TABLE 24a-continued

| Spray composition | Lecithin g/l | % w/w Fluorad FC-135 | Components sonicated with lecithin |
|---|---|---|---|
| 24-04 | 0.2 | | none |
| 24-05 | 0.1 | | none |
| 24-06 | 2.5 | 0.25 | none |
| 24-07 | 0.5 | 0.05 | none |
| 24-08 | 0.2 | 0.02 | none |
| 24-09 | 0.2 | 0.02 | glyphosate |
| 24-10 | 0.2 | 0.02 | FC-135 |
| 24-11 | 0.1 | 0.01 | none |
| 24-12 | 0.1 | 0.01 | glyphosate |
| 24-13 | 0.1 | 0.02 | FC-135 |
| 24-14 | 0.5 | 0.02 | none |
| 24-15 | 0.5 | 0.02 | glyphosate |
| 24-16 | 0.5 | 0.02 | FC-135 |

Yellow nutsedge (*Cyperus esculentus*, CYPES) plants were grown and treated by the standard procedures given above. Applications of spray compositions were made 29 days after planting, and evaluation of herbicidal inhibition was done 33 days after application.

In addition to compositions 24-01 to 24-16, spray compositions were prepared by tank mixing Formulations B and C with Fluorad FC-135 at various concentrations. Formulations B and C alone were applied as comparative treatments. Results, averaged for all replicates of each treatment, are shown in Table 24b.

TABLE 24b

| Spray composition | Glyphosate rate g a.e./ha | % Inhibition CYPES |
|---|---|---|
| Formulation B | 400 | 32 |
| | 750 | 68 |
| | 1000 | 70 |
| Formulation C | 400 | 25 |
| | 750 | 66 |
| | 1000 | 89 |
| Formulation B + Fluorad FC-135 0.25% w/v | 400 | 49 |
| | 750 | 75 |
| | 1000 | 82 |
| Formulation B + Fluorad FC-135 0.05% w/v | 400 | 53 |
| | 750 | 74 |
| | 1000 | 64 |
| Formulation B + Fluorad FC-135 0.02% w/v | 400 | 56 |
| | 750 | 83 |
| | 1000 | 83 |
| Formulation B + Fluorad FC-135 0.01% w/v | 400 | 61 |
| | 750 | 67 |
| | 1000 | 88 |
| Formulation C + Fluorad FC-135 0.25% w/v | 400 | 73 |
| | 750 | 47 |
| | 1000 | 79 |
| Formulation C + Fluorad FC-135 0.05% w/v | 400 | 50 |
| | 750 | 73 |
| | 1000 | 81 |
| Formulation C + Fluorad FC-135 0.02% w/v | 400 | 41 |
| | 750 | 79 |
| | 1000 | 81 |
| Formulation C + Fluorad FC-135 0.01% w/v | 400 | 67 |
| | 750 | 77 |
| | 1000 | 72 |
| 24-01 | 400 | 62 |
| | 750 | 73 |
| | 1000 | 100 |
| 24-02 | 400 | 61 |
| | 750 | 85 |
| | 1000 | 92 |
| 24-03 | 400 | 81 |
| | 750 | 83 |
| | 1000 | 87 |
| 24-04 | 400 | 59 |
| | 750 | 79 |
| | 1000 | 79 |
| 24-05 | 400 | 69 |
| | 750 | 69 |
| | 1000 | 91 |
| 24-06 | 400 | 75 |
| | 750 | 80 |
| | 1000 | 96 |
| 24-07 | 400 | 65 |
| | 750 | 69 |
| | 1000 | 89 |
| 24-08 | 400 | 67 |
| | 750 | 69 |
| | 1000 | 87 |
| 24-09 | 400 | 76 |
| | 750 | 77 |
| | 1000 | 80 |
| 24-10 | 400 | 71 |
| | 750 | 75 |
| | 1000 | 86 |
| 24-11 | 400 | 69 |
| | 750 | 77 |
| | 1000 | 85 |
| 24-12 | 400 | 59 |
| | 750 | 85 |
| | 1000 | 95 |
| 24-13 | 400 | 61 |
| | 750 | 75 |
| | 1000 | 81 |
| 24-14 | 400 | 64 |
| | 750 | 83 |
| | 1000 | 90 |
| 24-15 | 400 | 53 |
| | 750 | 81 |
| | 1000 | 86 |
| 24-16 | 400 | 85 |
| | 750 | 86 |
| | 1000 | 81 |

The tank-mix treatments of this Example show surprisingly little effect on herbicidal effectiveness on CYPES of reducing Fluorad FC-135 concentration from 0.25% all the way down to 0.01%. At this extraordinarily low concentration, the tank mix of Formulation B with Fluorad FC-135 still performed equal or better than Formulation C alone. Lecithin alone was an unexpectedly effective excipient for glyphosate in this test (see compositions 24-01 to 24-05) and the addition of Fluorad FC-135 to lecithin did not in every case give further enhancement of herbicidal efficacy.

Example 25

Glyphosate-containing spray compositions were prepared by tank-mixing Formulation B with excipients as shown in Table 25. Soybean lecithin (20% phospholipid, Avanti) was used in the form of a 10% dispersion prepared by sonication as in process (iii).

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and 21 days after planting ECHCF, and evaluation of herbicidal inhibition was done 21 days after application. Results, averaged for all replicates of each treatment, are shown in Table 25.

TABLE 25

| Glyphosate composition | Glyphosate rate g a.e./ha | Additive | Add rate % w/v | % Inhibition ABUTH | ECHCF |
|---|---|---|---|---|---|
| Formulation B | 56 | | | 3 | 17 |
| | 112 | | | 7 | 38 |
| | 224 | | | 30 | 58 |
| | 336 | | | 60 | 67 |
| None | 0 | MON 0818 | 5.0 | 7 | 30 |
| | | Fluorad FC-135 | 5.0 | 5 | 3 |
| | | lecithin | 5.0 | 0 | 0 |
| Formulation B | 56 | MON 0818 | 0.005 | 0 | 48 |
| | 112 | | | 3 | 60 |
| | 224 | | | 53 | 85 |
| | 336 | | | 58 | 87 |
| Formulation B | 56 | MON 0818 | 0.01 | 3 | 50 |
| | 112 | | | 10 | 67 |
| | 224 | | | 52 | 87 |
| | 336 | | | 67 | 92 |
| Formulation B | 56 | MON 0818 | 0.05 | 7 | 52 |
| | 112 | | | 10 | 67 |
| | 224 | | | 60 | 93 |
| | 336 | | | 68 | 96 |
| Formulation B | 56 | MON 0818 | 0.1 | 10 | 55 |
| | 112 | | | 12 | 70 |
| | 224 | | | 57 | 97 |
| | 336 | | | 80 | 97 |
| Formulation B | 56 | MON 0818 | 0.2 | 10 | 65 |
| | 112 | | | 22 | 70 |
| | 224 | | | 58 | 97 |
| | 336 | | | 85 | 97 |
| Formulation B | 56 | MON 0818 | 0.5 | 13 | 65 |
| | 112 | | | 33 | 77 |
| | 224 | | | 72 | 99 |
| | 336 | | | 88 | 100 |
| Formulation B | 56 | MON 0818 | 1.0 | 15 | 68 |
| | 112 | | | 55 | 80 |
| | 224 | | | 78 | 98 |
| | 336 | | | 95 | 100 |
| Formulation B | 56 | MON 0818 | 2.0 | 27 | 75 |
| | 112 | | | 62 | 78 |
| | 224 | | | 83 | 100 |
| | 336 | | | 100 | 99 |
| Formulation B | 56 | MON 0818 | 5.0 | 23 | 55 |
| | 112 | | | 53 | 77 |
| | 224 | | | 72 | 90 |
| | 336 | | | 97 | 88 |
| Formulation B | 56 | Fluorad FC-135 | 0.005 | 2 | 47 |
| | 112 | | | 10 | 50 |
| | 224 | | | 25 | 70 |
| | 336 | | | 55 | 78 |
| Formulation B | 56 | Fluorad FC-135 | 0.01 | 7 | 40 |
| | 112 | | | 15 | 57 |
| | 224 | | | 70 | 67 |
| | 336 | | | 80 | 80 |
| Formulation B | 56 | Fluorad FC-135 | 0.05 | 2 | 48 |
| | 112 | | | 15 | 57 |
| | 224 | | | 70 | 78 |
| | 336 | | | 78 | 88 |
| Formulation B | 56 | Fluorad FC-135 | 0.1 | 5 | 45 |
| | 112 | | | 18 | 58 |
| | 224 | | | 75 | 87 |
| | 336 | | | 80 | 90 |
| Formulation B | 56 | Fluorad FC-135 | 0.2 | 12 | 48 |
| | 112 | | | 27 | 60 |
| | 224 | | | 75 | 90 |
| | 336 | | | 97 | 93 |
| Formulation B | 56 | Fluorad FC-135 | 0.5 | 3 | 47 |
| | 112 | | | 12 | 57 |
| | 224 | | | 75 | 80 |
| | 336 | | | 78 | 83 |
| Formulation B | 56 | Fluorad FC-135 | 1.0 | 5 | 43 |
| | 112 | | | 10 | 52 |
| | 224 | | | 77 | 75 |
| | 336 | | | 78 | 77 |
| Formulation B | 56 | Fluorad FC-135 | 2.0 | 7 | 42 |
| | 112 | | | 10 | 47 |
| | 224 | | | 65 | 65 |
| | 336 | | | 72 | 77 |

TABLE 25-continued

| Glyphosate composition | Glyphosate rate g a.e./ha | Additive | Add rate % w/v | % Inhibition ABUTH | ECHCF |
|---|---|---|---|---|---|
| Formulation B | 56 | Fluorad FC-135 | 5.0 | 2 | 38 |
| | 112 | | | 5 | 47 |
| | 224 | | | 63 | 60 |
| | 336 | | | 67 | 63 |
| Formulation B | 56 | lecithin | 0.005 | 0 | 10 |
| | 112 | | | 10 | 45 |
| | 224 | | | 67 | 70 |
| | 336 | | | 67 | 77 |
| Formulation B | 56 | lecithin | 0.01 | 2 | 20 |
| | 112 | | | 12 | 47 |
| | 224 | | | 63 | 70 |
| | 336 | | | 68 | 85 |
| Formulation B | 56 | lecithin | 0.05 | 3 | 32 |
| | 112 | | | 12 | 52 |
| | 224 | | | 63 | 73 |
| | 336 | | | 72 | 82 |
| Formulation B | 56 | lecithin | 0.1 | 8 | 37 |
| | 112 | | | 10 | 50 |
| | 224 | | | 65 | 73 |
| | 336 | | | 78 | 83 |
| Formulation B | 56 | lecithin | 0.2 | 5 | 45 |
| | 112 | | | 43 | 63 |
| | 224 | | | 68 | 82 |
| | 336 | | | 80 | 92 |
| Formulation B | 56 | lecithin | 0.5 | 13 | 50 |
| | 112 | | | 42 | 65 |
| | 224 | | | 67 | 88 |
| | 336 | | | 68 | 87 |
| Formulation B | 56 | lecithin | 1.0 | 13 | 52 |
| | 112 | | | 50 | 72 |
| | 224 | | | 67 | 80 |
| | 336 | | | 68 | 88 |
| Formulation B | 56 | lecithin | 2.0 | 10 | 53 |
| | 112 | | | 37 | 72 |
| | 224 | | | 72 | 88 |
| | 336 | | | 87 | 97 |
| Formulation B | 56 | lecithin | 5.0 | 10 | 50 |
| | 112 | | | 55 | 73 |
| | 224 | | | 72 | 80 |
| | 336 | | | 78 | 95 |
| | 336 | | | 67 | 63 |
| Formulation B | 56 | lecithin | 0.005 | 0 | 10 |
| | 112 | | | 10 | 45 |
| | 224 | | | 67 | 70 |
| | 336 | | | 67 | 77 |
| Formulation B | 56 | lecithin | 0.01 | 2 | 20 |
| | 112 | | | 12 | 47 |
| | 224 | | | 63 | 70 |
| | 336 | | | 68 | 85 |
| Formulation B | 56 | lecithin | 0.05 | 3 | 32 |
| | 112 | | | 12 | 52 |
| | 224 | | | 63 | 73 |
| | 336 | | | 72 | 82 |
| Formulation B | 56 | lecithin | 0.1 | 8 | 37 |
| | 112 | | | 10 | 50 |
| | 224 | | | 65 | 73 |
| | 336 | | | 78 | 83 |
| Formulation B | 56 | lecithin | 0.2 | 5 | 45 |
| | 112 | | | 43 | 63 |
| | 224 | | | 68 | 82 |
| | 336 | | | 80 | 92 |
| Formulation B | 56 | lecithin | 0.5 | 13 | 50 |
| | 112 | | | 42 | 65 |
| | 224 | | | 67 | 88 |
| | 336 | | | 68 | 87 |
| Formulation B | 56 | lecithin | 1.0 | 13 | 52 |
| | 112 | | | 50 | 72 |
| | 224 | | | 67 | 80 |
| | 336 | | | 68 | 88 |
| Formulation B | 56 | lecithin | 2.0 | 10 | 53 |
| | 112 | | | 37 | 72 |
| | 224 | | | 72 | 88 |
| | 336 | | | 87 | 97 |

TABLE 25-continued

| Glyphosate composition | Glyphosate rate g a.e./ha | Additive | Add rate % w/v | % Inhibition ABUTH | ECHCF |
|---|---|---|---|---|---|
| Formulation B | 56 | lecithin | 5.0 | 10 | 50 |
|  | 112 |  |  | 55 | 73 |
|  | 224 |  |  | 72 | 80 |
|  | 336 |  |  | 78 | 95 |

This test was an expanded rate titration study of MON 0818, Fluorad FC-135 and lecithin as tank-mix adjuvants for glyphosate as Formulation B. On ABUTH, the optimum adjuvant concentration was 2.0% for MON 0818, 0.2% for Fluorad FC-135 and 0.2% or higher for lecithin. On ECHCF, the optimum adjuvant concentration was 0.5% to 2.0% for MON 0818, 0.2% for Fluorad FC-135 and 2.0% for lecithin.

Example 26

Aqueous spray compositions were prepared containing glyphosate IPA salt and excipient ingredients as shown in Table 26a. Process (iii) was followed for all compositions, using soybean lecithin (20% phospholipid, Avanti). The pH of all compositions was adjusted to approximately 7.

TABLE 26a

| Spray composition | Lecithin g/l | % w/w Fluorad FC-135 | Aerosol OT |
|---|---|---|---|
| 26-01 |  |  | 0.1 |
| 26-02 |  |  | 0.05 |
| 26-03 |  |  | 0.02 |
| 26-04 |  | 0.1 | 0.1 |
| 26-05 |  | 0.05 | 0.05 |
| 26-06 |  | 0.02 | 0.02 |
| 26-07 | 1.0 |  | 0.10 |
| 26-08 | 1.0 | 0.10 | 0.10 |
| 26-09 | 1.0 |  |  |
| 26-10 | 1.0 | 0.10 |  |
| 26-11 | 0.5 |  |  |
| 26-12 | 0.5 |  | 0.05 |
| 26-13 | 0.5 | 0.05 |  |
| 26-14 | 0.5 | 0.05 | 0.05 |
| 26-15 | 0.2 |  |  |
| 26-16 | 0.2 |  | 0.02 |
| 26-17 | 0.2 | 0.02 |  |
| 26-18 | 0.2 | 0.02 | 0.02 |

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 16 days after planting ABUTH, 19 days after planting ECHCF, and 26 days after planting SIDSP. Evaluation of herbicidal inhibition was done for ABUTH and ECHCF 15 days after application and for SIDSP 21 days after application.

In addition to compositions 26-01 to 26-18, spray compositions were prepared by tank mixing Formulations B and C with Fluorad FC-135 at various concentrations. Formulations B and C alone were applied as comparative treatments. Results, averaged for all replicates of each treatment, are shown in Table 26b.

TABLE 26b

| Spray composition | Glyphosate rate g a.e./ha | % Inhibition ABUTH | ECHCF | SIDSP |
|---|---|---|---|---|
| Formulation B | 150 | 37 | 71 | 57 |
|  | 250 | 57 | 79 | 69 |
|  | 400 | 74 | 86 | 80 |
|  | 500 | 79 | 89 | 74 |
| Formulation C | 150 | 48 | 42 | 58 |
|  | 250 | 71 | 80 | 81 |
|  | 400 | 88 | 100 | 88 |
|  | 500 | 92 | 100 | 86 |
| Formulation B + Fluorad FC-135 0.1% w/v | 150 | 87 | 62 | 66 |
|  | 250 | 87 | 96 | 70 |
|  | 400 | 91 | 94 | 75 |
| Formulation B + Fluorad FC-135 0.05% w/v | 150 | 61 | 48 | 65 |
|  | 250 | 81 | 69 | 71 |
|  | 400 | 90 | 91 | 67 |
| Formulation B + Fluorad FC-135 0.02% w/v | 150 | 58 | 32 | 62 |
|  | 250 | 75 | 49 | 51 |
|  | 400 | 81 | 83 | 73 |
| Formulation C + Fluorad FC-135 0.1% w/v | 150 | 78 | 61 | 76 |
|  | 250 | 79 | 77 | 81 |
|  | 400 | 93 | 100 | 78 |
| Formulation C + Fluorad FC-135 0.05% w/v | 150 | 43 | 86 | 69 |
|  | 250 | 79 | 100 | 80 |
|  | 400 | 95 | 98 | 84 |
| Formulation C + Fluorad FC-135 0.02% w/v | 150 | 39 | 56 | 77 |
|  | 250 | 77 | 100 | 86 |
|  | 400 | 88 | 100 | 80 |
| 26-01 | 150 | 63 | 48 | 49 |
|  | 250 | 70 | 69 | 66 |
| 26-02 | 150 | 32 | 36 | 55 |
|  | 250 | 64 | 74 | 65 |
|  | 400 | 77 | 92 | 69 |
| 26-03 | 150 | 30 | 78 | 51 |
|  | 250 | 59 | 79 | 66 |
|  | 400 | 83 | 93 | 74 |
| 26-04 | 150 | 86 | 50 | 65 |
|  | 250 | 74 | 98 | 71 |
|  | 400 | 81 | 89 | 75 |
| 26-05 | 150 | 85 | 55 | 60 |
|  | 250 | 81 | 75 | 73 |
|  | 400 | 82 | 81 | 64 |
| 26-06 | 150 | 61 | 67 | 45 |
|  | 250 | 66 | 78 | 61 |
|  | 400 | 83 | 77 | 67 |
| 26-07 | 150 | 46 | 38 | 44 |
|  | 250 | 56 | 85 | 64 |
|  | 400 | 75 | 96 | 78 |
| 26-08 | 150 | 88 | 63 | 70 |
|  | 250 | 87 | 73 | 79 |
|  | 400 | 91 | 82 | 75 |
| 26-09 | 150 | 63 | 72 | 61 |
|  | 250 | 87 | 73 | 71 |
|  | 400 | 89 | 87 | 80 |
| 26-10 | 150 | 81 | 72 | 61 |
|  | 250 | 85 | 62 | 82 |
|  | 400 | 87 | 89 | 76 |
| 26-11 | 150 | 54 | 57 | 68 |
|  | 250 | 80 | 90 | 74 |
|  | 400 | 84 | 95 | 66 |

TABLE 26b-continued

| Spray composition | Glyphosate rate g a.e./ha | % Inhibition ABUTH | ECHCF | SIDSP |
|---|---|---|---|---|
| 26-12 | 150 | 27 | 53 | 47 |
|  | 250 | 57 | 71 | 67 |
|  | 400 | 72 | 91 | 70 |
| 26-13 | 150 | 78 | 59 | 64 |
|  | 250 | 80 | 84 | 80 |
|  | 400 | 89 | 76 | 77 |
| 26-14 | 150 | 84 | 52 | 68 |
|  | 250 | 88 | 69 | 75 |
|  | 400 | 90 | 84 | 66 |
| 26-15 | 150 | 51 | 57 | 55 |
|  | 250 | 81 | 55 | 71 |
|  | 400 | 88 | 83 | 69 |
| 26-16 | 150 | 40 | 68 | 46 |
|  | 250 | 74 | 89 | 60 |
|  | 400 | 77 | 98 | 63 |
| 26-17 | 150 | 64 | 44 | 58 |
|  | 250 | 80 | 93 | 81 |
|  | 400 | 87 | 99 | 69 |
| 26-18 | 150 | 64 | 87 | 50 |
|  | 250 | 77 | 75 | 70 |
|  | 400 | 90 | 89 | 50 |

This test was designed in part to explore the relative contribution of Fluorad FC-135 and lecithin to the herbicidal effectiveness of glyphosate compositions comprising both of these excipient substances. Fluorad FC-135 was applied as sole excipient at concentrations of 1.0%, 0.5% and 0.2% (see tank-mix treatments with Formulation B). Lecithin was applied as sole excipient at the same three concentrations in compositions 26-09, 26-11 and 26-15. Combinations of the two excipients at equal concentrations were applied in corresponding compositions 26-10, 26-13 and 26-17. The data are highly variable but an overall trend can be discerned. When only one of the two excipients was present, herbicidal effectiveness tended to drop off as the concentration of that excipient was reduced. When both excipients were present, there was scarcely any decline in herbicidal effectiveness as excipient concentration was reduced. Although averages of data from three glyphosate rates across three species can be misleading, it is helpful in this case to reduce the mass of individual data to the following such averages of percent inhibition:

| | |
|---|---|
| Glyphosate (Formulation B) | 68% |
| Glyphosate + 0.1% Fluorad FC-135 | 81% |
| Glyphosate + 0.05% Fluorad FC-135 | 71% |
| Glyphosate + 0.02% Fluorad FC-135 | 63% |
| Glyphosate + 0 1% lecithin | 76% |
| Glyphosate + 0.05% lecithin | 74% |
| Glyphosate + 0.02% lecithin | 68% |
| Glyphosate + 0.1% Fluorad FC-135 + 0.1% lecithin | 77% |
| Glyphosate + 0.05% Fluorad FC-135 + 0.05% lecithin | 76% |
| Glyphosate + 0.02% Fluorad FC-135 + 0.02% lecithin | 75% |
| Glyphosate commercial standard (Formulation C) | 73% |

Thus, when both excipients are used together, a fivefold decrease in excipient concentration results in a decline in overall herbicidal effectiveness of only 2 percentage points, still retaining overall effectiveness at least equal to that of the commercial standard.

Example 27

Glyphosate-containing spray compositions were prepared by tank-mixing Formulations B with excipients as shown in Table 27. Soybean lecithin (20% phospholipid, Avanti) was used in the form of a 10% dispersion prepared by sonication as in process (iii).

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 15 days after planting ECHCF, and evaluation of herbicidal inhibition was done 19 days after application. Results, averaged for all replicates of each treatment, are shown in Table 27.

TABLE 27

| Glyphosate composition | Glyphosate rate g a.e./ha | Additive | Additive rate % v/v | % Inhibition ABUTH | ECHCF |
|---|---|---|---|---|---|
| Formulation B | 56 | none |  | 0 | 3 |
|  | 112 |  |  | 5 | 13 |
|  | 224 |  |  | 40 | 40 |
|  | 336 |  |  | 83 | 77 |
| Formulation B | 56 | Fluorad FC-135 | 0.005 | 0 | 7 |
|  | 112 |  |  | 3 | 10 |
|  | 224 |  |  | 45 | 53 |
|  | 336 |  |  | 58 | 78 |
| Formulation B | 56 | Fluorad FC-135 | 0.01 | 0 | 8 |
|  | 112 |  |  | 2 | 12 |
|  | 224 |  |  | 45 | 60 |
|  | 336 |  |  | 67 | 87 |
| Formulation B | 56 | Fluorad FC-135 | 0.05 | 2 | 8 |
|  | 112 |  |  | 20 | 23 |
|  | 224 |  |  | 72 | 88 |
|  | 336 |  |  | 90 | 93 |
| Formulation B | 56 | Fluorad FC-135 | 0.1 | 3 | 10 |
|  | 112 |  |  | 33 | 38 |
|  | 224 |  |  | 73 | 88 |
|  | 336 |  |  | 93 | 92 |
| Formulation B | 56 | Fluorad FC-135 | 0.2 | 10 | 17 |
|  | 112 |  |  | 33 | 47 |
|  | 224 |  |  | 77 | 85 |
|  | 336 |  |  | 93 | 92 |

TABLE 27-continued

| Glyphosate composition | Glyphosate rate g a.e./ha | Additive | Additive rate % v/v | % Inhibition ABUTH | ECHCF |
|---|---|---|---|---|---|
| Formulation B | 56 | Fluorad FC-135 | 0.5 | 7 | 13 |
| | 112 | | | 37 | 37 |
| | 224 | | | 80 | 85 |
| | 336 | | | 96 | 95 |
| Formulation B | 56 | Fluorad FC-135 | 1.0 | 3 | 7 |
| | 112 | | | 27 | 35 |
| | 224 | | | 72 | 87 |
| | 336 | | | 88 | 92 |
| Formulation B | 56 | Fluorad FC-135 | 2.0 | 0 | 0 |
| | 112 | | | 27 | 18 |
| | 224 | | | 72 | 75 |
| | 336 | | | 87 | 87 |
| Formulation B | 56 | Fluorad FC-135 | 5.0 | 0 | 0 |
| | 112 | | | 12 | 13 |
| | 224 | | | 43 | 50 |
| | 336 | | | 58 | 53 |
| Formulation B | 56 | lecithin/FC-135 (1:1) | 0.005 | 0 | 2 |
| | 112 | | | 7 | 13 |
| | 224 | | | 65 | 63 |
| | 336 | | | 83 | 82 |
| Formulation B | 56 | lecithin/FC-135 (1:1) | 0.01 | 0 | 0 |
| | 112 | | | 3 | 10 |
| | 224 | | | 45 | 53 |
| | 336 | | | 58 | 78 |
| Formulation B | 56 | lecithin/FC-135 (1:1) | 0.05 | 0 | 0 |
| | 112 | | | 42 | 13 |
| | 224 | | | 68 | 73 |
| | 336 | | | 98 | 73 |
| Formulation B | 56 | lecithin/FC-135 (1:1) | 0.1 | 0 | 0 |
| | 112 | | | 37 | 20 |
| | 224 | | | 62 | 68 |
| | 336 | | | 94 | 77 |
| Formulation B | 56 | lecithin/FC-135 (1:1) | 0.2 | 0 | 2 |
| | 112 | | | 33 | 28 |
| | 224 | | | 67 | 68 |
| | 336 | | | 100 | 78 |
| Formulation B | 56 | lecithin/FC-135 (1:1) | 0.5 | 7 | 0 |
| | 112 | | | 40 | 18 |
| | 224 | | | 68 | 68 |
| | 336 | | | 90 | 73 |
| Formulation B | 56 | lecithin/FC-135 (1:1) | 1.0 | 17 | 3 |
| | 112 | | | 43 | 45 |
| | 224 | | | 83 | 88 |
| | 336 | | | 95 | 94 |
| Formulation B | 56 | lecithin/FC-135 (1:1) | 2.0 | 10 | 23 |
| | 112 | | | 32 | 42 |
| | 224 | | | 63 | 73 |
| | 336 | | | 88 | 87 |
| Formulation B | 56 | lecithin/FC-135 (1:1) | 5.0 | 2 | 3 |
| | 112 | | | 18 | 28 |
| | 224 | | | 50 | 72 |
| | 336 | | | 85 | 87 |
| Formulation B | 56 | lecithin | 0.005 | 2 | 2 |
| | 112 | | | 3 | 10 |
| | 224 | | | 45 | 50 |
| | 336 | | | 58 | 72 |
| Formulation B | 56 | lecithin | 0.01 | 0 | 2 |
| | 112 | | | 2 | 12 |
| | 224 | | | 40 | 52 |
| | 336 | | | 65 | 75 |
| Formulation B | 56 | lecithin | 0.05 | 2 | 2 |
| | 112 | | | 0 | 10 |
| | 224 | | | 40 | 45 |
| | 336 | | | 57 | 70 |
| Formulation B | 56 | lecithin | 0.1 | 2 | 7 |
| | 112 | | | 2 | 13 |
| | 224 | | | 33 | 37 |
| | 336 | | | 48 | 67 |
| Formulation B | 56 | lecithin | 0.2 | 3 | 3 |
| | 112 | | | 3 | 13 |
| | 224 | | | 32 | 35 |
| | 336 | | | 47 | 68 |

TABLE 27-continued

| Glyphosate composition | Glyphosate rate g a.e./ha | Additive | Additive rate % v/v | % Inhibition ABUTH | ECHCF |
|---|---|---|---|---|---|
| Formulation B | 56 | lecithin | 0.5 | 2 | 3 |
|  | 112 |  |  | 8 | 15 |
|  | 224 |  |  | 47 | 53 |
|  | 336 |  |  | 67 | 65 |
| Formulation B | 56 | lecithin | 1.0 | 2 | 5 |
|  | 112 |  |  | 10 | 15 |
|  | 224 |  |  | 33 | 55 |
|  | 336 |  |  | 70 | 77 |
| Formulation B | 56 | lecithin | 2.0 | 5 | 8 |
|  | 112 |  |  | 12 | 17 |
|  | 224 |  |  | 48 | 52 |
|  | 336 |  |  | 68 | 77 |
| Formulation B | 56 | lecithin | 5.0 | 5 | 17 |
|  | 12 |  |  | 23 | 17 |
|  | 224 |  |  | 52 | 55 |
|  | 336 |  |  | 73 | 78 |

This tank-mix study more clearly demonstrates the surprising interaction seen in Example 26 between lecithin and Fluorad FC-135 as excipients for glyphosate. For example, glyphosate alone over four rates gave average inhibition of ABUTH of 32%. Adding Fluorad FC-135 at a concentration of 0.5% boosted the average inhibition to 55%, but adding lecithin at the same concentration did not raise average inhibition above 32%. A 1:1 combination of both excipients at the same total concentration gave an average inhibition of 51%. At a concentration of 0.1%, Fluorad FC-135 gave average inhibition of 50%, lecithin 21% (i.e. a reduction in effectiveness of glyphosate) and the 1:1 combination 48%. Thus, as in Example 26, the decline in herbicidal effectiveness with reducing excipient rate was much less pronounced with the combination than with either excipient on its own.

Example 28

Aqueous concentrate compositions were prepared containing glyphosate IPA salt and excipient ingredients as shown in Table 28a. Process (i) was followed for compositions 28-01 to 28-06. Process (iv) was followed for compositions 28-07 to 28-11, using soybean lecithin (20% phospholipid, Avanti). For compositions 28-12 and 28-13, process (iv) was also used, but Aerosol TO was the aggregate-forming material employed in place of lecithin. The pH of all compositions was approximately 5.

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 38 days after application.

Formulations B and C were applied as comparative treatments. Results, averaged for all replicates of each treatment, as shown in Table 28b.

TABLE 28b

| Concentrate composition | Glyphosate rate g a.e./ha | % Inhibition ABUTH | ECHCF |
|---|---|---|---|
| Formulation B | 56 | 0 | 8 |
|  | 112 | 4 | 33 |
|  | 224 | 45 | 40 |
|  | 336 | 69 | 65 |
| Formulation C | 56 | 0 | 10 |
|  | 112 | 5 | 43 |
|  | 224 | 68 | 73 |
|  | 336 | 87 | 94 |
| 28-01 | 112 | 0 | 40 |
|  | 224 | 50 | 76 |
|  | 336 | 76 | 85 |

TABLE 28a

| Concentrate composition | % w/w | | | | | |
|---|---|---|---|---|---|---|
|  | Glyphosate a.e. | Lecithin | Fluorad FC-135 | MON 0818 | Other (*) | (*) Other components |
| 28-01 | 20 |  |  |  | 1.0 | PVA |
| 28-02 | 20 |  | 5.0 |  | 1.0 | PVA |
| 28-03 | 20 |  | 2.0 |  | 1.0 | PVA |
| 28-04 | 20 |  | 1.0 |  | 1.0 | PVA |
| 28-05 | 20 |  |  |  | 0.5 | Kelzan |
| 28-06 | 20 |  | 2.0 |  | 0.5 | Kelzan |
| 28-07 | 20 | 2.0 |  | 0.04 |  |  |
| 28-08 | 20 | 2.0 | 2.0 | 0.04 |  |  |
| 28-09 | 20 | 2.0 | 2.0 | 0.02 |  |  |
| 28-10 | 20 | 2.0 |  | 0.04 | 25.0 | Silwet 800 |
| 28-11 | 20 | 2.0 | 2.0 | 0.04 | 25.0 | Silwet 800 |
| 28-12 | 20 |  |  |  | 5.0 | Aerosol OT |
| 28-13 | 20 |  |  |  | 5.0 + 25.0 | Aerosol OT + Silwet 800 |

TABLE 28b-continued

| Concentrate composition | Glyphosate rate g a.e./ha | % Inhibition ABUTH | ECHCF |
|---|---|---|---|
| 28-02 | 112 | 1 | 35 |
|  | 224 | 30 | 70 |
|  | 336 | 69 | 96 |
| 28-03 | 112 | 6 | 35 |
|  | 224 | 35 | 58 |
|  | 336 | 65 | 84 |
| 28-04 | 112 | 1 | 35 |
|  | 224 | 70 | 60 |
|  | 336 | 69 | 85 |
| 28-05 | 112 | 1 | 35 |
|  | 224 | 63 | 68 |
|  | 336 | 80 | 88 |
| 28-06 | 112 | 0 | 25 |
|  | 224 | 40 | 55 |
|  | 336 | 66 | 73 |
| 28-07 | 112 | 11 | 35 |
|  | 224 | 45 | 68 |
|  | 336 | 65 | 86 |
| 28-08 | 112 | 9 | 38 |
|  | 224 | 65 | 60 |
|  | 336 | 66 | 75 |
| 28-09 | 112 | 10 | 33 |
|  | 224 | 56 | 60 |
|  | 336 | 78 | 75 |
| 28-10 | 112 | 30 | 5 |
|  | 224 | 79 | 30 |
|  | 336 | 90 | 35 |
| 28-11 | 112 | 60 | 5 |
|  | 224 | 79 | 33 |
|  | 336 | 96 | 30 |
| 28-12 | 112 | 8 | 11 |
|  | 224 | 53 | 40 |
|  | 336 | 66 | 64 |
| 28-13 | 112 | 40 | 6 |
|  | 224 | 91 | 33 |
|  | 336 | 98 | 38 |

Concentrate compositions 28-08 and 28-09 did not in this test exhibit herbicidal effectiveness equal to Formulation C.

Example 29

Aqueous spray compositions were prepared containing glyphosate IPA salt and excipient ingredients as shown in Table 29a. Process (iii) was followed for all compositions, using soybean lecithin (20% or 45% phospholipid as indicated below, both sourced from Avanti). The pH of all compositions was adjusted to approximately 7.

TABLE 29a

| Spray composition | Lecithin g/l | phospholipid % | % w/w Fluorad FC-135 |
|---|---|---|---|
| 29-01 | 0.25 | 20 |  |
| 29-02 | 0.05 | 20 |  |
| 29-03 | 0.02 | 20 |  |
| 29-04 | 0.01 | 20 |  |
| 29-05 | 0.25 | 20 | 0.25 |
| 29-06 | 0.05 | 20 | 0.05 |
| 29-07 | 0.02 | 20 | 0.02 |
| 29-08 | 0.01 | 20 | 0.01 |
| 29-09 | 0.25 | 45 |  |
| 29-10 | 0.05 | 45 |  |
| 29-11 | 0.02 | 45 |  |
| 29-12 | 0.01 | 45 |  |
| 29-13 | 0.25 | 45 | 0.25 |
| 29-14 | 0.05 | 45 | 0.05 |
| 29-15 | 0.02 | 45 | 0.02 |
| 29-16 | 0.01 | 45 | 0.01 |

Yellow nutsedge (*Cyperus esculentus*, CYPES) plants were grown and treated by the standard procedures given above. Applications of spray compositions were made 27 days after planting CYPES. Evaluation was done 27 days after application.

In addition to compositions 29-01 to 29-16, spray compositions were prepared by tank mixing Formulations B and C with Fluorad FC-135 at various concentrations. Formulations B and C were applied as comparative treatments. Results, averaged for all replicates of each treatment, are shown in Table 29b.

TABLE 29b

| Spray composition | Glyphosate rate g a.e./ha | % Inhibition CYPES |
|---|---|---|
| Formulation B | 500 | 25 |
|  | 800 | 41 |
|  | 1200 | 59 |
| Formulation C | 500 | 29 |
|  | 800 | 43 |
|  | 1200 | 62 |
| Formulation B + Fluorad FC-135 0.25% w/v | 500 | 60 |
|  | 800 | 57 |
|  | 1200 | 79 |
| Formulation B + Fluorad FC-135 0.05% w/v | 500 | 63 |
|  | 800 | 54 |
|  | 1200 | 65 |
| Formulation B + Fluorad FC-135 0.02% w/v | 500 | 50 |
|  | 800 | 71 |
|  | 1200 | 60 |
| Formulation B + Fluorad FC-135 0.01% w/v | 500 | 27 |
|  | 800 | 35 |
|  | 1200 | 81 |
| Formulation C + Fluorad FC-135 0.25% w/v | 500 | 41 |
|  | 800 | 72 |
|  | 1200 | 75 |
| Formulation C + Fluorad FC-135 0.05% w/v | 500 | 52 |
|  | 800 | 43 |
|  | 1200 | 63 |
| Formulation C + Fluorad FC-135 0.02% w/v | 500 | 76 |
|  | 800 | 72 |
|  | 1200 | 82 |
| Formulation C + Fluorad FC-135 0.01% w/v | 500 | 38 |
|  | 800 | 59 |
|  | 1200 | 72 |
| 29-01 | 500 | 51 |
|  | 800 | 70 |
|  | 1200 | 64 |
| 29-02 | 500 | 58 |
|  | 800 | 69 |
|  | 1200 | 77 |
| 29-03 | 500 | 49 |
|  | 800 | 67 |
|  | 1200 | 85 |
| 29-04 | 500 | 51 |
|  | 800 | 76 |
|  | 1200 | 77 |
| 29-05 | 500 | 37 |
|  | 800 | 73 |
|  | 1200 | 100 |
| 29-06 | 400 | 72 |
|  | 750 | 62 |
|  | 1000 | 67 |
| 29-07 | 400 | 68 |
|  | 750 | 75 |
|  | 1000 | 86 |
| 29-08 | 400 | 59 |
|  | 750 | 78 |
|  | 1000 | 88 |
| 29-09 | 400 | 72 |
|  | 750 | 80 |
|  | 1000 | 88 |
| 29-10 | 400 | 67 |
|  | 750 | 77 |
|  | 1000 | 89 |
| 29-11 | 400 | 67 |
|  | 750 | 75 |
|  | 1000 | 66 |

TABLE 29b-continued

| Spray composition | Glyphosate rate g a.e./ha | % Inhibition CYPES |
|---|---|---|
| 29-12 | 400 | 55 |
|  | 750 | 75 |
|  | 1000 | 83 |
| 29-13 | 400 | 33 |
|  | 750 | 59 |
|  | 1000 | 73 |
| 29-14 | 400 | 63 |
|  | 750 | 77 |
|  | 1000 | 76 |
| 29-15 | 400 | 35 |
|  | 750 | 75 |
|  | 1000 | 88 |
| 29-16 | 400 | 77 |
|  | 750 | 66 |
|  | 1000 | 86 |

This test was conducted to investigate the effect of phospholipid content of lecithin on herbicidal efficacy of lecithin-containing glyphosate compositions. No clear pattern emerged from this study, but overall it appeared that the crude lecithin (20% phospholipid) provided greater herbicidal effectiveness on CYPES than the de-oiled lecithin (45% phospholipid), suggesting that the oil present in crude lecithin might be having an adjuvant effect on this species.

Example 30

Aqueous spray compositions were prepared containing glyphosate IPA salt and excipient ingredients as shown in Table 30a. Process (iii) was followed for all compositions, using soybean lecithin (20%, 45% or 95% phospholipid as indicated below, all sourced from Avanti). The pH of all compositions was adjusted to approximately 7.

TABLE 30a

| Spray composition | Lecithin g/l | phospholipid % | % w/w Fluorad FC-135 |
|---|---|---|---|
| 30-01 | 0.5 | 20 |  |
| 30-02 | 0.2 | 20 |  |
| 30-03 | 0.1 | 20 |  |
| 30-04 | 0.5 | 45 |  |
| 30-05 | 0.2 | 45 |  |
| 30-06 | 0.1 | 45 |  |
| 30-07 | 0.5 | 95 |  |
| 30-08 | 0.2 | 95 |  |
| 30-09 | 0.1 | 95 |  |
| 30-10 | 0.5 | 20 | 0.05 |
| 30-11 | 0.5 | 45 | 0.05 |
| 30-12 | 0.5 | 95 | 0.05 |
| 30-13 | 0.2 | 20 | 0.02 |
| 30-14 | 0.2 | 45 | 0.02 |
| 30-15 | 0.2 | 95 | 0.02 |
| 30-16 | 0.1 | 20 | 0.01 |
| 30-17 | 0.1 | 45 | 0.01 |
| 30-18 | 0.1 | 95 | 0.01 |

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 17 days after planting ABUTH, 19 days after planting ECHCF, and 23 days after planting SIDSP. Evaluation of herbicidal inhibition was done 15 days after application.

In addition to compositions 30-01 to 30-18, spray compositions were prepared by tank mixing Formulations B and C with Fluorad FC-135 at various concentrations. Formulations B and C alone were applied as comparative treatments. Results, averaged for all replicates of each treatment, are shown in Table 30b.

TABLE 30b

| Spray composition | Glyphosate rate g a.e./ha | % Inhibition ABUTH | ECHCF | SIDSP |
|---|---|---|---|---|
| Formulation B | 100 | 10 | 25 | 33 |
|  | 200 | 22 | 29 | 49 |
|  | 300 | 50 | 62 | 61 |
|  | 400 | 62 | 62 | 64 |
| Formulation C | 100 | 14 | 40 | 34 |
|  | 200 | 53 | 98 | 66 |
|  | 300 | 74 | 100 | 84 |
|  | 400 | 86 | 100 | 93 |
| Formulation B + Fluorad FC-135 0.05% w/v | 100 | 18 | 25 | 34 |
|  | 200 | 50 | 58 | 52 |
|  | 300 | 68 | 83 | 70 |
| Formulation B + Fluorad FC-135 0.02% w/v | 100 | 10 | 21 | 29 |
|  | 200 | 64 | 40 | 46 |
|  | 300 | 79 | 62 | 64 |
| Formulation B + Fluorad FC-135 0.01% w/v | 100 | 10 | 21 | 34 |
|  | 200 | 34 | 27 | 44 |
|  | 300 | 73 | 74 | 69 |
| Formulation C + Fluorad FC-135 0.05% w/v | 100 | 65 | 53 | 58 |
|  | 200 | 73 | 77 | 65 |
|  | 300 | 94 | 99 | 73 |
| Formulation C + Fluorad FC-135 0.02% w/v | 100 | 68 | 94 | 61 |
|  | 200 | 63 | 93 | 66 |
|  | 300 | 85 | 90 | 79 |
| Formulation C + Fluorad FC-135 0.01% w/v | 100 | 72 | 67 | 53 |
|  | 200 | 69 | 99 | 61 |
|  | 300 | 81 | 99 | 83 |
| 30-01 | 100 | 32 | 26 | 39 |
|  | 200 | 72 | 60 | 56 |
|  | 300 | 84 | 72 | 69 |
| 30-02 | 100 | 14 | 23 | 43 |
|  | 200 | 70 | 42 | 63 |
|  | 300 | 83 | 74 | 68 |
| 30-03 | 100 | 6 | 25 | 42 |
|  | 200 | 55 | 47 | 57 |
|  | 300 | 65 | 64 | 72 |
| 30-04 | 100 | 29 | 31 | 42 |
|  | 200 | 55 | 65 | 60 |
|  | 300 | 82 | 54 | 73 |
| 30-05 | 100 | 14 | 22 | 41 |
|  | 200 | 32 | 35 | 66 |
|  | 300 | 81 | 98 | 70 |
| 30-06 | 100 | 9 | 26 | 29 |
|  | 200 | 47 | 48 | 57 |
|  | 300 | 69 | 71 | 71 |
| 30-07 | 100 | 30 | 22 | 50 |
|  | 200 | 73 | 50 | 69 |
|  | 300 | 82 | 86 | 67 |
| 30-08 | 100 | 41 | 23 | 53 |
|  | 200 | 57 | 38 | 69 |
|  | 300 | 76 | 46 | 84 |
| 30-09 | 100 | 32 | 17 | 45 |
|  | 200 | 60 | 37 | 67 |
|  | 300 | 78 | 77 | 73 |
| 30-10 | 100 | 58 | 27 | 62 |
|  | 200 | 91 | 42 | 79 |
|  | 300 | 93 | 95 | 77 |
| 30-11 | 100 | 66 | 58 | 63 |
|  | 200 | 91 | 79 | 69 |
|  | 300 | 91 | 84 | 84 |
| 30-12 | 100 | 61 | 27 | 67 |
|  | 200 | 90 | 72 | 77 |
|  | 300 | 93 | 83 | 84 |
| 30-13 | 100 | 61 | 24 | 51 |
|  | 200 | 88 | 48 | 69 |
|  | 300 | 94 | 54 | 75 |
| 30-14 | 100 | 66 | 25 | 56 |
|  | 200 | 90 | 49 | 72 |
|  | 300 | 93 | 73 | 85 |

TABLE 30b-continued

| Spray composition | Glyphosate rate g a.e./ha | % Inhibition | | |
|---|---|---|---|---|
| | | ABUTH | ECHCF | SIDSP |
| 30-15 | 100 | 63 | 23 | 61 |
| | 200 | 88 | 33 | 72 |
| | 300 | 95 | 75 | 81 |
| 30-16 | 100 | 75 | 25 | 56 |
| | 200 | 87 | 37 | 74 |
| | 300 | 93 | 71 | 77 |
| 30-17 | 100 | 63 | 17 | 59 |
| | 200 | 92 | 27 | 73 |
| | 300 | 92 | 83 | 78 |
| 30-18 | 100 | 67 | 22 | 53 |
| | 200 | 91 | 38 | 68 |
| | 300 | 91 | 46 | 77 |

In general, across the three species included in this test, compositions containing the 45% phospholipid grade of soybean lecithin provided slightly greater herbicidal effectiveness than those containing the 20% grade. Any further improvement obtained by using the 95% grade was minimal and would likely not justify the considerably increased cost of this grade. The data of this test clearly show a non-additive interaction between lecithin and Fluorad FC-135. To take just one example for illustration, glyphosate alone (Formulation B) at 200 g a.e./ha gave 22% inhibition of ABUTH, 29% inhibition of ECHCF and 49% inhibition of SIDSP. Adding 0.02% Fluorad FC-135 brought these percentage inhibitions to 64%, 40% and 46% respectively. Alternatively, adding the 45% grade of lecithin at 0.02% (composition 30-05) resulted in percentage inhibitions of 32%, 135% and 36% respectively. Adding both these excipients, each at 0.02% (composition 30-14) gave percentage inhibitions of 90%, 49% and 72% respectively. Even adding both excipients so that the total excipient concentration was 0.02% (composition 30-17) resulted in percentage inhibitions of 92%, 27% and 73% respectively. Thus at least on the broadleaf species (ABUTH and SIDSP) there is strong evidence of a synergistic interaction between these two excipient substances.

Example 31

Aqueous spray compositions were prepared containing glyphosate IPA salt and excipient ingredients as shown in Table 31a. Process (iii) was followed for all compositions, using lecithin (20% or 95% phospholipid from soybean, or 95% phospholipid from egg yolk, all sourced from Avanti). The pH of all compositions was adjusted to approximately 7.

TABLE 31a

| Spray composition | Lecithin | | | % w/w | |
|---|---|---|---|---|---|
| | g/l | phospholipid % | source | Fluorad FC-135 | Fluorad FC-754 |
| 31-01 | 0.05 | 95 | egg yolk | | |
| 31-02 | 0.02 | 95 | egg yolk | | |
| 31-03 | 0.01 | 95 | egg yolk | | |
| 31-04 | 0.05 | 95 | soybean | | |
| 31-05 | 0.02 | 95 | soybean | | |
| 31-06 | 0.01 | 95 | soybean | | |
| 31-07 | 0.05 | 95 | egg yolk | 0.05 | |
| 31-08 | 0.02 | 95 | egg yolk | 0.02 | |
| 31-09 | 0.01 | 95 | egg yolk | 0.01 | |
| 31-10 | 0.05 | 95 | soybean | 0.05 | |
| 31-11 | 0.02 | 95 | soybean | 0.02 | |
| 31-12 | 0.01 | 95 | soybean | 0.01 | |
| 31-13 | 0.05 | 20 | soybean | | 0.05 |
| 31-14 | 0.02 | 20 | soybean | | 0.02 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 19 days after planting ECHCF, and evaluation of herbicidal inhibition was done 15 days after application.

In addition to compositions 31-01 to 31-14, spray compositions were prepared by tank mixing Formulations B and C with Fluorad FC-135 or Fluorad FC-754 at various concentrations. Formulations B and C alone were applied as comparative treatments. Results, averaged for all replicates of each treatment, are shown in Table 31b.

TABLE 31b

| Spray composition | Glyphosate rate g a.e./ha | % Inhibition | |
|---|---|---|---|
| | | ABUTH | ECHCF |
| Formulation B | 100 | 1 | 27 |
| | 200 | 6 | 28 |
| | 300 | 2 | 35 |
| | 400 | 31 | 46 |
| Formulation C | 100 | 10 | 31 |
| | 200 | 28 | 36 |
| | 300 | 62 | 66 |
| | 400 | 77 | 74 |
| Formulation B + Fluorad FC-135 0.05% w/v | 100 | 19 | 24 |
| | 200 | 37 | 40 |
| | 300 | 62 | 52 |
| Formulation B + Fluorad FC-135 0.02% w/v | 100 | 7 | 13 |
| | 200 | 42 | 27 |
| | 300 | 56 | 57 |
| Formulation B + Fluorad FC-135 0.01% w/v | 100 | 23 | 19 |
| | 200 | 43 | 24 |
| | 300 | 60 | 40 |
| Formulation B + Fluorad FC-754 0.05% w/v | 100 | 19 | 23 |
| | 200 | 41 | 33 |
| | 300 | 67 | 62 |
| Formulation B + Fluorad FC-754 0.02% w/v | 100 | 12 | 19 |
| | 200 | 31 | 44 |
| | 300 | 61 | 45 |
| Formulation C + Fluorad FC-135 0.05% w/v | 100 | 37 | 39 |
| | 200 | 49 | 43 |
| | 300 | 66 | 62 |
| Formulation C + Fluorad FC-135 0.02% w/v | 100 | 18 | 31 |
| | 200 | 47 | 44 |
| | 300 | 68 | 49 |
| Formulation C + Fluorad FC-135 0.01% w/v | 100 | 26 | 27 |
| | 200 | 36 | 44 |
| | 300 | 54 | 82 |
| Formulation C + Fluorad FC-754 0.05% w/v | 100 | 34 | 32 |
| | 200 | 47 | 37 |
| | 300 | 62 | 62 |
| Formulation C + Fluorad FC-754 0.02% w/v | 100 | 28 | 32 |
| | 200 | 45 | 60 |
| | 300 | 43 | 75 |
| 31-01 | 100 | 6 | 36 |
| | 200 | 54 | 56 |
| | 300 | 66 | 61 |
| 31-02 | 100 | 23 | 43 |
| | 200 | 45 | 45 |
| | 300 | 65 | 51 |

TABLE 31b-continued

| Spray composition | Glyphosate rate g a.e./ha | % Inhibition ABUTH | % Inhibition ECHCF |
|---|---|---|---|
| 31-03 | 100 | 31 | 35 |
|  | 200 | 37 | 45 |
|  | 300 | 53 | 60 |
| 31-04 | 100 | 24 | 35 |
|  | 200 | 43 | 43 |
|  | 300 | 78 | 50 |
| 31-05 | 100 | 24 | 36 |
|  | 200 | 45 | 44 |
|  | 300 | 58 | 66 |
| 31-06 | 100 | 31 | 24 |
|  | 200 | 46 | 34 |
|  | 300 | 52 | 51 |
| 31-07 | 100 | 49 | 33 |
|  | 200 | 65 | 39 |
|  | 300 | 73 | 63 |
| 31-08 | 100 | 48 | 25 |
|  | 200 | 70 | 49 |
|  | 300 | 73 | 69 |
| 31-09 | 100 | 45 | 27 |
|  | 200 | 59 | 53 |
|  | 300 | 71 | 84 |
| 31-10 | 100 | 60 | 30 |
|  | 200 | 64 | 89 |
|  | 300 | 75 | 99 |
| 31-11 | 100 | 47 | 51 |
|  | 200 | 66 | 65 |
|  | 300 | 80 | 78 |
| 31-12 | 100 | 49 | 39 |
|  | 200 | 60 | 59 |
|  | 300 | 67 | 84 |
| 31-13 | 100 | 50 | 30 |
|  | 200 | 70 | 51 |
|  | 300 | 68 | 66 |
| 31-14 | 100 | 54 | 33 |
|  | 200 | 61 | 44 |
|  | 300 | 79 | 66 |

In this test, glyphosate compositions containing egg yolk lecithin (31-01 to 31-03) performed similarly to those containing soybean lecithin (31-04 to 31-06) on ABUTH but were generally more effective than those containing soybean lecithin on ECHCF, at least in the absence of Fluorad FC-135. Addition of Fluorad FC-135, as in compositions 31-07 to 31-12, enhanced effectiveness of all compositions.

Example 32

Aqueous spray compositions were prepared containing glyphosate IPA salt and excipient ingredients as shown in Table 32a. Process (iii) was followed for all compositions, using soybean lecithin (20% phospholipid, Avanti). The pH of all compositions was adjusted to approximately 7.

TABLE 32a

| Spray composition | Lecithin g/l | % w/w fluoro-organic | Type of fluoro-organic |
|---|---|---|---|
| 32-01 | 0.20 |  | none |
| 32-02 | 0.20 | 0.02 | Fluorad FC-135 |
| 32-03 | 0.20 | 0.02 | Fluorad FC-431 |
| 32-04 | 0.20 | 0.02 | Fluorad FC-751 |
| 32-05 | 0.20 | 0.02 | Fluorad FC-170C |
| 32-06 | 0.20 | 0.02 | Fluorad FC-171 |
| 32-07 | 0.20 | 0.02 | Fluorad FC-754 |
| 32-08 | 0.50 |  | none |
| 32-09 | 0.10 |  | none |
| 32-10 | 0.04 |  | none |
| 32-11 | 0.02 |  | none |

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 18 days after planting ABUTH and ECHCF, and 27 days after planting SIDSP. Evaluation of herbicidal inhibition was done 15 days after application.

In addition to compositions 32-01 to 32-11, spray compositions were prepared by tank mixing Formulations B and C with various fluoro-organic surfactants of the Fluorad range, all at 0.02%. Formulations B and C alone were applied as comparative treatments. Results, averaged for all replicates of each treatment, are shown in Table 32b.

TABLE 32b

| Spray composition | Glyphosate rate g a.e./ha | % Inhibition ABUTH | % Inhibition ECHCF | % Inhibition SIDSP |
|---|---|---|---|---|
| Formulation B | 150 | 8 | 35 | 35 |
|  | 250 | 21 | 47 | 37 |
|  | 350 | 31 | 36 | 56 |
|  | 450 | 57 | 52 | 64 |
| Formulation C | 150 | 29 | 69 | 49 |
|  | 250 | 55 | 90 | 67 |
|  | 350 | 75 | 91 | 75 |
|  | 450 | 82 | 91 | 85 |
| Formulation B + Fluorad FC-135 0.02% w/v | 150 | 17 | 43 | 36 |
|  | 250 | 39 | 58 | 53 |
|  | 350 | 52 | 53 | 68 |
| Formulation B + Fluorad FC-170C 0.02% w/v | 150 | 13 | 25 | 32 |
|  | 250 | 31 | 47 | 36 |
|  | 350 | 31 | 85 | 61 |
| Formulation B + Fluorad FC-171 0.02% w/v | 150 | 52 | 15 |  |
|  | 250 | 10 | 47 | 44 |
|  | 350 | 15 | 58 | 55 |
| Formulation B + Fluorad FC-431 0.02% w/v | 150 | 4 | 36 | 34 |
|  | 250 | 23 | 53 | 53 |
|  | 350 | 37 | 61 | 62 |
| Formulation B + Fluorad FC-751 0.02% w/v | 150 | 12 | 29 | 29 |
|  | 250 | 30 | 38 | 41 |
|  | 350 | 43 | 36 | 58 |
| Formulation B + Fluorad FC-754 0.02% w/v | 150 | 21 | 27 | 33 |
|  | 250 | 3 | 36 | 49 |
|  | 350 | 38 | 51 | 59 |
| Formulation C + Fluorad FC-135 0.02% w/v | 150 | 35 | 3 | 46 |
|  | 250 | 66 | 87 | 58 |
|  | 350 | 78 | 99 | 80 |
| Formulation C + Fluorad FC-170C 0.02% w/v | 150 | 29 | 68 | 41 |
|  | 250 | 54 | 78 | 61 |
|  | 350 | 59 | 86 | 78 |
| Formulation C + Fluorad FC-171 0.02% w/v | 150 | 20 | 96 | 35 |
|  | 250 | 37 | 99 | 62 |
|  | 350 | 55 | 100 | 65 |
| Formulation C + Fluorad FC-431 0.02% w/v | 150 | 20 | 94 | 41 |
|  | 250 | 51 | 85 | 68 |
|  | 350 | 66 | 97 | 74 |
| Formulation C + Fluorad FC-751 0.02% w/v | 150 | 15 | 67 | 38 |
|  | 250 | 36 | 85 | 56 |
|  | 350 | 60 | 100 | 72 |
| Formulation C + Fluorad FC-754 0.02% w/v | 150 | 33 | 78 | 37 |
|  | 250 | 75 | 85 | 66 |
|  | 350 | 82 | 94 | 80 |
| 32-01 | 150 | 25 | 35 | 45 |
|  | 250 | 43 | 52 | 63 |
|  | 350 | 60 | 90 | 77 |
| 32-02 | 150 | 65 | 37 | 58 |
|  | 250 | 69 | 69 | 67 |
|  | 350 | 66 | 69 | 78 |
| 32-03 | 150 | 14 | 40 | 41 |
|  | 250 | 45 | 78 | 63 |
|  | 350 | 55 | 92 | 75 |
| 32-04 | 150 | 19 | 48 | 48 |
|  | 250 | 36 | 51 | 63 |
|  | 350 | 65 | 69 | 70 |
| 32-05 | 150 | 47 | 34 | 45 |
|  | 250 | 55 | 43 | 55 |
|  | 350 | 63 | 58 | 75 |

TABLE 32b-continued

| Spray composition | Glyphosate rate g a.e./ha | % Inhibition ABUTH | ECHCF | SIDSP |
|---|---|---|---|---|
| 32-06 | 150 | 23 | 36 | 46 |
|  | 250 | 57 | 52 | 59 |
|  | 350 | 61 | 73 | 67 |
| 32-07 | 150 | 67 | 59 | 58 |
|  | 250 | 81 | 73 | 72 |
|  | 350 | 80 | 76 | 76 |
| 32-08 | 150 | 37 | 49 | 60 |
|  | 250 | 60 | 83 | 69 |
|  | 350 | 67 | 93 | 49 |
| 32-09 | 150 | 19 | 63 | 51 |
|  | 250 | 53 | 71 | 62 |
|  | 350 | 55 | 74 | 82 |
| 32-10 | 150 | 19 | 70 | 51 |
|  | 250 | 39 | 94 | 61 |
|  | 350 | 63 | 87 | 73 |
| 32-11 | 150 | 6 | 51 | 50 |
|  | 250 | 58 | 67 | 66 |
|  | 350 | 69 | 92 | 73 |

Composition 32-07, containing 0.02% lecithin and 0.02% Fluorad FC-754, was equal or superior to composition 32-02, containing 02% lecithin and 0.02% Fluorad FC-135, in herbicidal effectiveness. This indicates that Fluorad FC-754 is an acceptable substitute for Fluorad FC-135 in such compositions. The other fluoro-organic surfactants tested in this Example, none of which is cationic, were less effective than the cationic fluoro-organics Fluorad FC-135 and Fluorad FC-754 as excipients in combination with lecithin. A possible exception was Fluorad FC-170C which gave good enhancement of glyphosate effectiveness on ECHCF only.

Example 33

Aqueous concentrate compositions were prepared containing glyphosate IPA salt and excipient ingredients as shown in Table 33a. Process (v) was followed for all compositions, using soybean lecithin (20% phospholipid, Avanti). The pH of all compositions was approximately 5.

TABLE 33a

| Concentrate composition | Glyphosate a.e. | Lecithin | MON 0818 | Agrimul PG-2069 | Fluorad FC-135 |
|---|---|---|---|---|---|
| 33-01 | 30 | 3.0 |  |  | 3.0 |
| 33-02 | 30 | 3.0 |  | 0.25 | 1.0 |
| 33-03 | 30 | 3.0 | 0.25 |  | 3.0 |
| 33-04 | 30 | 1.0 | 0.50 |  | 3.0 |
| 33-05 | 30 | 1.0 |  | 0.50 | 3.0 |
| 33-06 | 30 | 1.0 |  |  | 1.0 |
| 33-07 | 30 | 1.0 |  | 0.25 | 1.0 |
| 33-08 | 30 | 3.0 |  | 0.50 | 2.0 |
| 33-09 | 30 | 2.0 |  |  | 3.0 |
| 33-10 | 30 | 3.0 | 0.50 |  |  |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 19 days after application.

Formulations C and J were applied as comparative treatments. Results, averaged for all replicates of each treatment, are shown in Table 33b.

TABLE 33b

| Concentrate composition | Glyphosate rate g a.e./ha | % Inhibition ABUTH | ECHCF |
|---|---|---|---|
| Formulation C | 56 | 3 | 5 |
|  | 112 | 49 | 48 |
|  | 224 | 79 | 83 |
|  | 448 | 99 | 99 |
| Formulation J | 56 | 16 | 20 |
|  | 112 | 40 | 43 |
|  | 224 | 80 | 81 |
|  | 448 | 97 | 99 |
| 33-01 | 56 | 4 | 5 |
|  | 112 | 35 | 20 |
|  | 224 | 81 | 51 |
|  | 448 | 99 | 80 |
| 33-02 | 56 | 0 | 5 |
|  | 112 | 4 | 20 |
|  | 224 | 66 | 55 |
|  | 448 | 94 | 80 |
| 33-03 | 56 | 1 | 5 |
|  | 112 | 6 | 20 |
|  | 224 | 78 | 74 |
|  | 448 | 93 | 80 |
| 33-04 | 56 | 1 | 5 |
|  | 112 | 1 | 15 |
|  | 224 | 75 | 65 |
|  | 448 | 95 | 80 |
| 33-05 | 56 | 0 | 5 |
|  | 112 | 1 | 15 |
|  | 224 | 75 | 65 |
|  | 448 | 91 | 80 |
| 33-06 | 56 | 0 | 5 |
|  | 112 | 3 | 15 |
|  | 224 | 55 | 63 |
|  | 448 | 91 | 79 |
| 33-07 | 56 | 1 | 5 |
|  | 112 | 3 | 15 |
|  | 224 | 48 | 55 |
|  | 448 | 88 | 81 |
| 33-08 | 56 | 3 | 9 |
|  | 112 | 3 | 20 |
|  | 224 | 66 | 60 |
|  | 448 | 89 | 80 |
| 33-09 | 56 | 0 | 5 |
|  | 112 | 5 | 10 |
|  | 224 | 78 | 55 |
|  | 448 | 97 | 80 |
| 33-10 | 56 | 0 | 5 |
|  | 112 | 4 | 15 |
|  | 224 | 21 | 55 |
|  | 448 | 88 | 79 |

Concentrate compositions containing lecithin and Fluorad FC-135 did not exhibit herbicidal effectiveness superior to commercial standard Formulations C and J in this test.

Example 34

Aqueous spray compositions were prepared containing glyphosate IPA salt and excipient ingredients as shown in Table 34a. Process (iii) was followed for all compositions, using soybean lecithin (20% phospholipid, Avanti). The pH of all compositions was adjusted to approximately 7.

TABLE 34a

| Spray composition | Lecithin g/l | % w/w Fluorad FC-135 |
|---|---|---|
| 34-01 | 0.25 |  |
| 34-02 | 0.05 |  |

TABLE 34a-continued

| Spray composition | Lecithin g/l | % w/w Fluorad FC-135 |
|---|---|---|
| 34-03 | 0.02 | |
| 34-04 | 0.01 | |
| 34-05 | 0.25 | 0.25 |
| 34-06 | 0.05 | 0.05 |
| 34-07 | 0.02 | 0.02 |
| 34-08 | 0.01 | 0.01 |

Guineagrass (*Panicum maximum*, PANMA) plants were grown and treated by the standard procedures given above. Applications of spray compositions were made 78 days after planting PANMA, and evaluation of herbicidal inhibition was done 20 days after application.

In addition to composition 34-01 to 34-08, spray compositions were prepared by tank mixing Formulation B and C with Fluorad FC-135 at various concentrations. Forumlations B and C alone were applied as comparative treatments. Results, averaged for all replicates of each treatment, are shown in Table 34b.

TABLE 34b

| Spray composition | Glyphosate rate g a.e./ha | % Inhibition PANMA |
|---|---|---|
| Formulation B | 400 | 61 |
| | 800 | 89 |
| | 1500 | 93 |
| | 2000 | 97 |
| Formulation C | 400 | 85 |
| | 800 | 94 |
| | 1500 | 100 |
| | 2000 | 100 |
| Formulation B + Fluorad FC-135 0.25% w/v | 400 | 76 |
| | 800 | 78 |
| | 1500 | 97 |
| Formulation B + Fluorad FC-135 0.05% w/v | 400 | 45 |
| | 800 | 69 |
| | 1500 | 89 |
| Formulation B + Fluorad FC-135 0.02% w/v | 400 | 39 |
| | 800 | 71 |
| | 1500 | 95 |
| Formulation B + Fluorad FC-135 0.01% w/v | 400 | 52 |
| | 800 | 78 |
| | 1500 | 99 |
| Formulation C + Fluorad FC-135 0.25% w/v | 400 | 82 |
| | 800 | 97 |
| | 1500 | 100 |
| Formulation C + Fluorad FC-135 0.05% w/v | 400 | 63 |
| | 800 | 93 |
| | 1500 | 100 |
| Formulation C + Fluorad FC-135 0.02% w/v | 400 | 73 |
| | 800 | 98 |
| | 1500 | 100 |
| Formulation C + Fluorad FC-135 0.01% w/v | 400 | 66 |
| | 800 | 97 |
| | 1500 | 100 |
| 34-01 | 400 | 38 |
| | 800 | 73 |
| | 1500 | 92 |
| 34-02 | 400 | 64 |
| | 800 | 83 |
| | 1500 | 90 |
| 34-03 | 400 | 50 |
| | 800 | 75 |
| | 1500 | 99 |
| 34-04 | 400 | 48 |
| | 800 | 88 |
| | 1500 | 98 |
| 34-05 | 400 | 60 |
| | 800 | 79 |
| | 1500 | 99 |

TABLE 34b-continued

| Spray composition | Glyphosate rate g a.e./ha | % Inhibition PANMA |
|---|---|---|
| 34-06 | 400 | 58 |
| | 800 | 86 |
| | 1500 | 99 |
| 34-07 | 400 | 55 |
| | 800 | 86 |
| | 1500 | 93 |
| 34-08 | 400 | 60 |
| | 800 | 91 |
| | 1500 | 98 |

Exceptionally high glyphosate activity was seen in this test even with Formulation B and no firm conclusions can be drawn. However, none of the compositions containing lecithin and Fluorad FC-135 exceeded the effectiveness of commercial standard Formulation C on PANMA under the conditions of this test.

Example 35

Aqueous concentrate compositions were prepared containing glyphosate IPA salt and excipient ingredients as shown in Table 35a. Process (v) was followed for all compositions, using soybean lecithin (20% phospholipid, Avanti). The pH of all compositions was approximately 5.

TABLE 35a

| Concentrate composition | % w/w | | | | | |
|---|---|---|---|---|---|---|
| | Glyphosate a.e. | Lecithin | Fluorad FC-135 | Fluorad FC-754 | MON 0818 | Agrimul PG-2069 |
| 35-01 | 30 | 3.0 | 3.0 | | | 0.25 |
| 35-02 | 30 | 3.0 | 1.0 | | | 0.25 |
| 35-03 | 30 | 3.0 | 3.0 | | 0.25 | |
| 35-04 | 30 | 1.0 | 3.0 | | 0.50 | |
| 35-05 | 30 | 1.0 | 3.0 | | | 0.50 |
| 35-06 | 30 | 1.0 | 1.0 | | | |
| 35-07 | 30 | 1.0 | 1.0 | | | 0.25 |
| 35-08 | 30 | 3.0 | 2.0 | | | 0.50 |
| 35-09 | 30 | 2.0 | 3.0 | | | |
| 35-10 | 30 | 3.0 | | | 0.50 | |
| 35-11 | 30 | 3.0 | | 3.0 | | 0.50 |
| 35-12 | 30 | 2.0 | 1.0 | | | 0.375 |
| 35-13 | 30 | 1.0 | | 2.0 | | 0.25 |
| 35-14 | 30 | 3.0 | 3.0 | | 0.50 | |
| 35-15 | 30 | 3.0 | 3.0 | | | 0.50 |
| 35-16 | 30 | 2.0 | 1.0 | | | 0.375 |
| 35-17 | 30 | 1.0 | | 2.0 | | 0.25 |
| 35-18 | 30 | 3.0 | 3.0 | | 0.50 | |

Quackgrass (*Elymus repens*, AGRRE) plants were grown and treated by the standard procedures given above. Applications of spray compositions were made 56 days after planting AGRRE, and evaluation of herbicidal inhibition was done 16 days after application.

Formulations B, C and J were applied as comparative treatments. Results, averaged for all replicates of each treatment, are shown in Table 35b.

TABLE 35b

| Concentrate composition | Glyphosate rate g a.e./ha | % Inhibition AGRRE |
|---|---|---|
| Formulation B | 400 | 41 |
| | 800 | 46 |
| | 1000 | 55 |
| | 1200 | 70 |

TABLE 35b-continued

| Concentrate composition | Glyphosate rate g a.e./ha | % Inhibition AGRRE |
|---|---|---|
| Formulation C | 400 | 38 |
|  | 800 | 47 |
|  | 1000 | 77 |
|  | 1200 | 77 |
| Formulation J | 400 | 60 |
|  | 800 | 84 |
|  | 1000 | 77 |
|  | 1200 | 85 |
| 35-01 | 400 | 27 |
|  | 800 | 76 |
|  | 1000 | 79 |
| 35-02 | 400 | 49 |
|  | 800 | 66 |
|  | 1000 | 78 |
| 35-03 | 400 | 42 |
|  | 800 | 80 |
|  | 1000 | 83 |
| 35-04 | 400 | 31 |
|  | 800 | 71 |
|  | 1000 | 64 |
| 35-05 | 400 | 32 |
|  | 800 | 53 |
|  | 1000 | 59 |
| 35-06 | 400 | 27 |
|  | 800 | 39 |
|  | 1000 | 65 |
| 35-07 | 400 | 29 |
|  | 800 | 54 |
|  | 1000 | 61 |
| 35-08 | 400 | 38 |
|  | 800 | 65 |
|  | 1000 | 81 |
| 35-09 | 400 | 31 |
|  | 800 | 55 |
|  | 1000 | 67 |
| 35-10 | 400 | 43 |
|  | 800 | 38 |
|  | 1000 | 58 |
| 35-11 | 400 | 34 |
|  | 800 | 56 |
|  | 1000 | 75 |
| 35-12 | 400 | 29 |
|  | 800 | 51 |
|  | 1000 | 65 |
| 35-13 | 400 | 51 |
|  | 800 | 69 |
|  | 1000 | 83 |
| 35-14 | 400 | 39 |
|  | 800 | 63 |
|  | 1000 | 65 |
| 35-15 | 400 | 53 |
|  | 800 | 65 |
|  | 1000 | 77 |
| 35-16 | 400 | 43 |
|  | 800 | 65 |
|  | 1000 | 82 |
| 35-17 | 400 | 69 |
|  | 800 | 84 |
|  | 1000 | 94 |
| 35-18 | 400 | 69 |
|  | 800 | 92 |
|  | 1000 | 92 |

Compositions of the invention exhibiting superior herbicidal effectiveness to commercial standard Formulation C in this test on AGRRE included 35-01, 35-02, 35-03, 35-13 and 35-15 to 35-18. Compositions 35-17 and 35-18 were the most effective in this test, outperforming commercial standard Formulation J as well as Formulation C.

Example 36

Aqueous concentrate compositions were prepared containing glyphosate IPA salt and excipient ingredients as shown in Table 36a. Process (v) was followed for all compositions, using soybean lecithin (20% phospholipid, Avanti). The order of addition of ingredients was varied in compositions 36-15 to 36-20 as shown below. The pH of all compositions was approximately 5.

TABLE 36a

| Conc. comp. | % w/w Glyphosate a.e. | Lecithin | Fluorad FC-135 | Agrimul PG-2069 | MON 0818 | Lecithin phospholipid % | order of addition (*) |
|---|---|---|---|---|---|---|---|
| 36-01 | 30 | 3.0 | 2.0 | 0.50 |  | 45 | A |
| 36-02 | 30 | 3.0 | 3.0 | 0.50 |  | 45 | A |
| 36-03 | 30 | 3.0 | 3.0 | 0.75 |  | 45 | A |
| 36-04 | 30 | 3.0 | 3.0 | 0.75 | 0.5 | 45 | A(**) |
| 36-05 | 30 | 3.0 | 3.0 | 1.00 |  | 45 | A |
| 36-06 | 30 | 3.0 | 3.0 | 2.00 |  | 45 | A |
| 36-07 | 30 | 3.0 | 3.0 | 3.00 |  | 45 | A |
| 36-08 | 30 | 3.0 | 3.0 | 4.00 |  | 45 | A |
| 36-09 | 30 | 3.0 | 2.0 | 0.50 |  | 20 | A |
| 36-10 | 30 | 3.0 | 2.0 | 0.50 |  | 20 | B |
| 36-11 | 30 | 3.0 | 2.0 | 0.50 |  | 20 | C |
| 36-12 | 30 | 3.0 | 2.0 | 0.50 |  | 20 | D |
| 36-13 | 30 | 3.0 | 2.0 | 0.50 |  | 20 | E |
| 36-14 | 30 | 3.0 | 2.0 | 0.50 |  | 20 | F |
| 36-15 | 30 | 3.0 | 3.0 | 0.50 |  | 20 | A |
| 36-16 | 30 | 3.0 | 3.0 | 0.50 |  | 20 | B |
| 36-17 | 30 | 3.0 | 3.0 | 0.50 |  | 20 | C |
| 36-18 | 30 | 3.0 | 3.0 | 0.50 |  | 20 | D |
| 36-19 | 30 | 3.0 | 3.0 | 0.50 |  | 20 | E |
| 36-20 | 30 | 3.0 | 3.0 | 0.50 |  | 20 | F |

TABLE 36a-continued (*) Order of addition:

| | 1st | 2nd | 3rd | 4th | 5th |
|---|---|---|---|---|---|
| A | lecithin | PG-2069 | FC-135 | water | glyphosate |
| B | lecithin | FC-135 | PG-2069 | water | glyphosate |
| C | glyphosate | water | FC-135 | PG-2069 | lecithin |
| D | glyphosate | water | PG-2069 | FC-135 | lecithin |
| E | glyphosate | lecithin | PG-2069 | FC-135 | water |
| F | glyphosate | lecithin | FC-135 | PG-2069 | water |

(**)where MON 0818 included, added with Agrimul PG-2069

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 22 days after planting ECHCF, and evaluation of herbicidal inhibition was done 17 days after application.

Formulations B, C and J were applied as comparative treatments. Results, average for all replicates of each treatment, are shown in Table 36b.

TABLE 36b

| Concentrate composition | Glyphosate rate g a.e./ha | % Inhibition ABUTH | % Inhibition ECHCF |
|---|---|---|---|
| Formulation B | 200 | 38 | 73 |
| | 400 | 51 | 64 |
| | 600 | 67 | 89 |
| | 800 | 72 | 86 |
| Formulation C | 200 | 57 | 75 |
| | 400 | 77 | 98 |
| | 600 | 92 | 97 |
| | 800 | 100 | 100 |
| Formulation J | 200 | 50 | 52 |
| | 400 | 73 | 99 |
| | 600 | 88 | 99 |
| | 800 | 98 | 98 |
| 36-01 | 200 | 49 | 64 |
| | 400 | 72 | 59 |
| | 600 | 78 | 87 |
| 36-02 | 200 | 54 | 72 |
| | 400 | 78 | 71 |
| | 600 | 97 | 90 |
| 36-03 | 200 | 57 | 62 |
| | 400 | 80 | 78 |
| | 600 | 89 | 87 |
| 36-04 | 200 | 46 | 39 |
| | 400 | 74 | 64 |
| | 600 | 86 | 78 |
| 36-05 | 200 | 49 | 29 |
| | 400 | 74 | 79 |
| | 600 | 83 | 90 |
| 36-06 | 200 | 49 | 65 |
| | 400 | 70 | 88 |
| | 600 | 87 | 88 |
| 36-07 | 200 | 49 | 51 |
| | 400 | 67 | 77 |
| | 600 | 81 | 83 |
| 36-08 | 200 | 42 | 59 |
| | 400 | 70 | 67 |
| | 600 | 78 | 80 |
| 36-09 | 200 | 45 | 28 |
| | 400 | 73 | 85 |
| | 600 | 87 | 98 |
| 36-10 | 200 | 57 | 82 |
| | 400 | 76 | 89 |
| | 600 | 87 | 98 |

TABLE 36b-continued

| Concentrate composition | Glyphosate rate g a.e./ha | % Inhibition ABUTH | % Inhibition ECHCF |
|---|---|---|---|
| 36-11 | 200 | 56 | 80 |
| | 400 | 84 | 84 |
| | 600 | 85 | 100 |
| 36-12 | 200 | 57 | 81 |
| | 400 | 78 | 98 |
| | 600 | 87 | 94 |
| 36-13 | 200 | 54 | 86 |
| | 400 | 73 | 72 |
| | 600 | 96 | 97 |
| 36-14 | 200 | 56 | 73 |
| | 400 | 69 | 98 |
| | 600 | 85 | 94 |
| 36-15 | 200 | 40 | 41 |
| | 400 | 85 | 88 |
| | 600 | 83 | 96 |
| 36-16 | 200 | 53 | 59 |
| | 400 | 73 | 76 |
| | 600 | 84 | 73 |
| 36-17 | 200 | 39 | 53 |
| | 400 | 65 | 86 |
| | 600 | 86 | 81 |
| 36-18 | 200 | 49 | 31 |
| | 400 | 69 | 52 |
| | 600 | 73 | 75 |
| 36-19 | 200 | 47 | 50 |
| | 400 | 74 | 86 |
| | 600 | 88 | 98 |
| 36-20 | 200 | 51 | 42 |
| | 400 | 68 | 94 |
| | 600 | 90 | 98 |

Order of addition of ingredients apparently had some influence on herbicidal effectiveness of compositions 36-09 to 36-20. However, as most of these compositions showed poor short-term stability, it is likely that in at least some cases the uniformity of spray application was affected and the results are therefore difficult to interpret.

Example 37

Aqueous concentrate compositions were prepared containing glyphosate IPA salt and excipient ingredients as shown in Table 37a. Process (iv) was followed for all compositions, using soybean lecithin (20% phospholipid, Avanti). The pH of all compositions was approximately 5.

TABLE 37a

| Concentrate composition | Glyphosate g a.e./l | % w/w | | | | | |
|---|---|---|---|---|---|---|---|
| | | Lecithin | Aerosol OT | MON 0818 | Fluorad FC-754 | Methyl caprate | PVA |
| 37-01 | 200 | 2.0 | | 0.25 | | | |
| 37-02 | 300 | 3.0 | | 0.50 | | | |
| 37-03 | 300 | 3.0 | | 0.50 | | | 2.0 |
| 37-04 | 200 | 2.0 | | 0.25 | | | 1.5 |
| 37-05 | 200 | 2.0 | | 0.25 | | 1.0 | 1.0 |
| 37-06 | 200 | 2.0 | | 0.25 | | 1.0 | 1.0 |
| 37-07 | 200 | 2.0 | | 0.25 | 2.0 | | |
| 37-08 | 200 | | 2.0 | 0.25 | | | |
| 37-09 | 300 | | 3.0 | 0.50 | | | |
| 37-10 | 300 | | 3.0 | 0.50 | | | 2.0 |
| 37-11 | 200 | | 2.0 | 0.25 | | | 1.5 |
| 37-12 | 200 | | 2.0 | 0.25 | | 1.0 | |
| 37-13 | 200 | | 2.0 | 0.25 | | 1.0 | |
| 37-14 | 200 | | 2.0 | 0.25 | | 1.0 | 1.5 |
| 37-15 | 200 | | 2.0 | 0.25 | 2.0 | | |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 13 days after planting ECHCF, and evaluation of herbicidal inhibition was done 20 days after application.

Composition containing PVA were too vicous to spray and were not tested for herbicidal effectiveness. Formulations B, C and J were applied as comparative treatments. Results, average for all replicates of each treatment, are shown in Table 37b.

TABLE 37b

| Concentrate composition | Glyphosate rate g a.e./ha | % Inhibition | |
|---|---|---|---|
| | | ABUTH | ECHCF |
| Formulation B | 112 | 5 | 4 |
| | 224 | 48 | 8 |
| | 336 | 73 | 20 |
| | 448 | 94 | 50 |
| Formulation C | 112 | 30 | 45 |
| | 224 | 91 | 81 |
| | 336 | 98 | 81 |
| | 448 | 100 | 99 |
| Formulation J | 112 | 50 | 35 |
| | 224 | 80 | 65 |
| | 336 | 97 | 88 |
| | 448 | 100 | 90 |
| 37-01 | 112 | 11 | 8 |
| | 224 | 50 | 40 |
| | 336 | 71 | 61 |
| | 448 | 93 | 78 |
| 37-02 | 112 | 5 | 6 |
| | 224 | 64 | 58 |
| | 336 | 78 | 60 |
| | 448 | 84 | 65 |
| 37-07 | 112 | 5 | 3 |
| | 224 | 46 | 38 |
| | 336 | 73 | 83 |
| | 448 | 93 | 66 |
| 37-08 | 112 | 8 | 13 |
| | 224 | 43 | 46 |
| | 336 | 73 | 65 |
| | 448 | 83 | 70 |
| 37-09 | 112 | 1 | 5 |
| | 224 | 23 | 25 |
| | 336 | 65 | 33 |
| | 448 | 91 | 58 |
| 37-12 | 112 | 0 | 5 |
| | 224 | 58 | 48 |
| | 336 | 73 | 63 |
| | 448 | 91 | 63 |
| 37-13 | 112 | 0 | 10 |
| | 224 | 53 | 38 |
| | 336 | 73 | 45 |
| | 448 | 88 | 50 |
| 37-15 | 112 | 28 | 10 |
| | 224 | 50 | 53 |
| | 336 | 80 | 63 |
| | 448 | 88 | 91 |

Concentrate compositions containing lecithin and Fluorad FC-754 or methyl caprate did not exhibit herbicidal effectiveness equal to that of the commercial standards in this test.

Example 38

Aqueous concentrate compositions were prepared containing glyphosate IPA salt and excipient ingredients as shown in Table 38a. Process (iii) was followed for all compositions, using soybean lecithin (20% phospholipid, Avanti). The pH of all compositions was approximately 5.

TABLE 38a

| Concentrate composition | Glyphosate a.e. | % w/w | | |
|---|---|---|---|---|
| | | Lecithin | Fluorad FC-135 | MON 0818 |
| 38-01 | 30 | 3.0 | 3.0 | 0.75 |
| 38-02 | 25 | 2.5 | 2.5 | 0.63 |
| 38-03 | 20 | 2.0 | 2.0 | 0.50 |
| 38-04 | 15 | 1.5 | 1.5 | 0.38 |
| 38-05 | 10 | 1.0 | 1.0 | 0.25 |
| 38-06 | 5 | 0.5 | 0.5 | 0.13 |
| 38-07 | 30 | 3.0 | 3.0 | 1.50 |
| 38-08 | 25 | 2.5 | 2.5 | 0.63 |
| 38-09 | 20 | 2.0 | 2.0 | 0.50 |
| 38-10 | 15 | 1.5 | 1.5 | 0.38 |
| 38-11 | 10 | 1.0 | 1.0 | 0.25 |

TABLE 38a-continued

| Concentrate composition | Glyphosate a.e. | Lecithin | Fluorad FC-135 | MON 0818 |
|---|---|---|---|---|
| | % w/w | | | |
| 38-12 | 5 | 0.5 | 0.5 | 0.13 |
| 38-13 | 25 | 2.5 | 2.5 | 0.94 |
| 38-14 | 20 | 2.0 | 2.0 | 0.75 |
| 38-15 | 15 | 1.5 | 1.5 | 0.56 |
| 38-16 | 10 | 1.0 | 1.0 | 0.38 |
| 38-17 | 5 | 0.5 | 0.5 | 0.19 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 14 days after application.

In addition to compositions 38-01 to 38-17, spray compositions were prepared by tank mixing Formulations B and C with Fluorad FC-135 at two concentrations. Formulations B and C alone were applied as comparative treatments. Results, averaged for all replicates of each treatment, are shown in Table 38b.

TABLE 38b

| Concentrate composition | Glyphosate rate g a.e./ha | % Inhibition ABUTH | ECHCF |
|---|---|---|---|
| Formulation C | 200 | 59 | 98 |
| | 400 | 96 | 96 |
| | 600 | 70 | 93 |
| | 800 | 100 | 97 |
| Formulation C + Fluorad FC-135 0.1% | 200 | 59 | 92 |
| | 400 | 93 | 93 |
| | 600 | 95 | 100 |
| | 800 | 100 | 97 |
| Formulation C + Fluorad FC-135 0.05% | 200 | 54 | 73 |
| | 400 | 95 | 76 |
| | 600 | 100 | 82 |
| | 800 | 100 | 95 |
| Formulation J | 200 | 55 | 87 |
| | 400 | 92 | 98 |
| | 600 | 97 | 94 |
| | 800 | 99 | 96 |
| Formulation J + Fluorad FC-135 0.1% | 200 | 67 | 88 |
| | 400 | 89 | 89 |
| | 600 | 94 | 87 |
| | 800 | 96 | 91 |
| Formulation J + Fluorad FC-135 0.05% | 200 | 71 | 81 |
| | 400 | 75 | 95 |
| | 600 | 96 | 99 |
| | 800 | 100 | 100 |
| 38-01 | 200 | 53 | 71 |
| | 400 | 74 | 87 |
| | 600 | 98 | 87 |
| 38-02 | 200 | 51 | 70 |
| | 400 | 88 | 96 |
| | 600 | 89 | 99 |
| 38-03 | 200 | 51 | 85 |
| | 400 | 81 | 97 |
| | 600 | 96 | 94 |
| 38-04 | 200 | 51 | 63 |
| | 400 | 81 | 82 |
| | 600 | 96 | 97 |
| 38-05 | 200 | 47 | 60 |
| | 400 | 73 | 91 |
| | 600 | 94 | 94 |
| 38-06 | 200 | 54 | 43 |
| | 400 | 73 | 88 |
| | 600 | 92 | 87 |

TABLE 38b-continued

| Concentrate composition | Glyphosate rate g a.e./ha | % Inhibition ABUTH | ECHCF |
|---|---|---|---|
| 38-07 | 200 | 60 | 70 |
| | 400 | 84 | 93 |
| | 600 | 90 | 98 |
| 38-08 | 200 | 49 | 55 |
| | 400 | 76 | 92 |
| | 600 | 88 | 83 |
| 38-09 | 200 | 57 | 53 |
| | 400 | 79 | 95 |
| | 600 | 91 | 87 |
| 38-10 | 200 | 55 | 85 |
| | 400 | 90 | 97 |
| | 600 | 94 | 96 |
| 38-11 | 200 | 64 | 43 |
| | 400 | 77 | 87 |
| | 600 | 93 | 96 |
| 38-12 | 200 | 54 | 72 |
| | 400 | 85 | 98 |
| | 600 | 96 | 100 |
| 38-13 | 200 | 61 | 61 |
| | 400 | 84 | 90 |
| | 600 | 95 | 99 |
| 38-14 | 200 | 57 | 86 |
| | 400 | 82 | 90 |
| | 600 | 99 | 98 |
| 38-15 | 200 | 59 | 89 |
| | 400 | 78 | 96 |
| | 600 | 93 | 97 |
| 38-16 | 200 | 53 | 87 |
| | 400 | 81 | 98 |
| | 600 | 96 | 98 |
| 38-17 | 200 | 48 | 87 |
| | 400 | 81 | 100 |
| | 600 | 91 | 100 |

As concentrate compositions in previous Examples have tended to exhibit weaker herbicidal effectiveness than has been seen with ready-made spray compositions, this test was conducted to determine if the degree of concentration at which a composition is prepared before dilution for spraying had an influence on effectiveness. No consistent trend was seen in this test.

Example 39

Aqueous concentrate compositions were prepared containing glyphosate IPA salt and excipient ingredients as shown in Table 39a. Process (iii) was followed for all compositions, using soybean lecithin (45% phospholipid, Avanti). The pH of all compositions was approximately 5.

TABLE 39a

| Conc. comp. | Glyphosate a.e. | Lecithin | Fluorad FC-135 or FC-754 | Amine surfactant | Type of amine surfactant |
|---|---|---|---|---|---|
| | | | % w/w | | |
| 39-01 | 20 | 2.0 | | 0.25 | MON 0818 |
| 39-02 | 20 | 3.0 | | 0.25 | MON 0818 |
| 39-03 | 20 | 3.0 | 3.0 (135) | 0.25 | MON 0818 |
| 39-04 | 20 | 3.0 | 3.0 (754) | 0.25 | MON 0818 |
| 39-05 | 20 | 2.0 | | 2.00 | Triton RW-20 |
| 39-06 | 20 | 2.0 | | 2.00 | Triton RW-50 |
| 39-07 | 20 | 2.0 | | 2.00 | Triton RW-75 |
| 39-08 | 20 | 2.0 | | 2.00 | Triton RW-100 |
| 39-09 | 20 | 2.0 | | 2.00 | Triton RW-150 |
| 39-10 | 20 | | | 2.00 | Triton RW-20 |
| 39-11 | 20 | | | 2.00 | Triton RW-50 |
| 39-12 | 20 | | | 2.00 | Triton RW-75 |
| 39-13 | 20 | | | 2.00 | Triton RW-100 |
| 39-14 | 20 | | | 2.00 | Triton RW-150 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 21 days after application.

Formulation C was applied as a comparative treatment. Results, averaged for all replicates of each treatment, are shown in Table 39b.

TABLE 39b

| Concentrate composition | Glyphosate rate g a.e./ha | % Inhibition ABUTH | % Inhibition ECHCF |
|---|---|---|---|
| Formulation C | 112 | 0 | 10 |
| | 224 | 10 | 20 |
| | 336 | 47 | 30 |
| | 448 | 63 | 40 |
| 39-01 | 112 | 8 | 15 |
| | 224 | 25 | 35 |
| | 336 | 55 | 56 |
| | 448 | 63 | 65 |
| 39-02 | 112 | 5 | 10 |
| | 224 | 23 | 33 |
| | 336 | 55 | 64 |
| | 448 | 66 | 60 |
| 39-03 | 112 | 28 | 15 |
| | 224 | 55 | 35 |
| | 336 | 74 | 58 |
| | 448 | 76 | 65 |
| 39-04 | 112 | 15 | 8 |
| | 224 | 53 | 45 |
| | 336 | 73 | 55 |
| | 448 | 75 | 64 |
| 39-05 | 112 | 0 | 8 |
| | 224 | 14 | 45 |
| | 336 | 45 | 70 |
| | 448 | 65 | 66 |
| 39-06 | 112 | 1 | 13 |
| | 224 | 5 | 43 |
| | 336 | 58 | 64 |
| | 448 | 66 | 75 |
| 39-07 | 112 | 0 | 15 |
| | 224 | 1 | 53 |
| | 336 | 45 | 78 |
| | 448 | 60 | 83 |
| 39-08 | 112 | 0 | 10 |
| | 224 | 25 | 45 |
| | 336 | 50 | 79 |
| | 448 | 68 | 88 |
| 39-09 | 112 | 0 | 13 |
| | 224 | 13 | 45 |
| | 336 | 50 | 75 |
| | 448 | 70 | 81 |
| 39-10 | 112 | 0 | 18 |
| | 224 | 18 | 35 |
| | 336 | 48 | 65 |
| | 448 | 66 | 76 |
| 39-11 | 112 | 1 | 0 |
| | 224 | 35 | 25 |
| | 336 | 38 | 55 |
| | 448 | 50 | 78 |
| 39-12 | 112 | 8 | 25 |
| | 224 | 10 | 38 |
| | 336 | 48 | 70 |
| | 448 | 73 | 81 |
| 39-13 | 112 | 0 | 25 |
| | 224 | 5 | 33 |
| | 336 | 30 | 70 |
| | 448 | 74 | 75 |
| 39-14 | 112 | 0 | 12 |
| | 224 | 0 | 30 |
| | 336 | 12 | 70 |
| | 448 | 40 | 80 |

No difference in herbicidal effectiveness was seen between compositions 39-03 and 39-04. The only difference between these compositions is that 39-03 contained Fluorad FC-135 and 39-04 contained Fluorad FC-754.

Example 40

Aqueous spray compositions were prepared containing glyphosate IPA salt and excipient ingredients as shown in Table 40a. Process (iii) was followed for all compositions, using soybean lecithin (20% or 45% phospholipid as indicated below, both sourced from Avanti). The pH of all compositions was adjusted to approximately 7.

TABLE 40a

| Spray composition | Lecithin g/l | Lecithin % purity | % w/w Fluorad FC-135 | Fluorad FC-754 |
|---|---|---|---|---|
| 40-01 | 1.0 | 20 | | |
| 40-02 | 0.5 | 20 | | |
| 40-03 | 0.2 | 20 | | |
| 40-04 | 1.0 | 20 | 0.10 | |
| 40-05 | 0.5 | 20 | 0.05 | |
| 40-06 | 0.2 | 20 | 0.02 | |
| 40-07 | 1.0 | 20 | | 0.10 |
| 40-08 | 0.5 | 20 | | 0.05 |
| 40-09 | 0.2 | 20 | 0.02 | 0.02 |
| 40-10 | 0.5 | 45 | 0.05 | |
| 40-11 | 0.5 | 45 | | 0.05 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 21 days after planting ECHCF, and evaluation of herbicidal inhibition was done 18 days after application.

In addition to compositions 40-01 to 40-11 spray compositions were prepared by tank mixing Formulations B and C with Fluorad FC-135 or FC-754 at various concentrations. Formulations B and C alone were applied as comparative treatments. Results, averaged for all replicates of each treatment, are shown in Table 40b.

TABLE 40b

| Spray composition | Glyphosate rate g a.e./ha | % Inhibition ABUTH | ECHCF |
|---|---|---|---|
| Formulation B | 150 | 49 | 100 |
| | 300 | 66 | 92 |
| | 500 | 80 | 76 |
| | 700 | 93 | 96 |
| Formulation C | 200 | 57 | 79 |
| | 400 | 93 | 98 |
| | 600 | 100 | 100 |
| | 800 | 100 | 100 |
| Formulation B + Fluorad FC-135 0.1% | 200 | 58 | 80 |
| | 400 | 63 | 100 |
| | 600 | 82 | 100 |
| Formulation B + Fluorad FC-135 0.05% | 200 | 37 | 49 |
| | 400 | 67 | 84 |
| | 600 | 74 | 100 |
| Formulation B + Fluorad FC-135 0.02% | 200 | 33 | 82 |
| | 400 | 58 | 94 |
| | 600 | 81 | 87 |
| Formation B + Fluorad FC-754 0.1% | 200 | 50 | 45 |
| | 400 | 77 | 82 |
| | 600 | 77 | 94 |
| Formulation B + Fluorad FC-754 0.05% | 200 | 44 | 45 |
| | 400 | 71 | 65 |
| | 600 | 74 | 90 |
| Formulation B + Fluorad FC-754 0.02% | 200 | 31 | 57 |
| | 400 | 67 | 83 |
| | 600 | 68 | 93 |
| Formulation C + Fluorad FC-135 0.1% | 200 | 69 | 65 |
| | 400 | 91 | 99 |
| | 600 | 97 | 100 |
| Formulation C + Fluorad FC-135 0.05% | 200 | 73 | 87 |
| | 400 | 89 | 100 |
| | 600 | 98 | 100 |
| Formulation C + Fluorad FC-135 0.02% | 200 | 51 | 60 |
| | 400 | 91 | 100 |
| | 600 | 98 | 100 |
| Formulation C + Fluorad FC-754 0.1% | 200 | 70 | 81 |
| | 400 | 85 | 99 |
| | 600 | 98 | 95 |
| Formulation C + Fluorad FC-754 0.05% | 200 | 68 | 54 |
| | 400 | 78 | 88 |
| | 600 | 91 | 88 |
| Formulation C + Fluorad FC-754 0.02% | 200 | 50 | 41 |
| | 400 | 89 | 91 |
| | 600 | 99 | 100 |
| 40-01 | 200 | 41 | 37 |
| | 400 | 78 | 84 |
| | 600 | 83 | 100 |
| 40-02 | 200 | 38 | 82 |
| | 400 | 74 | 94 |
| | 600 | 82 | 98 |
| 40-03 | 200 | 38 | 62 |
| | 400 | 69 | 85 |
| | 600 | 86 | 100 |
| 40-04 | 200 | 63 | 69 |
| | 400 | 79 | 75 |
| | 600 | 93 | 89 |
| 40-05 | 200 | 69 | 66 |
| | 400 | 85 | 81 |
| | 600 | 84 | 86 |
| 40-06 | 200 | 64 | 38 |
| | 400 | 79 | 74 |
| | 600 | 93 | 99 |
| 40-07 | 200 | 61 | 43 |
| | 400 | 76 | 71 |
| | 600 | 85 | 85 |
| 40-08 | 200 | 71 | 52 |
| | 400 | 82 | 85 |
| | 600 | 82 | 100 |
| 40-09 | 200 | 63 | 55 |
| | 400 | 83 | 73 |
| | 600 | 79 | 97 |
| 40-10 | 200 | 65 | 54 |
| | 400 | 78 | 80 |
| | 600 | 85 | 99 |
| 40-11 | 200 | 55 | 33 |
| | 400 | 77 | 74 |
| | 600 | 91 | 97 |

There was a tendency, although not consistently so, for compositions of this Example containing Fluorad FC-754 to show slightly weaker herbicidal effectiveness than corresponding compositions containing Fluorad FC-135.

Example 41

Aqueous concentrate compositions were prepared containing glyphosate IPA salt and excipient ingredients as shown in Table 41a. Process (v) was followed for all compositions, using soybean lecithin (45% phospholipid, Avanti). The pH of all compositions was approximately 5.

TABLE 41a

| Concentrate composition | Glyphosate a.e. | Lecithin | Fluorad FC-135 | Fluorad FC-754 | MON 0818 |
|---|---|---|---|---|---|
| 41-01 | 15.0 | 4.0 | 8.0 | | 0.5 |
| 41-02 | 15.0 | 6.0 | 8.0 | | 0.5 |
| 41-03 | 15.0 | 8.0 | 8.0 | | 0.5 |
| 41-04 | 10.0 | 4.0 | 8.0 | | 0.5 |
| 41-05 | 10.0 | 6.0 | 8.0 | | 0.5 |
| 41-06 | 10.0 | 8.0 | 8.0 | | 0.5 |
| 41-07 | 5.0 | 4.0 | 8.0 | | 0.5 |
| 41-08 | 5.0 | 6.0 | 8.0 | | 0.5 |

TABLE 41a-continued

| Concentrate composition | Glyphosate a.e. | Lecithin | Fluorad FC-135 | Fluorad FC-754 | MON 0818 |
|---|---|---|---|---|---|
| 41-09 | 5.0 | 8.0 | 8.0 | | 0.5 |
| 41-10 | 15.0 | 4.0 | | 8.0 | 0.5 |
| 41-11 | 15.0 | 6.0 | | 8.0 | 0.5 |
| 41-12 | 15.0 | 8.0 | | 8.0 | 0.5 |
| 41-13 | 10.0 | 4.0 | | 8.0 | 0.5 |
| 41-14 | 10.0 | 6.0 | | 8.0 | 0.5 |
| 41-15 | 10.0 | 8.0 | | 8.0 | 0.5 |
| 41-16 | 5.0 | 4.0 | | 8.0 | 0.5 |
| 41-17 | 5.0 | 6.0 | | 8.0 | 0.5 |
| 41-18 | 5.0 | 8.0 | | 8.0 | 0.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 20 days after planting ECHCF, and evaluation of herbicidal inhibition was done 15 days after application.

In addition to compositions 41-01 to 41-18, spray compositions were prepared by tank mixing Formulations B and J with Fluorad FC-135 at two concentrations. Formulations B and J alone were applied as comparative treatments. Results, averaged for all replicates of each treatment, are shown in Table 41b.

TABLE 41b

| Spray composition | Glyphosate rate g a.e./ha | % Inhibition ABUTH | % Inhibition ECHCF |
|---|---|---|---|
| Formulation B | 150 | 49 | 41 |
| | 300 | 41 | 55 |
| | 500 | 76 | 98 |
| | 700 | 82 | 100 |
| Formulation J | 150 | 59 | 66 |
| | 300 | 79 | 99 |
| | 500 | 93 | 99 |
| | 700 | 98 | 100 |
| Formulation B + Fluorad FC-135 0.1% | 150 | 52 | 85 |
| | 300 | 69 | 93 |
| | 500 | 89 | 97 |
| Formulation B + Fluorad FC-135 0.05% | 150 | 9 | 61 |
| | 300 | 71 | 77 |
| | 500 | 77 | 100 |
| Forrnulation J + Fluorad FC-135 0.1% | 150 | 52 | 99 |
| | 300 | 74 | 100 |
| | 500 | 82 | 99 |
| Formulation J + Fluorad FC-135 0.05% | 150 | 41 | 52 |
| | 300 | 77 | 83 |
| | 500 | 91 | 100 |
| 41-01 | 150 | 66 | 51 |
| | 300 | 86 | 91 |
| | 500 | 93 | 100 |
| 41-02 | 150 | 72 | 88 |
| | 300 | 89 | 93 |
| | 500 | 96 | 92 |
| 41-03 | 150 | 71 | 91 |
| | 300 | 89 | 95 |
| | 500 | 91 | 100 |
| 41-04 | 150 | 63 | 90 |
| | 300 | 89 | 89 |
| | 500 | 96 | 99 |
| 41-05 | 150 | 70 | 79 |
| | 300 | 84 | 94 |
| | 500 | 88 | 98 |
| 41-06 | 150 | 69 | 76 |
| | 300 | 89 | 84 |
| | 500 | 94 | 100 |
| 41-07 | 150 | 71 | 87 |
| | 300 | 77 | 82 |
| | 500 | 99 | 92 |
| 41-08 | 150 | 81 | 87 |
| | 300 | 88 | 94 |
| | 500 | 92 | 98 |
| 41-09 | 150 | 72 | 83 |
| | 300 | 87 | 83 |
| | 500 | 94 | 94 |
| 41-10 | 150 | 72 | 70 |
| | 300 | 81 | 80 |
| | 500 | 89 | 93 |
| 41-11 | 150 | 74 | 85 |
| | 300 | 87 | 96 |
| | 500 | 91 | 98 |
| 41-12 | 150 | 66 | 92 |
| | 300 | 78 | 98 |
| | 500 | 93 | 100 |
| 41-13 | 150 | 71 | 76 |
| | 300 | 86 | 95 |
| | 500 | 94 | 99 |
| 41-14 | 150 | 72 | 75 |
| | 300 | 90 | 97 |
| | 500 | 91 | 99 |
| 41-15 | 150 | 69 | 82 |
| | 300 | 85 | 98 |
| | 500 | 94 | 100 |
| 41-16 | 150 | 76 | 87 |
| | 300 | 86 | 100 |
| | 500 | 90 | 99 |
| 41-17 | 150 | 71 | 83 |
| | 300 | 87 | 94 |
| | 500 | 96 | 100 |
| 41-18 | 150 | 70 | 81 |
| | 300 | 77 | 98 |
| | 500 | 89 | 98 |

Good herbicidal effectiveness was obtained with the concentrate compositions of this Example containing lecithin and Fluorad FC-135 or Fluorad FC-754. No great or consistent difference was seen between compositions containing Fluorad FC-135 and their counterparts containing Fluorad FC-754.

Example 42

Aqueous concentrate compositions were prepared containing glyphosate IPA salt and excipient ingredients as shown in Table 42a. Process (v) was followed for all compositions. using soybean lecithin (95% phospholipid, Avanti). The pH of all compositions was approximately 5.

TABLE 42a

| Conc. comp. | Glyphosate a.e. | Lecithin | MON 0818 | Agrimul PG-2069 | Fluorad FC-135 | Fluorad FC-754 | Westvaco H-240 |
|---|---|---|---|---|---|---|---|
| 42-01 | 30 | 3.0 | | 0.25 | 3.0 | | 9.0 |
| 42-02 | 30 | 3.0 | | 0.25 | 1.0 | | 9.0 |
| 42-03 | 30 | 3.0 | 0.25 | | 3.0 | | 9.0 |
| 42-04 | 30 | 1.0 | 0.50 | | 3.0 | | 9.0 |
| 42-05 | 30 | 1.0 | | 0.50 | 3.0 | | 9.0 |
| 42-06 | 30 | 1.0 | | | 1.0 | | 9.0 |
| 42-07 | 30 | 1.0 | | 0.25 | 1.0 | | 9.0 |
| 42-08 | 30 | 3.0 | | 0.50 | 2.0 | | 9.0 |
| 42-09 | 30 | 2.0 | | | 3.0 | | 9.0 |
| 42-10 | 30 | 3.0 | | | | | 5.0 |
| 42-11 | 30 | 3.0 | | 0.50 | | 3.0 | 9.0 |
| 42-12 | 30 | 2.0 | | 0.38 | | 2.0 | 9.0 |
| 42-13 | 30 | 1.0 | | 0.25 | | 1.0 | 9.0 |
| 42-14 | 30 | 3.0 | 0.50 | | 3.0 | | 9.0 |
| 42-15 | 15 | 6.0 | 2.00 | | 8.3 | | |
| 42-16 | 15 | 6.0 | 4.00 | | 8.3 | | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 20 days after planting ECHCF, and evaluation of herbicidal inhibition was done 15 days after application.

In addition to compositions 42-01 to 42-16, spray compositions were prepared by tank mixing Formulations B and J with Fluorad FC-135 at two concentrations. Formulations B and J alone were applied as comparative treatments. Results, averaged for all replicates of each treatment, are shown in Table 42b.

TABLE 42b

| Concentrate composition | Glyphosate rate g a.e./ha | % Inhibition ABUTH | % Inhibition ECHCF |
|---|---|---|---|
| Formulation B | 150 | 3 | 33 |
| | 300 | 12 | 90 |
| | 500 | 65 | 98 |
| | 700 | 79 | 100 |
| Formulation J | 150 | 2 | 46 |
| | 300 | 76 | 100 |
| | 500 | 98 | 100 |
| | 700 | 98 | 100 |
| Formulation B + Fluorad FC-135 0.1% | 150 | 10 | 38 |
| | 300 | 50 | 85 |
| | 500 | 65 | 68 |
| Formulation B + Fluorad FC-135 0.05% | 150 | 3 | 27 |
| | 300 | 36 | 82 |
| | 500 | 68 | 99 |
| Formulation J + Fluorad FC-135 0.1% | 150 | 18 | 79 |
| | 300 | 57 | 98 |
| | 500 | 79 | 100 |
| Formulation J + Fluorad FC-135 0.05% | 150 | 2 | 37 |
| | 300 | 56 | 97 |
| | 500 | 96 | 98 |
| 42-01 | 150 | 2 | 27 |
| | 300 | 2 | 74 |
| | 500 | 46 | 78 |
| 42-02 | 150 | 2 | 52 |
| | 300 | 41 | 64 |
| | 500 | 40 | 85 |
| 42-03 | 150 | 3 | 38 |
| | 300 | 39 | 47 |
| | 500 | 73 | 98 |
| 42-04 | 150 | 3 | 38 |
| | 300 | 42 | 63 |
| | 500 | 78 | 84 |
| 42-05 | 150 | 5 | 29 |
| | 300 | 37 | 89 |
| | 500 | 70 | 99 |
| 42-06 | 150 | 8 | 37 |
| | 300 | 30 | 89 |
| | 500 | 69 | 97 |
| 42-07 | 150 | 5 | 53 |
| | 300 | 32 | 80 |
| | 500 | 83 | 99 |
| 42-08 | 150 | 3 | 26 |
| | 300 | 10 | 40 |
| | 500 | 12 | 55 |
| 42-09 | 150 | 7 | 21 |
| | 300 | 57 | 86 |
| | 500 | 91 | 97 |
| 42-10 | 150 | 21 | 61 |
| | 300 | 73 | 89 |
| | 500 | 85 | 98 |
| 42-11 | 150 | 6 | 23 |
| | 300 | 53 | 70 |
| | 500 | 85 | 83 |
| 42-12 | 150 | 33 | 25 |
| | 300 | 34 | 43 |
| | 500 | 83 | 97 |
| 42-13 | 150 | 7 | 34 |
| | 300 | 62 | 39 |
| | 500 | 77 | 73 |
| 42-14 | 150 | 10 | 27 |
| | 300 | 59 | 40 |
| | 500 | 84 | 73 |
| 42-15 | 150 | 71 | 48 |
| | 300 | 97 | 65 |
| | 500 | 99 | 92 |
| 42-16 | 150 | 83 | 40 |
| | 300 | 98 | 89 |
| | 500 | 100 | 95 |

The only concentrate compositions in this test exhibiting excellent performance, at least on ABUTH, were 42-15 and 42-16.

Example 43

Aqueous concentrate compositions were prepared containing glyphosate IPA salt and excipient ingredients as shown in Table 43a. Process (viii) was followed for composition 43-02 and process (ix) for compositions 43-03 to 43-13 which contain a colloidal particulate together with surfactant. Composition 43-01 contains colloidal particulate but no surfactant. The pH of all compositions was approximately 5.

TABLE 43a

| Concentrate composition | % w/w | | | |
|---|---|---|---|---|
| | Glyphosate a.e. | Fluorad FC-135 | Aerosil 90 | Emphos PS-21A |
| 43-01 | 20 | | 3.3 | |
| 43-02 | 20 | 3.3 | | |
| 43-03 | 31 | 1.1 | 3.3 | 1.1 |
| 43-04 | 31 | 1.1 | 3.3 | 2.2 |
| 43-05 | 31 | 1.1 | 3.3 | 3.3 |
| 43-06 | 31 | 2.2 | 3.3 | 1.1 |
| 43-07 | 31 | 2.2 | 3.3 | 2.2 |
| 43-08 | 31 | 2.2 | 3.3 | 3.3 |
| 43-09 | 31 | 3.3 | 3.3 | 1.1 |
| 43-10 | 31 | 3.3 | 3.3 | 2.2 |
| 43-11 | 31 | 3.3 | 3.3 | 3.3 |
| 43-12 | 31 | 3.3 | 3.3 | |
| 43-13 | 31 | | 3.3 | 3.3 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 23 days after application.

Formulations B, C and J were applied as comparative treatments. Results, averaged for all replicates of each treatment, are shown in Table 43b.

TABLE 43b

| Concentrate composition | Glyphosate rate g a.e./ha | % Inhibition | |
|---|---|---|---|
| | | ABUTH | ECHCF |
| Formulation B | 150 | 0 | 8 |
| | 250 | 18 | 25 |
| | 350 | 35 | 40 |
| | 450 | 75 | 50 |
| Formulation C | 150 | 30 | 85 |
| | 250 | 92 | 95 |
| | 350 | 100 | 100 |
| | 450 | 100 | 100 |
| Formulation J | 150 | 40 | 70 |
| | 250 | 70 | 83 |
| | 350 | 93 | 92 |
| | 450 | 100 | 98 |
| 43-01 | 150 | 20 | 25 |
| | 250 | 35 | 30 |
| | 350 | 65 | 43 |
| | 450 | 73 | 35 |
| 43-02 | 150 | 5 | 5 |
| | 250 | 20 | 25 |
| | 350 | 45 | 35 |
| | 450 | 66 | 83 |
| 43-03 | 150 | 20 | 11 |
| | 250 | 40 | 30 |
| | 350 | 73 | 64 |
| | 450 | 88 | 83 |
| 43-04 | 150 | 15 | 3 |
| | 250 | 30 | 25 |
| | 350 | 40 | 35 |
| | 450 | 71 | 75 |

TABLE 43b-continued

| Concentrate composition | Glyphosate rate g a.e./ha | % Inhibition | |
|---|---|---|---|
| | | ABUTH | ECHCF |
| 43-05 | 150 | 15 | 10 |
| | 250 | 33 | 30 |
| | 350 | 69 | 45 |
| | 450 | 78 | 65 |
| 43-06 | 150 | 11 | 8 |
| | 250 | 28 | 30 |
| | 350 | 30 | 35 |
| | 450 | 69 | 61 |
| 43-07 | 150 | 5 | 8 |
| | 250 | 13 | 20 |
| | 350 | 51 | 30 |
| | 450 | 74 | 43 |
| 43-08 | 150 | 15 | 8 |
| | 250 | 30 | 15 |
| | 350 | 35 | 30 |
| | 450 | 56 | 45 |
| 43-09 | 150 | 15 | 15 |
| | 250 | 28 | 20 |
| | 350 | 43 | 33 |
| | 450 | 45 | 40 |
| 43-10 | 150 | 5 | 3 |
| | 250 | 25 | 20 |
| | 350 | 50 | 40 |
| | 450 | 48 | 58 |
| 43-11 | 150 | 14 | 6 |
| | 250 | 25 | 40 |
| | 350 | 64 | 76 |
| | 450 | 78 | 79 |
| 43-12 | 150 | 9 | 20 |
| | 250 | 20 | 33 |
| | 350 | 46 | 73 |
| | 450 | 59 | 80 |
| 43-13 | 150 | 15 | 11 |
| | 250 | 20 | 28 |
| | 350 | 30 | 59 |
| | 450 | 68 | 48 |

Most concentrate compositions containing Fluorad FC-135 showed enhanced herbicidal effectiveness by comparison with Formulation B but did not equal the performance of commercial standard Formulations C and J under the conditions of this test.

Example 44

Aqueous concentrate compositions were prepared containing glyphosate IPA salt and excipient ingredients as shown in Table 44a. Process (viii) was followed for compositions 44-01, 44-03, 44-06, 44-07, 44-10, 44-14, 44-15, 44-18 and 44-19 process (ix) for compositions 44-02, 44-08, 44-09, 44-16 and 44-17 which contain a colloidal particulate together with surfactant. Compositions 44-04, 44-05, 44-12 and 44-13 contain colloidal particulate but no surfactant. The pH of all compositions was approximately 5.

TABLE 44a

| Concentrate composition | Glyphosate a.e. | Fluorad FC-135 | Ethomeen T/25 | Aluminum oxide C | Titanium dioxide P25 | Aerosol OT |
|---|---|---|---|---|---|---|
| | | | % w/w | | | |
| 44-01 | 20 | | 3.30 | | | |
| 44-02 | 20 | | | | | 3.30 |
| 44-03 | 20 | 3.30 | | | | |
| 44-04 | 20 | | | 3.30 | | |
| 44-05 | 20 | | | 0.67 | | |
| 44-06 | 20 | | 3.30 | 3.30 | | |
| 44-07 | 20 | | 3.30 | 0.67 | | |
| 44-08 | 20 | | | 3.30 | | 3.30 |
| 44-09 | 20 | | | 0.67 | | 3.30 |
| 44-10 | 20 | 3.30 | | 3.30 | | |
| 44-11 | 20 | 3.30 | | 0.67 | | |
| 44-12 | 20 | | | | 3.30 | |
| 44-13 | 20 | | | | 0.67 | |
| 44-14 | 20 | | 3.30 | | 3.30 | |
| 44-15 | 20 | | 3.30 | | 0.67 | |
| 44-16 | 20 | | | | 3.30 | 3.30 |
| 44-17 | 20 | | | | 0.67 | 3.30 |
| 44-18 | 20 | 3.30 | | | 3.30 | |
| 44-19 | 20 | 3.30 | | | 0.67 | |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 20 days after planting ECHCF, and evaluation of herbicidal inhibition was done 25 days after application.

Formulations B, C and J were applied as comparative treatments. Results, averaged for all replicates of each treatment. are shown in Table 44b.

TABLE 44b

| Concentrate composition | Glyphosate rate g a.e./ha | % Inhibition ABUTH | % Inhibition ECHCF |
|---|---|---|---|
| Formulation B | 150 | 8 | 45 |
| | 250 | 37 | 55 |
| | 350 | 40 | 60 |
| | 450 | 50 | 70 |
| Formulation C | 150 | 27 | 72 |
| | 250 | 73 | 92 |
| | 350 | 90 | 99 |
| | 450 | 92 | 99 |
| Formulation J | 150 | 25 | 66 |
| | 250 | 45 | 88 |
| | 350 | 78 | 99 |
| | 450 | 91 | 100 |
| 44-01 | 150 | 40 | 82 |
| | 250 | 55 | 93 |
| | 350 | 74 | 100 |
| | 450 | 83 | 100 |
| 44-02 | 150 | 9 | 20 |
| | 250 | 30 | 73 |
| | 350 | 38 | 73 |
| | 450 | 55 | 97 |
| 44-03 | 150 | 13 | 23 |
| | 250 | 35 | 79 |
| | 350 | 45 | 78 |
| | 450 | 75 | 100 |
| 44-04 | 150 | 18 | 45 |
| | 250 | 35 | 65 |
| | 350 | 35 | 70 |
| | 450 | 68 | 81 |
| 44-05 | 150 | 11 | 43 |
| | 250 | 35 | 50 |
| | 350 | 50 | 55 |
| | 450 | 59 | 78 |
| 44-06 | 150 | 25 | 75 |
| | 250 | 58 | 93 |
| | 350 | 88 | 100 |
| | 450 | 95 | 100 |
| 44-07 | 150 | 15 | 88 |
| | 250 | 68 | 100 |
| | 350 | 79 | 100 |
| | 450 | 90 | 100 |
| 44-08 | 150 | 28 | 38 |
| | 250 | 25 | 38 |
| | 350 | 35 | 55 |
| | 450 | 71 | 79 |
| 44-09 | 112 | 5 | 13 |
| | 224 | 23 | 48 |
| | 336 | 25 | 70 |
| | 448 | 45 | 64 |
| 44-10 | 150 | 1 | 20 |
| | 250 | 40 | 74 |
| | 350 | 65 | 55 |
| | 450 | 84 | 96 |
| 44-11 | 150 | 25 | 25 |
| | 250 | 35 | 65 |
| | 350 | 45 | 61 |
| | 450 | 76 | 92 |
| 44-12 | 150 | 14 | 28 |
| | 250 | 40 | 43 |
| | 350 | 45 | 70 |
| | 450 | 65 | 79 |
| 44-13 | 150 | 20 | 45 |
| | 250 | 48 | 33 |
| | 350 | 60 | 55 |
| | 450 | 80 | 79 |
| 44-14 | 150 | 23 | 79 |
| | 250 | 73 | 100 |
| | 350 | 76 | 99 |
| | 450 | 85 | 99 |
| 44-15 | 150 | 25 | 83 |
| | 250 | 69 | 99 |
| | 350 | 75 | 99 |
| | 450 | 91 | 100 |
| 44-16 | 150 | 14 | 28 |
| | 250 | 23 | 40 |
| | 350 | 30 | 79 |
| | 450 | 69 | 86 |

TABLE 44b-continued

| Concentrate composition | Glyphosate rate g a.e./ha | % Inhibition ABUTH | ECHCF |
|---|---|---|---|
| 44-17 | 150 | 1 | 20 |
|  | 250 | 23 | 33 |
|  | 350 | 16 | 45 |
|  | 450 | 40 | 68 |
| 44-18 | 150 | 8 | 15 |
|  | 250 | 49 | 56 |
|  | 350 | 55 | 58 |
|  | 450 | 83 | 83 |
| 44-19 | 150 | 6 | 15 |
|  | 250 | 35 | 60 |
|  | 350 | 61 | 63 |
|  | 450 | 63 | 70 |

Concentrate compositions containing Fluorad FC-135 showed enhanced herbicidal effectiveness by comparison with Formulation B but did not provide herbicidal effectiveness equal to commercial standard Formulations C and J in this test.

Example 45

Aqueous spray compositions were prepared containing glyphosate IPA salt and excipient ingredients as shown in Table 45a. Process (i) was followed for compositions 45-10 to 45-12 and process (iii) for compositions 45-01 to 45-09 using soybean lecithin (45% phospholipid, Avanti). The pH of all compositions was adjusted to approximately 7.

TABLE 45a

| Spray composition | % w/w Lecithin | Fluorad FC-135 | Surf H1 |
|---|---|---|---|
| 45-01 | 0.10 |  |  |
| 45-02 | 0.05 |  |  |
| 45-03 | 0.02 |  |  |
| 45-04 | 0.10 | 0.10 |  |
| 45-05 | 0.05 | 0.05 |  |
| 45-06 | 0.02 | 0.02 |  |
| 45-07 | 0.10 |  | 0.10 |
| 45-08 | 0.05 |  | 0.05 |
| 45-09 | 0.02 |  | 0.02 |
| 45-10 |  | 0.10 |  |
| 45-11 |  | 0.05 |  |
| 45-12 |  | 0.02 |  |

Velvetleaf (*Abutilon theophrasti*, ABUTH) and Japanese millet (*Echinochloa crus-galli*, ECHCF) plants were grown and treated by the standard procedures given above. Applications of spray compositions were made 23 days after planting ABUTH and 21 days after planting ECHCF, and evaluation of herbicidal inhibition was done 15 days after application.

In addition to compositions 45-01 to 45-12. spray compositions were prepared by tank mixing Formulations B and C with Fluorad FC-135 at various concentrations. Formulations B and C alone and Formulation J were applied as comparative treatments. Results, averaged for all replicates of each treatment, are shown in Table 45b.

TABLE 45b

| Spray composition | Glyphosate rate g a.e./ha | % Inhibition ABUTH | ECHCF |
|---|---|---|---|
| Formulation B | 150 | 16 | 21 |
|  | 250 | 68 | 32 |
|  | 350 | 68 | 63 |
|  | 450 | 67 | 69 |
| Formulation C | 150 | 29 | 47 |
|  | 250 | 76 | 74 |
|  | 350 | 98 | 94 |
|  | 450 | 100 | 85 |
| Formulation J | 150 | 37 | 31 |
|  | 250 | 79 | 72 |
|  | 350 | 93 | 82 |
|  | 450 | 97 | 97 |
| Formulation B + Fluorad FC-135 0.1% w/v | 150 | 55 | 15 |
|  | 250 | 73 | 28 |
|  | 350 | 85 | 57 |
|  | 450 | 83 | 83 |
| Formulation B + Fluorad FC-135 0.05% w/v | 150 | 59 | 15 |
|  | 250 | 77 | 41 |
|  | 350 | 81 | 72 |
|  | 450 | 77 | 51 |
| Formulation B + Fluorad FC-135 0.02% w/v | 150 | 25 | 12 |
|  | 250 | 54 | 27 |
|  | 350 | 82 | 38 |
|  | 450 | 75 | 47 |
| Formulation C + Fluorad FC-135 0.1% w/v | 150 | 51 | 26 |
|  | 250 | 78 | 63 |
|  | 350 | 86 | 71 |
|  | 450 | 89 | 79 |
| Formulation C + Fluorad FC-135 0.05% w/v | 150 | 58 | 23 |
|  | 250 | 74 | 89 |
|  | 350 | 93 | 78 |
|  | 450 | 89 | 91 |
| 45-01 | 150 | 29 | 26 |
|  | 250 | 61 | 47 |
|  | 350 | 73 | 48 |
|  | 450 | 82 | 62 |
| 45-02 | 150 | 34 | 34 |
|  | 250 | 67 | 34 |
|  | 350 | 73 | 54 |
|  | 450 | 85 | 43 |
| 45-03 | 150 | 20 | 29 |
|  | 250 | 60 | 49 |
|  | 350 | 68 | 84 |
|  | 450 | 74 | 64 |
| 45-04 | 150 | 78 | 24 |
|  | 250 | 83 | 33 |
|  | 350 | 96 | 64 |
|  | 450 | 97 | 59 |
| 45-05 | 150 | 81 | 21 |
|  | 250 | 89 | 27 |
|  | 350 | 82 | 34 |
|  | 450 | 99 | 31 |
| 45-06 | 150 | 92 | 14 |
|  | 250 | 85 | 64 |
|  | 350 | 86 | 31 |
|  | 450 | 90 | 60 |
| 45-07 | 150 | 71 | 27 |
|  | 250 | 81 | 46 |
|  | 350 | 84 | 66 |
|  | 450 | 88 | 62 |
| 45-08 | 150 | 46 | 29 |
|  | 250 | 70 | 43 |
|  | 350 | 78 | 61 |
|  | 450 | 86 | 58 |
| 45-09 | 150 | 55 | 25 |
|  | 250 | 76 | 33 |
|  | 350 | 80 | 50 |
|  | 450 | 78 | 62 |
| 45-10 | 150 | 65 | 26 |
|  | 250 | 85 | 28 |
|  | 350 | 91 | 37 |
|  | 450 | 89 | 53 |

TABLE 45b-continued

| Spray composition | Glyphosate rate g a.e./ha | % Inhibition ABUTH | % Inhibition ECHCF |
|---|---|---|---|
| 45-11 | 150 | 73 | 27 |
|  | 250 | 77 | 28 |
|  | 350 | 92 | 41 |
|  | 450 | 92 | 49 |
| 45-12 | 150 | 71 | 20 |
|  | 250 | 74 | 31 |
|  | 350 | 79 | 39 |
|  | 450 | 93 | 53 |

Extremely high herbicidal effectiveness was noted on ABUTH with compositions 45-04 to 45-06, containing lecithin and Fluorad FC-135. Replacement of Fluorad FC-135 by "Surf H1", a hydrocarbon-based surfactant of formula $C_{12}H_{25}SO_2NH(CH_2)_3N^+(CH_3)_3I^-$, gave (in compositions 45-07 to 45-09) effectiveness on ABUTH still superior at low glyphosate rates to commercial standard Formulations C and J but not quite as great as that of compositions 45-04 to 45-06. Performance of compositions 45-04 to 45-12 on ECHCF was relatively low in this test but performance on ABUTH was remarkably high considering the very low surfactant concentrations present.

Example 46

Aqueous spray compositions were prepared containing glyphosate IPA or tetrabutylammonium salt and excipient ingredients as shown in Table 46a. Process (i) was followed for compositions 46-10 to 46-13 and 46-15 and process (iii) for compositions 46-01 to 46-09 using soybean lecithin (45% phospholipid, Avanti). The pH of all compositions was adjusted to approximately 7.

TABLE 46a

| Spray composition | % w/w Lecithin | LI-700 | Fluorad FC-135 | Surf H1 | Glyphosate salt |
|---|---|---|---|---|---|
| 46-01 | 0.10 |  |  |  | IPA |
| 46-02 | 0.05 |  |  |  | IPA |
| 46-03 | 0.02 |  |  |  | IPA |
| 46-04 | 0.10 |  | 0.10 |  | IPA |
| 46-05 | 0.05 |  | 0.05 |  | IPA |
| 46-06 | 0.02 |  | 0.02 |  | IPA |
| 46-07 | 0.10 |  |  | 0.10 | IPA |
| 46-08 | 0.05 |  |  | 0.05 | IPA |
| 46-09 | 0.02 |  |  | 0.02 | IPA |
| 46-10 |  | 0.10 |  |  | IPA |
| 46-11 |  | 0.05 |  |  | IPA |
| 46-12 |  | 0.02 |  |  | IPA |
| 46-13 |  |  |  |  | $(BU)_4N$ |
| 46-14 | 0.05 |  | 0.05 |  | $(BU)_4N$ |
| 46-15 |  |  | 0.05 |  | $(BU)_4N$ |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 14 days after application.

In addition to compositions 46-01 to 46-15. spray compositions were prepared by tank mixing Formulations B and C with Fluorad FC-135 at various concentrations. Formulations B and C alone and Formulation J were applied as comparative treatments. Results, averaged for all replicates of each treatment, are shown in Table 46b.

TABLE 46b

| Spray composition | Glyphosate rate g a.e./ha | % Inhibition ABUTH | % Inhibition ECHCF |
|---|---|---|---|
| Formulation B | 150 | 33 | 24 |
|  | 300 | 51 | 27 |
|  | 500 | 68 | 36 |
|  | 700 | 83 | 43 |
| Formulation C | 150 | 32 | 30 |
|  | 300 | 78 | 68 |
|  | 500 | 90 | 81 |
|  | 700 | 96 | 89 |
| Formulation J | 150 | 16 | 27 |
|  | 300 | 74 | 56 |
|  | 500 | 88 | 79 |
|  | 700 | 93 | 92 |
| Formulation B + Fluorad FC-135 0.1% w/v | 150 | 22 | 18 |
|  | 300 | 71 | 26 |
|  | 500 | 73 | 51 |
| Formulation B + Fluorad FC-135 0.05% w/v | 150 | 19 | 16 |
|  | 300 | 60 | 28 |
|  | 500 | 72 | 33 |
| Formulation B + Fluorad FC-135 0.02% w/v | 150 | 14 | 14 |
|  | 300 | 23 | 26 |
|  | 500 | 69 | 38 |
| Formulation C + Fluorad FC-135 0.1% w/v | 150 | 31 | 11 |
|  | 300 | 73 | 27 |
|  | 500 | 82 | 48 |
| Formulation C + Fluorad FC-135 0.05% w/v | 150 | 43 | 23 |
|  | 300 | 71 | 49 |
|  | 500 | 93 | 50 |
| 46-01 | 150 | 20 | 18 |
|  | 300 | 65 | 29 |
|  | 500 | 85 | 34 |
| 46-02 | 150 | 22 | 19 |
|  | 300 | 63 | 35 |
|  | 500 | 83 | 51 |
| 46-03 | 150 | 24 | 29 |
|  | 300 | 64 | 35 |
|  | 500 | 85 | 40 |
| 46-04 | 150 | 63 | 21 |
|  | 300 | 75 | 31 |
|  | 500 | 84 | 46 |
| 46-05 | 150 | 68 | 10 |
|  | 300 | 82 | 29 |
|  | 500 | 81 | 53 |
| 46-06 | 150 | 68 | 21 |
|  | 300 | 84 | 30 |
|  | 500 | 85 | 46 |
| 46-07 | 150 | 41 | 35 |
|  | 300 | 51 | 39 |
|  | 500 | 93 | 61 |
| 46-08 | 150 | 34 | 22 |
|  | 300 | 77 | 27 |
|  | 500 | 85 | 35 |
| 46-09 | 150 | 24 | 17 |
|  | 300 | 78 | 39 |
|  | 500 | 91 | 58 |
| 46-10 | 150 | 16 | 19 |
|  | 300 | 62 | 28 |
|  | 500 | 72 | 53 |
| 46-11 | 150 | 38 | 25 |
|  | 300 | 59 | 38 |
|  | 500 | 82 | 59 |
| 46-12 | 150 | 7 | 23 |
|  | 300 | 61 | 40 |
|  | 500 | 77 | 63 |
| 46-13 | 150 | 81 | 48 |
|  | 300 | 92 | 51 |
|  | 500 | 90 | 46 |
| 46-14 | 150 | 87 | 30 |
|  | 300 | 91 | 69 |
|  | 500 | 95 | 89 |
| 46-15 | 150 | 81 | 37 |
|  | 300 | 94 | 41 |
|  | 500 | 92 | 63 |

As in the previous Example. compositions containing "Surf H1" did not show as strong enhancement of glyphosate effectiveness as counterpart compositions containing Fluorad FC-135. The tetrabutylammonium salt of glyphosate (compositions 46-13 to 46-15) exhibited extremely high herbicidal effectiveness in this test.

EXAMPLE 47

Aqueous concentrate compositions were prepared containing glyphosate IPA salt and excipient ingredients as shown in Table 47a. Process (v) was followed for all compositions using soybean lecithin (45% phospholipid, Avanti), except that various orders of addition were tried as indicated below. The pH of all compositions was approximately 5.

TABLE 47a

| Concentrate composition | Glyphosate a.e. | Lecithin | Fluorad FC-135 | Fluorad FC-754 | MON 0818 | Agrimul PG-2069 | Order of addition (*) |
|---|---|---|---|---|---|---|---|
| 47-01 | 30 | 3.0 | 3.0 |  | 0.75 |  | A |
| 47-02 | 30 | 3.0 | 3.0 |  | 0.75 |  | B |
| 47-03 | 30 | 3.0 | 3.0 |  | 0.75 |  | C |
| 47-04 | 30 | 3.0 | 3.0 |  | 0.75 |  | D |
| 47-05 | 30 | 3.0 | 3.0 |  | 0.75 |  | E |
| 47-06 | 30 | 3.0 | 3.0 |  | 0.75 |  | F |
| 47-07 | 30 | 3.0 |  | 3.0 | 0.75 |  | A |
| 47-08 | 30 | 3.0 |  | 3.0 | 0.75 |  | B |
| 47-09 | 30 | 3.0 |  | 3.0 | 0.75 |  | C |
| 47-10 | 30 | 3.0 |  | 3.0 | 0.75 |  | D |
| 47-11 | 30 | 3.0 |  | 3.0 | 0.75 |  | E |
| 47-12 | 30 | 3.0 |  | 3.0 | 0.75 |  | F |
| 47-13 | 30 | 3.0 | 3.0 |  |  | 0.5 | A |
| 47-14 | 30 | 3.0 | 3.0 |  |  | 0.5 | B |
| 47-15 | 30 | 3.0 | 3.0 |  |  | 0.5 | C |
| 47-16 | 30 | 3.0 | 3.0 |  |  | 0.5 | D |
| 47-17 | 30 | 3.0 | 3.0 |  |  | 0.5 | E |
| 47-18 | 30 | 3.0 | 3.0 |  |  | 0.5 | F |

(*) Order of addition:

|   | 1st | 2nd | 3rd | 4th | 5th |
|---|---|---|---|---|---|
| A | lecithin | MON/PG | FC-135/754 | water | glyphosate |
| B | lecithin | FC-135 | MON/PG | water | glyphosate |
| C | glyphosate | water | FC-135/754 | MON/PG | lecithin |
| D | glyphosate | water | MON/PG | FC-135/754 | lecithin |
| E | glyphosate | lecithin | MON/PG | FC-135/754 | water |
| F | glyphosate | lecithin | FC-135/754 | MON/PG | water |

MON/PG means MON 0818 or Agrimul PG-2069

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and 18 days after planting ECHCF, and evaluation of herbicidal inhibition was done 15 days after application.

Formulations C and J were applied as comparative treatments. Results, averaged for all replicates of each treatment, are shown in Table 47b.

TABLE 47b

| Concentrate composition | Glyphosate rate g a.e./ha | % Inhibition ABUTH | % Inhibition ECHCF |
|---|---|---|---|
| Formulation C | 150 | 26 | 69 |
|  | 300 | 75 | 100 |
|  | 500 | 85 | 99 |
|  | 700 | 94 | 100 |
| Formulation J | 150 | 38 | 78 |
|  | 300 | 76 | 87 |
|  | 500 | 87 | 100 |
|  | 700 | 90 | 100 |
| 47-01 | 150 | 10 | 35 |
|  | 300 | 51 | 56 |
|  | 500 | 71 | 91 |
|  | 700 | 77 | 100 |
| 47-02 | 150 | 24 | 35 |
|  | 300 | 57 | 71 |
|  | 500 | 77 | 93 |
|  | 700 | 94 | 100 |
| 47-03 | 150 | 11 | 33 |
|  | 300 | 48 | 55 |
|  | 500 | 73 | 87 |
|  | 700 | 83 | 93 |
| 47-04 | 150 | 37 | 36 |
|  | 300 | 50 | 38 |
|  | 500 | 68 | 94 |
| 47-05 | 150 | 24 | 32 |
|  | 300 | 48 | 47 |
|  | 500 | 77 | 85 |
|  | 700 | 76 | 100 |

TABLE 47b-continued

| Concentrate composition | Glyphosate rate g a.e./ha | % Inhibition ABUTH | ECHCF |
|---|---|---|---|
| 47-06 | 150 | 12 | 32 |
|  | 300 | 61 | 40 |
|  | 500 | 83 | 86 |
|  | 700 | 88 | 95 |
| 47-07 | 150 | 17 | 25 |
|  | 300 | 58 | 77 |
|  | 500 | 73 | 97 |
|  | 700 | 86 | 81 |
| 47-08 | 150 | 12 | 34 |
|  | 300 | 53 | 47 |
|  | 500 | 69 | 72 |
|  | 700 | 79 | 100 |
| 47-09 | 150 | 10 | 33 |
|  | 300 | 47 | 70 |
|  | 500 | 67 | 99 |
|  | 700 | 83 | 81 |
| 47-10 | 150 | 13 | 25 |
|  | 300 | 49 | 51 |
|  | 500 | 70 | 73 |
|  | 700 | 85 | 92 |
| 47-11 | 150 | 10 | 22 |
|  | 300 | 56 | 37 |
|  | 500 | 77 | 47 |
|  | 700 | 85 | 85 |
| 47-12 | 150 | 13 | 27 |
|  | 300 | 61 | 68 |
|  | 500 | 78 | 52 |
|  | 700 | 86 | 85 |
| 47-13 | 150 | 14 | 27 |
|  | 300 | 62 | 35 |
|  | 500 | 72 | 46 |
|  | 700 | 87 | 67 |
| 47-14 | 150 | 15 | 27 |
|  | 300 | 59 | 37 |
|  | 500 | 76 | 63 |
|  | 700 | 85 | 61 |
| 47-15 | 150 | 10 | 25 |
|  | 300 | 40 | 46 |
|  | 500 | 72 | 88 |
|  | 700 | 79 | 51 |
| 47-16 | 150 | 12 | 27 |
|  | 300 | 53 | 41 |
|  | 500 | 63 | 49 |
|  | 700 | 71 | 85 |
| 47-17 | 150 | 23 | 25 |
|  | 300 | 59 | 35 |
|  | 500 | 70 | 79 |
|  | 700 | 75 | 86 |
| 47-18 | 150 | 10 | 27 |
|  | 300 | 56 | 39 |
|  | 500 | 69 | 57 |
|  | 700 | 74 | 93 |

No great or consistent differences in herbicidal effectiveness were seen with different orders of addition of ingredients.

Example 48

Aqueous concentrate compositions were prepared containing glyphosate IPA salt and excipient ingredients as shown in Table 48a. Process (v) was followed for all compositions using soybean lecithin (45% phospholipid, Avanti). Order of addition of ingredients was varied as indicated below. The pH of all compositions was approximately 5.

TABLE 48a

| Concentrate composition | Glyphosate a.e. | Lecithin | Fluorad FC-135 | MON 0818 | Order of addition (*) |
|---|---|---|---|---|---|
| 48-01 | 20 | 6.0 | 6.0 | 2.0 | A |
| 48-02 | 20 | 6.0 | 6.0 | 2.0 | B |
| 48-03 | 20 | 6.0 | 6.0 | 2.0 | C |
| 48-04 | 20 | 6.0 | 3.0 | 2.0 | A |
| 48-05 | 20 | 6.0 | 3.0 | 2.0 | B |
| 48-06 | 20 | 6.0 | 3.0 | 2.0 | C |
| 48-07 | 20 | 6.0 | 1.0 | 2.0 | A |
| 48-08 | 20 | 6.0 | 1.0 | 2.0 | B |
| 48-09 | 20 | 6.0 | 1.0 | 2.0 | C |
| 48-10 | 20 | 6.0 | 0.0 | 2.0 | A |
| 48-11 | 20 | 6.0 | 0.0 | 2.0 | B |
| 48-12 | 20 | 6.0 | 0.0 | 2.0 | C |
| 48-13 | 20 | 2.0 | 2.0 | 0.5 | A |
| 48-14 | 20 | 2.0 | 2.0 | 0.5 | B |
| 48-15 | 20 | 2.0 | 2.0 | 0.5 | C |

(*) Order of addition:

| | 1st | 2nd | 3rd | 4th | 5th |
|---|---|---|---|---|---|
| A | lecithin | MON 0818 | FC-135 | water | glyphosate |
| B | lecithin | MON 0818 | water | FC-135 | glyphosate |
| C | lecithin | water | MON 0818 | FC-135 | glyphosate |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 16 days after planting ECHCF, and evaluation of herbicidal inhibition was done 15 days after application.

Formulations B, C and J were applied as comparative treatments. Results, averaged for all replicates of each treatment, are shown in Table 48b.

TABLE 48b

| Concentrate composition | Glyphosate rate g a.e./ha | % Inhibition ABUTH | ECHCF |
|---|---|---|---|
| Formulation B | 100 | 0 | 3 |
|  | 200 | 17 | 28 |
|  | 300 | 38 | 37 |
|  | 500 | 78 | 68 |
| Formulation C | 100 | 8 | 63 |
|  | 200 | 43 | 96 |
|  | 300 | 88 | 96 |
|  | 500 | 99 | 98 |
| Formulation J | 100 | 12 | 10 |
|  | 200 | 35 | 60 |
|  | 300 | 85 | 90 |
|  | 500 | 98 | 92 |
| 48-01 | 100 | 10 | 0 |
|  | 200 | 38 | 13 |
|  | 300 | 73 | 28 |
|  | 500 | 90 | 75 |
| 48-02 | 100 | 8 | 0 |
|  | 200 | 40 | 23 |
|  | 300 | 87 | 43 |
|  | 500 | 98 | 62 |
| 48-03 | 100 | 12 | 0 |
|  | 200 | 40 | 25 |
|  | 300 | 83 | 47 |
|  | 500 | 95 | 73 |
| 48-04 | 100 | 5 | 5 |
|  | 200 | 45 | 38 |
|  | 300 | 83 | 65 |
|  | 500 | 98 | 83 |

TABLE 48b-continued

| Concentrate composition | Glyphosate rate g a.e./ha | % Inhibition ABUTH | % Inhibition ECHCF |
|---|---|---|---|
| 48-05 | 100 | 10 | 3 |
|  | 200 | 42 | 48 |
|  | 300 | 82 | 53 |
|  | 500 | 97 | 91 |
| 48-06 | 100 | 28 | 0 |
|  | 200 | 67 | 43 |
|  | 300 | 85 | 68 |
|  | 500 | 97 | 93 |
| 48-07 | 100 | 8 | 8 |
|  | 200 | 37 | 35 |
|  | 300 | 75 | 72 |
|  | 500 | 97 | 90 |
| 48-08 | 100 | 0 | 1 |
|  | 200 | 37 | 45 |
|  | 300 | 57 | 68 |
|  | 500 | 96 | 97 |
| 48-09 | 100 | 0 | 7 |
|  | 200 | 35 | 40 |
|  | 300 | 78 | 60 |
|  | 500 | 96 | 93 |
| 48-10 | 100 | 0 | 3 |
|  | 200 | 33 | 57 |
|  | 300 | 82 | 72 |
|  | 500 | 96 | 94 |
| 48-11 | 100 | 0 | 5 |
|  | 200 | 35 | 50 |
|  | 300 | 78 | 82 |
|  | 500 | 97 | 87 |
| 48-12 | 100 | 3 | 5 |
|  | 200 | 40 | 37 |
|  | 300 | 77 | 78 |
|  | 500 | 97 | 85 |
| 48-13 | 100 | 3 | 0 |
|  | 200 | 45 | 33 |
|  | 300 | 83 | 38 |
|  | 500 | 95 | 75 |
| 48-14 | 100 | 0 | 0 |
|  | 200 | 43 | 33 |
|  | 300 | 77 | 50 |
|  | 500 | 96 | 68 |
| 48-15 | 100 | 0 | 0 |
|  | 200 | 42 | 30 |
|  | 300 | 78 | 47 |
|  | 500 | 88 | 73 |

No great or consistent differences were seen with different orders of addition of ingredients.

Example 49

Aqueous concentrate compositions were prepared containing glyphosate IPA salt and excipient ingredients as shown in Table 49a. Process (v) was followed for all compositions using soybean lecithin (45% phospholipid, Avanti). The pH of all compositions was approximately 5.

TABLE 49a

| Concentrate composition | Glyphosate a.e. | Lecithin | Fluorad FC-135 | Fluorad FC-754 | MON 0818 |
|---|---|---|---|---|---|
| 49-01 | 15 | 4.0 |  | 8.0 | 0.5 |
| 49-02 | 15 | 6.0 |  | 8.0 | 0.5 |
| 49-03 | 15 | 8.0 |  | 8.0 | 0.5 |
| 49-04 | 10 | 4.0 |  | 8.0 | 0.5 |
| 49-05 | 10 | 6.0 |  | 8.0 | 0.5 |
| 49-06 | 10 | 8.0 |  | 8.0 | 0.5 |
| 49-07 | 15 | 4.0 | 8.00 |  | 0.5 |
| 49-08 | 15 | 6.0 | 8.00 |  | 0.5 |
| 49-09 | 15 | 8.0 | 8.00 |  | 0.5 |
| 49-10 | 15 | 6.0 | 8.25 |  | 0.5 |
| 49-11 | 15 | 6.0 | 8.25 |  | 4.0 |
| 49-12 | 15 | 8.0 | 4.00 | 4.0 | 0.5 |
| 49-13 | 10 | 8.0 | 8.00 |  | 0.5 |
| 49-14 | 10 | 8.0 | 4.00 | 4.0 | 0.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 22 days after planting ABUTH and 23 days after planting ECHCF, and evaluation of herbicidal inhibition was done 17 days after application.

Formulations B and J were applied as comparative treatments. Results, averaged for all replicates of each treatment, are shown in Table 49b.

TABLE 49b

| Concentrate composition | Glyphosate rate g a.e./ha | % Inhibition ABUTH | % Inhibition ECHCF |
|---|---|---|---|
| Formulation B | 150 | 0 | 20 |
|  | 250 | 17 | 37 |
|  | 350 | 47 | 47 |
|  | 450 | 53 | 60 |
| Formulation J | 150 | 27 | 38 |
|  | 250 | 68 | 80 |
|  | 350 | 78 | 95 |
|  | 450 | 87 | 95 |
| 49-01 | 150 | 15 | 30 |
|  | 250 | 78 | 68 |
|  | 350 | 97 | 87 |
|  | 450 | 97 | 78 |
| 49-02 | 150 | 47 | 30 |
|  | 250 | 92 | 80 |
|  | 350 | 97 | 97 |
|  | 450 | 98 | 85 |
| 49-03 | 150 | 30 | 35 |
|  | 250 | 83 | 45 |
|  | 350 | 97 | 57 |
|  | 450 | 97 | 67 |
| 49-04 | 150 | 47 | 32 |
|  | 250 | 80 | 57 |
|  | 350 | 95 | 87 |
|  | 450 | 97 | 96 |
| 49-05 | 150 | 32 | 30 |
|  | 250 | 81 | 89 |
|  | 350 | 94 | 95 |
|  | 450 | 98 | 94 |
| 49-06 | 150 | 60 | 28 |
|  | 250 | 80 | 96 |
|  | 350 | 92 | 95 |
|  | 450 | 98 | 96 |
| 49-07 | 150 | 50 | 23 |
|  | 250 | 70 | 72 |
|  | 350 | 92 | 78 |
|  | 450 | 97 | 60 |
| 49-08 | 150 | 45 | 40 |
|  | 250 | 72 | 72 |
|  | 350 | 90 | 89 |
|  | 450 | 97 | 77 |
| 49-09 | 150 | 53 | 25 |
|  | 250 | 80 | 78 |
|  | 350 | 89 | 89 |
|  | 450 | 96 | 93 |

TABLE 49b-continued

| Concentrate composition | Glyphosate rate g a.e./ha | % Inhibition ABUTH | % Inhibition ECHCF |
|---|---|---|---|
| 49-10 | 150 | 72 | 48 |
|  | 250 | 89 | 83 |
|  | 350 | 98 | 95 |
|  | 450 | 98 | 80 |
| 49-11 | 150 | 50 | 27 |
|  | 250 | 77 | 63 |
|  | 350 | 93 | 83 |
|  | 450 | 97 | 72 |
| 49-12 | 150 | 52 | 15 |
|  | 250 | 83 | 57 |
|  | 350 | 94 | 68 |
|  | 450 | 98 | 63 |
| 49-13 | #50 | 50 | 30 |
|  | 250 | 75 | 32 |
|  | 350 | 88 | 84 |
|  | 450 | 97 | 77 |
| 49-14 | 150 | 67 | 23 |
|  | 250 | 84 | 77 |
|  | 350 | 97 | 73 |
|  | 450 | 97 | 72 |

In this test compositions prepared with Fluorad FC-754 tended to provide greater herbicidal effectiveness on ECHCF than their counterparts prepared with Fluorad FC-135.

Example 50

Aqueous concentrate compositions were prepared containing glyphosate IPA salt and excipient ingredients as shown in Table 50a. Process (v) was followed for all compositions using soybean lecithin (45% phospholipid, Avanti). The pH of all compositions was approximately 5.

TABLE 50a

| Concentrate composition | Glyphosate a.e. | Lecithin | Fluorad FC-135 | Fluorad FC-754 | MON 0818 | Iso-propanol |
|---|---|---|---|---|---|---|
| 50-01 | 15 | 6.0 | 8.25 |  | 4.0 |  |
| 50-02 | 15 | 6.0 |  | 8.25 | 4.0 |  |
| 50-03 | 10 | 8.0 | 8.00 |  | 0.5 |  |
| 50-04 | 10 | 8.0 |  | 8.00 | 0.5 |  |
| 50-05 | 20 | 2.0 | 2.00 |  | 0.5 |  |
| 50-06 | 20 | 2.0 |  | 2.00 | 0.5 |  |
| 50-07 | 30 | 3.0 | 3.00 |  | 0.5 |  |
| 50-08 | 30 | 3.0 |  | 3.00 | 0.5 |  |
| 50-09 | 30 | 1.0 | 1.00 |  | 0.5 |  |
| 50-10 | 30 | 1.0 |  | 1.00 | 0.5 |  |
| 50-11 | 15 | 6.0 | 8.25 |  | 4.0 | 5.0 |
| 50-12 | 15 | 6.0 |  | 8.25 | 4.0 | 5.0 |
| 50-13 | 10 | 8.0 | 8.00 |  | 2.0 | 5.0 |
| 50-14 | 10 | 8.0 |  | 8.00 | 2.0 | 5.0 |
| 50-15 | 30 | 3.0 |  | 3.00 | 0.8 |  |
| 50-16 | 30 | 3.0 | 3.00 |  | 0.8 |  |
| 50-17 | 10 | 8.0 | 8.00 |  | 2.0 | 7.5 |
| 50-18 | 10 | 8.0 |  | 8.00 | 2.0 | 7.5 |
| 50-19 | 10 | 8.0 | 8.00 |  | 2.0 | 10.0 |
| 50-20 | 10 | 8.0 |  | 8.00 | 2.0 | 10.0 |
| 50-21 | 10 | 8.0 | 8.00 |  | 4.0 | 5.0 |
| 50-22 | 10 | 8.0 |  | 8.00 | 4.0 | 5.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 15 days after application.

Formulations B, C and J were applied as comparative treatments. Results, averaged for all replicates of each treatment, are shown in Table 50b.

TABLE 50b

| Concentrate composition | Glyphosate rate g a.e./ha | % Inhibition ABUTH | % Inhibition ECHCF |
|---|---|---|---|
| Formulation B | 150 | 2 | 22 |
|  | 250 | 25 | 28 |
|  | 350 | 63 | 38 |
|  | 450 | 70 | 58 |
| Formulation C | 150 | 30 | 47 |
|  | 250 | 75 | 82 |
|  | 350 | 97 | 97 |
|  | 450 | 100 | 99 |
| Formulation J | 150 | 10 | 43 |
|  | 250 | 58 | 88 |
|  | 350 | 87 | 96 |
|  | 450 | 98 | 93 |
| 50-01 | 150 | 63 | 15 |
|  | 250 | 78 | 32 |
|  | 350 | 83 | 70 |
| 50-02 | 150 | 60 | 28 |
|  | 250 | 80 | 32 |
|  | 350 | 88 | 65 |
| 50-03 | 150 | 53 | 37 |
|  | 250 | 80 | 42 |
|  | 350 | 91 | 27 |
| 50-04 | 150 | 72 | 18 |
|  | 250 | 83 | 50 |
|  | 350 | 96 | 80 |
| 50-05 | 150 | 50 | 2 |
|  | 250 | 77 | 25 |
|  | 350 | 78 | 43 |
| 50-06 | 150 | 22 | 25 |
|  | 250 | 77 | 27 |
|  | 350 | 87 | 40 |
| 50-07 | 150 | 27 | 20 |
|  | 250 | 58 | 32 |
|  | 350 | 87 | 37 |
| 50-08 | 150 | 32 | 3 |
|  | 250 | 78 | 30 |
|  | 350 | 82 | 52 |
| 50-09 | 150 | 5 | 0 |
|  | 250 | 42 | 28 |
|  | 350 | 68 | 43 |
| 50-10 | 150 | 2 | 23 |
|  | 250 | 52 | 28 |
|  | 350 | 75 | 42 |
| 50-11 | 150 | 72 | 27 |
|  | 250 | 80 | 42 |
|  | 350 | 85 | 73 |
| 50-12 | 150 | 58 | 23 |
|  | 250 | 82 | 58 |
|  | 350 | 87 | 97 |
| 50-13 | 150 | 70 | 8 |
|  | 250 | 83 | 38 |
|  | 350 | 85 | 45 |
| 50-14 | 150 | 68 | 37 |
|  | 250 | 90 | 27 |
|  | 350 | 89 | 67 |
| 50-15 | 150 | 28 | 28 |
|  | 250 | 63 | 40 |
|  | 350 | 87 | 35 |
| 50-16 | 150 | 23 | 13 |
|  | 250 | 45 | 48 |
|  | 350 | 82 | 68 |
| 50-17 | 150 | 67 | 2 |
|  | 250 | 88 | 30 |
|  | 350 | 87 | 58 |
| 50-18 | 150 | 60 | 38 |
|  | 250 | 85 | 22 |
|  | 350 | 95 | 53 |

TABLE 50b-continued

| Concentrate composition | Glyphosate rate g a.e./ha | % Inhibition ABUTH | ECHCF |
|---|---|---|---|
| 50-19 | 150 | 74 | 38 |
| | 250 | 80 | 47 |
| | 350 | 95 | 28 |
| 50-20 | 150 | 70 | 25 |
| | 250 | 85 | 70 |
| | 350 | 97 | 81 |
| 50-21 | 150 | 78 | 5 |
| | 250 | 83 | 50 |
| | 350 | 90 | 83 |
| 50-22 | 150 | 73 | 33 |
| | 250 | 82 | 33 |
| | 350 | 95 | 83 |

Concentrate compositions having a high (20–30% a.e.) loading of glyphosate and consequently a relatively low loading of excipients showed enhancement of herbicidal effectiveness over that obtained with Formulation B, but in this test did not provide efficacy equal to commercial standard Formulations C and J.

Example 51

Aqueous concentrate compositions were prepared containing glyphosate IPA salt and excipient ingredients as shown in Table 51a. Process (i) was followed for compositions 51-13 to 51-20 and process (v) for compositions 51-01 to 51-12 using soybean lecithin (45% phospholipid, Avanti). Compositions were stored in different conditions as indicated below before testing for herbicidal effectiveness. The pH of all compositions was approximately 5.

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 18 days after planting ECHCF, and evaluation of herbicidal inhibition was done 18 days after application.

Formulations B and J were applied as comparative treatments. Results, averaged for all replicates of each treatment, are shown in Table 51b.

TABLE 51b

| Spray composition | Glyphosate rate g a.e./ha | % Inhibition ABUTH | ECHCF |
|---|---|---|---|
| Formulation B | 150 | 27 | 30 |
| | 250 | 37 | 38 |
| | 350 | 60 | 42 |
| | 450 | 69 | 45 |
| Formulation J | 150 | 45 | 61 |
| | 250 | 81 | 92 |
| | 350 | 93 | 97 |
| | 450 | 96 | 97 |
| 51-01 | 150 | 45 | 25 |
| | 250 | 49 | 41 |
| | 350 | 66 | 47 |
| | 450 | 75 | 63 |
| 51-02 | 150 | 49 | 65 |
| | 250 | 74 | 67 |
| | 350 | 83 | 88 |
| | 450 | 92 | 87 |
| 51-03 | 150 | 32 | 25 |
| | 250 | 71 | 70 |
| | 350 | 75 | 65 |
| | 450 | 77 | 67 |
| 51-04 | 150 | 54 | 68 |
| | 250 | 82 | 82 |
| | 350 | 91 | 95 |
| | 450 | 87 | 96 |

TABLE 51a

| Concentrate composition | Glyphosate a.e. | Lecithin | LI-700 | Fluorad FC-135 | Fluorad FC-754 | MON 0818 | Storage conditions |
|---|---|---|---|---|---|---|---|
| 51-01 | 20.0 | 2.0 | | | 2.0 | 0.5 | 60° C., 4d |
| 51-02 | 15.0 | 6.0 | | 8.25 | | 4.0 | 60° C., 4d |
| 51-03 | 20.0 | 2.0 | | | 2.0 | 0.5 | −10° C., 4d |
| 51-04 | 15.0 | 6.0 | | 8.25 | | 4.0 | −10° C., 4d |
| 5I-05 | 20.0 | 2.0 | | | 2.0 | 0.5 | room temperature, 4d |
| 51-06 | 15.0 | 6.0 | | 8.25 | | 4.0 | room temperature, 4d |
| 51-07 | 20.0 | 2.0 | | | 2.0 | 0.5 | 60° C., 8 h then −10° C., 4d |
| 51-08 | 15.0 | 6.0 | | 8.25 | | 4.0 | 60° C., 8 h then −10° C., 4d |
| 51-09 | 20.0 | 2.0 | | | 2.0 | 0.5 | freshly made |
| 51-10 | 15.0 | 6.0 | | 8.25 | | 4.0 | freshly made |
| 51-11 | 20.0 | 2.0 | | | 2.0 | 0.5 | room temperature, 42 d |
| 51-12 | 15.0 | 6.0 | | 8.25 | | 4.0 | room temperature, 42 d |
| 51-13 | 15.0 | | 18.25 | | | | |
| 51-14 | 20.0 | | 4.50 | | | | |
| 51-15 | 15.0 | | 14.25 | | | 4.0 | |
| 51-16 | 20.0 | | 4.00 | | | 0.5 | |
| 51-17 | 15.0 | | 10.00 | 8.25 | | | |
| 51-18 | 20.0 | | 2.50 | | 2.0 | | |
| 51-19 | 15.0 | | 6.00 | 8.25 | | 4.0 | |
| 51-20 | 20.0 | | 2.00 | 2.00 | | 0.5 | |

TABLE 51b-continued

| Spray composition | Glyphosate rate g a.e./ha | % Inhibition ABUTH | % Inhibition ECHCF |
|---|---|---|---|
| 51-05 | 150 | 39 | 52 |
|  | 250 | 63 | 65 |
|  | 350 | 83 | 90 |
|  | 450 | 85 | 93 |
| 51-06 | 150 | 67 | 81 |
|  | 250 | 89 | 97 |
|  | 350 | 94 | 100 |
|  | 450 | 96 | 100 |
| 51-07 | 150 | 39 | 52 |
|  | 250 | 60 | 88 |
|  | 350 | 87 | 94 |
|  | 450 | 85 | 96 |
| 51-08 | 150 | 54 | 82 |
|  | 250 | 87 | 98 |
|  | 350 | 93 | 100 |
|  | 450 | 92 | 100 |
| 51-09 | 150 | 45 | 53 |
|  | 250 | 67 | 88 |
|  | 350 | 84 | 89 |
|  | 450 | 93 | 93 |
| 51-10 | 150 | 56 | 63 |
|  | 250 | 86 | 97 |
|  | 350 | 94 | 99 |
|  | 450 | 92 | 98 |
| 51-11 | 150 | 48 | 40 |
|  | 250 | 69 | 55 |
|  | 350 | 74 | 91 |
| 51-12 | 150 | 60 | 41 |
|  | 250 | 86 | 91 |
|  | 350 | 95 | 98 |
| 51-13 | 150 | 30 | 44 |
|  | 250 | 37 | 76 |
|  | 350 | 59 | 94 |
| 51-14 | 150 | 0 | 40 |
|  | 250 | 49 | 55 |
|  | 350 | 59 | 85 |
| 51-15 | 150 | 42 | 61 |
|  | 250 | 71 | 90 |
|  | 350 | 83 | 97 |
| 51-16 | 150 | 27 | 42 |
|  | 250 | 49 | 58 |
|  | 350 | 61 | 86 |
| 51-17 | 150 | 37 | 45 |
|  | 250 | 52 | 70 |
|  | 350 | 76 | 60 |
| 51-18 | 150 | 28 | 32 |
|  | 250 | 53 | 77 |
|  | 350 | 70 | 71 |
| 51-19 | 150 | 47 | 36 |
|  | 250 | 69 | 97 |
|  | 350 | 83 | 89 |
| 51-20 | 150 | 26 | 20 |
|  | 250 | 56 | 74 |
|  | 350 | 62 | 82 |

No great or consistent effect of storage conditions on herbicidal effectiveness of compositions was seen in this test.

Example 52

Aqueous concentrate compositions were prepared containing glyphosate IPA salt and excipient ingredients as shown in Table 52a. Process (v) was followed for all compositions using soybean lecithin (45% phospholipid, Avanti). The pH of all compositions was approximately 5.

TABLE 52a

| Concentrate composition | Glyphosate a.e. | Lecithin | Butyl stearate | Fluorad FC-754 | MON 0818 | Ethomeen T/25 | Ethanol |
|---|---|---|---|---|---|---|---|
| 52-01 | 20 | 2.0 | 0.5 |  |  | 1.25 | 1.0 |
| 52-02 | 20 | 2.0 | 0.5 | 1.00 |  | 1.00 | 1.0 |
| 52-03 | 20 | 2.0 | 0.5 |  | 1.25 |  | 1.0 |
| 52-04 | 20 | 6.0 | 1.5 |  |  | 3.00 | 3.0 |
| 52-05 | 20 | 6.0 | 1.5 | 2.00 |  | 2.00 | 2.0 |
| 52-06 | 20 | 6.0 | 1.5 |  | 3.00 |  | 3.0 |
| 52-07 | 20 | 2.0 | 0.5 |  |  | 0.50 |  |
| 52-08 | 20 | 2.0 | 0.5 |  |  | 2.50 |  |
| 52-09 | 20 | 2.0 | 0.5 |  | 1.25 | 1.25 |  |
| 52-10 | 20 | 6.0 | 1.5 |  |  | 0.50 |  |
| 52-11 | 20 | 6.0 | 1.5 |  |  | 3.00 |  |
| 52-12 | 20 | 6.0 | 1.5 |  |  | 6.00 |  |
| 52-13 | 20 | 6.0 | 1.5 |  | 3.00 | 3.00 |  |
| 52-14 | 20 | 2.0 |  | 2.0 | 0.50 |  |  |
| 52-15 | 20 | 6.0 |  | 3.0 | 6.00 |  |  |
| 52-16 | 20 | 6.0 |  | 6.0 | 6.00 |  |  |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulation J was applied as a comparative treatment. Results, averaged for all replicates of each treatment, are shown in Table 52b.

TABLE 52b

| Concentrate composition | Glyphosate rate g a.e./ha | % Inhibition ABUTH | % Inhibition ECHCF |
|---|---|---|---|
| Formulation J | 150 | 38 | 45 |
|  | 250 | 80 | 63 |
|  | 350 | 78 | 82 |
|  | 450 | 75 | 55 |
| 52-01 | 150 | 23 | 27 |
|  | 250 | 57 | 53 |
|  | 350 | 70 | 85 |
|  | 450 | 70 | 83 |
| 52-02 | 150 | 7 | 25 |
|  | 250 | 52 | 45 |
|  | 350 | 82 | 88 |
|  | 450 | 82 | 90 |
| 52-03 | 150 | 38 | 35 |
|  | 250 | 50 | 40 |
|  | 350 | 82 | 92 |
|  | 450 | 83 | 93 |
| 52-04 | 150 | 40 | 48 |
|  | 250 | 73 | 75 |
|  | 350 | 78 | 92 |
|  | 450 | 88 | 92 |
| 52-05 | 150 | 50 | 53 |
|  | 250 | 68 | 80 |
|  | 350 | 85 | 98 |
|  | 450 | 89 | 96 |
| 52-06 | 150 | 50 | 43 |
|  | 250 | 55 | 80 |
|  | 350 | 78 | 97 |
|  | 450 | 85 | 91 |
| 52-07 | 150 | 3 | 28 |
|  | 250 | 22 | 43 |
|  | 350 | 67 | 72 |
|  | 450 | 73 | 75 |
| 52-08 | 150 | 43 | 33 |
|  | 250 | 77 | 63 |
|  | 350 | 89 | 78 |
|  | 450 | 97 | 85 |
| 52-09 | 150 | 57 | 27 |
|  | 250 | 95 | 63 |
|  | 350 | 89 | 86 |
|  | 450 | 98 | 88 |
| 52-10 | 150 | 32 | 23 |
|  | 250 | 33 | 55 |
|  | 350 | 73 | 82 |
|  | 450 | 67 | 60 |

TABLE 52b-continued

| Concentrate composition | Glyphosate rate g a.e./ha | % Inhibition ABUTH | % Inhibition ECHCF |
|---|---|---|---|
| 52-11 | 150 | 45 | 32 |
|  | 250 | 78 | 72 |
|  | 350 | 95 | 92 |
|  | 450 | 98 | 96 |
| 52-12 | 150 | 67 | 42 |
|  | 250 | 80 | 75 |
|  | 350 | 96 | 88 |
|  | 450 | 97 | 90 |
| 52-13 | 150 | 73 | 42 |
|  | 250 | 83 | 77 |
|  | 350 | 96 | 91 |
|  | 450 | 98 | 88 |
| 52-14 | 150 | 57 | 30 |
|  | 250 | 77 | 72 |
|  | 350 | 84 | 80 |
|  | 450 | 96 | 75 |
| 52-15 | 150 | 72 | 38 |
|  | 250 | 88 | 82 |
|  | 350 | 98 | 92 |
|  | 450 | 98 | 87 |
| 52-16 | 150 | 85 | 49 |
|  | 250 | 97 | 47 |
|  | 350 | 97 | 83 |
|  | 450 | 98 | 85 |

Very high herbicidal effectiveness was obtained in this test with concentrate compositions containing lecithin and Fluorad FC-754. Composition 52-14, containing each of these excipients at the very low weight/weight ratio to glyphosate a.e. of 1:10, was at least as effective as commercial standard Formulation J, while compositions 52-15 and 52-16 were still more effective. Also performing very well in this test, particularly on ECHCF, were a number of concentrate compositions containing lecithin and butyl stearate.

Example 53

Aqueous concentrate compositions were prepared containing glyphosate IPA salt and excipient ingredients as shown in Table 53a. Process (v) was followed for all compositions using soybean lecithin (45% phospholipid, Avanti). Order of addition of ingredients was varied for certain compositions as indicated below. The pH of all compositions was approximately 5.

TABLE 53a

| Concentrate composition | Glyphosate g/l a.e. | Lecithin | Fluorad FC-754/135 | Benzalkonium Cl | Butyl stearate | MON 0818 | Order of addition (*) |
|---|---|---|---|---|---|---|---|
| 53-01 | 345 | 4.0 |  | 0.66 |  |  |  |
| 53-02 | 345 | 4.0 |  | 1.00 |  |  |  |
| 53-03 | 347 | 3.0 |  | 3.00 |  |  |  |
| 53-04 | 347 | 4.0 |  | 4.00 |  |  |  |
| 53-05 | 347 | 4.0 |  | 5.00 |  |  |  |
| 53-06 | 345 | 4.6 |  | 4.60 |  |  |  |
| 53-07 | 348 | 4.0 | 2.0 (754) | 1.10 |  |  |  |
| 53-08 | 351 | 4.0 | 4.0 (754) | 1.00 |  |  | A |

TABLE 53a-continued

| Concentrate composition | Glyphosate g/l a.e. | Lecithin | Fluorad FC-754/135 | Benzalkonium Cl | Butyl stearate | MON 0818 | Order of addition (*) |
|---|---|---|---|---|---|---|---|
| 53-09 | 346 | 3.9 | 4.2 (754) | 1.00 | | | B |
| 53-10 | 350 | 4.0 | 2.0 (135) | 1.10 | | | |
| 53-11 | 352 | 4.0 | 4.0 (135) | 1.00 | | | A |
| 53-12 | 349 | 4.0 | 4.0 (135) | 1.00 | | | B |
| 53-13 | 348 | 4.0 | 4.0 (754) | 0.50 | 0.57 | | |
| 53-14 | 347 | 4.0 | | 0.50 | 0.52 | | |
| 53-15 | 348 | 3.7 | | 0.48 | | 3.7 | |
| 53-16 | 348 | 4.0 | | 0.58 | | 4.0 | |

(*) Order of addition:

| | 1st | 2nd | 3rd | 4th | 5th |
|---|---|---|---|---|---|
| A | lecithin | water | Benzalkonium Cl | FC-135/754 | glyphosate |
| B | glyphosate | FC-135/754 | Benzalkonium Cl | water | glyphosate |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 21 days after application.

Formulations B and J were applied as comparative treatments. Results, averaged for all replicates of each treatment, are shown in Table 53b.

TABLE 53b

| Concentrate composition | Glyphosate rate g a.e./ha | % Inhibition ABUTH | % Inhibition ECHCF |
|---|---|---|---|
| Formulation B | 100 | 5 | 5 |
| | 200 | 15 | 20 |
| | 300 | 47 | 30 |
| | 400 | 65 | 37 |
| Formulation J | 100 | 0 | 8 |
| | 200 | 70 | 37 |
| | 300 | 78 | 70 |
| | 400 | 83 | 73 |
| 53-01 | 100 | 3 | 10 |
| | 200 | 17 | 27 |
| | 300 | 45 | 37 |
| | 400 | 75 | 40 |
| 53-02 | 100 | 2 | 5 |
| | 200 | 13 | 30 |
| | 300 | 43 | 40 |
| | 400 | 75 | 47 |
| 53-03 | 100 | 0 | 8 |
| | 200 | 17 | 43 |
| | 300 | 65 | 78 |
| | 400 | 78 | 83 |
| 53-04 | 100 | 2 | 10 |
| | 200 | 30 | 37 |
| | 300 | 68 | 72 |
| | 400 | 75 | 88 |
| 53-05 | 100 | 2 | 20 |
| | 200 | 25 | 65 |
| | 300 | 63 | 88 |
| | 400 | 82 | 83 |
| 53-06 | 100 | 10 | 17 |
| | 200 | 25 | 33 |
| | 300 | 47 | 77 |
| | 400 | 83 | 75 |
| 53-07 | 100 | 0 | 10 |
| | 200 | 48 | 30 |
| | 300 | 73 | 37 |
| | 400 | 83 | 43 |
| 53-08 | 100 | 3 | 10 |
| | 200 | 33 | 30 |
| | 300 | 68 | 37 |
| | 400 | 78 | 40 |
| 53-09 | 100 | 5 | 10 |
| | 200 | 40 | 27 |
| | 300 | 65 | 50 |
| | 400 | 70 | 57 |
| 53-10 | 100 | 0 | 10 |
| | 200 | 30 | 27 |
| | 300 | 67 | 40 |
| | 400 | 73 | 40 |
| 53-11 | 100 | 0 | 10 |
| | 200 | 33 | 27 |
| | 300 | 52 | 37 |
| | 400 | 82 | 40 |
| 53-12 | 100 | 0 | 10 |
| | 200 | 40 | 20 |
| | 300 | 65 | 40 |
| | 400 | 72 | 40 |
| 53-13 | 100 | 0 | 10 |
| | 200 | 40 | 20 |
| | 300 | 60 | 33 |
| | 400 | 78 | 33 |
| 53-14 | 100 | 0 | 10 |
| | 200 | 7 | 47 |
| | 300 | 28 | 33 |
| | 400 | 43 | 43 |
| 53-15 | 100 | 0 | 13 |
| | 200 | 27 | 33 |
| | 300 | 73 | 53 |
| | 400 | 77 | 67 |
| 53-16 | 100 | 0 | 13 |
| | 200 | 30 | 37 |
| | 300 | 75 | 47 |
| | 400 | 77 | 68 |

Most concentrate compositions of this Example showed enhanced glyphosate effectiveness by comparison with Formulation B but did not equal the efficacy of commercial standard Formulation J in this test.

Example 54

Aqueous spray and concentrate compositions were prepared containing glyphosate IPA salt and excipient ingredients as shown in Table 54a. Process (i) was followed for spray compositions 54-37 to 54-60 and process (iii) for spray compositions 54-01 to 54-36 using soybean lecithin (45% phospholipid, Avanti). Process (v) was followed for concentrate compositions 54-61 to 54-63 using soybean lecithin (45% phospholipid, Avanti). The pH of all compositions was approximately 5.

TABLE 54a

| Composition | Glyphosate g a.e./l | % w/w Lecithin | % w/w Fluoro-organic | Type of fluoro-organic |
|---|---|---|---|---|
| Spray composition | | | | |
| 54-01 | 1.60 | 0.027 | 0.027 | Fluorad FC-754 |
| 54-02 | 2.66 | 0.045 | 0.045 | Fluorad FC-754 |
| 54-03 | 3.72 | 0.062 | 0.062 | Fluorad FC-754 |
| 54-04 | 4.79 | 0.080 | 0.080 | Fluorad FC-754 |
| 54-05 | 1.60 | 0.027 | 0.027 | Fluorad FC-750 |
| 54-06 | 2.66 | 0.045 | 0.045 | Fluorad FC-750 |
| 54-07 | 3.72 | 0.062 | 0.062 | Fluorad FC-750 |
| 54-08 | 4.79 | 0.080 | 0.080 | Fluorad FC-750 |
| 54-09 | 1.60 | 0.027 | 0.027 | Fluorad FC-751 |
| 54-10 | 2.66 | 0.045 | 0.045 | Fluorad FC-751 |
| 54-11 | 3.72 | 0.062 | 0.062 | Fluorad FC-751 |
| 54-12 | 4.79 | 0.080 | 0.080 | Fluorad FC-751 |
| 54-13 | 1.60 | 0.027 | 0.027 | Fluorad FC-760 |
| 54-14 | 2.66 | 0.045 | 0.045 | Fluorad FC-760 |
| 54-15 | 3.72 | 0.062 | 0.062 | Fluorad FC-760 |
| 54-16 | 4.79 | 0.080 | 0.080 | Fluorad FC-760 |
| 54-17 | 1.60 | 0.027 | 0.027 | Fluorad FC-120 |
| 54-18 | 2.66 | 0.045 | 0.045 | Fluorad FC-120 |
| 54-19 | 3.72 | 0.062 | 0.062 | Fluorad FC-120 |
| 54-20 | 4.79 | 0.080 | 0.080 | Fluorad FC-120 |
| 54-21 | 1.60 | 0.027 | 0.027 | Fluorad FC-171 |
| 54-22 | 2.66 | 0.045 | 0.045 | Fluorad FC-171 |
| 54-23 | 3.72 | 0.062 | 0.062 | Fluorad FC-171 |
| 54-24 | 4.79 | 0.080 | 0.080 | Fluorad FC-171 |
| 54-25 | 1.60 | 0.027 | 0.027 | Fluorad FC-129 |
| 54-26 | 2.66 | 0.045 | 0.045 | Fluorad FC-129 |
| 54-27 | 3.72 | 0.062 | 0.062 | Fluorad FC-129 |
| 54-28 | 4.79 | 0.080 | 0.080 | Fluorad FC-129 |
| 54-29 | 1.60 | 0.027 | 0.027 | Fluorad FC-170C |
| 54-30 | 2.66 | 0.045 | 0.045 | Fluorad FC-170C |
| 54-31 | 3.72 | 0.062 | 0.062 | Fluorad FC-170C |
| 54-32 | 4.79 | 0.080 | 0.080 | Fluorad FC-170C |
| 54-33 | 1.60 | | 0.027 | Fluorad FC-754 |
| 54-34 | 2.66 | | 0.045 | Fluorad FC-754 |
| 54-35 | 3.72 | | 0.062 | Fluorad FC-754 |
| 54-36 | 4.79 | | 0.080 | Fluorad FC-754 |
| 54-37 | 1.60 | | 0.027 | Fluorad FC-750 |
| 54-38 | 2.66 | | 0.045 | Fluorad FC-750 |
| 54-39 | 3.72 | | 0.062 | Fluorad FC-750 |
| 54-40 | 4.79 | | 0.080 | Fluorad FC-750 |
| 54-41 | 1.60 | | 0.027 | Fluorad FC-760 |
| 54-42 | 2.66 | | 0.045 | Fluorad FC-760 |
| 54-43 | 3.72 | | 0.062 | Fluorad FC-760 |
| 54-44 | 4.79 | | 0.080 | Fluorad FC-760 |
| 54-45 | 1.60 | | 0.027 | Fluorad FC-120 |
| 54-46 | 2.66 | | 0.045 | Fluorad FC-120 |
| 54-47 | 3.72 | | 0.062 | Fluorad FC-120 |
| 54-48 | 4.79 | | 0.080 | Fluorad FC-120 |
| 54-49 | 1.60 | | 0.027 | Fluorad FC-171 |
| 54-50 | 2.66 | | 0.045 | Fluorad FC-171 |
| 54-51 | 3.72 | | 0.062 | Fluorad FC-171 |
| 54-52 | 4.79 | | 0.080 | Fluorad FC-171 |
| 54-53 | 1.60 | | 0.027 | Fluorad FC-129 |
| 54-54 | 2.66 | | 0.045 | Fluorad FC-129 |
| 54-55 | 3.72 | | 0.062 | Fluorad FC-129 |
| 54-56 | 4.79 | | 0.080 | Fluorad FC-129 |
| 54-57 | 1.60 | | 0.027 | Fluorad FC-170C |
| 54-58 | 2.66 | | 0.045 | Fluorad FC-170C |
| 54-59 | 3.72 | | 0.062 | Fluorad FC-170C |
| 54-60 | 4.79 | | 0.080 | Fluorad FC-170C |
| Concentrate compositions: | | | | |
| 54-61 | 180 | 1.5 | 1.5 | Fluorad FC-754 |
| 54-62 | 180 | 2.5 | 2.5 | Fluorad FC-754 |
| 54-63 | 180 | 3.0 | 6.0 | Fluorad FC-754 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 19 days after planting ECHCF, and evaluation of herbicidal inhibition was done 16 days after application.

Formulations B and J were applied as comparative treatments. Results, averaged for all replicates of each treatment, are shown in Table 54b.

TABLE 54b

| Spray or concentrate composition | Glyphosate rate g a.e./ha | % Inhibition ABUTH | % Inhibition ECHCF |
|---|---|---|---|
| Formulation B | 150 | 47 | 88 |
| | 250 | 68 | 96 |
| | 350 | 86 | 98 |
| | 450 | 93 | 100 |
| Formulation J | 150 | 68 | 89 |
| | 250 | 94 | 97 |
| | 350 | 98 | 100 |
| | 450 | 100 | 99 |
| 54-01 | 150 | 94 | 83 |
| 54-02 | 250 | 97 | 99 |
| 54-03 | 350 | 97 | 99 |
| 54-04 | 450 | 99 | 100 |
| 54-05 | 150 | 93 | 77 |
| 54-06 | 250 | 94 | 96 |
| 54-07 | 350 | 97 | 94 |
| 54-08 | 450 | 98 | 99 |
| 54-09 | 150 | 53 | 72 |
| 54-10 | 250 | 68 | 86 |
| 54-11 | 350 | 73 | 99 |
| 54-12 | 450 | 91 | 96 |
| 54-13 | 150 | 58 | 70 |
| 54-14 | 250 | 72 | 94 |
| 54-15 | 350 | 89 | 95 |
| 54-16 | 450 | 93 | 92 |
| 54-17 | 150 | 50 | 62 |
| 54-18 | 250 | 58 | 78 |
| 54-19 | 350 | 85 | 93 |
| 54-20 | 450 | 84 | 96 |
| 54-21 | 150 | 53 | 63 |
| 54-22 | 250 | 83 | 85 |
| 54-23 | 350 | 89 | 90 |
| 54-24 | 450 | 96 | 86 |
| 54-25 | 150 | 53 | 57 |
| 54-26 | 250 | 78 | 85 |
| 54-27 | 350 | 90 | 91 |
| 54-28 | 450 | 96 | 93 |
| 54-29 | 150 | 62 | 70 |
| 54-30 | 250 | 84 | 92 |
| 54-31 | 350 | 97 | 97 |
| 54-32 | 450 | 97 | 98 |
| 54-33 | 150 | 94 | 79 |
| 54-34 | 250 | 96 | 97 |
| 54-35 | 350 | 97 | 99 |
| 54-36 | 450 | 98 | 99 |
| 54-37 | 150 | 90 | 84 |
| 54-38 | 250 | 99 | 96 |
| 54-39 | 350 | 98 | 100 |
| 54-40 | 450 | 99 | 100 |
| 54-41 | 150 | 68 | 75 |
| 54-42 | 250 | 73 | 88 |
| 54-43 | 350 | 83 | 92 |
| 54-44 | 450 | 92 | 98 |
| 54-45 | 150 | 48 | 53 |
| 54-46 | 250 | 60 | 88 |
| 54-47 | 350 | 82 | 97 |
| 54-48 | 450 | 95 | 95 |
| 54-49 | 150 | 50 | 47 |
| 54-50 | 250 | 63 | 89 |
| 54-51 | 350 | 83 | 91 |
| 54-52 | 450 | 91 | 90 |
| 54-53 | 150 | 48 | 52 |
| 54-54 | 250 | 63 | 75 |
| 54-55 | 350 | 91 | 92 |
| 54-56 | 450 | 97 | 97 |

TABLE 54b-continued

| Spray or concentrate composition | Glyphosate rate g a.e./ha | % Inhibition ABUTH | % Inhibition ECHCF |
|---|---|---|---|
| 54-57 | 150 | 50 | 83 |
| 54-58 | 250 | 73 | 94 |
| 54-59 | 350 | 91 | 98 |
| 54-60 | 450 | 94 | 98 |

TABLE 54b-continued

| Spray or concentrate composition | Glyphosate rate g a.e./ha | % Inhibition ABUTH | % Inhibition ECHCF |
|---|---|---|---|
| 54-61 | 150 | 63 | 52 |
|  | 250 | 96 | 96 |
|  | 350 | 97 | 96 |
| 54-62 | 150 | 77 | 77 |
|  | 250 | 93 | 87 |
|  | 350 | 98 | 98 |
| 54-63 | 150 | 83 | 89 |
|  | 250 | 96 | 96 |
|  | 350 | 98 | 98 |

Outstanding herbicidal efficacy, even by comparison with Formulation J, was obtained in this test from spray compositions containing lecithin and Fluorad FC-754 (54-01 to 54-04). Substitution of other fluoro-organic surfactants for Fluorad FC-754 gave varying results. Fluorad FC-750 (compositions 54-05 to 54-08) was an acceptable substitute; however Fluorad FC-751, Fluorad FC-760, Fluorad FC-120, Fluorad FC-171, Fluorad FC-129 and Fluorad FC-170C (compositions 54-09 to 54-32) provided less enhancement. A similar pattern was seen with spray compositions (54-33 to 54-60) containing the same fluoro-organic surfactants as above with the exception of Fluorad FC-751, but no lecithin. It is noteworthy that of all the fluoro-organic surfactants included in this test, only Fluorad FC-754 and Fluorad FC-750 are cationic. Excellent herbicidal efficacy was also noted in this test from concentrate glyphosate compositions containing lecithin and Fluorad FC-754, especially composition 54-63.

Example 55

Aqueous concentrate compositions were prepared containing glyphosate IPA salt and excipient ingredients as shown in Table 55a. Concentrate compositions 55-01 to 55-07, 55-17 and 55-18 were prepared by process (v). Concentrate compositions 55-08 to 55-15 were prepared by process (x). The other concentrate compositions of this Example were included for comparison purposes.

TABLE 55a

| Conc. comp. | Glyphosate g a.e./l | Lecithin | Fluorad FC-754 | Butyl stearate | Ethomeen T/25 | Ceteareth-20 | Arcosolve DPM | Ceteareth-27 |
|---|---|---|---|---|---|---|---|---|
| 55-01 | 348 | 3.0 | 3.00 |  | 0.75 |  |  |  |
| 55-02 | 348 | 3.8 | 3.75 |  | 5.00 |  |  |  |
| 55-03 | 348 | 3.8 | 3.75 |  | 7.50 |  |  |  |
| 55-04 | 348 | 2.0 | 5.00 |  | 0.75 |  |  |  |
| 55-05 | 348 | 5.0 | 5.00 |  | 0.75 |  |  |  |
| 55-06 | 348 | 2.0 | 2.00 |  |  |  |  |  |
| 55-07 | 348 | 1.0 | 1.00 |  |  |  |  |  |
| 55-08 | 220 | 1.5 |  | 1.5 | 3.00 | 3.0 |  |  |
| 55-09 | 220 | 1.5 |  | 1.5 | 3.00 |  |  | 3.0 |
| 55-10 | 220 | 1.5 |  | 1.5 | 6.00 | 3.0 |  |  |
| 55-11 | 220 | 1.5 |  | 1.5 | 6.00 |  |  | 3.0 |
| 55-12 | 220 | 3.0 |  | 1.5 | 3.00 | 3.0 |  |  |
| 55-13 | 220 | 3.0 |  | 1.5 | 3.00 |  |  | 3.0 |
| 55-14 | 348 | 1.5 |  | 1.5 | 6.00 | 3.0 |  |  |
| 55-15 | 348 | 3.0 |  | 1.5 | 3.00 | 3.0 |  |  |
| 55-16 | 348 |  | 3.00 |  |  |  |  |  |
| 55-17 | 348 | 3.0 |  |  |  |  | 3.0 |  |
| 55-18 | 348 | 5.0 |  |  | 13.00 |  | 5.0 |  |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and J were applied as comparative treatments. Results, averaged for all replicates of each treatment, are shown in Table 55b.

TABLE 55b

| Concentrate composition | Glyphosate rate g a.e./ha | % Inhibition ABUTH | % Inhibition ECHCF |
|---|---|---|---|
| Formulation B | 100 | 28 | 32 |
|  | 200 | 41 | 37 |
|  | 300 | 73 | 64 |
|  | 400 | 22 | 30 |
| Formulation J | 100 | 38 | 32 |
|  | 200 | 82 | 73 |
|  | 300 | 89 | 91 |
|  | 400 | 97 | 89 |
| 55-01 | 100 | 73 | 28 |
|  | 200 | 90 | 66 |
|  | 300 | 97 | 92 |
|  | 400 | 100 | 96 |
| 55-02 | 100 | 77 | 32 |
|  | 200 | 87 | 67 |
|  | 300 | 84 | 78 |
|  | 400 | 98 | 84 |

TABLE 55b-continued

| Concentrate composition | Glyphosate rate g a.e./ha | % Inhibition ABUTH | ECHCF |
|---|---|---|---|
| 55-03 | 100 | 79 | 33 |
|  | 200 | 82 | 66 |
|  | 300 | 99 | 81 |
|  | 400 | 97 | 88 |
| 55-04 | 100 | 69 | 35 |
|  | 200 | 95 | 59 |
|  | 300 | 96 | 84 |
|  | 400 | 92 | 91 |
| 55-05 | 100 | 82 | 32 |
|  | 200 | 92 | 55 |
|  | 300 | 96 | 71 |
|  | 400 | 94 | 87 |
| 55-06 | 100 | 83 | 33 |
|  | 200 | 100 | 52 |
|  | 300 | 100 | 68 |
|  | 400 | 99 | 75 |
| 55-07 | 100 | 77 | 35 |
|  | 200 | 90 | 58 |
|  | 300 | 95 | 71 |
|  | 400 | 94 | 90 |
| 55-08 | 100 | 51 | 40 |
|  | 200 | 89 | 75 |
|  | 300 | 96 | 92 |
|  | 400 | 95 | 98 |
| 55-09 | 100 | 76 | 57 |
|  | 200 | 98 | 81 |
|  | 300 | 97 | 86 |
|  | 400 | 96 | 98 |
| 55-10 | 100 | 69 | 60 |
|  | 200 | 98 | 63 |
|  | 300 | 95 | 82 |
|  | 400 | 99 | 90 |
| 55-11 | 100 | 61 | 60 |
|  | 200 | 94 | 84 |
|  | 300 | 97 | 89 |
|  | 400 | 99 | 97 |
| 55-12 | 100 | 64 | 53 |
|  | 200 | 95 | 82 |
|  | 300 | 96 | 90 |
|  | 400 | 95 | 98 |
| 55-13 | 100 | 61 | 58 |
|  | 200 | 94 | 78 |
|  | 300 | 88 | 87 |
|  | 400 | 100 | 94 |
| 55-14 | 100 | 56 | 61 |
|  | 200 | 88 | 77 |
|  | 300 | 91 | 82 |
|  | 400 | 97 | 89 |
| 55-15 | 100 | 42 | 52 |
|  | 200 | 82 | 80 |
|  | 300 | 86 | 90 |
|  | 400 | 97 | 92 |
| 55-16 | 100 | 64 | 49 |
|  | 200 | 86 | 75 |
|  | 300 | 97 | 88 |
|  | 400 | 100 | 82 |
| 55-17 | 100 | 57 | 32 |
|  | 200 | 88 | 66 |
|  | 300 | 95 | 73 |
|  | 400 | 100 | 88 |
| 55-18 | 100 | 52 | 35 |
|  | 200 | 70 | 77 |
|  | 300 | 82 | 79 |
|  | 400 | 97 | 73 |

Concentrate compositions 55-01 to 55-07, containing lecithin and Fluorad FC-754, exhibited postanding herbicidal effectiveness. On ABUTH, several of these were about as effective at 100 g a.e./ha as commercial standard Formulation J at 200 g a.e./ha. On ECHCF, all exhibited strong enhancement over Formulation B but most did not equal Formulation J on this species. The performance of composition 55-07, containing lecithin and Fluorad FC-754 each at the extremely low weight/weight ratio to glyphosate a.e. of about 1:30, was remarkably high. The inclusion of a relatively high concentration of Ethomeen T/25, as in compositions 55-02 and 55-03, was not helpful to herbicidal effectiveness in the presence of lecithin and Fluorad FC-754, and may even have been detrimental. The relatively poor performance of composition 55-18, having a high Ethomeen T/25 concentration but in this case no Fluorad FC-754, is consistent with this observation. Without being bound by theory, it is believed that the presence of such high concentrations of Ethomeen T/25 together with lecithin results in the formation of mixed micelles rather than liposomes in aqueous dispersion. Composition 55-16, containing Fluorad FC-754 at a weight/weight ratio to glyphosate a.e. of about 1:10, but II no lecithin, exhibited herbicidal effectiveness similar to that of composition 55-01, suggesting that under the conditions of this test a large part of the enhancement due to the lecithin/Fluorad FC-754 combination was attributable to the Fluorad FC-754 component.

Compositions 55-08 to 55-15, containing lecithin, butyl stearate, Ethomeen T/25 and a $C_{16-18}$ alkylether surfactant (ceteareth-20 or ceteareth-27) exhibited a very high degree of herbicidal effectiveness. Not only was performance, at least of 55-08 to 55-13, on ABUTH substantially better than that of Formulation J, these compositions performed considerably better than Formulation J on ECHCF as well.

Example 56

Aqueous spray compositions were prepared containing glyphosate IPA salt and excipient ingredients as shown in Table 56a. Process (i) was followed for compositions 56-61 to 56-64, 56-67, 56-69 and 56-71 and process (iii) for compositions 56-01 to 56-60, 56-66, 56-68, 56-70 and 56-72 using soybean lecithin (45% phospholipid, Avanti). The pH of all compositions was approximately 5.

TABLE 56a

| Spray composition | % w/w |  |  |  |  |
|---|---|---|---|---|---|
|  | Lecithin | MON 0818 | Fluorad FC-754 | Ethomeen T/25 | Ethomeen C/12 |
| 56-01 | 0.020 | 0.025 | 0.02 |  |  |
| 56-02 | 0.030 | 0.025 | 0.02 |  |  |
| 56-03 | 0.050 | 0.025 | 0.02 |  |  |
| 56-04 | 0.020 | 0.025 | 0.03 |  |  |
| 56-05 | 0.030 | 0.025 | 0.03 |  |  |
| 56-06 | 0.050 | 0.025 | 0.03 |  |  |
| 56-07 | 0.020 | 0.025 | 0.04 |  |  |
| 56-08 | 0.030 | 0.025 | 0.04 |  |  |
| 56-09 | 0.050 | 0.025 | 0.04 |  |  |
| 56-10 | 0.020 | 0.025 | 0.05 |  |  |
| 56-11 | 0.030 | 0.025 | 0.05 |  |  |
| 56-12 | 0.050 | 0.025 | 0.05 |  |  |
| 56-13 | 0.020 |  | 0.02 |  |  |
| 56-14 | 0.030 |  | 0.02 |  |  |
| 56-15 | 0.050 |  | 0.02 |  |  |
| 56-16 | 0.020 |  | 0.03 |  |  |
| 56-17 | 0.030 |  | 0.03 |  |  |
| 56-18 | 0.050 |  | 0.03 |  |  |
| 56-19 | 0.020 |  | 0.04 |  |  |
| 56-20 | 0.030 |  | 0.04 |  |  |
| 56-21 | 0.050 |  | 0.04 |  |  |
| 56-22 | 0.020 |  | 0.05 |  |  |
| 56-23 | 0.030 |  | 0.05 |  |  |
| 56-24 | 0.050 |  | 0.05 |  |  |
| 56-25 | 0.020 |  | 0.02 | 0.025 |  |
| 56-26 | 0.030 |  | 0.02 | 0.025 |  |
| 56-27 | 0.050 |  | 0.02 | 0.025 |  |
| 56-28 | 0.020 |  | 0.03 | 0.025 |  |
| 56-29 | 0.030 |  | 0.03 | 0.025 |  |
| 56-30 | 0.050 |  | 0.03 | 0.025 |  |
| 56-31 | 0.020 |  | 0.04 | 0.025 |  |
| 56-32 | 0.030 |  | 0.04 | 0.025 |  |

TABLE 56a-continued

| | | | % w/w | | |
|---|---|---|---|---|---|
| Spray composition | Lecithin | MON 0818 | Fluorad FC-754 | Ethomeen T/25 | Ethomeen C/12 |
| 56-33 | 0.050 | | 0.04 | 0.025 | |
| 56-34 | 0.020 | | 0.05 | 0.025 | |
| 56-35 | 0.030 | | 0.05 | 0.025 | |
| 56-36 | 0.050 | | 0.05 | 0.025 | |
| 56-37 | 0.020 | | 0.02 | | 0.025 |
| 56-38 | 0.030 | | 0.02 | | 0.025 |
| 56-39 | 0.050 | | 0.02 | | 0.025 |
| 56-40 | 0.020 | | 0.03 | | 0.025 |
| 56-41 | 0.030 | | 0.03 | | 0.025 |
| 56-42 | 0.050 | | 0.03 | | 0.025 |
| 56-43 | 0.020 | | 0.04 | | 0.025 |
| 56-44 | 0.030 | | 0.04 | | 0.025 |
| 56-45 | 0.050 | | 0.04 | | 0.025 |
| 56-46 | 0.020 | | 0.05 | | 0.025 |
| 56-47 | 0.030 | | 0.05 | | 0.025 |
| 56-48 | 0.050 | | 0.05 | | 0.025 |
| 56-49 | 0.020 | | 0.02 | 0.050 | |
| 56-50 | 0.025 | | 0.03 | 0.050 | |
| 56-51 | 0.050 | | 0.02 | 0.050 | |
| 56-52 | 0.020 | | 0.03 | 0.050 | |
| 56-53 | 0.030 | | 0.03 | 0.050 | |
| 56-54 | 0.050 | | 0.03 | 0.050 | |
| 56-55 | 0.020 | 0.050 | 0.02 | | |
| 56-56 | 0.025 | 0.050 | 0.03 | | |
| 56-57 | 0.050 | 0.050 | 0.02 | | |
| 56-58 | 0.020 | 0.050 | 0.03 | | |
| 56-59 | 0.030 | 0.050 | 0.03 | | |
| 56-60 | 0.050 | 0.050 | 0.03 | | |
| 56-61 | | 0.050 | | | |
| 56-62 | | | | 0.050 | |
| 56-63 | | | | | 0.025 |
| 56-64 | | 0.025 | | | |
| 56-65 | 0.050 | | 0.08 | 0.025 | |
| 56-66 | 0.025 | | 0.03 | | 0.025 |
| 56-67 | | | 0.05 | | |
| 56-68 | 0.050 | | | | |
| 56-69 | | | 0.05 | 0.050 | |
| 56-70 | 0.050 | | | 0.050 | |
| 56-71 | | 0.050 | 0.05 | | |
| 56-72 | 0.050 | 0.050 | | | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulation J was applied as a comparative treatment. Results, averaged for all replicates of each treatment, are shown in Table 56b.

TABLE 56b

| Spray composition | Glyphosate rate g a.e./ha | % Inhibition ABUTH | % Inhibition ECHCF |
|---|---|---|---|
| Formulation J | 100 | 14 | 42 |
| | 187 | 44 | 87 |
| | 300 | 71 | 90 |
| | 400 | 92 | 97 |
| 56-01 | 187 | 80 | 80 |
| 56-02 | 187 | 80 | 97 |
| 56-03 | 187 | 79 | 94 |
| 56-04 | 187 | 79 | 91 |
| 56-05 | 187 | 81 | 80 |
| 56-06 | 187 | 73 | 88 |
| 56-07 | 187 | 86 | 90 |
| 56-08 | 187 | 88 | 91 |
| 56-09 | 187 | 77 | 85 |
| 56-10 | 187 | 81 | 80 |
| 56-11 | 187 | 88 | 68 |
| 56-12 | 187 | 87 | 72 |
| 56-13 | 187 | 85 | 61 |
| 56-14 | 187 | 83 | 47 |
| 56-15 | 187 | 86 | 61 |
| 56-16 | 187 | 86 | 57 |
| 56-17 | 187 | 85 | 44 |
| 56-18 | 187 | 81 | 62 |
| 56-19 | 187 | 82 | 63 |
| 56-20 | 187 | 87 | 62 |
| 56-21 | 187 | 84 | 48 |
| 56-22 | 187 | 80 | 67 |
| 56-23 | 187 | 86 | 89 |
| 56-24 | 187 | 78 | 64 |
| 56-25 | 187 | 84 | 87 |
| 56-26 | 187 | 81 | 81 |
| 56-27 | 187 | 74 | 85 |
| 56-28 | 187 | 71 | 90 |
| 56-29 | 187 | 76 | 74 |
| 56-30 | 187 | 81 | 89 |
| 56-31 | 187 | 78 | 80 |
| 56-32 | 187 | 79 | 84 |
| 56-33 | 187 | 82 | 84 |
| 56-34 | 187 | 74 | 87 |
| 56-35 | 187 | 81 | 89 |
| 56-36 | 187 | 85 | 79 |
| 56-37 | 187 | 68 | 89 |
| 56-38 | 187 | 69 | 85 |
| 56-39 | 187 | 86 | 85 |
| 56-40 | 187 | 83 | 89 |
| 56-41 | 187 | 77 | 76 |
| 56-42 | 187 | 83 | 76 |
| 56-43 | 187 | 74 | 83 |
| 56-44 | 187 | 84 | 69 |
| 56-45 | 187 | 85 | 71 |
| 56-46 | 187 | 80 | 86 |
| 56-47 | 187 | 83 | 96 |
| 56-48 | 187 | 81 | 87 |
| 56-49 | 187 | 75 | 99 |
| 56-50 | 187 | 78 | 97 |
| 56-51 | 187 | 76 | 97 |
| 56-52 | 187 | 77 | 92 |
| 56-53 | 187 | 74 | 88 |
| 56-54 | 187 | 73 | 81 |
| 56-55 | 187 | 70 | 87 |
| 56-56 | 187 | 79 | 88 |
| 56-57 | 187 | 72 | 89 |
| 56-58 | 187 | 72 | 79 |
| 56-59 | 187 | 53 | 80 |
| 56-60 | 187 | 80 | 73 |
| 56-61 | 187 | 46 | 78 |
| 56-62 | 187 | 54 | 94 |
| 56-63 | 187 | 48 | 98 |
| 56-64 | 187 | 59 | 97 |
| 56-65 | 187 | 87 | 84 |
| 56-66 | 187 | 89 | 96 |
| 56-67 | 187 | 86 | 69 |
| 56-68 | 187 | 46 | 43 |
| 56-69 | 187 | 75 | 90 |
| 56-70 | 187 | 55 | 83 |
| 56-71 | 187 | 79 | 80 |
| 56-72 | 187 | 55 | 82 |

All compositions of this Example containing Fluorad FC-754 showed much greater herbicidal effectiveness on ABUTH at 187 g a.e./ha than did Formulation J at the same rate, in many cases giving inhibition of ABUTH equal to or greater than provided by Formulation J at 300 g a.e./ha. The only compositions of the Example not showing strong improvement over Formulation J on ABUTH were 56-61 to 56-64, 56-68, 56-70 and 56-72. These are the only formulations of the Example not containing Fluorad FC-754.

Example 57

Aqueous spray compositions were prepared containing glyphosate IPA salt and excipient ingredients as shown in Table 57a. Process (i) was followed for compositions 57-02, 57-04, 57-06, 57-08, 57-10, 57-12, 57-14 and 57-16 to 57-18, and process (iii) for compositions 57-01, 57-03, 57-05, 57-07, 57-09, 57-11 and 57-13 using soybean lecithin (45% phospholipid, Avanti). The pH of all compositions was approximately 5.

TABLE 57a

| Spray composition | % w/w Lecithin | % w/w Surfactant | Type of surfactant |
|---|---|---|---|
| 57-01 | 0.05 | 0.05 | Surf H2 |
| 57-02 |  | 0.05 | Surf H2 |
| 57-03 | 0.05 | 0.05 | Surf H3 |
| 57-04 |  | 0.05 | Surf H3 |
| 57-05 | 0.05 | 0.05 | Surf H4 |
| 57-06 |  | 0.05 | Surf H4 |
| 57-07 | 0.05 | 0.05 | Surf H5 |
| 57-08 |  | 0.05 | Surf H5 |
| 57-09 | 0.05 | 0.05 | Fluorad FC-754 |
| 57-10 |  | 0.05 | Fluorad FC-754 |
| 57-11 | 0.05 | 0.05 | Surf H1 |
| 57-12 |  | 0.05 | Surf H1 |
| 57-13 | 0.05 | 0.05 | MON 0818 |
| 57-14 |  | 0.05 | MON 0818 |
| 57-15 | 0.05 | 0.05 | Ethomeen T/25 |
| 57-16 |  | 0.05 | Ethomeen T/25 |
| 57-17 |  | 0.10 | MON 0818 |
| 57-18 |  | 0.10 | Ethomeen T/25 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF. and evaluation of herbicidal inhibition was done 16 days after application.

Formulations B and J were applied as comparative treatments. Results, averaged for all replicates of each treatment, are shown in Table 57b.

TABLE 57b

| Spray composition | Glyphosate rate g a.e./ha | % Inhibition ABUTH | % Inhibition ECHCF |
|---|---|---|---|
| Formulation B | 100 | 12 | 22 |
|  | 200 | 43 | 43 |
|  | 300 | 63 | 78 |
|  | 400 | 75 | 82 |
| Formulation J | 100 | 47 | 27 |
|  | 200 | 89 | 83 |
|  | 300 | 98 | 98 |
|  | 400 | 99 | 97 |
| 57-01 | 100 | 65 | 60 |
|  | 200 | 94 | 84 |
|  | 300 | 99 | 97 |
|  | 400 | 100 | 98 |
| 57-02 | 100 | 40 | 45 |
|  | 200 | 77 | 75 |
|  | 300 | 91 | 90 |
|  | 400 | 94 | 98 |
| 57-03 | 100 | 63 | 37 |
|  | 200 | 82 | 82 |
|  | 300 | 97 | 99 |
|  | 400 | 99 | 97 |
| 57-04 | 100 | 52 | 38 |
|  | 200 | 79 | 73 |
|  | 300 | 95 | 98 |
|  | 400 | 99 | 97 |
| 57-05 | 100 | 73 | 68 |
|  | 200 | 85 | 94 |
|  | 300 | 98 | 99 |
|  | 400 | 100 | 99 |
| 57-06 | 100 | 38 | 58 |
|  | 200 | 73 | 92 |
|  | 300 | 85 | 100 |
|  | 400 | 100 | 98 |
| 57-07 | 100 | 50 | 43 |
|  | 200 | 80 | 78 |
|  | 300 | 94 | 86 |
|  | 400 | 94 | 95 |
| 57-08 | 100 | 50 | 48 |
|  | 200 | 75 | 62 |
|  | 300 | 89 | 77 |
|  | 400 | 90 | 79 |
| 57-09 | 100 | 91 | 47 |
|  | 200 | 98 | 75 |
|  | 300 | 99 | 97 |
|  | 400 | 99 | 94 |
| 57-10 | 100 | 87 | 38 |
|  | 200 | 89 | 73 |
|  | 300 | 99 | 83 |
|  | 400 | 100 | 94 |
| 57-11 | 100 | 77 | 73 |
|  | 200 | 93 | 79 |
|  | 300 | 98 | 96 |
|  | 400 | 99 | 98 |
| 57-12 | 100 | 55 | 52 |
|  | 200 | 82 | 89 |
|  | 300 | 96 | 99 |
|  | 400 | 99 | 100 |
| 57-13 | 100 | 75 | 63 |
|  | 200 | 93 | 92 |
|  | 300 | 98 | 99 |
|  | 400 | 99 | 99 |
| 57-14 | 100 | 78 | 82 |
|  | 200 | 88 | 86 |
|  | 300 | 96 | 99 |
|  | 400 | 99 | 100 |
| 57-15 | 100 | 77 | 68 |
|  | 200 | 94 | 95 |
|  | 300 | 98 | 97 |
|  | 400 | 99 | 98 |
| 57-16 | 100 | 75 | 75 |
|  | 200 | 88 | 99 |
|  | 300 | 98 | 99 |
|  | 400 | 99 | 100 |
| 57-17 | 100 | 72 | 77 |
|  | 200 | 85 | 98 |
|  | 300 | 98 | 100 |
|  | 400 | 99 | 99 |
| 57-18 | 100 | 77 | 77 |
|  | 200 | 90 | 96 |
|  | 300 | 97 | 99 |
|  | 400 | 99 | 100 |

Herbicidal activity with compositions 57-13 to 57-18, based on alkylamine based surfactants known in the art, was very high in this test. Compositions 57-01 to 57-12 of the present invention also exhibited excellent herbicidal effectiveness. Overall, surfactants "Surf H1" to "Surf H5" having hydrocarbon hydrophobes were not quite as effective as Fluorad FC-754 having a fluorocarbon hydrophobe, either when used as sole excipient substance or together with lecithin.

Example 58

Aqueous concentrate compositions were prepared containing glyphosate IPA salt and excipient ingredients as shown in Table 58a. These compositions are water-in-oil-in-water multiple emulsions and were prepared by process (vi) described above.

TABLE 58a

| Conc. comp. | Glyphosate a.e. | Butyl stearate | Emulsifier #1 | Emulsifier #2 | % in inner aq. phase Water | % in inner aq. phase Glyphosate | Emulsifier #1 | Emulsifier #2 |
|---|---|---|---|---|---|---|---|---|
| 58-01 | 10 | 18.0 | 3.0 | 5.0 | 9.0 | 20 | Span 80 | Tween 20 |
| 58-02 | 10 | 7.5 | 3.0 | 5.0 | 4.5 | 20 | Span 80 | Tween 20 |
| 58-03 | 10 | 7.5 | 3.0 | 10.0 | 4.5 | 0 | Surfynol 104 | Neodol 25-12 |
| 58-04 | 10 | 7.5 | 3.0 | 10.0 | 4.5 | 0 | Surfynol 104 | Neodol 25-20 |
| 58-05 | 10 | 7.5 | 3.0 | 10.0 | 4.5 | 0 | Surfynol 104 | Tergitol 15-S-15 |
| 58-06 | 10 | 7.5 | 3.0 | 10.0 | 4.5 | 0 | Surfynol 104 | Tergitol 15-S-20 |
| 58-07 | 10 | 7.5 | 3.0 | 10.0 | 4.5 | 0 | Surfynol 104 | Tween 20 |
| 58-08 | 10 | 7.5 | 3.0 | 10.0 | 4.5 | 0 | Surfynol 104 | ceteareth-55 |
| 58-09 | 10 | 7.5 | 3.0 | 10.0 | 4.5 | 0 | Surfynol 104 | Tergitol 15-S-30 |
| 58-10 | 10 | 7.5 | 3.0 | 10.0 | 4.5 | 0 | Neodol 25-3 | ceteareth-55 |
| 58-11 | 10 | 7.5 | 3.0 | 10.0 | 4.5 | 0 | Neodol 25-3 | Tergitol 15-S-30 |
| 58-12 | 10 | 7.5 | 3.0 | 10.0 | 4.5 | 0 | Span 60 | ceteareth-55 |
| 58-13 | 10 | 7.5 | 3.0 | 10.0 | 4.5 | 0 | Span 60 | Tergitol 15-S-30 |
| 58-14 | 10 | 7.5 | 3.0 | 10.0 | 4.5 | 0 | oleth-2 | ceteareth-55 |
| 58-15 | 10 | 7.5 | 3.0 | 10.0 | 4.5 | 0 | oleth-2 | Tergitol 15-S-30 |
| 58-16 | 10 | 7.5 | 3.0 | 10.0 | 4.5 | 0 | Emid 6545 | ceteareth-55 |
| 58-17 | 10 | 7.5 | 3.0 | 10.0 | 4.5 | 0 | Emid 6545 | Tergitol 15-S-30 |

Velvetleaf (*Abutilon theophrasti*, ABUTH) and Japanese millet (*Echinochloa crus-galli*, ECHCF) plants were grown and treated by the standard procedures given above. Applications of spray compositions were made 35 days after planting ABUTH and 33 days after planting ECHCF, and evaluation of herbicidal inhibition was done 17 days after application.

Formulations B, C and J were applied as comparative treatments. Results, averaged for all replicates of each treatment, are shown in Table 58b.

TABLE 58b

| Spray composition | Glyphosate rate g a.e./ha | % Inhibition ABUTH | % Inhibition ECHCF |
|---|---|---|---|
| Formulation B | 150 | 0 | 0 |
|  | 250 | 35 | 40 |
|  | 350 | 50 | 63 |
|  | 450 | 60 | 43 |
| Formulation C | 150 | 63 | 63 |
|  | 250 | 80 | 96 |
|  | 350 | 92 | 98 |
|  | 450 | 98 | 87 |
| Formulation J | 150 | 43 | 30 |
|  | 250 | 75 | 85 |
|  | 350 | 82 | 98 |
|  | 450 | 96 | 95 |
| 58-01 | 150 | 65 | 53 |
|  | 250 | 85 | 70 |
|  | 350 | 90 | 87 |
|  | 450 | 98 | 73 |
| 58-02 | 150 | 63 | 5 |
|  | 250 | 78 | 53 |
|  | 350 | 88 | 80 |
|  | 450 | 97 | 87 |
| 58-03 | 150 | 75 | 0 |
|  | 250 | 87 | 22 |
|  | 350 | 88 | 72 |
|  | 450 | 97 | 17 |
| 58-04 | 150 | 84 | 0 |
|  | 250 | 90 | 10 |
|  | 350 | 95 | 70 |
|  | 450 | 98 | 60 |

TABLE 58b-continued

| Spray composition | Glyphosate rate g a.e./ha | % Inhibition ABUTH | % Inhibition ECHCF |
|---|---|---|---|
| 58-05 | 150 | 77 | 0 |
|  | 250 | 83 | 3 |
|  | 350 | 93 | 30 |
|  | 450 | 95 | 10 |
| 58-06 | 150 | 72 | 0 |
|  | 250 | 83 | 47 |
|  | 350 | 94 | 60 |
|  | 450 | 98 | 20 |
| 58-07 | 150 | 75 | 0 |
|  | 250 | 77 | 40 |
|  | 350 | 96 | 47 |
|  | 450 | 96 | 50 |
| 58-08 | 150 | 87 | 40 |
|  | 250 | 97 | 82 |
|  | 350 | 99 | 83 |
|  | 450 | 100 | 77 |
| 58-09 | 150 | 82 | 10 |
|  | 250 | 82 | 40 |
|  | 350 | 96 | 67 |
|  | 450 | 97 | 67 |
| 58-10 | 150 | 82 | 13 |
|  | 250 | 94 | 83 |
|  | 350 | 99 | 85 |
|  | 450 | 99 | 83 |
| 58-11 | 150 | 73 | 17 |
|  | 250 | 83 | 60 |
|  | 350 | 88 | 73 |
|  | 450 | 96 | 63 |
| 58-12 | 150 | 80 | 20 |
|  | 250 | 93 | 85 |
|  | 350 | 96 | 82 |
|  | 450 | 96 | 82 |
| 58-13 | 150 | 78 | 20 |
|  | 250 | 83 | 50 |
|  | 350 | 92 | 90 |
|  | 450 | 92 | 85 |
| 58-14 | 150 | 80 | 30 |
|  | 250 | 97 | 85 |
|  | 350 | 99 | 99 |
|  | 450 | 97 | 96 |
| 58-15 | 150 | 82 | 30 |
|  | 250 | 87 | 75 |
|  | 350 | 99 | 92 |
|  | 450 | 99 | 93 |

TABLE 58b-continued

| Spray composition | Glyphosate rate g a.e./ha | % Inhibition ABUTH | ECHCF |
|---|---|---|---|
| 58-16 | 150 | 82 | 53 |
|  | 250 | 96 | 82 |
|  | 350 | 96 | 97 |
|  | 450 | 87 | 82 |
| 58-17 | 150 | 72 | 20 |
|  | 250 | 80 | 63 |
|  | 350 | 92 | 75 |
|  | 450 | 95 | 87 |

Considerable variation was seen in herbicidal effectiveness of water-in-oil-in-water multiple emulsions of this Example, especially on ECHCF. Among the most efficacious were 58-08, 58-10, 58-12, 58-14 and 58-16. All of these contained a $C_{16-18}$ alkylether surfactant, ceteareth-55. When Tergitol 15-S-30, a $C_{12-15}$ secondary alkylether surfactant, replaced ceteareth-55, as in 58-09, 58-11, 58-13, 58-15 and 58-17, herbicidal effectiveness, at least on ECHCF, was in most cases markedly reduced.

Example 59

Aqueous concentrate compositions were prepared containing glyphosate IPA salt and excipient ingredients as shown in Table 59a. Concentrate compositions 59-01 and 59-02 are water-in-oil-in-water multiple emulsions and were prepared by process (vi), using Span 80 as emulsifier #1. Concentrate compositions 59-03 to 59-12 and 59-14 to 59-17 are oil-in-water emulsions and were prepared by process (vii). Concentrate composition 59-13 is an aqueous solution concentrate and was prepared by process (viii), the component indicated below as "emulsifier #2" being the surfactant component.

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 18 days after application.

Formulations B, C and J were applied as comparative treatments. Results, average for all replicates of each treatment, are shown in Table 59b.

TABLE 59b

| Concentrate composition | Glyphosate rate g a.e./ha | % Inhibition ABUTH | ECHCF |
|---|---|---|---|
| Formulation B | 150 | 0 | 30 |
|  | 250 | 10 | 40 |
|  | 350 | 37 | 73 |
|  | 450 | 58 | 68 |
| Formulation C | 150 | 42 | 79 |
|  | 250 | 77 | 98 |
|  | 350 | 99 | 97 |
|  | 450 | 97 | 93 |
| Formulation J | 150 | 43 | 67 |
|  | 250 | 73 | 90 |
|  | 350 | 94 | 98 |
|  | 450 | 77 | 78 |
| 59-01 | 150 | 58 | 76 |
|  | 250 | 75 | 77 |
|  | 350 | 88 | 93 |
|  | 450 | 95 | 83 |
| 59-02 | 150 | 27 | 63 |
|  | 250 | 60 | 87 |
|  | 350 | 82 | 98 |
|  | 450 | 77 | 92 |
| 59-03 | 150 | 47 | 76 |
|  | 250 | 65 | 92 |
|  | 350 | 94 | 99 |
|  | 450 | 95 | 91 |

TABLE 59a

| Conc. comp. | Glyphosate a.e. | Butyl stearate | Span 80 | Emulsifier #2 | % in inner aq. Phase Water | Glyphosate | Emulsifier #2 |
|---|---|---|---|---|---|---|---|
| 59-01 | 10 | 18.0 | 3.0 | 5.0 | 12.2 | 20 | Tween 20 |
| 59-02 | 10 | 7.5 | 3.0 | 5.0 | 5.3 | 20 | Tween 20 |
| 59-03 | 10 | 1.0 |  | 10.0 |  |  | Neodol 25-20 |
| 59-04 | 10 | 3.0 |  | 10.0 |  |  | Neodol 25-20 |
| 59-05 | 10 | 1.0 |  | 5.0 |  |  | Neodol 25-20 |
| 59-06 | 10 | 3.0 |  | 5.0 |  |  | Neodol 25-20 |
| 59-07 | 15 | 1.0 |  | 10.0 |  |  | Neodol 25-20 |
| 59-08 | 15 | 3.0 |  | 10.0 |  |  | Neodol 25-20 |
| 59-09 | 15 | 1.0 |  | 5.0 |  |  | Neodol 25-20 |
| 59-10 | 15 | 3.0 |  | 5.0 |  |  | Neodol 25-20 |
| 59-11 | 20 | 1.0 |  | 5.0 |  |  | Neodol 25-20 |
| 59-12 | 20 | 1.0 |  | 10.0 |  |  | Neodol 25-20 |
| 59-13 | 10 |  |  | 10.0 |  |  | Neodol 25-20 |
| 59-14 | 10 | 7.5 |  | 10.0 |  |  | Neodol 25-20 |
| 59-15 | 10 | 7.5 |  | 10.0 |  |  | Neodol 25-12 |
| 59-16 | 10 | 7.5 |  | 10.0 |  |  | steareth-20 |
| 59-17 | 10 | 7.5 |  | 10.0 |  |  | oleth-20 |

TABLE 59b-continued

| Concentrate composition | Glyphosate rate g a.e./ha | % Inhibition ABUTH | % Inhibition ECHCF |
|---|---|---|---|
| 59-04 | 150 | 70 | 86 |
|  | 250 | 86 | 95 |
|  | 350 | 97 | 98 |
|  | 450 | 99 | 90 |
| 59-05 | 150 | 42 | 80 |
|  | 250 | 72 | 90 |
|  | 350 | 90 | 93 |
|  | 450 | 99 | 96 |
| 59-06 | 150 | 48 | 57 |
|  | 250 | 78 | 92 |
|  | 350 | 94 | 99 |
|  | 450 | 96 | 92 |
| 59-07 | 150 | 78 | 95 |
|  | 250 | 96 | 96 |
|  | 350 | 98 | 98 |
|  | 450 | 100 | 97 |
| 59-08 | 150 | 88 | 96 |
|  | 250 | 98 | 98 |
|  | 350 | 100 | 99 |
|  | 450 | 100 | 99 |
| 59-09 | 150 | 82 | 93 |
|  | 250 | 94 | 96 |
|  | 350 | 99 | 97 |
|  | 450 | 99 | 93 |
| 59-10 | 150 | 72 | 83 |
|  | 250 | 97 | 93 |
|  | 350 | 99 | 100 |
|  | 450 | 100 | 98 |
| 59-11 | 150 | 87 | 83 |
|  | 250 | 98 | 97 |
|  | 350 | 100 | 99 |
|  | 450 | 100 | 99 |
| 59-12 | 150 | 93 | 99 |
|  | 250 | 99 | 99 |
|  | 350 | 99 | 97 |
|  | 450 | 100 | 99 |
| 59-13 | 150 | 70 | 90 |
|  | 250 | 91 | 88 |
|  | 350 | 97 | 94 |
|  | 450 | 99 | 86 |
| 59-14 | 150 | 67 | 76 |
|  | 250 | 93 | 80 |
|  | 350 | 98 | 95 |
|  | 450 | 95 | 78 |
| 59-15 | 150 | 68 | 65 |
|  | 250 | 90 | 87 |
|  | 350 | 97 | 80 |
|  | 450 | 98 | 93 |
| 59-16 | 150 | 83 | 73 |
|  | 250 | 90 | 93 |
|  | 350 | 99 | 100 |
|  | 450 | 100 | 100 |
| 59-17 | 150 | 80 | 66 |
|  | 250 | 98 | 77 |
|  | 350 | 99 | 83 |
|  | 450 | 100 | 85 |

Very high herbicidal activity was evident in compositions 59-13 to 59-17, which have a very high ratio of surfactant to glyphosate a.e. of 1:1. Activity was too high to clearly distinguish among these compositions, but 59-16 and 59-17, containing steareth-20 and oleth-20 respectively, exbited greater effectiveness on ABUTH at the lowest glyphosate rate than 59-14 and 59-15, containing Neodol 25-20 and Neodol 25-12 respectively.

Example 60

Aqueous concentrate compositions were prepared containing glyphosate IPA salt and excipient ingredients as shown in Table 60a. Concentrate compositions 60-01 and 60-02 are water-in-oil-in-water multiple emulsions and were prepared by process (vi), using Span 80 as emulsifier #1. Concentrate compositions 60-03 to 60-12 and 60-14 to 60-17 are oil-in-water emulsions and were prepared by process (vii). Concentrate composition 60-13 is an aqueous solution concentrate and was prepared by process (viii), the component indicated below as "emulsifier #2" being the surfactant component.

TABLE 60a

| Conc. comp. | % w/w Glyphosate a.e. | % w/w Butyl stearate | % w/w Span 80 | % w/w Emulsifier #2 | % in inner aq. Phase Water | % in inner aq. Phase Glyphosate | Emulsifier #2 |
|---|---|---|---|---|---|---|---|
| 60-01 | 10 | 18.0 | 3.0 | 5.0 | 12.2 | 20 | Tween 20 |
| 60-02 | 10 | 7.5 | 3.0 | 5.0 | 5.3 | 20 | Tween 20 |
| 60-03 | 10 | 1.0 |  | 10.0 |  |  | Tween 80 |
| 60-04 | 10 | 3.0 |  | 10.0 |  |  | Tween 80 |
| 60-05 | 10 | 1.0 |  | 5.0 |  |  | Tween 80 |
| 60-06 | 10 | 3.0 |  | 5.0 |  |  | Tween 80 |
| 60-07 | 15 | 1.0 |  | 10.0 |  |  | Tween 80 |
| 60-08 | 15 | 3.0 |  | 10.0 |  |  | Tween 80 |
| 60-09 | 15 | 1.0 |  | 5.0 |  |  | Tween 80 |
| 60-10 | 15 | 3.0 |  | 5.0 |  |  | Tween 80 |
| 60-11 | 20 | 1.0 |  | 5.0 |  |  | Tween 80 |
| 60-12 | 20 | 1.0 |  | 10.0 |  |  | Tween 80 |
| 60-13 | 10 |  |  | 10.0 |  |  | Tween 80 |
| 60-14 | 10 | 7.5 |  | 10.0 |  |  | Tween 80 |
| 60-15 | 10 | 7.5 |  | 10.0 |  |  | Neodol 25-20 |
| 60-16 | 10 | 7.5 |  | 10.0 |  |  | steareth-20 |
| 60-17 | 10 | 7.5 |  | 10.0 |  |  | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 18 days after application.

Formulations B, C and J were applied as comparative treatments. Results, averaged for all replicates of each treatment, are shown in Table 60b.

TABLE 60b

| Composition applied | Glyphosate rate g a.e./ha | % Inhibition ABUTH | ECHCF |
|---|---|---|---|
| Formulation B | 150 | 0 | 0 |
| | 250 | 3 | 10 |
| | 350 | 17 | 20 |
| | 450 | 20 | 30 |
| Formulation C | 150 | 70 | 33 |
| | 250 | 80 | 70 |
| | 350 | 85 | 80 |
| | 450 | 97 | 77 |
| Formulation J | 150 | 7 | 20 |
| | 250 | 70 | 80 |
| | 350 | 78 | 80 |
| | 450 | 83 | 80 |
| 60-01 | 150 | 40 | 7 |
| | 250 | 48 | 20 |
| | 350 | 73 | 23 |
| | 450 | 75 | 30 |
| 60-02 | 150 | 3 | 0 |
| | 250 | 10 | 17 |
| | 350 | 47 | 23 |
| | 450 | 50 | 30 |
| 60-03 | 150 | 0 | 2 |
| | 250 | 33 | 13 |
| | 350 | 63 | 40 |
| | 450 | 68 | 43 |
| 60-04 | 150 | 17 | 7 |
| | 250 | 43 | 20 |
| | 350 | 78 | 63 |
| | 450 | 78 | 63 |
| 60-05 | 150 | 10 | 3 |
| | 250 | 20 | 13 |
| | 350 | 58 | 40 |
| | 450 | 75 | 40 |
| 60-06 | 150 | 3 | 0 |
| | 250 | 27 | 20 |
| | 350 | 60 | 23 |
| | 450 | 72 | 23 |
| 60-07 | 150 | 32 | 10 |
| | 250 | 68 | 20 |
| | 350 | 75 | 50 |
| | 450 | 86 | 60 |
| 60-08 | 150 | 27 | 20 |
| | 250 | 68 | 30 |
| | 350 | 82 | 40 |
| | 450 | 90 | 73 |
| 60-09 | 150 | 43 | 10 |
| | 250 | 60 | 33 |
| | 350 | 72 | 63 |
| | 450 | 75 | 73 |
| 60-10 | 150 | 33 | 10 |
| | 250 | 62 | 30 |
| | 350 | 77 | 60 |
| | 450 | 83 | 70 |
| 60-11 | 150 | 48 | 13 |
| | 250 | 72 | 63 |
| | 350 | 83 | 80 |
| | 450 | 87 | 80 |
| 60-12 | 150 | 23 | 13 |
| | 250 | 60 | 50 |
| | 350 | 75 | 80 |
| | 450 | 86 | 78 |

TABLE 60b-continued

| Composition applied | Glyphosate rate g a.e./ha | % Inhibition ABUTH | ECHCF |
|---|---|---|---|
| 60-13 | 150 | 32 | 13 |
| | 250 | 47 | 40 |
| | 350 | 75 | 50 |
| | 450 | 78 | 70 |
| 60-14 | 150 | 27 | 20 |
| | 250 | 75 | 53 |
| | 350 | 82 | 70 |
| | 450 | 92 | 67 |
| 60-15 | 150 | 70 | 20 |
| | 250 | 78 | 30 |
| | 350 | 92 | 80 |
| | 450 | 93 | 80 |
| 60-16 | 150 | 68 | 40 |
| | 250 | 73 | 30 |
| | 350 | 93 | 80 |
| | 450 | 93 | 77 |
| 60-17 | 150 | 73 | 20 |
| | 250 | 85 | 30 |
| | 350 | 93 | 60 |
| | 450 | 95 | 63 |

Compositions 60-16 and 60-17, containing steareth-20 and oleth-20 respectively, exhibited very high herbicidal activity on ABUTH. At the very high surfactant to glyphosate a.e. ratio (1:1) of these compositions, no difference was evident between these compositions and an otherwise similar composition (60-15) containing Neodol 25-20 in place of steareth-20 or oleth-20.

Example 61

Aqueous concentrate compositions were prepared containing glyphosate IPA salt and excipient ingredients as shown in Table 61a. All are oil-in-water emulsions and were prepared by process (vii).

TABLE 61a

| Concentrate composition | Glyphosate g a.e./l | % w/w Butyl stearate | Surfactant | Type of surfactant |
|---|---|---|---|---|
| 61-01 | 163 | 1.00 | 10.0 | Tween 80 |
| 61-02 | 163 | 1.00 | 10.0 | Neodol 25-12 |
| 61-03 | 163 | 1.00 | 10.0 | Neodol 25-20 |
| 61-04 | 163 | 1.00 | 10.0 | steareth-20 |
| 61-05 | 163 | 1.00 | 10.0 | oleth-20 |
| 61-06 | 163 | 1.00 | 10.0 | Tergitol 15-S-40 |
| 61-07 | 163 | 1.00 | 10.0 | Tergitol 15-S-15 |
| 61-08 | 163 | 1.00 | 10.0 | Tergitol 15-S-20 |
| 61-09 | 163 | 0.50 | 10.0 | Tergitol 15-S-40 |
| 61-10 | 163 | 0.50 | 10.0 | Tergitol 15-S-15 |
| 61-11 | 163 | 0.50 | 10.0 | Tergitol 15-S-20 |
| 61-12 | 163 | 0.50 | 5.0 | Tergitol 15-S-40 |
| 61-13 | 163 | 0.50 | 5.0 | Tergitol 15-S-15 |
| 61-14 | 163 | 0.50 | 5.0 | Tergitol 15-S-20 |
| 61-15 | 163 | 0.25 | 10.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 61b.

TABLE 61b

| Concentrate composition | Glyphosate rate g a.e./ha | % Inhibition ABUTH | % Inhibition ECHCF |
|---|---|---|---|
| Formulation B | 150 | 2 | 20 |
|  | 250 | 2 | 30 |
|  | 350 | 5 | 53 |
|  | 450 | 45 | 75 |
| Formulation C | 150 | 45 | 63 |
|  | 250 | 77 | 93 |
|  | 350 | 83 | 99 |
|  | 450 | 93 | 100 |
| Formulation J | 150 | 15 | 40 |
|  | 250 | 70 | 73 |
|  | 350 | 78 | 98 |
|  | 450 | 92 | 99 |
| 61-01 | 150 | 42 | 50 |
|  | 250 | 72 | 89 |
|  | 350 | 80 | 96 |
|  | 450 | 93 | 98 |
| 61-02 | 150 | 45 | 80 |
|  | 250 | 72 | 83 |
|  | 350 | 85 | 91 |
|  | 450 | 97 | 98 |
| 61-03 | 150 | 60 | 80 |
|  | 250 | 75 | 87 |
|  | 350 | 82 | 96 |
|  | 450 | 86 | 99 |
| 61-04 | 150 | 65 | 60 |
|  | 250 | 82 | 70 |
|  | 350 | 93 | 80 |
|  | 450 | 98 | 87 |
| 61-05 | 150 | 72 | 60 |
|  | 250 | 83 | 87 |
|  | 350 | 95 | 93 |
|  | 450 | 98 | 97 |
| 61-06 | 150 | 50 | 45 |
|  | 250 | 68 | 70 |
|  | 350 | 77 | 85 |
|  | 450 | 83 | 90 |
| 61-07 | 150 | 25 | 40 |
|  | 250 | 65 | 50 |
|  | 350 | 80 | 77 |
|  | 450 | 83 | 80 |
| 61-08 | 150 | 37 | 33 |
|  | 250 | 72 | 80 |
|  | 350 | 77 | 87 |
|  | 450 | 80 | 90 |
| 61-09 | 150 | 32 | 47 |
|  | 250 | 65 | 73 |
|  | 350 | 77 | 75 |
|  | 450 | 80 | 94 |
| 61-10 | 150 | 17 | 30 |
|  | 250 | 65 | 70 |
|  | 350 | 75 | 70 |
|  | 450 | 78 | 89 |
| 61-11 | 150 | 35 | 33 |
|  | 250 | 68 | 68 |
|  | 350 | 77 | 77 |
|  | 450 | 92 | 75 |
| 61-12 | 150 | 13 | 35 |
|  | 250 | 57 | 40 |
|  | 350 | 75 | 57 |
|  | 450 | 77 | 83 |
| 61-13 | 150 | 35 | 40 |
|  | 250 | 63 | 43 |
|  | 350 | 77 | 77 |
|  | 450 | 83 | 75 |
| 61-14 | 150 | 30 | 25 |
|  | 250 | 67 | 53 |
|  | 350 | 78 | 85 |
|  | 450 | 83 | 77 |
| 61-15 | 150 | 13 | 37 |
|  | 250 | 65 | 50 |
|  | 350 | 77 | 57 |
|  | 450 | 87 | 82 |

At a surfactant to glyphosate a.e. weight/weight ratio of about 1:1.5, compositions containing steareth-20 or oleth-20 (61-04 and 61-05 respectively) exhibited herbicidal effectiveness on ABUTH similar to one containing Neodol 25-20 (61-03).

Example 62

Aqueous concentrate compositions were prepared containing glyphosate IPA salt and excipient ingredients as shown in Table 62a. All are oil-in-water emulsions and were prepared by process (vii).

TABLE 62a

| Concentrate composition | Glyphosate g a.e./l | Butyl stearate % w/w | Surfactant % w/w | Type of surfactant |
|---|---|---|---|---|
| 62-01 | 163 | 1.0 | 10.0 | Tween 80 |
| 62-02 | 163 | 1.0 | 10.0 | Neodol 25-12 |
| 62-03 | 163 | 1.0 | 10.0 | Neodol 25-20 |
| 62-04 | 163 | 1.0 | 10.0 | steareth-20 |
| 62-05 | 163 | 1.0 | 10.0 | oleth-20 |
| 62-06 | 163 | 1.0 | 10.0 | Tergitol 15-S-40 |
| 62-06 | 163 | 1.0 | 10.0 | Tergitol 15-S-15 |
| 62-08 | 163 | 1.0 | 10.0 | Tergitol 15-S-20 |
| 62-09 | 163 | 0.5 | 10.0 | Tergitol 15-S-40 |
| 62-10 | 163 | 0.3 | 10.0 | Tergitol 15-S-15 |
| 62-11 | 163 | 0.3 | 10.0 | Tergitol 15-S-20 |
| 62-12 | 163 | 0.3 | 10.0 | Tergitol 15-S-40 |
| 62-13 | 163 | 0.3 | 5.0 | Tergitol 15-S-15 |
| 62-14 | 163 | 0.3 | 5.0 | Tergitol 15-S-20 |
| 62-15 | 163 | 0.3 | 5.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 21 days after application.

Formulations B, C and J were applied as comparative treatments. Results, averaged for all replicates of each treatment, are shown in Table 62b.

TABLE 62b

| Concentrate composition | Glyphosate rate g a.e./ha | % Inhibition ABUTH | % Inhibition ECHCF |
|---|---|---|---|
| Formulation B | 150 | 0 | 23 |
|  | 250 | 0 | 40 |
|  | 350 | 5 | 53 |
|  | 450 | 13 | 57 |
| Formulation C | 150 | 0 | 47 |
|  | 250 | 28 | 87 |
|  | 350 | 72 | 98 |
|  | 450 | 97 | 97 |
| Formulation J | 150 | 5 | 40 |
|  | 250 | 20 | 63 |
|  | 350 | 67 | 93 |
|  | 450 | 82 | 92 |
| 62-01 | 150 | 2 | 40 |
|  | 250 | 30 | 50 |
|  | 350 | 50 | 70 |
|  | 450 | 57 | 85 |
| 62-02 | 150 | 10 | 50 |
|  | 250 | 33 | 50 |
|  | 350 | 75 | 72 |
|  | 450 | 75 | 88 |
| 62-03 | 150 | 17 | 53 |
|  | 250 | 60 | 60 |
|  | 350 | 70 | 92 |
|  | 450 | 78 | 94 |

TABLE 62b-continued

| Concentrate composition | Glyphosate rate g a.e./ha | % Inhibition ABUTH | ECHCF |
|---|---|---|---|
| 62-04 | 150 | 57 | 45 |
|  | 250 | 70 | 70 |
|  | 350 | 82 | 93 |
|  | 450 | 83 | 95 |
| 62-05 | 150 | 47 | 45 |
|  | 250 | 70 | 80 |
|  | 350 | 80 | 88 |
|  | 450 | 88 | 92 |
| 62-06 | 150 | 2 | 42 |
|  | 250 | 20 | 60 |
|  | 350 | 35 | 75 |
|  | 450 | 58 | 89 |
| 62-07 | 150 | 0 | 42 |
|  | 250 | 30 | 68 |
|  | 350 | 40 | 75 |
|  | 450 | 77 | 82 |
| 62-08 | 150 | 2 | 40 |
|  | 250 | 25 | 60 |
|  | 350 | 50 | 83 |
|  | 450 | 75 | 86 |
| 62-09 | 150 | 2 | 43 |
|  | 250 | 27 | 83 |
|  | 350 | 40 | 73 |
|  | 450 | 70 | 78 |
| 62-10 | 150 | 2 | 42 |
|  | 250 | 32 | 47 |
|  | 350 | 43 | 63 |
|  | 450 | 70 | 82 |
| 62-11 | 150 | 0 | 30 |
|  | 250 | 25 | 53 |
|  | 350 | 35 | 75 |
|  | 450 | 70 | 75 |
| 62-12 | 150 | 2 | 40 |
|  | 250 | 13 | 57 |
|  | 350 | 25 | 75 |
|  | 450 | 40 | 83 |
| 62-13 | 150 | 5 | 42 |
|  | 250 | 23 | 62 |
|  | 350 | 38 | 63 |
|  | 450 | 67 | 60 |
| 62-14 | 150 | 2 | 33 |
|  | 250 | 13 | 48 |
|  | 350 | 30 | 53 |
|  | 450 | 70 | 88 |
| 62-15 | 150 | 2 | 33 |
|  | 250 | 18 | 48 |
|  | 350 | 30 | 75 |
|  | 450 | 43 | 65 |

In this test, herbicidal effectiveness overall was lower than in the previous Example, particularly on ABUTH. In these circumstances, at a surfactant to glyphosate a.e. weight/weight ratio of about 1:1.5, compositions containing steareth-20 or oleth-20 (62-04 and 62-05 respectively) exhibited greater herbicidal effectiveness on both ABUTH and ECHCF than one containing Neodol 25-20 (62-03).

Example 63

Aqueous concentrate compositions were prepared containing glyphosate ammonium or IPA salt and excipient ingredients as shown in Table 63a. Concentrate composition 63-01 is a water-in-oil-in-water multiple emulsion and was prepared by process (vi), using Span 80 as emulsifier #1. Concentrate compositions 63-02 to 63-11 and 63-17 are oil-in-water emulsions and were prepared by process (vii). Concentrate compositions 63-12 to 63-16 are aqueous solution concentrates and were prepared by process (viii), the component indicated below as "emulsifier #2" being the surfactant component.

TABLE 63a

| | % w/w | | | | | % in inner aq. phase | | | |
|---|---|---|---|---|---|---|---|---|---|
| Conc. comp. | Glyphosate a.e. | Butyl stearate | Span 80 | Emulsifier #2 | Water | Glyphosate | Emulsifier #2 | Glyphosate salt |
| 63-01 | 10 | 18.0 | 3.0 | 5.0 | 9.0 | 20 | Tween 20 | IPA |
| 63-02 | 15 | 1.0 | | 10.0 | | | Tween 80 | IPA |
| 63-03 | 15 | 1.0 | | 10.0 | | | Neodol 25-12 | IPA |
| 63-04 | 15 | 1.0 | | 10.0 | | | Neodol 25-20 | IPA |
| 63-05 | 15 | 1.0 | | 10.0 | | | steareth-20 | IPA |
| 63-06 | 15 | 1.0 | | 10.0 | | | oleth-20 | IPA |
| 63-07 | 15 | 1.0 | | 10.0 | | | Tween 80 | ammonium |
| 63-08 | 15 | 1.0 | | 10.0 | | | Neodol 25-12 | ammonium |
| 63-09 | 15 | 1.0 | | 10.0 | | | Neodol 25-20 | ammonium |
| 63-10 | 15 | 1.0 | | 10.0 | | | steareth-20 | ammonium |
| 63-11 | 15 | 1.0 | | 10.0 | | | oleth-20 | ammonium |
| 63-12 | 15 | | | 10.0 | | | Tween 80 | IPA |
| 63-13 | 15 | | | 10.0 | | | Neodol 25-12 | IPA |
| 63-14 | 15 | | | 10.0 | | | Neodol 25-20 | IPA |
| 63-15 | 15 | | | 10.0 | | | steareth-20 | IPA |
| 63-16 | 15 | | | 10.0 | | | oleth-20 | IPA |
| 63-17 | 15 | 1.0 | | 10.0 | | | Emerest 2661 | IPA |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 20 days after application.

Formulations B, C and J were applied as comparative treatments. Results, averaged for all replicates of each treatment, are shown in Table 63b.

TABLE 63b

| Concentrate composition | Glyphosate rate g a.e./ha | % Inhibition ABUTH | ECHCF |
|---|---|---|---|
| Formulation B | 150 | 2 | 5 |
|  | 250 | 3 | 25 |
|  | 350 | 28 | 30 |
|  | 450 | 53 | 50 |
| Formulation C | 150 | 5 | 25 |
|  | 250 | 60 | 50 |
|  | 350 | 85 | 83 |
|  | 450 | 88 | 88 |
| Formulation J | 150 | 2 | 10 |
|  | 250 | 70 | 40 |
|  | 350 | 82 | 53 |
|  | 450 | 87 | 83 |
| 63-01 | 150 | 23 | 20 |
|  | 250 | 72 | 30 |
|  | 350 | 80 | 80 |
|  | 450 | 85 | 69 |

TABLE 63b-continued

| Concentrate composition | Glyphosate rate g a.e./ha | % Inhibition ABUTH | ECHCF |
|---|---|---|---|
| 63-02 | 150 | 5 | 18 |
|  | 250 | 72 | 38 |
|  | 350 | 82 | 63 |
|  | 450 | 85 | 83 |
| 63-03 | 150 | 25 | 20 |
|  | 250 | 70 | 57 |
|  | 350 | 85 | 68 |
|  | 450 | 90 | 83 |
| 63-04 | 150 | 25 | 27 |
|  | 250 | 77 | 67 |
|  | 350 | 85 | 62 |
|  | 450 | 88 | 70 |
| 63-05 | 150 | 60 | 25 |
|  | 250 | 82 | 62 |
|  | 350 | 87 | 73 |
|  | 450 | 85 | 80 |
| 63-06 | 150 | 50 | 32 |
|  | 250 | 78 | 78 |
|  | 350 | 91 | 91 |
|  | 450 | 98 | 98 |
| 63-07 | 150 | 5 | 25 |
|  | 250 | 55 | 77 |
|  | 350 | 77 | 86 |
|  | 450 | 83 | 99 |
| 63-08 | 150 | 0 | 13 |
|  | 250 | 58 | 78 |
|  | 350 | 80 | 85 |
|  | 450 | 85 | 87 |
| 63-09 | 150 | 7 | 25 |
|  | 250 | 57 | 72 |
|  | 350 | 77 | 83 |
|  | 450 | 91 | 92 |
| 63-10 | 150 | 50 | 25 |
|  | 250 | 80 | 55 |
|  | 350 | 86 | 87 |
|  | 450 | 92 | 82 |
| 63-11 | 150 | 53 | 30 |
|  | 250 | 78 | 80 |
|  | 350 | 87 | 89 |
|  | 450 | 95 | 98 |
| 63-12 | 150 | 0 | 25 |
|  | 250 | 50 | 77 |
|  | 350 | 77 | 90 |
|  | 450 | 83 | 94 |
| 63-13 | 150 | 2 | 30 |
|  | 250 | 55 | 75 |
|  | 350 | 72 | 92 |
|  | 450 | 85 | 80 |
| 63-14 | 150 | 12 | 30 |
|  | 250 | 75 | 78 |
|  | 350 | 84 | 90 |
|  | 450 | 96 | 94 |
| 63-15 | 150 | 55 | 35 |
|  | 250 | 78 | 80 |
|  | 350 | 80 | 94 |
|  | 450 | 86 | 98 |
| 63-16 | 150 | 50 | 35 |
|  | 250 | 73 | 63 |
|  | 350 | 84 | 83 |
|  | 450 | 89 | 95 |
| 63-17 | 150 | 0 | 10 |
|  | 250 | 10 | 53 |
|  | 350 | 53 | 83 |
|  | 450 | 62 | 87 |

Compositions containing steareth-20 or oleth-20 (63-05, 63-06, 63-10, 63-11, 63-15, 63-16) generally exhibited superior herbicidal effectiveness to counterparts containing Neodol 25-20 (63-04, 63-09, 63-14), at least on ABUTH. The presence of a small amount of butyl stearate tended to enhance effectiveness on ABUTH (compare 63-05 and 63-06 with 63-15 and 63-16).

Example 64

Aqueous concentrate compositions were prepared containing glyphosate IPA salt and excipient ingredients as shown in Table 64a. Concentrate composition 64-01 is a water-in-oil-in-water multiple emulsion and was prepared by process (vi), using Span 80 as emulsifier #1. Concentrate compositions 64-02 to 64-08, 64-14, 64-16 and 64-17 are oil-in-water emulsions and were prepared by process (vii). Concentrate compositions 64-09 to 64-13 and 64-15 are aqueous solution concentrates and were prepared by process (viii), the component indicated below as "emulsifier #2" being the surfactant component.

TABLE 64a

| | % w/w | | | | % in inner aq. phase | | |
|---|---|---|---|---|---|---|---|
| Conc. comp. | Glyphosate a.e. | Butyl stearate | Span 80 | Emulsifier #2 | Water | Glyphosate a.e. | Emulsifier #2 |
| 64-01 | 10 | 18.0 | 3.0 | 2.5 | 9.0 | 20 | Tween 20 |
| 64-02 | 15 | 1.0 |  | 10.0 |  |  | Emerest 2661 |
| 64-03 | 15 | 1.0 |  | 10.0 |  |  | Tween 80 |
| 64-04 | 15 | 1.0 |  | 10.0 |  |  | oleth-20 |
| 64-05 | 15 | 1.0 |  | 10.0 |  |  | Neodol 25-20 |
| 64-06 | 15 | 1.0 |  | 10.0 |  |  | ceteareth-27 |
| 64-07 | 15 | 1.0 |  | 10.0 |  |  | ceteareth-55 |
| 64-08 | 15 | 1.0 |  | 10.0 |  |  | Genapol UD-110 |
| 64-09 | 15 |  |  | 10.0 |  |  | ceteareth-27 |
| 64-10 | 15 |  |  | 10.0 |  |  | ceteareth-55 |
| 64-11 | 15 |  |  | 10.0 |  |  | Genapol UD-110 |
| 64-12 | 15 |  |  | 10.0 |  |  | oleth-20 |
| 64-13 | 10 |  |  | 10.0 |  |  | oleth-20 |
| 64-14 | 10 | 1.0 |  | 10.0 |  |  | oleth-20 |
| 64-15 | 20 |  |  | 10.0 |  |  | oleth-20 |
| 64-16 | 15 | 0.5 |  | 5.0 |  |  | oleth-20 |
| 64-17 | 15 | 0.5 |  | 10.0 |  |  | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B, C and J were applied as comparative treatments. Results, averaged for all replicates of each treatment, are shown in Table 64b.

TABLE 64b

| Concentrate composition | Glyphosate rate g a.e./ha | % Inhibition ABUTH | ECHCF |
|---|---|---|---|
| Formulation B | 150 | 0 | 0 |
|  | 250 | 8 | 20 |
|  | 350 | 27 | 40 |
|  | 450 | 62 | 50 |
| Formulation C | 150 | 27 | 50 |
|  | 250 | 75 | 70 |
|  | 350 | 92 | 80 |
|  | 450 | 97 | 92 |
| Formulation J | 150 | 23 | 30 |
|  | 250 | 72 | 50 |
|  | 350 | 94 | 63 |
|  | 450 | 95 | 80 |
| 64-01 | 150 | 22 | 30 |
|  | 250 | 60 | 40 |
|  | 350 | 83 | 57 |
|  | 450 | 90 | 67 |

TABLE 64b-continued

| Concentrate composition | Glyphosate rate g a.e./ha | % Inhibition ABUTH | % Inhibition ECHCF |
|---|---|---|---|
| 64-02 | 150 | 12 | 33 |
|  | 250 | 45 | 50 |
|  | 350 | 73 | 63 |
|  | 450 | 83 | 83 |
| 64-03 | 150 | 27 | 43 |
|  | 250 | 68 | 50 |
|  | 350 | 80 | 63 |
|  | 450 | 87 | 87 |
| 64-04 | 150 | 68 | 47 |
|  | 250 | 95 | 73 |
|  | 350 | 99 | 78 |
|  | 450 | 95 | 90 |
| 64-05 | 150 | 50 | 50 |
|  | 250 | 77 | 77 |
|  | 350 | 90 | 83 |
|  | 450 | 98 | 83 |
| 64-06 | 150 | 78 | 67 |
|  | 250 | 93 | 82 |
|  | 350 | 97 | 87 |
|  | 450 | 99 | 97 |
| 64-07 | 150 | 87 | 57 |
|  | 250 | 96 | 73 |
|  | 350 | 99 | 85 |
|  | 450 | 99 | 97 |
| 64-08 | 150 | 42 | 30 |
|  | 250 | 73 | 53 |
|  | 350 | 82 | 85 |
|  | 450 | 95 | 89 |
| 64-09 | 150 | 67 | 40 |
|  | 250 | 95 | 73 |
|  | 350 | 99 | 95 |
|  | 450 | 99 | 98 |
| 64-10 | 150 | 85 | 60 |
|  | 250 | 96 | 68 |
|  | 350 | 96 | 91 |
|  | 450 | 100 | 88 |
| 64-11 | 150 | 13 | 10 |
|  | 250 | 67 | 50 |
|  | 350 | 78 | 60 |
|  | 450 | 88 | 73 |
| 64-12 | 150 | 72 | 43 |
|  | 250 | 97 | 68 |
|  | 350 | 98 | 83 |
|  | 450 | 99 | 93 |
| 64-13 | 150 | 73 | 57 |
|  | 250 | 88 | 70 |
|  | 350 | 98 | 87 |
|  | 450 | 99 | 96 |
| 64-14 | 150 | 80 | 50 |
|  | 250 | 96 | 70 |
|  | 350 | 99 | 85 |
|  | 450 | 98 | 88 |
| 64-15 | 150 | 70 | 43 |
|  | 250 | 96 | 53 |
|  | 350 | 97 | 82 |
|  | 450 | 99 | 89 |
| 64-16 | 150 | 62 | 53 |
|  | 250 | 88 | 72 |
|  | 350 | 99 | 81 |
|  | 450 | 99 | 91 |
| 64-17 | 150 | 72 | 58 |
|  | 250 | 95 | 68 |
|  | 350 | 100 | 89 |
|  | 450 | 100 | 93 |

The greatest herbicidal effectiveness in this test was exhibited by compositions containing a $C_{16-18}$ alkylether surfactant (oleth-20, ceteareth-27 or ceteareth-55).

Example 65

Aqueous concentrate compositions were prepared containing glyphosate IPA salt and excipient ingredients as shown in Table 65a. All are oil-in-water emulsions and were prepared by process (vii).

TABLE 65a

| Concentrate composition | Glyphosate g a.e./l | Butyl stearate % w/w | Surfactant % w/w | Type of surfactant |
|---|---|---|---|---|
| 65-01 | 163 | 1.00 | 10.0 | Tween 80 |
| 65-02 | 163 | 1.00 | 10.0 | Emerest 2661 |
| 65-03 | 326 | 1.00 | 10.0 | Genapol UD-110 |
| 65-04 | 326 | 0.50 | 10.0 | Genapol UD-110 |
| 65-05 | 326 | 0.25 | 10.0 | Genapol UD-110 |
| 65-06 | 163 | 0.25 | 10.0 | Genapol UD-110 |
| 65-07 | 163 | 1.00 | 10.0 | Genapol UD-110 |
| 65-08 | 163 | 1.00 | 10.0 | Neodol 1-9 |
| 65-09 | 163 | 1.00 | 10.0 | Neodol 1-12 |
| 65-10 | 163 | 1.00 | 10.0 | Neodol 25-20 |
| 65-11 | 163 | 1.00 | 10.0 | Neodol 25-12 |
| 65-12 | 163 | 1.00 | 10.0 | Neodox 25-11 |
| 65-13 | 163 | 1.00 | 10.0 | laureth-23 |
| 65-14 | 163 | 1.00 | 10.0 | ceteth-20 |
| 65-15 | 163 | 1.00 | 10.0 | steareth-20 |
| 65-16 | 163 | 1.00 | 10.0 | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 23 days after application.

Formulations B, C and J were applied as comparative treatments. Results, averaged for all replicates of each treatment, are shown in Table 65b.

TABLE 65b

| Concentrate composition | Glyphosate rate g a.e./ha | % Inhibition ABUTH | % Inhibition ECHCF |
|---|---|---|---|
| Formulation B | 150 | 0 | 0 |
|  | 250 | 25 | 22 |
|  | 350 | 60 | 40 |
|  | 450 | 65 | 52 |
| Formulation C | 150 | 43 | 52 |
|  | 250 | 72 | 83 |
|  | 350 | 87 | 98 |
|  | 450 | 97 | 95 |
| Formulation J | 150 | 50 | 43 |
|  | 250 | 75 | 91 |
|  | 350 | 86 | 96 |
|  | 450 | 95 | 97 |
| 65-01 | 150 | 50 | 30 |
|  | 250 | 75 | 75 |
|  | 350 | 85 | 87 |
|  | 450 | 90 | 92 |
| 65-02 | 150 | 35 | 47 |
|  | 250 | 58 | 77 |
|  | 350 | 75 | 85 |
|  | 450 | 80 | 96 |
| 65-03 | 150 | 33 | 32 |
|  | 250 | 57 | 53 |
|  | 350 | 75 | 78 |
|  | 450 | 84 | 94 |
| 65-04 | 150 | 20 | 25 |
|  | 250 | 55 | 68 |
|  | 350 | 78 | 91 |
|  | 450 | 82 | 97 |
| 65-05 | 150 | 37 | 12 |
|  | 250 | 58 | 42 |
|  | 350 | 81 | 70 |
|  | 450 | 86 | 73 |

TABLE 65b-continued

| Concentrate composition | Glyphosate rate g a.e./ha | % Inhibition ABUTH | ECHCF |
|---|---|---|---|
| 65-06 | 150 | 50 | 8 |
| | 250 | 65 | 40 |
| | 350 | 81 | 65 |
| | 450 | 92 | 85 |
| 65-07 | 150 | 50 | 30 |
| | 250 | 63 | 48 |
| | 350 | 84 | 68 |
| | 450 | 98 | 84 |
| 65-08 | 150 | 43 | 35 |
| | 250 | 52 | 65 |
| | 350 | 73 | 85 |
| | 450 | 84 | 85 |
| 65-09 | 150 | 55 | 40 |
| | 250 | 68 | 58 |
| | 350 | 79 | 65 |
| | 450 | 97 | 73 |
| 65-10 | 150 | 69 | 40 |
| | 250 | 81 | 68 |
| | 350 | 94 | 92 |
| | 450 | 99 | 96 |
| 65-11 | 150 | 58 | 50 |
| | 250 | 84 | 60 |
| | 350 | 90 | 83 |
| | 450 | 94 | 93 |
| 65-12 | 150 | 50 | 40 |
| | 250 | 57 | 67 |
| | 350 | 65 | 84 |
| | 450 | 75 | 98 |
| 65-13 | 150 | 57 | 53 |
| | 250 | 78 | 73 |
| | 350 | 89 | 97 |
| | 450 | 98 | 97 |
| 65-14 | 150 | 68 | 67 |
| | 250 | 85 | 73 |
| | 350 | 97 | 98 |
| | 450 | 100 | 97 |
| 65-15 | 150 | 72 | 50 |
| | 250 | 88 | 89 |
| | 350 | 89 | 98 |
| | 450 | 99 | 97 |
| 65-16 | 150 | 65 | 53 |
| | 250 | 87 | 72 |
| | 350 | 97 | 85 |
| | 450 | 100 | 95 |

Activity overall in this test was very high, and differences among compositions in herbicidal effectiveness are difficult to discern clearly.

Example 66

Aqueous concentrate compositions were prepared containing glyphosate IPA salt and excipient ingredients as shown in Table 66a. All are oil-in-water emulsions and were prepared by process (vii). The pH of all compositions was approximately 5.

TABLE 66a

| | | % w/w | | |
|---|---|---|---|---|
| Concentrate composition | Glyphosate g a.e./l | Butyl Stearate | Surfactant | Type of surfactant |
| 66-01 | 163 | 1.00 | 10.0 | Tween 80 |
| 66-02 | 163 | 1.00 | 10.0 | Emerest 2661 |
| 66-03 | 163 | 1.00 | 10.0 | Neodol 25-20 |
| 66-04 | 163 | 1.00 | 10.0 | oleth-20 |
| 66-05 | 163 | 0.50 | 5.0 | oleth-20 |
| 66-06 | 163 | 0.25 | 2.5 | oleth-20 |
| 66-07 | 163 | 0.50 | 2.5 | oleth-20 |
| 66-08 | 163 | 0.50 | 1.0 | oleth-20 |
| 66-09 | 163 | 0.25 | 5.0 | oleth-20 |
| 66-10 | 326 | 1.00 | 10.0 | Neodol 1-12 |
| 66-11 | 326 | 0.50 | 10.0 | Neodol 1-12 |
| 66-12 | 326 | 0.25 | 10.0 | Neodol 1-12 |
| 66-13 | 326 | 1.00 | 5.0 | Neodol 1-12 |
| 66-14 | 326 | 0.50 | 5.0 | Neodol 1-12 |
| 66-15 | 326 | 0.25 | 5.0 | Neodol 1-12 |
| 66-16 | 326 | 0.10 | 5.0 | Neodol 1-12 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 20 days after application.

Formulations B, C and J were applied as comparative treatments. Results, averaged for all replicates of each treatment, are shown in Table 66b.

TABLE 66b

| Concentrate composition | Glyphosate rate g a.e./ha | % Inhibition ABUTH | ECHCF |
|---|---|---|---|
| Formulation B | 150 | 7 | 50 |
| | 250 | 45 | 60 |
| | 350 | 73 | 73 |
| | 450 | 80 | 78 |
| Formulation C | 150 | 75 | 77 |
| | 250 | 87 | 100 |
| | 350 | 96 | 99 |
| | 450 | 99 | 97 |
| Formulation J | 150 | 72 | 77 |
| | 250 | 83 | 89 |
| | 350 | 97 | 99 |
| | 450 | 97 | 98 |
| 66-01 | 150 | 60 | 75 |
| | 250 | 80 | 85 |
| | 350 | 93 | 97 |
| | 450 | 98 | 98 |
| 66-02 | 150 | 57 | 75 |
| | 250 | 70 | 83 |
| | 350 | 87 | 83 |
| | 450 | 90 | 94 |
| 66-03 | 150 | 77 | 80 |
| | 250 | 87 | 92 |
| | 350 | 97 | 87 |
| | 450 | 99 | 98 |
| 66-04 | 150 | 80 | 89 |
| | 250 | 93 | 92 |
| | 350 | 99 | 99 |
| | 450 | 100 | 99 |
| 66-05 | 150 | 83 | 83 |
| | 250 | 92 | 93 |
| | 350 | 97 | 90 |
| | 450 | 100 | 93 |
| 66-06 | 150 | 77 | 77 |
| | 250 | 80 | 91 |
| | 350 | 90 | 99 |
| | 450 | 98 | 99 |
| 66-07 | 150 | 77 | 83 |
| | 250 | 82 | 89 |
| | 350 | 90 | 91 |
| | 450 | 97 | 98 |
| 66-08 | 150 | 47 | 82 |
| | 250 | 73 | 82 |
| | 350 | 80 | 97 |
| | 450 | 92 | 91 |

TABLE 66b-continued

| Concentrate composition | Glyphosate rate g a.e./ha | % Inhibition ABUTH | % Inhibition ECHCF |
|---|---|---|---|
| 66-09 | 150 | 73 | 78 |
|  | 250 | 87 | 88 |
|  | 350 | 97 | 94 |
|  | 450 | 99 | 99 |
| 66-10 | 150 | 52 | 67 |
|  | 250 | 70 | 80 |
|  | 350 | 93 | 88 |
|  | 450 | 93 | 94 |
| 66-11 | 150 | 40 | 68 |
|  | 250 | 72 | 85 |
|  | 350 | 87 | 96 |
|  | 450 | 93 | 96 |
| 66-12 | 150 | 37 | 60 |
|  | 250 | 68 | 83 |
|  | 350 | 85 | 85 |
|  | 450 | 93 | 75 |
| 66-13 | 150 | 28 | 63 |
|  | 250 | 53 | 80 |
|  | 350 | 85 | 97 |
|  | 450 | 88 | 97 |
| 66-14 | 150 | 37 | 63 |
|  | 250 | 58 | 73 |
|  | 350 | 83 | 96 |
|  | 450 | 90 | 91 |
| 66-15 | 150 | 30 | 70 |
|  | 250 | 47 | 83 |
|  | 350 | 82 | 89 |
|  | 450 | 87 | 89 |
| 66-16 | 150 | 40 | 53 |
|  | 250 | 53 | 82 |
|  | 350 | 80 | 80 |
|  | 450 | 88 | 77 |

Composition 66-04, containing 1% butyl stearate and 10% oleth-20 (surfactant to glyphosate a.e. weight/weight ratio about 1:1.5), exhibited marginally greater herbicidal effectiveness than composition 66-03, containing 1% butyl stearate and 10% Neodol 25-20. At this very high surfactant to glyphosate ratio, however, both performed extremely well. Surprisingly, when the butyl stearate and oleth-20 concentrations were significantly lowered, this high level of performance was maintained to a remarkable degree. Even when butyl stearate was reduced to 0.25% and oleth-20 to 2.5% (surfactant to glyphosate a.e. ratio about 1:6), as in composition 66-06, herbicidal effectiveness was still similar to that obtained with commercial standard Formulations C and J.

Example 67

Aqueous concentrate compositions were prepared containing glyphosate IPA salt and excipient ingredients as shown in Table 67a. Concentrate compositions 67-01 to 67-08 and 67-11 to 67-16 are oil-in-water emulsions and were prepared by process (vii). Concentrate compositions 67-09 and 67-10 are aqueous solution concentrates and were prepared by process (viii). The pH of all compositions was approximately 5.

TABLE 67a

| Concentrate composition | % w/w Glyphosate a.e. | % w/w Butyl stearate | % w/w Surfactant | Type of surfactant |
|---|---|---|---|---|
| 67-01 | 15.0 | 0.25 | 5.0 | Emerest 2661 |
| 67-02 | 15.0 | 0.25 | 5.0 | Tween 80 |
| 67-03 | 15.0 | 0.25 | 5.0 | Neodol 25-20 |
| 67-04 | 15.0 | 0.25 | 5.0 | laureth-23 |
| 67-05 | 15.0 | 0.25 | 5.0 | ceteth-20 |
| 67-06 | 15.0 | 0.25 | 2.5 | Tween 80 |
| 67-07 | 15.0 | 0.10 | 1.0 | Tween 80 |
| 67-08 | 15.0 | 1.00 | 10.0 | Tween 80 |
| 67-09 | 15.0 |  | 5.0 | laureth-23 |
| 67-10 | 15.0 |  | 5.0 | ceteth-20 |
| 67-11 | 15.0 | 1.00 | 10.0 | Neodol 25-20 |
| 67-12 | 15.0 | 1.00 | 10.0 | oleth-20 |
| 67-13 | 15.0 | 0.50 | 5.0 | oleth-20 |
| 67-14 | 15.0 | 0.25 | 5.0 | oleth-20 |
| 67-15 | 15.0 | 0.25 | 2.5 | oleth-20 |
| 67-16 | 15.0 | 0.25 | 5.0 | Genapol UD-110 |

Velvetleaf (*Abutilon theophrasti*, ABUTH) and Japanese millet (*Echinochloa crus-galli*, ECHCF) plants were grown and treated by the standard procedures given above. Applications of spray compositions were made 12 days after planting ABUTH and ECHCF, and evaluation of herbicidal inhibition was done 16 days after application.

Formulations B, C and J were applied as comparative treatments. Results, averaged for all replicates of each treatment, are shown in Table 67b.

TABLE 67b

| Concentrate composition | Glyphosate rate g a.e./ha | % Inhibition ABUTH | % Inhibition ECHCF |
|---|---|---|---|
| Formulation B | 150 | 2 | 10 |
|  | 250 | 5 | 20 |
|  | 350 | 43 | 30 |
|  | 450 | 58 | 43 |
| Formulation C | 150 | 68 | 50 |
|  | 250 | 92 | 79 |
|  | 350 | 96 | 90 |
|  | 450 | 98 | 85 |
| Formulation J | 150 | 57 | 43 |
|  | 250 | 90 | 63 |
|  | 350 | 95 | 80 |
|  | 450 | 95 | 95 |
| 67-01 | 150 | 7 | 33 |
|  | 250 | 50 | 43 |
|  | 350 | 77 | 53 |
|  | 450 | 80 | 93 |
| 67-02 | 150 | 17 | 50 |
|  | 250 | 72 | 70 |
|  | 350 | 80 | 80 |
|  | 450 | 80 | 93 |
| 67-03 | 150 | 43 | 40 |
|  | 250 | 75 | 68 |
|  | 350 | 87 | 75 |
|  | 450 | 96 | 95 |
| 67-04 | 150 | 33 | 47 |
|  | 250 | 73 | 63 |
|  | 350 | 80 | 77 |
|  | 450 | 90 | 93 |
| 67-05 | 150 | 73 | 37 |
|  | 250 | 92 | 57 |
|  | 350 | 95 | 88 |
|  | 450 | 95 | 73 |
| 67-06 | 150 | 25 | 35 |
|  | 250 | 68 | 47 |
|  | 350 | 80 | 92 |
|  | 450 | 88 | 85 |

TABLE 67b-continued

| Concentrate composition | Glyphosate rate g a.e./ha | % Inhibition ABUTH | ECHCF |
|---|---|---|---|
| 67-07 | 150 | 3 | 30 |
| | 250 | 57 | 40 |
| | 350 | 77 | 53 |
| | 450 | 80 | 67 |
| 67-08 | 150 | 53 | 43 |
| | 250 | 77 | 62 |
| | 350 | 80 | 88 |
| | 450 | 93 | 80 |
| 67-09 | 150 | 32 | 60 |
| | 250 | 77 | 53 |
| | 350 | 93 | 73 |
| | 450 | 97 | 93 |
| 67-10 | 150 | 75 | 35 |
| | 250 | 92 | 77 |
| | 350 | 96 | 77 |
| | 450 | 97 | 93 |
| 67-11 | 150 | 75 | 53 |
| | 250 | 90 | 78 |
| | 350 | 95 | 89 |
| | 450 | 98 | 97 |
| 67-12 | 150 | 80 | 43 |
| | 250 | 95 | 73 |
| | 350 | 96 | 92 |
| | 450 | 98 | 89 |
| 67-13 | 150 | 75 | 53 |
| | 250 | 92 | 97 |
| | 350 | 97 | 99 |
| | 450 | 96 | 93 |
| 67-14 | 150 | 78 | 70 |
| | 250 | 90 | 92 |
| | 350 | 93 | 97 |
| | 450 | 95 | 93 |
| 67-15 | 150 | 70 | 60 |
| | 250 | 83 | 98 |
| | 350 | 95 | 99 |
| | 450 | 97 | 99 |
| 67-16 | 150 | 27 | 52 |
| | 250 | 75 | 73 |
| | 350 | 80 | 98 |
| | 450 | 83 | 99 |

Extremely high herbicidal effectiveness was again observed with a composition (67-15) containing 15% glyphosate a.e. and just 2.5% oleth-20 together with 0.25% butyl stearate. A comparison of 15% glyphosate a.e. compositions containing 5% alkylether surfactant and 0.25% butyl stearate provided the following ranking of alkylethers in descending order of effectiveness: oleth-20 (67-14)>ceteth-20 (67-05)>Neodol 25-20 (67-03)=laureth-23 (67-04).

Example 68

Aqueous concentrate compositions were prepared containing glyphosate IPA salt and excipient ingredients as shown in Table 68a. All are oil-in-water emulsions and were prepared by process (vii).

TABLE 68a

| Concentrate composition | Glyphosate g a.e./l | Butyl stearate % w/w | Surfactant | Type of surfactant |
|---|---|---|---|---|
| 68-01 | 163 | 0.50 | 5.0 | oleth-20 |
| 68-02 | 163 | 0.25 | 5.0 | oleth-20 |
| 68-03 | 163 | 0.25 | 2.5 | oleth-20 |
| 68-04 | 163 | 1.00 | 10.0 | oleth-20 |
| 68-05 | 163 | 0.50 | 5.0 | steareth-20 |
| 68-06 | 163 | 0.25 | 5.0 | steareth-20 |
| 68-07 | 163 | 0.25 | 2.5 | steareth-20 |
| 68-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 16 days after application.

Formulations B, C and J were applied as comparative treatments. Results, averaged for all replicates of each treatment, are shown in Table 68b.

TABLE 68b

| Concentrate composition | Glyphosate rate g a.e./ha | % Inhibition ABUTH | ECHCF |
|---|---|---|---|
| Formulation B | 150 | 0 | 30 |
| | 250 | 20 | 43 |
| | 350 | 43 | 53 |
| | 450 | 68 | 57 |
| Formulation C | 150 | 60 | 47 |
| | 250 | 75 | 53 |
| | 350 | 87 | 80 |
| | 450 | 87 | 78 |
| Formulation J | 150 | 42 | 43 |
| | 250 | 83 | 60 |
| | 350 | 87 | 73 |
| | 450 | 93 | 87 |
| 68-01 | 150 | 60 | 60 |
| | 250 | 78 | 63 |
| | 350 | 87 | 89 |
| | 450 | 92 | 78 |
| 68-02 | 150 | 70 | 43 |
| | 250 | 80 | 91 |
| | 350 | 87 | 86 |
| | 450 | 96 | 87 |
| 68-03 | 150 | 52 | 43 |
| | 250 | 75 | 72 |
| | 350 | 83 | 93 |
| | 450 | 87 | 94 |
| 68-04 | 150 | 72 | 50 |
| | 250 | 93 | 73 |
| | 350 | 97 | 95 |
| | 450 | 97 | 91 |
| 68-05 | 150 | 72 | 43 |
| | 250 | 80 | 78 |
| | 350 | 87 | 91 |
| | 450 | 93 | 85 |
| 68-06 | 150 | 68 | 40 |
| | 250 | 80 | 50 |
| | 350 | 93 | 75 |
| | 450 | 95 | 85 |
| 68-07 | 150 | 63 | 37 |
| | 250 | 78 | 55 |
| | 350 | 87 | 84 |
| | 450 | 83 | 82 |
| 68-08 | 150 | 70 | 50 |
| | 250 | 80 | 70 |
| | 350 | 92 | 84 |
| | 450 | 94 | 98 |

All compositions containing butyl stearate and either oleth-20 or steareth-20 showed a very high level of performance by comparison with commercial standard Formulations C and J.

Example 69

Aqueous concentrate compositions were prepared containing glyphosate IPA salt and excipient ingredients as shown in Table 69a. All are oil-in-water emulsions and were prepared by process (vii).

TABLE 69a

| Concentrate composition | Glyphosate g a.e./l | % w/w stearate | % w/w Surfactant | Type of surfactant |
|---|---|---|---|---|
| 69-01 | 163 | 0.50 | 5.0 | oleth-20 |
| 69-02 | 163 | 0.25 | 5.0 | oleth-20 |
| 69-03 | 163 | 0.25 | 2.5 | oleth-20 |
| 69-04 | 163 | 1.00 | 10.0 | oleth-20 |
| 69-05 | 163 | 0.50 | 5.0 | steareth-20 |
| 69-06 | 163 | 0.25 | 5.0 | steareth-20 |
| 69-07 | 163 | 0.25 | 2.5 | steareth-20 |
| 69-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 18 days after application.

Formulations B, C and J were applied as comparative treatments. Results, averaged for all replicates of each treatment, are shown in Table 69b.

TABLE 69b

| Concentrate composition | Glyphosate rate g a.e./ha | % Inhibition ABUTH | % Inhibition ECHCF |
|---|---|---|---|
| Formulation B | 150 | 3 | 10 |
| | 250 | 28 | 23 |
| | 350 | 72 | 37 |
| | 450 | 73 | 50 |
| Formulation C | 150 | 57 | 43 |
| | 250 | 87 | 62 |
| | 350 | 93 | 83 |
| | 450 | 99 | 95 |
| Formulation J | 150 | 27 | 47 |
| | 250 | 70 | 53 |
| | 350 | 92 | 75 |
| | 450 | 94 | 92 |

TABLE 69b-continued

| Concentrate composition | Glyphosate rate g a.e./ha | % Inhibition ABUTH | % Inhibition ECHCF |
|---|---|---|---|
| 69-01 | 150 | 68 | 50 |
| | 250 | 85 | 47 |
| | 350 | 97 | 70 |
| | 450 | 99 | 83 |
| 69-02 | 150 | 67 | 40 |
| | 250 | 78 | 50 |
| | 350 | 96 | 63 |
| | 450 | 99 | 68 |
| 69-03 | 150 | 52 | 40 |
| | 250 | 72 | 50 |
| | 350 | 95 | 63 |
| | 450 | 97 | 85 |
| 69-04 | 150 | 72 | 40 |
| | 250 | 97 | 53 |
| | 350 | 97 | 77 |
| | 450 | 99 | 90 |
| 69-05 | 150 | 75 | 40 |
| | 250 | missing | 53 |
| | 350 | 88 | 53 |
| | 450 | 96 | 78 |
| 69-06 | 150 | 98 | 40 |
| | 250 | 93 | 50 |
| | 350 | 97 | 68 |
| | 450 | 97 | 82 |
| 69-07 | 150 | 73 | 40 |
| | 250 | 92 | 50 |
| | 350 | 98 | 63 |
| | 450 | 98 | 80 |
| 69-08 | 150 | 77 | 43 |
| | 250 | 93 | 57 |
| | 350 | 97 | 77 |
| | 450 | 98 | 88 |

All compositions containing butyl stearate and either oleth-20 or steareth-20 showed a very high level of performance by comparison with commercial standard Formulations C and J.

Example 70

Aqueous concentrate compositions were prepared containing glyphosate IPA salt and excipient ingredients as shown in Table 70a. All contain colloidal particulates and were prepared by process (ix).

All compositions of this example showed acceptable storage stability. The compositions containing oleth-20 were not acceptably storage-stable in the absence of the colloidal particulate.

TABLE 70a

| Concentrate composition | Glyphosate g a.e./l | Butyl stearate (% w/w) | Oleth-20 (% w/w) | Aerosil (% w/w) | Type of Aerosil |
|---|---|---|---|---|---|
| 70-01 | 488 |  | 3.0 | 0.4 | OX-50 |
| 70-02 | 488 |  | 3.0 | 0.8 | OX-50 |
| 70-03 | 488 |  | 3.0 | 1.5 | OX-50 |
| 70-04 | 488 |  |  | 0.4 | OX-50 |
| 70-05 | 488 |  |  | 0.8 | OX-50 |
| 70-06 | 488 |  |  | 1.5 | OX-50 |
| 70-07 | 488 |  | 3.0 | 0.4 | MOX-80 |
| 70-08 | 488 |  | 3.0 | 0.8 | MOX-80 |
| 70-09 | 488 |  | 3.0 | 1.5 | MOX-80 |
| 70-10 | 488 |  |  | 0.4 | MOX-80 |
| 70-11 | 488 |  |  | 0.8 | MOX-80 |
| 70-12 | 488 |  |  | 1.5 | MOX-80 |
| 70-13 | 488 |  | 3.0 | 0.4 | MOX-170 |
| 70-14 | 488 |  | 3.0 | 0.8 | MOX-170 |

TABLE 70a-continued

| Concentrate composition | Glyphosate g a.e./l | % w/w Butyl stearate | Oleth-20 | Aerosil | Type of Aerosil |
|---|---|---|---|---|---|
| 70-15 | 488 | | 3.0 | 1.5 | MOX-170 |
| 70-16 | 488 | | | 0.4 | MOX-170 |
| 70-17 | 488 | | | 0.8 | MOX-170 |
| 70-18 | 488 | | | 1.5 | MOX-170 |
| 70-19 | 488 | 3.0 | 3.0 | 1.5 | MOX-80 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 20 days after application.

Formulations B and J were applied as comparative treatments. Results, averaged for all replicates of each treatment, are shown in Table 70b.

TABLE 70b

| Concentrate composition | Glyphosate rate g a.e./ha | % Inhibition ABUTH | ECHCF |
|---|---|---|---|
| Formulation B | 150 | 0 | 27 |
| | 250 | 17 | 37 |
| | 350 | 47 | 57 |
| | 450 | 60 | 60 |
| Formulation J | 150 | 57 | 50 |
| | 250 | 82 | 87 |
| | 350 | 95 | 99 |
| | 450 | 98 | 99 |
| 70-01 | 150 | 37 | 60 |
| | 250 | 73 | 70 |
| | 350 | 96 | 97 |
| | 450 | 96 | 99 |
| 70-02 | 150 | 43 | 50 |
| | 250 | 73 | 63 |
| | 350 | 93 | 96 |
| | 450 | 98 | 99 |
| 70-03 | 150 | 53 | 60 |
| | 250 | 83 | 87 |
| | 350 | 87 | 97 |
| | 450 | 98 | 98 |
| 70-04 | 150 | 45 | 40 |
| | 250 | 57 | 60 |
| | 350 | 78 | 95 |
| | 450 | 94 | 100 |
| 70-05 | 150 | 47 | 50 |
| | 250 | 60 | 82 |
| | 350 | 92 | 96 |
| | 450 | 95 | 99 |
| 70-06 | 150 | 38 | 53 |
| | 250 | 68 | 96 |
| | 350 | 82 | 99 |
| | 450 | 83 | 95 |
| 70-07 | 150 | 50 | 57 |
| | 250 | 87 | 88 |
| | 350 | 91 | 99 |
| | 450 | 98 | 98 |
| 70-08 | 150 | 53 | 50 |
| | 250 | 88 | 85 |
| | 350 | 96 | 97 |
| | 450 | 97 | 100 |
| 70-09 | 150 | 40 | 30 |
| | 250 | 37 | 47 |
| | 350 | 57 | 80 |
| | 450 | 77 | 94 |

TABLE 70b-continued

| Concentrate composition | Glyphosate rate g a.e./ha | % Inhibition ABUTH | ECHCF |
|---|---|---|---|
| 70-10 | 150 | 47 | 50 |
| | 250 | 70 | 95 |
| | 350 | 75 | 99 |
| | 450 | 77 | 98 |
| 70-11 | 150 | 27 | 60 |
| | 250 | 72 | 85 |
| | 350 | 82 | 98 |
| | 450 | 75 | 99 |
| 70-12 | 150 | 37 | 57 |
| | 250 | 73 | 86 |
| | 350 | 80 | 99 |
| | 450 | 85 | 100 |
| 70-13 | 150 | 45 | 53 |
| | 250 | 85 | 94 |
| | 350 | 95 | 100 |
| | 450 | 98 | 99 |
| 70-14 | 150 | 50 | 50 |
| | 250 | 78 | 83 |
| | 350 | 94 | 98 |
| | 450 | 98 | 99 |
| 70-15 | 150 | 53 | 67 |
| | 250 | 75 | 88 |
| | 350 | 93 | 97 |
| | 450 | 96 | 99 |
| 70-16 | 150 | 42 | 50 |
| | 250 | 47 | 96 |
| | 350 | 70 | 98 |
| | 450 | 90 | 99 |
| 70-17 | 150 | 27 | 83 |
| | 250 | 57 | 98 |
| | 350 | 87 | 99 |
| | 450 | 87 | 100 |
| 70-18 | 150 | 33 | 60 |
| | 250 | 47 | 94 |
| | 350 | 83 | 99 |
| | 450 | 93 | 99 |
| 70-19 | 150 | 45 | 47 |
| | 250 | 80 | 73 |
| | 350 | 96 | 94 |
| | 450 | 99 | 98 |

Remarkably high levels of herbicidal effectiveness were obtained in this test with compositions containing oleth-20 at a weight/weight ratio to glyphosate a.e. of about 1:14, and stabilized with colloidal particulates. In some cases the colloidal particulate alone contributed a major part of the efficacy enhancement. Results with composition 70-09 are out of line with other data and an application problem is suspected.

Example 71

Aqueous concentrate compositions were prepared containing glyphosate IPA salt and excipient ingredients as shown in Table 71a. Concentrate compositions 71-01 to 71-04, 71-06, 71-08, 71-09, 71-11, 71-12, 71-14 and 71-16 are oil-in-water emulsions and were prepared by process (vii). Concentrate compositions 71-05, 71-07, 71-10, 71-13, 71-15 and 71-17 are aqueous solution concentrates and were prepared by process (viii).

TABLE 71a

| Concentrate composition | Glyphosate g a.e./l | Butyl stearate | Surfactant | Type of surfactant |
|---|---|---|---|---|
| 71-01 | 163 | 0.25 | 2.5 | Neodol 1-12 |
| 71-02 | 163 | 0.25 | 2.5 | laureth-23 |
| 71-03 | 163 | 0.25 | 2.5 | steareth-10 |
| 71-04 | 163 | 0.25 | 2.5 | steareth-20 |
| 71-05 | 163 |  | 2.5 | steareth-20 |
| 71-06 | 163 | 0.25 | 2.5 | steareth-100 |
| 71-07 | 163 |  | 2.5 | steareth-100 |
| 71-08 | 163 | 0.25 | 2.5 | oleth-10 |
| 71-09 | 163 | 0.25 | 2.5 | oleth-20 |
| 71-10 | 163 |  | 2.5 | oleth-20 |
| 71-11 | 163 | 0.25 | 2.5 | ceteth-10 |
| 71-12 | 163 | 0.25 | 2.5 | ceteth-20 |
| 71-13 | 163 |  | 2.5 | ceteth-20 |
| 71-14 | 326 | 0.50 | 5.0 | ceteareth-27 |
| 71-15 | 326 |  | 5.0 | ceteareth-27 |
| 71-16 | 163 | 0.25 | 2.5 | ceteareth-55 |
| 71-17 | 163 |  | 2.5 | ceteareth-55 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulations B, C and J were applied as comparative treatments. Results, averaged for all replicates of each treatment, are shown in Table 71b.

TABLE 71b

| Concentrate composition | Glyphosate rate g a.e./ha | % Inhibition ABUTH | % Inhibition ECHCF |
|---|---|---|---|
| Formulation B | 150 | 0 | 33 |
|  | 250 | 20 | 43 |
|  | 350 | 63 | 63 |
|  | 450 | 75 | 70 |
| Formulation C | 150 | 53 | 55 |
|  | 250 | 80 | 87 |
|  | 350 | 94 | 97 |
|  | 450 | 98 | 99 |
| Formulation J | 150 | 40 | 57 |
|  | 250 | 80 | 90 |
|  | 350 | 96 | 99 |
|  | 450 | 98 | 99 |
| 71-01 | 150 | 52 | 40 |
|  | 250 | 65 | 73 |
|  | 350 | 77 | 70 |
|  | 450 | 77 | 70 |
| 71-02 | 150 | 37 | 70 |
|  | 250 | 75 | 80 |
|  | 350 | 83 | 97 |
|  | 450 | 95 | 99 |
| 71-03 | 150 | 47 | 53 |
|  | 250 | 77 | 86 |
|  | 350 | 83 | 97 |
|  | 450 | 93 | 100 |
| 71-04 | 150 | 80 | 60 |
|  | 250 | 93 | 83 |
|  | 350 | 96 | 85 |
|  | 450 | 99 | 99 |

TABLE 71b-continued

| Concentrate composition | Glyphosate rate g a.e./ha | % Inhibition ABUTH | % Inhibition ECHCF |
|---|---|---|---|
| 71-05 | 150 | 80 | 43 |
|  | 250 | 93 | 79 |
|  | 350 | 96 | 94 |
|  | 450 | 98 | 96 |
| 71-06 | 150 | 77 | 53 |
|  | 250 | 85 | 83 |
|  | 350 | 94 | 99 |
|  | 450 | 97 | 99 |
| 71-07 | 150 | 63 | 50 |
|  | 250 | 80 | 88 |
|  | 350 | 85 | 96 |
|  | 450 | 96 | 99 |
| 71-08 | 150 | 27 | 45 |
|  | 250 | 75 | 83 |
|  | 350 | 77 | 99 |
|  | 450 | 96 | 98 |
| 71-09 | 150 | 75 | 57 |
|  | 250 | 80 | 82 |
|  | 350 | 97 | 95 |
|  | 450 | 99 | 98 |
| 71-10 | 150 | 70 | 40 |
|  | 250 | 85 | 83 |
|  | 350 | 97 | 98 |
|  | 450 | 99 | 99 |
| 71-11 | 150 | 53 | 37 |
|  | 250 | 75 | 63 |
|  | 350 | 88 | 93 |
|  | 450 | 92 | 98 |
| 71-12 | 150 | 70 | 40 |
|  | 250 | 78 | 75 |
|  | 350 | 90 | 91 |
|  | 450 | 98 | 98 |
| 71-13 | 150 | 72 | 40 |
|  | 250 | 92 | 80 |
|  | 350 | 97 | 90 |
|  | 450 | 99 | 97 |
| 71-14 | 150 | 78 | 53 |
|  | 250 | 89 | 88 |
|  | 350 | 97 | 95 |
|  | 450 | 99 | 100 |
| 71-15 | 150 | 80 | 60 |
|  | 250 | 95 | 97 |
|  | 350 | 98 | 100 |
|  | 450 | 99 | 99 |
| 71-16 | 150 | 60 | 63 |
|  | 250 | 87 | 78 |
|  | 350 | 96 | 94 |
|  | 450 | 98 | 99 |
| 71-17 | 150 | 73 | 60 |
|  | 250 | 85 | 57 |
|  | 350 | 93 | 80 |
|  | 450 | 99 | 85 |

In combination with butyl stearate, steareth-20 (composition 71-04) gave greater herbicidal effectiveness than steareth-10 (71-03) on ABUTH. Similarly, oleth-20 (71-09) was more efficacious than oleth-10 (71-08) and ceteth-20 (71-12) than ceteth-10 (71-11). In the absence of butyl stearate, ceteareth-55 (71-17) was noticeably weaker on ECHCF than ceteareth-27 (71-15) but inclusion of butyl stearate (71-16) tended to correct this weakness. Note that while compositions 71-14 and 71-15 contained twice as high a concentration of excipients as the other compositions of the test, the concentration of glyphosate was also twice as high, thus the concentrations as sprayed were the same.

Example 72

Aqueous concentrate compositions were prepared containing glyphosate IPA salt and excipient ingredients as shown in Table 72a. Concentrate compositions 72-01 to 72-05, 72-07, 72-08, 72-10 and 72-12 to 72-16 are oil-inwater emulsions and were prepared by process (vii). Concentrate compositions 72-06, 72-09 and 72-11 are aqueous solution concentrates and were prepared by process (viii).

TABLE 72a

| Concentrate composition | Glyphosate g a.e./l | % w/w | | |
|---|---|---|---|---|
| | | Butyl stearate | Surfactant | Type of surfactant |
| 72-01 | 163 | 0.25 | 2.5 | Neodol 1-12 |
| 72-02 | 163 | 0.25 | 2.5 | laureth-23 |
| 72-03 | 163 | 0.25 | 2.5 | steareth-10 |
| 72-04 | 163 | 0.25 | 2.5 | steareth-20 |
| 72-05 | 163 | 0.25 | 2.5 | Pluronic F-68 |
| 72-06 | 163 | | 2.5 | Pluronic F-68 |
| 72-07 | 326 | 1.00 | 5.0 | Pluronic F-108 |
| 72-08 | 326 | 0.50 | 5.0 | Pluronic F-108 |
| 72-09 | 326 | | 5.0 | Pluronic F-108 |
| 72-10 | 163 | 0.25 | 2.5 | Pluronic F-127 |
| 72-11 | 163 | | 2.5 | Pluronic F-127 |
| 72-12 | 326 | 0.50 | 5.0 | ceteareth-27 |
| 72-13 | 163 | 0.25 | 2.5 | ceteareth-55 |
| 72-14 | 163 | 0.25 | 2.5 | oleth-20 |
| 72-15 | 163 | 0.25 | 2.5 | ceteth-20 |
| 72-16 | 163 | 0.25 | 2.5 | steareth-100 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulations B, C and J were applied as comparative treatments. Results, averaged for all replicates of each treatment, are shown in Table 72b.

TABLE 72b

| Concentrate composition | Glyphosate rate g a.e./ha | % Inhibition | |
|---|---|---|---|
| | | ABUTH | ECHCF |
| Formulation B | 150 | 5 | 0 |
| | 250 | 47 | 5 |
| | 350 | 70 | 23 |
| | 450 | 75 | 43 |
| Formulation C | 150 | 73 | 47 |
| | 250 | 99 | 50 |
| | 350 | 98 | 67 |
| | 450 | 99 | 75 |
| Formulation J | 150 | 73 | 43 |
| | 250 | 89 | 50 |
| | 350 | 97 | 83 |
| | 450 | 98 | 77 |
| 72-01 | 150 | 37 | 30 |
| | 250 | 70 | 33 |
| | 350 | 77 | 40 |
| | 450 | 90 | 47 |
| 72-02 | 150 | 52 | 37 |
| | 250 | 77 | 67 |
| | 350 | 90 | 77 |
| | 450 | 92 | 75 |
| 72-03 | 150 | 40 | 30 |
| | 250 | 77 | 70 |
| | 350 | 80 | 82 |
| | 450 | 90 | 83 |
| 72-04 | 150 | 75 | 37 |
| | 250 | 95 | 53 |
| | 350 | 99 | 91 |
| | 450 | 99 | 82 |
| 72-05 | 150 | 58 | 37 |
| | 250 | 65 | 53 |
| | 350 | 80 | 80 |
| | 450 | 75 | 68 |
| 72-06 | 150 | 40 | 30 |
| | 250 | 75 | 33 |
| | 350 | 78 | 43 |
| | 450 | 80 | 43 |
| 72-07 | 150 | 50 | 30 |
| | 250 | 75 | 33 |
| | 350 | 78 | 53 |
| | 450 | 86 | 53 |
| 72-08 | 150 | 47 | 30 |
| | 250 | 75 | 33 |
| | 350 | 77 | 40 |
| | 450 | 80 | 50 |
| 72-09 | 150 | 43 | 33 |
| | 250 | 77 | 40 |
| | 350 | 78 | 63 |
| | 450 | 83 | 50 |
| 72-10 | 150 | 27 | 40 |
| | 250 | 77 | 43 |
| | 350 | 80 | 50 |
| | 450 | 92 | 40 |
| 72-11 | 150 | 37 | 30 |
| | 250 | 72 | 33 |
| | 350 | 80 | 60 |
| | 450 | 95 | 40 |
| 72-12 | 150 | 78 | 37 |
| | 250 | 98 | 40 |
| | 350 | 99 | 53 |
| | 450 | 100 | 50 |
| 72-13 | 150 | 75 | 30 |
| | 250 | 88 | 40 |
| | 350 | 98 | 47 |
| | 450 | 100 | 65 |
| 72-14 | 150 | 73 | 30 |
| | 250 | 87 | 40 |
| | 350 | 98 | 50 |
| | 450 | 99 | 53 |
| 72-15 | 150 | 72 | 30 |
| | 250 | 93 | 40 |
| | 350 | 96 | 43 |
| | 450 | 99 | 50 |
| 72-16 | 150 | 73 | 40 |
| | 250 | 83 | 40 |
| | 350 | 98 | 40 |
| | 450 | 100 | 47 |

Composition 72-04 containing steareth-20 outperformed its counterpart 72-03 containing stearth-10, though both gave greater herbicidal effectiveness, especially on ECHCF, than 72-02 containing laureth-23 or 72-01 containing Neodol 1-12.

Example 73

Aqueous concentrate compositions were prepared containing glyphosate IPA salt and excipient ingredients as shown in Table 73a. Concentrate compositions 73-01 to 73-07 and 73-09 to 73-15 are oil-in-water emulsions and were prepared by process (vii). Concentrate compositions 73-08 and 73-16 are aqueous solution concentrates and were prepared by process (viii).

TABLE 73a

| Concentrate composition | Glyphosate g a.e./l | % w/w Oil | % w/w Surfactant | Type of oil | Type of surfactant |
|---|---|---|---|---|---|
| 73-01 | 163 | 0.5 | 5.0 | methyl stearate | oleth-20 |
| 73-02 | 163 | 0.5 | 5.0 | butyl stearate | oleth-20 |
| 73-03 | 163 | 0.5 | 5.0 | methyl oleate | oleth-20 |
| 73-04 | 163 | 0.5 | 5.0 | butyl oleate | oleth-20 |
| 73-05 | 163 | 0.5 | 5.0 | methyl laurate | oleth-20 |
| 73-06 | 163 | 0.5 | 5.0 | butyl laurate | oleth-20 |
| 73-07 | 163 | 0.5 | 5.0 | Orchex 796 | oleth-20 |
| 73-08 | 163 |  | 5.0 | none | oleth-20 |
| 73-09 | 163 | 0.5 | 5.0 | methyl stearate | Neodol 1-9 |
| 73-10 | 163 | 0.5 | 5.0 | butyl stearate | Neodol 1-9 |
| 73-11 | 163 | 0.5 | 5.0 | methyl oleate | Neodol 1-9 |
| 73-12 | 163 | 0.5 | 5.0 | butyl oleate | Neodol 1-9 |
| 73-13 | 163 | 0.5 | 5.0 | methyl laurate | Neodol 1-9 |
| 73-14 | 163 | 0.5 | 5.0 | butyl laurate | Neodol 1-9 |
| 73-15 | 163 | 0.5 | 5.0 | Orchex 796 | Neodol 1-9 |
| 73-16 | 163 |  | 5.0 | none | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 73b.

TABLE 73b

| Concentrate composition | Glyphosate rate g a.e./ha | % Inhibition ABUTH | % Inhibition ECHCF |
|---|---|---|---|
| Formulation B | 150 | 3 | 10 |
|  | 250 | 58 | 57 |
|  | 350 | 78 | 53 |
|  | 450 | 77 | 53 |
| Formulation C | 150 | 60 | 98 |
|  | 250 | 87 | 99 |
|  | 350 | 95 | 98 |
|  | 450 | 99 | 100 |
| Formulation J | 150 | 60 | 75 |
|  | 250 | 89 | 87 |
|  | 350 | 93 | 90 |
|  | 450 | 98 | 99 |
| 73-01 | 150 | 75 | 96 |
|  | 250 | 99 | 97 |
|  | 350 | 97 | 99 |
|  | 450 | 99 | 100 |
| 73-02 | 150 | 60 | 60 |
|  | 250 | 97 | 67 |
|  | 350 | 99 | 98 |
|  | 450 | 100 | 95 |
| 73-03 | 150 | 63 | 40 |
|  | 250 | 83 | 82 |
|  | 350 | 97 | 86 |
|  | 450 | 97 | 88 |
| 73-04 | 150 | 73 | 40 |
|  | 250 | 94 | 82 |
|  | 350 | 97 | 100 |
|  | 450 | 99 | 100 |
| 73-05 | 150 | 67 | 47 |
|  | 250 | 86 | 67 |
|  | 350 | 97 | 88 |
|  | 450 | 99 | 100 |
| 73-06 | 150 | 60 | 43 |
|  | 250 | 78 | 91 |
|  | 350 | 97 | 83 |
|  | 450 | 94 | 86 |
| 73-07 | 150 | 70 | 53 |
|  | 250 | 80 | 53 |
|  | 350 | 97 | 82 |
|  | 450 | 97 | 92 |
| 73-08 | 150 | 70 | 62 |
|  | 250 | 83 | 83 |
|  | 350 | 91 | 87 |
|  | 450 | 98 | 98 |
| 73-09 | 150 | 45 | 42 |
|  | 250 | 72 | 72 |
|  | 350 | 77 | 73 |
|  | 450 | 78 | 89 |
| 73-10 | 150 | 40 | 30 |
|  | 250 | 82 | 80 |
|  | 350 | 78 | 98 |
|  | 450 | 89 | 93 |
| 73-11 | 150 | 40 | 30 |
|  | 250 | 65 | 60 |
|  | 350 | 77 | 90 |
|  | 450 | 96 | 92 |
| 73-12 | 150 | 20 | 30 |
|  | 250 | 63 | 73 |
|  | 350 | 80 | 75 |
|  | 450 | 93 | 86 |
| 73-13 | 150 | 20 | 27 |
|  | 250 | 67 | 60 |
|  | 350 | 82 | 91 |
|  | 450 | 88 | 92 |
| 73-14 | 150 | 7 | 30 |
|  | 250 | 72 | 81 |
|  | 350 | 87 | 78 |
|  | 450 | 80 | 85 |
| 73-15 | 150 | 20 | 23 |
|  | 250 | 65 | 60 |
|  | 350 | 77 | 81 |
|  | 450 | 87 | 88 |
| 73-16 | 150 | 12 | 30 |
|  | 250 | 57 | 53 |
|  | 350 | 68 | 85 |
|  | 450 | 85 | 85 |

Composition 73-08, containing as sole excipient substance oleth-20 at a 1:3 weight/weight ratio to glyphosate a.e., exhibited high herbicidal effectiveness, at least equal to commercial standard Formulations C and J on ABUTH but a little weaker on ECHCF. By comparison, composition 73-16, wherein the sole excipient substance was Neodol 1-9 at the same ratio to glyphosate, had much weaker activity.

Addition of a small amount of fatty acid ester in most cases enhanced effectiveness, especially on ECHCF. In this study the most efficacious composition was 73-01, containing oleth-20 and methyl stearate. When added to Neodol 1-9, butyl stearate was more efficacious than methyl stearate, methyl oleate or butyl oleate. The mineral oil Orchex 796 did not substitute effectively for butyl stearate, either with oleth-20 or with Neodol 1-9.

Example 74

Aqueous concentrate compositions were prepared containing glyphosate IPA salt and excipient ingredients as shown in Table 74a. Concentrate compositions 74-01, 74-03, 74-05 to 74-08, 74-10 and 74-14 to 74-17 are oil-in-water emulsions and were prepared by process (vii). Concentrate compositions 74-02, 74-04, 74-09 and 74-11 to 74-13 are aqueous solution concentrates and were prepared by process (viii). Some compositions contained a coupling agent as indicated in Table 74a; the coupling agent was added with the surfactant.

TABLE 74a

| Conc. comp. | Glyphosate g a.e./l | Butyl stearate | Surfactant | Coupling agent | Type of coupling agent | Type of surfactant |
|---|---|---|---|---|---|---|
| | | | % w/w | | | |
| 74-01 | 326 | 1.0 | 5.0 | 2.5 | Arcosolve DPM | oleth-20 |
| 74-02 | 326 | | 5.0 | 2.5 | Arcosolve DPM | oleth-20 |
| 74-03 | 163 | 0.5 | 2.5 | | none | oleth-20 |
| 74-04 | 163 | | 2.5 | | none | oleth-20 |
| 74-05 | 326 | 1.0 | 5.0 | | none | ceteareth-27 |
| 74-06 | 326 | 1.0 | 5.0 | 2.5 | PEG-400 | ceteareth-27 |
| 74-07 | 326 | 1.0 | 5.0 | 2.5 | Dowanol TPNB | ceteareth-27 |
| 74-08 | 326 | 1.0 | 5.0 | 2.5 | Dowanol PNB | ceteareth-27 |
| 74-09 | 163 | | 2.5 | | none | ceteareth-27 |
| 74-10 | 326 | 0.5 | 5.0 | | none | ceteareth-27 |
| 74-11 | 326 | | 5.0 | 2.5 | PEG-400 | ceteareth-27 |
| 74-12 | 326 | | 5.0 | 2.5 | Dowanol TPNB | ceteareth-27 |
| 74-13 | 326 | | 5.0 | 2.5 | Dowanol PNB | ceteareth-27 |
| 74-14 | 163 | 0.5 | 2.5 | | none | Neodol 1-9 |
| 74-15 | 163 | 0.5 | 2.5 | | none | laureth-23 |
| 74-16 | 163 | 0.5 | 2.5 | | none | steareth-20 |
| 74-17 | 163 | 0.5 | 2.5 | | none | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 18 days after application.

Formulations B, C and J were applied as comparative treatments. Results, averaged for all replicates of each treatment, are shown in Table 74b.

TABLE 74b

| Concentrate composition | Glyphosate rate g a.e./ha | % Inhibition ABUTH | % Inhibition ECHCF |
|---|---|---|---|
| Formulation B | 150 | 0 | 5 |
| | 250 | 38 | 20 |
| | 350 | 63 | 30 |
| | 450 | 70 | 70 |
| Formulation C | 150 | 70 | 75 |
| | 250 | 92 | 94 |
| | 350 | 99 | 99 |
| | 450 | 99 | 98 |
| Formulation J | 150 | 65 | 50 |
| | 250 | 88 | 92 |
| | 350 | 97 | 99 |
| | 450 | 98 | 97 |
| 74-01 | 150 | 58 | 83 |
| | 250 | 77 | 88 |
| | 350 | 93 | 96 |
| | 450 | 93 | 99 |
| 74-02 | 150 | 40 | 76 |
| | 250 | 75 | 100 |
| | 350 | 92 | 100 |
| | 450 | 92 | 100 |
| 74-03 | 150 | 48 | 75 |
| | 250 | 83 | 96 |
| | 350 | 92 | 100 |
| | 450 | 99 | 100 |
| 74-04 | 150 | 40 | 82 |
| | 250 | 78 | 99 |
| | 350 | 87 | 99 |
| | 450 | 98 | 100 |
| 74-05 | 150 | 68 | 92 |
| | 250 | 87 | 99 |
| | 350 | 95 | 99 |
| | 450 | 99 | 99 |
| 74-06 | 150 | 55 | 60 |
| | 250 | 83 | 99 |
| | 350 | 97 | 99 |
| | 450 | 98 | 98 |
| 74-07 | 150 | 63 | 57 |
| | 250 | 80 | 96 |
| | 350 | 95 | 97 |
| | 450 | 99 | 98 |
| 74-08 | 150 | 73 | 75 |
| | 250 | 90 | 90 |
| | 350 | 95 | 97 |
| | 450 | 100 | 97 |

TABLE 74b-continued

| Concentrate composition | Glyphosate rate g a.e./ha | % Inhibition ABUTH | % Inhibition ECHCF |
|---|---|---|---|
| 74-09 | 150 | 73 | 68 |
|  | 250 | 87 | 73 |
|  | 350 | 92 | 90 |
|  | 450 | 97 | 95 |
| 74-10 | 150 | 70 | 63 |
|  | 250 | 87 | 80 |
|  | 350 | 98 | 94 |

TABLE 74b-continued

| Concentrate composition | Glyphosate rate g a.e./ha | % Inhibition ABUTH | % Inhibition ECHCF |
|---|---|---|---|
|  | 450 | 99 | 96 |
| 74-11 | 150 | 73 | 60 |
|  | 250 | 90 | 77 |
|  | 350 | 99 | 93 |
|  | 450 | 100 | 95 |
| 74-12 | 150 | 72 | 67 |
|  | 250 | 83 | 75 |
|  | 350 | 90 | 82 |
|  | 450 | 99 | 94 |
| 74-13 | 150 | 73 | 70 |
|  | 250 | 80 | 83 |
|  | 350 | 99 | 94 |
|  | 450 | 100 | 92 |
| 74-14 | 150 | 5 | 20 |
|  | 250 | 55 | 63 |
|  | 350 | 77 | 93 |
|  | 450 | 78 | 99 |
| 74-15 | 150 | 43 | 57 |
|  | 250 | 78 | 88 |
|  | 350 | 88 | 98 |
|  | 450 | 90 | 98 |
| 74-16 | 150 | 65 | 57 |
|  | 250 | 83 | 82 |
|  | 350 | 88 | 98 |
|  | 450 | 95 | 97 |
| 74-17 | 150 | 72 | 50 |
|  | 250 | 80 | 93 |
|  | 350 | 88 | 90 |
|  | 450 | 95 | 97 |

The superiority of herbicidal effectiveness provided by $C_{16-18}$ alkylethers (oleth-20, ceteareth-27, steareth-20) over that provided by shorter chain alkylethers (Neodol 1-9, laureth-23) was very pronounced in this test.

Example 75

Aqueous concentrate compositions were prepared containing glyphosate IPA salt and excipient ingredients as shown in Table 75a. Concentrate compositions 75-01 to 75-07 and 75-09 to 75-15 are oil-in-water emulsions and were prepared by process (vii). Concentrate compositions 75-08 and 75-16 are aqueous solution concentrates and were prepared by process (viii).

TABLE 75a

| Concentrate composition | Glyphosate g a.e./l | % w/w Oil | % w/w Surfactant | Type of oil | Type of surfactant |
|---|---|---|---|---|---|
| 75-01 | 163 | 0.5 | 5.0 | methyl stearate | steareth-20 |
| 75-02 | 163 | 0.5 | 5.0 | butyl stearate | steareth-20 |
| 75-03 | 163 | 0.5 | 5.0 | methyl oleate | steareth-20 |
| 75-04 | 163 | 0.5 | 5.0 | butyl oleate | steareth-20 |
| 75-05 | 163 | 0.5 | 5.0 | methyl laurate | steareth-20 |
| 75-06 | 163 | 0.5 | 5.0 | butyl laurate | steareth-20 |
| 75-07 | 163 | 0.5 | 5.0 | Orchex 796 | steareth-20 |
| 75-08 | 163 |  | 5.0 | none | steareth-20 |
| 75-09 | 163 | 0.5 | 5.0 | methyl stearate | ceteareth-27 |
| 75-10 | 163 | 0.5 | 5.0 | butyl stearate | ceteareth-27 |
| 75-11 | 163 | 0.5 | 5.0 | methyl oleate | ceteareth-27 |
| 75-12 | 163 | 0.5 | 5.0 | butyl oleate | ceteareth-27 |
| 75-13 | 163 | 0.5 | 5.0 | methyl laurate | ceteareth-27 |
| 75-14 | 163 | 0.5 | 5.0 | butyl laurate | ceteareth-27 |
| 75-15 | 163 | 0.5 | 5.0 | Orchex 796 | ceteareth-27 |
| 75-16 | 163 |  | 5.0 | none | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 18 days after application.

Formulations B, C and J were applied as comparative treatments. Results, averaged for all replicates of each treatment, are shown in Table 75b.

TABLE 75b

| Concentrate composition | Glyphosate rate g a.e./ha | % Inhibition ABUTH | % Inhibition ECHCF |
|---|---|---|---|
| Formulation B | 150 | 15 | 5 |
|  | 250 | 57 | 20 |
|  | 350 | 83 | 50 |
|  | 450 | 78 | 73 |
| Formulation C | 150 | 65 | 63 |
|  | 250 | 87 | 93 |
|  | 350 | 92 | 94 |
|  | 450 | 98 | 100 |
| Formulation J | 150 | 50 | 73 |
|  | 250 | 90 | 90 |
|  | 350 | 94 | 98 |
|  | 450 | 98 | 99 |
| 75-01 | 150 | 72 | 70 |
|  | 250 | 88 | 85 |
|  | 350 | 96 | 83 |
|  | 450 | 99 | 86 |
| 75-02 | 150 | 73 | 53 |
|  | 250 | 83 | 87 |
|  | 350 | 97 | 99 |
|  | 450 | 97 | 98 |

TABLE 75b-continued

| Concentrate composition | Glyphosate rate g a.e./ha | % Inhibition ABUTH | % Inhibition ECHCF |
|---|---|---|---|
| 75-03 | 150 | 68 | 33 |
|  | 250 | 87 | 92 |
|  | 350 | 93 | 97 |
|  | 450 | 98 | 93 |
| 75-04 | 150 | 72 | 50 |
|  | 250 | 87 | 88 |
|  | 350 | 94 | 86 |
|  | 450 | 98 | 97 |
| 75-05 | 150 | 72 | 67 |
|  | 250 | 83 | 82 |
|  | 350 | 99 | 97 |
|  | 450 | 98 | 98 |
| 75-06 | 150 | 73 | 33 |
|  | 250 | 95 | 83 |
|  | 350 | 99 | 95 |
|  | 450 | 99 | 88 |
| 75-07 | 150 | 73 | 55 |
|  | 250 | 93 | 73 |
|  | 350 | 95 | 83 |
|  | 450 | 98 | 91 |
| 75-08 | 150 | 75 | 40 |
|  | 250 | 94 | 60 |
|  | 350 | 98 | 86 |
|  | 450 | 99 | 92 |
| 75-09 | 150 | 77 | 50 |
|  | 250 | 90 | 50 |
|  | 350 | 98 | 92 |
|  | 450 | 99 | 98 |
| 75-10 | 150 | 72 | 53 |
|  | 250 | 92 | 77 |
|  | 350 | 96 | 86 |
|  | 450 | 99 | 99 |
| 75-11 | 150 | 72 | 60 |
|  | 250 | 87 | 87 |
|  | 350 | 97 | 97 |
|  | 450 | 97 | 99 |
| 75-12 | 150 | 70 | 57 |
|  | 250 | 90 | 90 |
|  | 350 | 96 | 96 |
|  | 450 | 98 | 99 |
| 75-13 | 150 | 68 | 40 |
|  | 250 | 90 | 77 |
|  | 350 | 99 | 95 |
|  | 450 | 99 | 98 |
| 75-14 | 150 | 77 | 33 |
|  | 250 | 94 | 70 |
|  | 350 | 96 | 82 |
|  | 450 | 99 | 93 |
| 75-15 | 150 | 75 | 30 |
|  | 250 | 96 | 75 |
|  | 350 | 97 | 88 |
|  | 450 | 99 | 92 |
| 75-16 | 150 | 77 | 40 |
|  | 250 | 99 | 47 |
|  | 350 | 98 | 67 |
|  | 450 | 98 | 78 |

Steareth-20 and ceteareth-27, as sole excipient substances (compositions 75-08 and 75-16 respectively) provided excellent herbicidal effectiveness, but further enhancements, especially on ECHCF, were obtained by inclusion of a small amount of fatty acid ester in the composition.

Example 76

Aqueous concentrate compositions were prepared containing glyphosate IPA salt and excipient ingredients as shown in Table 76a. Concentrate compositions 76-13 and 76-14 are aqueous solution concentrates and were prepared by process (viii). Concentrate compositions 76-01 to 76-12 and 76-15 are aqueous solution concentrates containing colloidal particulates and were prepared by process (ix). Concentrate compositions 76-16 and 76-17 contained colloidal particulates but no surfactant.

Compositions 76-13 and 76-14 (both containing 162 g a.e./l glyphosate) showed acceptable storage stability. However, at glyphosate loadings >480 g a.e./l (as in compositions 76-01 to 76-12 and 76-15) storage-stable compositions containing 3% oleth-20 could not be made except with the addition of colloidal particulate as shown below.

TABLE 76a

| Concentrate composition | Glyphosate g a.e./l | Oleth-20 % w/w | Glycerin % w/w | Aerosil % w/w | Type of Aerosil |
|---|---|---|---|---|---|
| 76-01 | 492 | 3.00 | 2.0 | 0.8 | 380 |
| 76-02 | 492 | 3.00 | 5.0 | 1.5 | 380 |
| 76-03 | 492 | 3.00 | 2.0 | 0.8 | 380 |
| 76-04 | 492 | 3.00 | 5.0 | 1.5 | 380 |
| 76-05 | 492 | 3.00 |  | 0.8 | OX-50 |
| 76-06 | 492 | 3.00 |  | 1.5 | OX-50 |
| 76-07 | 492 | 3.00 |  | 0.8 | 380/OX-50 blend |
| 76-08 | 492 | 3.00 |  | 1.5 | 380/OX-50 blend |
| 76-09 | 492 | 3.00 |  | 0.8 | 380 |
| 76-10 | 492 | 3.00 |  | 1.5 | 380 |
| 76-11 | 492 | 3.00 |  | 0.8 | 380 |
| 76-12 | 492 | 3.00 |  | 1.5 | 380 |
| 76-13 | 162 | 1.13 |  |  | none |
| 76-14 | 162 | 1.13 |  |  | none |
| 76-15 | 492 | 3.00 | 2.0 | 1.5 | 380 |
| 76-16 | 488 |  |  | 0.8 | 380 |
| 76-17 | 488 |  |  | 1.5 | 380 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and J were applied as comparative treatments. Results, averaged for all replicates of each treatment, are shown in Table 76b.

TABLE 76b

| Concentrate composition | Glyphosate rate g a.e./ha | % Inhibition ABUTH | % Inhibition ECHCF |
|---|---|---|---|
| Formulation B | 150 | 18 | 40 |
|  | 250 | 57 | 53 |
|  | 350 | 72 | 63 |
|  | 450 | 83 | 85 |
| Formulation J | 150 | 70 | 65 |
|  | 250 | 85 | 95 |
|  | 350 | 98 | 98 |
|  | 450 | 100 | 99 |
| 76-01 | 150 | 62 | 67 |
|  | 250 | 72 | 93 |
|  | 350 | 99 | 96 |
|  | 450 | 99 | 97 |
| 76-02 | 150 | 57 | 50 |
|  | 250 | 70 | 91 |
|  | 350 | 92 | 97 |
|  | 450 | 99 | 99 |
| 76-03 | 150 | 48 | 40 |
|  | 250 | 68 | 67 |
|  | 350 | 97 | 97 |
|  | 450 | 98 | 98 |
| 76-04 | 150 | 55 | 50 |
|  | 250 | 82 | 83 |
|  | 350 | 95 | 90 |
|  | 450 | 99 | 94 |
| 76-05 | 150 | 65 | 43 |
|  | 250 | 87 | 87 |
|  | 350 | 100 | 94 |
|  | 450 | 96 | 95 |
| 76-06 | 150 | 55 | 53 |
|  | 250 | 75 | 82 |
|  | 350 | 95 | 95 |
|  | 450 | 100 | 96 |
| 76-07 | 150 | 45 | 83 |
|  | 250 | 78 | 82 |
|  | 350 | 90 | 93 |
|  | 450 | 95 | 99 |
| 76-08 | 150 | 55 | 47 |
|  | 250 | 75 | 88 |
|  | 350 | 93 | 99 |
|  | 450 | 99 | 97 |
| 76-09 | 150 | 47 | 47 |
|  | 250 | 65 | 82 |
|  | 350 | 78 | 99 |
|  | 450 | 97 | 97 |
| 76-10 | 150 | 47 | 40 |
|  | 250 | 72 | 96 |
|  | 350 | 77 | 80 |
|  | 450 | 85 | 97 |

TABLE 76b-continued

| Concentrate composition | Glyphosate rate g a.e./ha | % Inhibition ABUTH | % Inhibition ECHCF |
|---|---|---|---|
| 76-11 | 150 | 37 | 53 |
|  | 250 | 73 | 82 |
|  | 350 | 80 | 83 |
|  | 450 | 90 | 92 |
| 76-12 | 150 | 35 | 57 |
|  | 250 | 70 | 82 |
|  | 350 | 80 | 97 |
|  | 450 | 90 | 99 |
| 76-13 | 150 | 50 | 40 |
|  | 250 | 68 | 75 |
|  | 350 | 95 | 92 |
|  | 450 | 99 | 95 |
| 76-14 | 150 | 40 | 33 |
|  | 250 | 70 | 82 |
|  | 350 | 93 | 89 |
|  | 450 | 98 | 93 |
| 76-15 | 150 | 23 | 33 |
|  | 250 | 67 | 73 |
|  | 350 | 83 | 91 |
|  | 450 | 94 | 92 |
| 76-16 | 150 | 13 | 40 |
|  | 250 | 45 | 50 |
|  | 350 | 62 | 72 |
|  | 450 | 77 | 77 |
| 76-17 | 150 | 7 | 33 |
|  | 250 | 50 | 50 |
|  | 350 | 60 | 70 |
|  | 450 | 75 | 73 |

Several high-loaded (492 g a.e./l) glyphosate compositions containing oleth-20 at just 3% exhibited surprisingly high herbicidal effectiveness, approaching or equalling that of commercial standard Formulation J, which is loaded at only about 360 g a.e./l and has a much higher surfactant to glyphosate ratio.

Example 77

Aqueous concentrate compositions were prepared containing glyphosate IPA salt and excipient ingredients as shown in Table 77a. Concentrate composition 77-08 to 77-14 are oil-in-water emulsions and were prepared by process (vii). Concentrate compositions 77-15 to 77-17 are aqueous solution concentrates and were prepared by process (viii). Concentrate compositions 77-01 to 77-07 contain colloidal particulates and were prepared by process (ix).

Compositions 77-08 to 77-17 (all containing 163 g a.e./l glyphosate) showed acceptable storage stability. However, at a glyphosate loading of 400 g a.e./l (as in compositions 77-01 to 77-07) storage-stable compositions containing 0.5–1% butyl stearate and 5–10% alkylether surfactant could not be made except with the addition of colloidal particulate as shown below.

TABLE 77a

| Concentrate composition | Glyphosate g a.e./l | Butyl stearate (% w/w) | Surfactant (% w/w) | Aerosil 90 (% w/w) | Type of surfactant |
|---|---|---|---|---|---|
| 77-01 | 400 | 1.0 | 10.0 | 1.0 | ceteareth-27 |
| 77-02 | 400 | 1.0 | 10.0 | 1.0 | steareth-20 |
| 77-03 | 400 | 0.5 | 5.0 | 1.0 | ceteareth-27 |
| 77-04 | 400 | 0.5 | 5.0 | 1.0 | steareth-20 |

TABLE 77a-continued

| Concentrate composition | Glyphosate g a.e./l | Butyl stearate | Surfactant | Aerosil 90 | Type of surfactant |
|---|---|---|---|---|---|
| | | | % w/w | | |
| 77-05 | 400 | 1.0 | 5.0 | 1.0 | ceteareth-27 |
| 77-06 | 400 | 1.0 | 5.0 | 1.0 | steareth-20 |
| 77-07 | 400 | 1.0 | 5.0 | 1.0 | steareth-30 |
| 77-08 | 163 | 0.5 | 5.0 | | oleth-20 |
| 77-09 | 163 | 0.5 | 5.0 | | steareth-20 |
| 77-10 | 163 | 0.5 | 5.0 | | ceteth-20 |
| 77-11 | 163 | 0.5 | 5.0 | | laureth-23 |
| 77-12 | 163 | 0.5 | 5.0 | | ceteareth-27 |
| 77-13 | 163 | 0.5 | 5.0 | | Neodol 25-12 |
| 77-14 | 163 | 0.5 | 5.0 | | Neodol 25-20 |
| 77-15 | 163 | | 5.0 | | steareth-20 |
| 77-16 | 163 | | 5.0 | | ceteth-20 |
| 77-17 | 163 | | 5.0 | | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 19 days after application.

Formulations B, C and J were applied as comparative treatments. Results, averaged for all replicates of each treatment, are shown in Table 77b.

TABLE 77b

| Composition applied | Glyphosate rate g a.e./ha | % Inhibition ABUTH | % Inhibition ECHCF |
|---|---|---|---|
| Formulation B | 150 | 0 | 40 |
| | 250 | 20 | 60 |
| | 350 | 68 | 82 |
| | 450 | 83 | 96 |
| Formulation C | 150 | 68 | 93 |
| | 250 | 93 | 99 |
| | 350 | 100 | 100 |
| | 450 | 100 | 100 |
| Formulation J | 150 | 43 | 89 |
| | 250 | 93 | 100 |
| | 350 | 100 | 100 |
| | 450 | 100 | 100 |
| 77-01 | 150 | 78 | 97 |
| | 250 | 96 | 100 |
| | 350 | 98 | 100 |
| | 450 | 100 | 100 |
| 77-02 | 150 | 91 | 98 |
| | 250 | 100 | 100 |
| | 350 | 100 | 100 |
| | 450 | 100 | 100 |
| 77-03 | 150 | 90 | 97 |
| | 250 | 99 | 99 |
| | 350 | 100 | 100 |
| | 450 | 100 | 100 |
| 77-04 | 150 | 77 | 98 |
| | 250 | 100 | 100 |
| | 350 | 100 | 100 |
| | 450 | 100 | 100 |
| 77-05 | 150 | 82 | 93 |
| | 250 | 100 | 99 |
| | 350 | 100 | 100 |
| | 450 | 100 | 100 |
| 77-06 | 150 | 83 | 85 |
| | 250 | 100 | 99 |
| | 350 | 100 | 100 |
| | 450 | 100 | 100 |
| 77-07 | 150 | 83 | 87 |
| | 250 | 100 | 100 |
| | 350 | 100 | 100 |
| | 450 | 100 | 100 |
| 77-08 | 150 | 90 | 92 |
| | 250 | 100 | 100 |
| | 350 | 100 | 100 |
| | 450 | 100 | 100 |
| 77-09 | 150 | 90 | 85 |
| | 250 | 100 | 98 |
| | 350 | 100 | 100 |
| | 450 | 100 | 100 |
| 77-10 | 150 | 80 | 85 |
| | 250 | 100 | 92 |
| | 350 | 100 | 100 |
| | 450 | 100 | 100 |
| 77-11 | 150 | 83 | 88 |
| | 250 | 96 | 99 |
| | 350 | 100 | 98 |
| | 450 | 100 | 100 |
| 77-12 | 150 | 93 | 85 |
| | 250 | 100 | 99 |
| | 350 | 100 | 100 |
| | 450 | 100 | 100 |
| 77-13 | 150 | 72 | 73 |
| | 250 | 92 | 97 |
| | 350 | 100 | 99 |
| | 450 | 100 | 100 |
| 77-14 | 150 | 72 | 80 |
| | 250 | 99 | 99 |
| | 350 | 100 | 100 |
| | 450 | 100 | 100 |
| 77-15 | 150 | 100 | 93 |
| | 250 | 100 | 99 |
| | 350 | 100 | 100 |
| | 450 | 100 | 100 |
| 77-16 | 150 | 100 | 98 |
| | 250 | 100 | 100 |
| | 350 | 100 | 100 |
| | 450 | 100 | 100 |
| 77-17 | 150 | 83 | 83 |
| | 250 | 100 | 99 |
| | 350 | 100 | 99 |
| | 450 | 100 | 99 |

Outstanding herbicidal effectiveness was provided by compositions containing $C_{16-18}$ alkylether surfactants (ceteareth-27, steareth-20, steareth-30, oleth-20, ceteth-20). High-loaded (400 g a.e./l) glyphosate compositions containing a $C_{16-18}$ alkylether surfactant, butyl stearate and a colloidal particulate (Aerosil 90) to stabilize the compositions performed especially impressively in this test.

Example 78

Aqueous concentrate compositions were prepared containing glyphosate IPA salt and excipient ingredients as shown in Table 78a. Concentrate composition 78-01 to 78-09, 78-11 to 78-14, 78-16 and 78-17 are oil-in-water emulsions and were prepared by process (vii). Concentrate compositions 78-10 and 78-15 are aqueous solution concentrates and were prepared by process (viii).

TABLE 78a

| Conc. comp. | Glyphosate g a.e./l | % w/w Oil | Oleth-20 | Other surfactant | Type of oil | Other surfactant |
|---|---|---|---|---|---|---|
| 78-01 | 163 | 0.25 | 2.5 | | methyl laurate | |
| 78-02 | 163 | 0.25 | 2.5 | | methyl myristate | |
| 78-03 | 163 | 0.25 | 2.5 | | methyl palmitoleate | |
| 78-04 | 163 | 0.25 | 2.5 | | methyl palmitate | |
| 78-05 | 163 | 0.25 | 2.5 | | methyl linoleate | |
| 78-06 | 163 | 0.25 | 2.5 | | methyl oleate | |
| 78-07 | 163 | 0.25 | 2.5 | | methyl stearate | |
| 78-08 | 163 | 0.25 | 2.5 | | ethyl stearate | |
| 78-09 | 163 | 0.25 | 2.5 | | butyl stearate | |
| 78-10 | 163 | | 2.5 | | none | |
| 78-11 | 163 | 0.25 | | 2.5 | methyl palmitoleate | MON 0818 |
| 78-12 | 163 | 0.25 | | 2.5 | methyl palmitate | MON 0818 |
| 78-13 | 163 | 0.25 | | 2.5 | methyl oleate | MON 0818 |
| 78-14 | 163 | 0.25 | | 2.5 | methyl stearate | MON 0818 |
| 78-15 | 163 | | | 2.5 | none | MON 0818 |
| 78-16 | 163 | 0.25 | | 2.5 | butyl stearate | laureth-23 |
| 78-17 | 163 | 0.25 | | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 78b.

TABLE 78b

| Concentrate composition | Glyphosate rate g a.e./ha | % Inhibition ABUTH | % Inhibition ECHCF |
|---|---|---|---|
| Formulation B | 100 | 2 | 35 |
| | 200 | 52 | 67 |
| | 300 | 77 | 83 |
| | 400 | 78 | 87 |
| Formulation C | 100 | 25 | 77 |
| | 200 | 72 | 99 |
| | 300 | 87 | 100 |
| | 400 | 99 | 100 |
| Formulation J | 100 | 13 | 73 |
| | 200 | 70 | 97 |
| | 300 | 90 | 100 |
| | 400 | 97 | 100 |
| 78-01 | 100 | 22 | 55 |
| | 200 | 65 | 86 |
| | 300 | 78 | 98 |
| | 400 | 89 | 98 |
| 78-02 | 100 | 20 | 63 |
| | 200 | 67 | 91 |
| | 300 | 83 | 99 |
| | 400 | 97 | 100 |
| 78-03 | 100 | 30 | 75 |
| | 200 | 63 | 98 |
| | 300 | 83 | 99 |
| | 400 | 94 | 100 |
| 78-04 | 100 | 23 | 63 |
| | 200 | 60 | 98 |
| | 300 | 90 | 99 |
| | 400 | 95 | 100 |
| 78-05 | 100 | 27 | 57 |
| | 200 | 62 | 91 |
| | 300 | 83 | 96 |
| | 400 | 93 | 98 |
| 78-06 | 100 | 23 | 50 |
| | 200 | 63 | 89 |
| | 300 | 83 | 99 |
| | 400 | 96 | 99 |
| 78-07 | 100 | 25 | 53 |
| | 200 | 65 | 94 |
| | 300 | 83 | 99 |
| | 400 | 92 | 99 |
| 78-08 | 100 | 13 | 47 |
| | 200 | 53 | 88 |
| | 300 | 89 | 97 |
| | 400 | 95 | 99 |
| 78-09 | 100 | 27 | 53 |
| | 200 | 60 | 85 |
| | 300 | 83 | 97 |
| | 400 | 97 | 98 |

TABLE 78b-continued

| Concentrate composition | Glyphosate rate g a.e./ha | % Inhibition ABUTH | % Inhibition ECHCF |
|---|---|---|---|
| 78-10 | 100 | 13 | 53 |
|  | 200 | 62 | 94 |
|  | 300 | 83 | 97 |
|  | 400 | 88 | 99 |
| 78-11 | 100 | 23 | 60 |
|  | 200 | 50 | 90 |
|  | 300 | 85 | 98 |
|  | 400 | 95 | 99 |

TABLE 78b-continued

| Concentrate composition | Glyphosate rate g a.e./ha | % Inhibition ABUTH | % Inhibition ECHCF |
|---|---|---|---|
| 78-12 | 100 | 17 | 55 |
|  | 200 | 35 | 94 |
|  | 300 | 78 | 98 |
|  | 400 | 94 | 99 |
| 78-13 | 100 | 8 | 50 |
|  | 200 | 43 | 90 |
|  | 300 | 73 | 98 |
|  | 400 | 90 | 99 |
| 78-14 | 100 | 30 | 63 |
|  | 200 | 45 | 92 |
|  | 300 | 80 | 98 |
|  | 400 | 94 | 98 |
| 78-15 | 100 | 20 | 63 |
|  | 200 | 70 | 96 |
|  | 300 | 82 | 99 |
|  | 400 | 94 | 98 |
| 78-16 | 100 | 18 | 62 |
|  | 200 | 62 | 83 |
|  | 300 | 80 | 97 |
|  | 400 | 97 | 97 |
| 78-17 | 100 | 17 | 52 |
|  | 200 | 58 | 85 |
|  | 300 | 75 | 90 |
|  | 400 | 95 | 98 |

No great or consistent enhancement of herbicidal effectiveness of glyphosate compositions containing oleth-20 was obtained by adding a small amount of any of a variety of fatty acid esters in this study (compare 78-10 with 78-01 to 78-09).

Example 79

Aqueous concentrate compositions were prepared containing glyphosate IPA salt and excipient ingredients as shown in Table 79a. Concentrate composition 79-01 to 79-09, 79-11 to 79-14, 79-16 and 79-17 are oil-in-water emulsions and were prepared by process (vii). Concentrate compositions 79-10 and 79-15 are aqueous solution concentrates and were prepared by process (viii).

TABLE 79a

| Concentrate composition | Glyphosate g a.e./l | % w/w Oil | % w/w Oleth-20 | % w/w Other surfactant | Type of oil | Other surfactant |
|---|---|---|---|---|---|---|
| 79-01 | 163 | 0.25 | 2.5 |  | isopropyl myristate |  |
| 79-02 | 163 | 0.25 | 2.5 |  | ethyl myristate |  |
| 79-03 | 163 | 0.25 | 2.5 |  | methyl palmitate |  |
| 79-04 | 163 | 0.25 | 2.5 |  | ethyl palmitate |  |
| 79-05 | 163 | 0.25 | 2.5 |  | ethyl linoleate |  |
| 79-06 | 163 | 0.25 | 2.5 |  | ethyl oleate |  |
| 79-07 | 163 | 0.25 | 2.5 |  | methyl stearate |  |
| 79-08 | 163 | 0.25 | 2.5 |  | ethyl stearate |  |
| 79-09 | 163 | 0.25 | 2.5 |  | butyl stearate |  |
| 79-10 | 163 |  | 2.5 |  | none |  |
| 79-11 | 163 | 0.25 |  | 2.5 | methyl palmitate | MON 0818 |
| 79-12 | 163 | 0.25 |  | 2.5 | methyl stearate | MON 0818 |
| 79-13 | 163 | 0.25 |  | 2.5 | ethyl stearate | MON 0818 |
| 79-14 | 163 | 0.25 |  | 2.5 | ethyl oleate | MON 0818 |
| 79-15 | 163 |  |  | 2.5 | none | MON 0818 |
| 79-16 | 163 | 0.25 |  | 2.5 | butyl stearate | laureth-23 |
| 79-17 | 163 | 0.25 |  | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 18 days after application.

Formulations B, C and J were applied as comparative treatments. Results, averaged for all replicates of each treatment, are shown in Table 79b.

TABLE 79b

| Concentrate composition | Glyphosate rate g a.e./ha | % Inhibition ABUTH | % Inhibition ECHCF |
|---|---|---|---|
| Formulation B | 100 | 12 | 33 |
|  | 200 | 45 | 43 |
|  | 300 | 73 | 63 |
|  | 400 | 80 | 63 |
| Formulation C | 100 | 43 | 57 |
|  | 200 | 75 | 88 |
|  | 300 | 95 | 99 |
|  | 400 | 100 | 99 |
| Formulation J | 100 | 53 | 60 |
|  | 200 | 77 | 75 |
|  | 300 | 96 | 95 |
|  | 400 | 99 | 98 |

TABLE 79b-continued

| Concentrate composition | Glyphosate rate g a.e./ha | % Inhibition ABUTH | % Inhibition ECHCF |
|---|---|---|---|
| 79-01 | 100 | 35 | 40 |
|  | 200 | 73 | 72 |
|  | 300 | 83 | 91 |
|  | 400 | 99 | 97 |
| 79-02 | 100 | 38 | 30 |
|  | 200 | 70 | 43 |
|  | 300 | 87 | 82 |
|  | 400 | 96 | 80 |
| 79-03 | 100 | 25 | 27 |
|  | 200 | 68 | 50 |
|  | 300 | 90 | 73 |
|  | 400 | 96 | 82 |
| 79-04 | 100 | 27 | 27 |
|  | 200 | 75 | 50 |
|  | 300 | 80 | 73 |
|  | 400 | 96 | 80 |
| 79-05 | 100 | 33 | 27 |
|  | 200 | 68 | 43 |
|  | 300 | 83 | 70 |
|  | 400 | 97 | 91 |
| 79-06 | 100 | 33 | 28 |
|  | 200 | 72 | 53 |
|  | 300 | 83 | 60 |
|  | 400 | 99 | 70 |
| 79-07 | 100 | 37 | 25 |
|  | 200 | 72 | 40 |
|  | 300 | 83 | 50 |
|  | 400 | 97 | 65 |
| 79-08 | 100 | 32 | 25 |
|  | 200 | 73 | 43 |
|  | 300 | 87 | 60 |
|  | 400 | 98 | 67 |
| 79-09 | 100 | 35 | 25 |
|  | 200 | 75 | 43 |
|  | 300 | 95 | 57 |
|  | 400 | 98 | 63 |
| 79-10 | 100 | 35 | 27 |
|  | 200 | 73 | 40 |
|  | 300 | 83 | 76 |
|  | 400 | 97 | 73 |
| 79-11 | 100 | 35 | 33 |
|  | 200 | 67 | 67 |
|  | 300 | 80 | 86 |
|  | 400 | 92 | 70 |
| 79-12 | 100 | 25 | 30 |
|  | 200 | 67 | 70 |
|  | 300 | 83 | 76 |
|  | 400 | 88 | 80 |
| 79-13 | 100 | 27 | 33 |
|  | 200 | 70 | 66 |
|  | 300 | 78 | 63 |
|  | 400 | 93 | 60 |
| 79-14 | 100 | 33 | 30 |
|  | 200 | 67 | 47 |
|  | 300 | 80 | 70 |
|  | 400 | 92 | 77 |
| 79-15 | 100 | 20 | 30 |
|  | 200 | 68 | 40 |
|  | 300 | 83 | 75 |
|  | 400 | 90 | 72 |
| 79-16 | 100 | 30 | 25 |
|  | 200 | 62 | 43 |
|  | 300 | 73 | 73 |
|  | 400 | 77 | 70 |
| 79-17 | 100 | 30 | 23 |
|  | 200 | 58 | 40 |
|  | 300 | 75 | 60 |
|  | 400 | 80 | 73 |

In this study, isopropyl myristate (composition 79-01) was the most effective of the fatty acid esters tested as additives to oleth-20 (79-10) in glyphosate compositions.

Example 80

Aqueous concentrate compositions were prepared containing glyphosate IPA salt and excipient ingredients as shown in Table 80a. Concentrate composition 80-01 to 80-13 are oil-in-water emulsions and were prepared by process (vii). Concentrate compositions 80-14 to 80-17 are aqueous solution concentrates and were prepared by process (viii).

TABLE 80a

| Concentrate composition | Glyphosate g a.e./l | % w/w Oil | % w/w Surfactant | Type of oil | Type of surfactant |
|---|---|---|---|---|---|
| 80-01 | 163 | 0.25 | 2.5 | butyl stearate | laureth-23 |
| 80-02 | 163 | 0.25 | 2.5 | butyl stearate | steareth-20 |
| 80-03 | 163 | 0.25 | 2.5 | butyl stearate | ceteareth-20 |
| 80-04 | 163 | 0.25 | 2.5 | butyl stearate | ceteareth-15 |
| 80-05 | 163 | 0.25 | 2.5 | butyl stearate | Neodol 45-13 |
| 80-06 | 163 | 0.25 | 2.5 | methyl stearate | steareth-20 |
| 80-07 | 163 | 0.25 | 2.5 | methyl stearate | ceteareth-20 |
| 80-08 | 163 | 0.25 | 2.5 | methyl stearate | ceteareth-15 |
| 80-09 | 163 | 0.25 | 2.5 | methyl stearate | Neodol 45-13 |
| 80-10 | 163 | 0.25 | 2.5 | methyl palmitate | steareth-20 |
| 80-11 | 163 | 0.25 | 2.5 | methyl palmitate | ceteareth-20 |
| 80-12 | 163 | 0.25 | 2.5 | methyl palmitate | ceteareth-15 |
| 80-13 | 163 | 0.25 | 2.5 | methyl palmitate | Neodol 45-13 |
| 80-14 | 163 |  | 2.5 | none | steareth-20 |
| 80-15 | 163 |  | 2.5 | none | ceteareth-20 |
| 80-16 | 163 |  | 2.5 | none | ceteareth-15 |
| 80-17 | 163 |  | 2.5 | none | Neodol 45-13 |

Velvetleaf (*Abutilon theophrasti*, ABUTH) and Japanese millet (*Echinochloa crus-galli*, ECHCF) plants were grown and treated by the standard procedures given above. Applications of spray compositions were made 24 days after planting ABUTH and ECHCF, and evaluation of herbicidal inhibition was done 16 days after application.

Formulations B, C and J were applied as comparative treatments. Results, averaged for all replicates of each treatment, are shown in Table 80b.

TABLE 80b

| Concentrate composition | Glyphosate rate g a.e./ha | % Inhibition ABUTH | % Inhibition ECHCF |
| --- | --- | --- | --- |
| Formulation B | 100 | 10 | 37 |
|  | 200 | 30 | 40 |
|  | 300 | 43 | 57 |
|  | 400 | 23 | 33 |
| Formulation C | 100 | 50 | 67 |
|  | 200 | 75 | 96 |
|  | 300 | 85 | 99 |
|  | 400 | 94 | 100 |
| Formulation J | 100 | 40 | 75 |
|  | 200 | 73 | 94 |
|  | 300 | 93 | 98 |
|  | 400 | 95 | 99 |
| 80-01 | 100 | 63 | 77 |
|  | 200 | 67 | 94 |
|  | 300 | 77 | 99 |
|  | 400 | 88 | 96 |
| 80-02 | 100 | 63 | 75 |
|  | 200 | 83 | 88 |
|  | 300 | 93 | 98 |
|  | 400 | 95 | 99 |
| 80-03 | 100 | 67 | 75 |
|  | 200 | 82 | 95 |
|  | 300 | 95 | 99 |
|  | 400 | 98 | 99 |
| 80-04 | 100 | 60 | 75 |
|  | 200 | 82 | 97 |
|  | 300 | 96 | 99 |
|  | 400 | 98 | 100 |
| 80-05 | 100 | 63 | 73 |
|  | 200 | 75 | 89 |
|  | 300 | 80 | 98 |
|  | 400 | 87 | 97 |
| 80-06 | 100 | 58 | 63 |
|  | 200 | 78 | 93 |
|  | 300 | 93 | 99 |
|  | 400 | 98 | 100 |
| 80-07 | 100 | 60 | 67 |
|  | 200 | 78 | 93 |
|  | 300 | 93 | 99 |
|  | 400 | 100 | 99 |
| 80-08 | 100 | missing | missing |
|  | 200 | missing | missing |
|  | 300 | 78 | 95 |
|  | 400 | 98 | 99 |
| 80-09 | 100 | 23 | 30 |
|  | 200 | 65 | 83 |
|  | 300 | 80 | 98 |
|  | 400 | 93 | 99 |
| 80-10 | 100 | 65 | 67 |
|  | 200 | 83 | 95 |
|  | 300 | 97 | 99 |
|  | 400 | 99 | 99 |
| 80-11 | 100 | 72 | 73 |
|  | 200 | 90 | 98 |
|  | 300 | 96 | 97 |
|  | 400 | 99 | 99 |
| 80-12 | 100 | 68 | 63 |
|  | 200 | 90 | 92 |
|  | 300 | 98 | 99 |
|  | 400 | 97 | 99 |
| 80-13 | 100 | 43 | 73 |
|  | 200 | 72 | 87 |
|  | 300 | 83 | 98 |
|  | 400 | 93 | 96 |
| 80-14 | 100 | 62 | 77 |
|  | 200 | 78 | 99 |
|  | 300 | 95 | 99 |
|  | 400 | 98 | 100 |
| 80-15 | 100 | 52 | 60 |
|  | 200 | 78 | 93 |
|  | 300 | 94 | 98 |
|  | 400 | 97 | 99 |
| 80-16 | 100 | 38 | 68 |
|  | 200 | 68 | 99 |
|  | 300 | 87 | 97 |
|  | 400 | 94 | 99 |
| 80-17 | 100 | 55 | 75 |
|  | 200 | 68 | 91 |
|  | 300 | 83 | 96 |
|  | 400 | 87 | 98 |

Herbicidal effectiveness exceeding that of commercial standard composition J, at least on ABUTH, was recorded with several compositions, including 80-02 (steareth-20 plus butyl stearate), 80-03 (ceteareth-20 plus butyl stearate), 80-04 (ceteareth-15 plus butyl stearate), 80-10 (steareth-20 plus methyl palmitate), 80-11 (ceteareth-20 plus methyl palmitate) and 80-12 (ceteareth-15 plus methyl palmitate). Compositions lacking fatty acid ester performed slightly less well overall than those containing butyl stearate or methyl palmitate.

Example 81

Spray compositions were prepared containing glyphosate IPA salt and excipient ingredients as shown in Table 81a. Compositions were prepared by simple mixing of ingredients. Soybean lecithin (45% phospholipid, Avanti), where included, was first prepared with sonication in water to make a homogeneous composition. Four different concentrations of glyphosate (not shown in Table 81a) were prepared, calculated to provide, when applied in a spray volume of 93 l/ha, the glyphosate rates shown in Table 81b.

TABLE 81a

| Spray comp. | % w/w Lecithin | FC-754 | Butyl stearate | Methyl oleate | Oleth-20 | Lecithin supplied as | Methyl oleate supplied as |
| --- | --- | --- | --- | --- | --- | --- | --- |
| 81-01 | 0.05 | 0.050 |  |  |  | soybean lecithin |  |
| 81-02 | 0.05 |  |  | 0.050 |  | soybean lecithin |  |

TABLE 81a-continued

| | | | % w/w | | | | |
|---|---|---|---|---|---|---|---|
| Spray comp. | Lecithin | FC-754 | Butyl stearate | Methyl oleate | Oleth-20 | Lecithin supplied as | Methyl oleate supplied as |
| 81-03 | 0.05 | | | | | soybean lecithin | |
| 81-04 | | 0.050 | | | | | |
| 81-05 | | | 0.050 | | | | |
| 81-06 | 0.05 | | | | | LI-700 | |
| 81-07 | | | 0.005 | | 0.05 | | |
| 81-08 | | | | 0.01 | 0.05 | | |
| 81-09 | | | | | 0.05 | | |
| 81-10 | | | 0.005 | | | | |
| 81-11 | | | | 0.01 | | | pure |
| 81-12 | | | | 0.01 | | | methylated seed oil |

Velvetleaf (*Abutilon theophrasti*, ABUTH), Japanese millet (*Echinochloa crus-galli*, ECHCF) and Prickly sida (*Sida spinosa*, SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Formulations B and C were applied as comparative treatments, representing technical glyphosate IPA salt and a commercial formulation of glyphosate IPA salt respectively. Results, averaged for all replicates of each treatment, are shown in Table 81b.

TABLE 81b

| | Glyphosate rate | % Inhibition | | |
|---|---|---|---|---|
| Composition applied | g a.e./ha | ABUTH | ECHCF | SIDSP |
| Formulation B (technical) | 50 | 0 | 0 | 0 |
| | 100 | 38 | 35 | 35 |
| | 200 | 87 | 50 | 90 |
| | 300 | 95 | 88 | 94 |
| Formulation C (commercial) | 50 | 0 | 2 | 0 |
| | 100 | 32 | 55 | 25 |
| | 200 | 85 | 97 | 93 |
| | 300 | 96 | 99 | 96 |
| 81-01 | 50 | 78 | 53 | 88 |
| | 100 | 90 | 60 | 95 |
| | 200 | 99 | 96 | 99 |
| | 300 | 99 | 97 | 98 |
| 81-02 | 50 | 25 | 15 | 43 |
| | 100 | 72 | 30 | 82 |
| | 200 | 94 | 62 | 93 |
| | 300 | 95 | 77 | 94 |
| 81-03 | 50 | 20 | 8 | 32 |
| | 100 | 52 | 22 | 78 |
| | 200 | 87 | 55 | 91 |
| | 300 | 95 | 65 | 93 |
| 81-04 | 50 | 62 | 37 | 85 |
| | 100 | 82 | 68 | 92 |
| | 200 | 97 | 96 | 95 |
| | 300 | 98 | 95 | 97 |
| 81-05 | 50 | 15 | 10 | 25 |
| | 100 | 47 | 27 | 23 |
| | 200 | 85 | 62 | 87 |
| | 300 | 90 | 63 | 92 |
| 81-06 | 50 | 0 | 2 | 0 |
| | 100 | 20 | 15 | 20 |
| | 200 | 85 | 60 | 82 |
| | 300 | 90 | 65 | 90 |
| 81-07 | 50 | 67 | 27 | 82 |
| | 100 | 87 | 55 | 93 |
| | 200 | 94 | 92 | 96 |
| | 300 | 97 | 99 | 97 |

TABLE 81b-continued

| | Glyphosate rate | % Inhibition | | |
|---|---|---|---|---|
| Composition applied | g a.e./ha | ABUTH | ECHCF | SIDSP |
| 81-08 | 50 | 62 | 30 | 75 |
| | 100 | 78 | 63 | 91 |
| | 200 | 93 | 96 | 96 |
| | 300 | 94 | 98 | 98 |
| 81-09 | 50 | 65 | 45 | 77 |
| | 100 | 80 | 73 | 95 |
| | 200 | 93 | 98 | 97 |
| | 300 | 95 | 99 | 99 |
| 81-10 | 50 | 10 | 25 | 5 |
| | 100 | 23 | 35 | 37 |
| | 200 | 90 | 50 | 93 |
| | 300 | 92 | 73 | 94 |
| 81-11 | 50 | 10 | 25 | 0 |
| | 100 | 52 | 33 | 43 |
| | 200 | 88 | 72 | 93 |
| | 300 | 94 | 78 | 94 |
| 81-12 | 50 | 0 | 15 | 0 |
| | 100 | 43 | 35 | 33 |
| | 200 | 91 | 70 | 90 |
| | 300 | 94 | 82 | 93 |

Results of this test using glyphosate as the exogenous chemical are summarized as follows:

At the low concentration of 0.05% used here. soybean lecithin containing 45% phospholipid (81-03) was a much more effective excipient than the lecithin-based adjuvant LI-700 (81-06) widely used in the art.

Butyl stearate alone at 0.05% (81-05) did not greatly enhance effectiveness.

The combination of lecithin and butyl stearate (81-02) gave surprisingly strong enhancement of effectiveness, suggesting a synergistic interaction between these two excipient substances.

Fluorad FC-754, either alone (81-04) or in combination with lecithin (81-01) gave extremely high effectiveness, superior to that obtained with the commercial standard.

Oleth-20 at the low concentration of 0.05% (81-09) gave extremely high effectiveness, superior to that obtained with the commercial standard. Addition of 0.005% butyl stearate (81-07) or 0.01% methyl oleate (81-08) did not provide further enhancement.

Example 82

Spray compositions were prepared containing paraquat dichloride and excipient ingredients. Compositions 82-01 to 82-12 were exactly like compositions 81-01 to 81-12 except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 12 days after application.

Standards included technical paraquat dichloride and Gramoxone, a commercial formulation of paraquat from Zeneca. Results, averaged for all replicates of each treatment, are shown in Table 82.

TABLE 82

| Spray composition | Paraquat rate g a.i./ha | % Inhibition ABUTH | ECHCF | SIDSP |
|---|---|---|---|---|
| Paraquat dichloride | 25 | 50 | 83 | 55 |
| (technical) | 50 | 57 | 78 | 60 |
|  | 100 | 73 | 84 | 69 |
|  | 200 | 85 | 95 | 99 |
| Gramoxone | 25 | 40 | 72 | 40 |
| (commercial) | 50 | 60 | 70 | 52 |
|  | 100 | 72 | 58 | 55 |
|  | 200 | 72 | 89 | 63 |
| 82-01 | 25 | 75 | 93 | 67 |
|  | 50 | 82 | 97 | 91 |
|  | 100 | 95 | 98 | 97 |
|  | 200 | 100 | 99 | 99 |
| 82-02 | 25 | 67 | 80 | 48 |
|  | 50 | 68 | 87 | 65 |
|  | 100 | 88 | 97 | 93 |
|  | 200 | 96 | 99 | 98 |
| 82-03 | 25 | 55 | 65 | 42 |
|  | 50 | 62 | 87 | 65 |
|  | 100 | 83 | 96 | 93 |
|  | 200 | 95 | 99 | 97 |
| 82-04 | 25 | 53 | 82 | 45 |
|  | 50 | 63 | 94 | 53 |
|  | 100 | 88 | 99 | 86 |
|  | 200 | 92 | 99 | 98 |
| 82-05 | 25 | 58 | 67 | 50 |
|  | 50 | 60 | 62 | 45 |
|  | 100 | 70 | 73 | 62 |
|  | 200 | 85 | 90 | 88 |
| 82-06 | 25 | 53 | 77 | 43 |
|  | 50 | 60 | 92 | 40 |
|  | 100 | 80 | 93 | 55 |
|  | 200 | 96 | 99 | 78 |
| 82-07 | 25 | 65 | 80 | 45 |
|  | 50 | 82 | 92 | 70 |
|  | 100 | 96 | 96 | 89 |
|  | 200 | 100 | 98 | 99 |
| 82-08 | 25 | 67 | 80 | 37 |
|  | 50 | 82 | 90 | 71 |
|  | 100 | 97 | 98 | 65 |
|  | 200 | 99 | 99 | 93 |
| 82-09 | 25 | 72 | 90 | 50 |
|  | 50 | 80 | 97 | 57 |
|  | 100 | 91 | 99 | 94 |
|  | 200 | 97 | 100 | 97 |
| 82-10 | 25 | 67 | 87 | 45 |
|  | 50 | 68 | 75 | 57 |
|  | 100 | 78 | 93 | 63 |
|  | 200 | 82 | 97 | 82 |
| 82-11 | 25 | 65 | 80 | 45 |
|  | 50 | 73 | 77 | 62 |
|  | 100 | 90 | 95 | 62 |
|  | 200 | 94 | 98 | 78 |

TABLE 82-continued

| Spray composition | Paraquat rate g a.i./ha | % Inhibition ABUTH | ECHCF | SIDSP |
|---|---|---|---|---|
| 82-12 | 25 | 67 | 78 | 37 |
|  | 50 | 75 | 90 | 55 |
|  | 100 | 77 | 97 | 90 |
|  | 200 | 85 | 99 | 92 |

Results of this test using paraquat as the exogenous chemical are summarized as follows:

At the low concentration of 0.05% used here, soybean lecithin containing 45% phospholipid (82-03) was a much more effective excipient on SIDSP than the lecithin-based adjuvant LI-700 (82-06) widely used in the art.

Butyl stearate alone at 0.05% (82-05) did not enhance effectiveness.

The combination of lecithin and butyl stearate (82-02) gave surprisingly strong enhancement of effectiveness, suggesting a synergistic interaction between these two excipient substances.

Fluorad FC-754 (82-04) gave extremely high effectiveness, superior to that obtained with the commercial standard. In the presence of lecithin (82-01), effectiveness was further increased dramatically, suggesting a synergistic interaction between these two excipient substances.

Oleth-20 at the low concentration of 0.05% (82-09) gave extremely high effectiveness, superior to that obtained with the commercial standard. Addition of 0.005% butyl stearate (82-07) or 0.01% methyl oleate (82-08) did not provide further enhancement.

Example 83

Spray compositions were prepared containing acifluorfen sodium salt and excipient ingredients. Compositions 83-01 to 83-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 15 days after planting ABUTH, 9 days after planting ECHCF and 22 days after planting SIDSP. Evaluation of herbicidal inhibition was done 10 days after application.

Standards included technical acifluorfen sodium and Blazer, a commercial formulation of acifluorfen from Rohm & Haas. Results, averaged for all replicates of each treatment, are shown in Table 83.

TABLE 83

| Spray composition | Acifluorfen rate g a.i./ha | % Inhibition ABUTH | ECHCF | SIDSP |
|---|---|---|---|---|
| Acifluorfen | 25 | 20 | 2 | 15 |
| (technical) | 50 | 32 | 7 | 17 |
|  | 100 | 52 | 18 | 35 |
|  | 200 | 62 | 35 | 40 |

TABLE 83-continued

| Spray composition | Acifluorfen rate g a.i./ha | % Inhibition ABUTH | ECHCF | SIDSP |
|---|---|---|---|---|
| Blazer | 25 | 30 | 30 | 5 |
| (commercial) | 50 | 53 | 53 | 12 |
| | 100 | 55 | 55 | 7 |
| | 200 | 65 | 65 | 32 |
| 83-01 | 25 | 60 | 7 | 20 |
| | 50 | 63 | 20 | 20 |
| | 100 | 65 | 43 | 33 |
| | 200 | 80 | 70 | 48 |
| 83-02 | 25 | 25 | 7 | 5 |
| | 50 | 42 | 12 | 25 |
| | 100 | 60 | 30 | 22 |
| | 200 | 68 | 68 | 50 |
| 83-03 | 25 | 22 | 5 | 10 |
| | 50 | 55 | 7 | 33 |
| | 100 | 62 | 25 | 27 |
| | 200 | 65 | 55 | 48 |
| 83-04 | 25 | 57 | 7 | 13 |
| | 50 | 67 | 10 | 32 |
| | 100 | 67 | 35 | 32 |
| | 200 | 70 | 70 | 45 |
| 83-05 | 25 | 30 | 3 | 15 |
| | 50 | 47 | 27 | 27 |
| | 100 | 55 | 42 | 37 |
| | 200 | 65 | 60 | 38 |
| 83-06 | 25 | 28 | 0 | 3 |
| | 50 | 50 | 0 | 10 |
| | 100 | 55 | 30 | 25 |
| | 200 | 67 | 58 | 47 |
| 83-07 | 25 | 35 | 20 | 17 |
| | 50 | 55 | 35 | 27 |
| | 100 | 58 | 63 | 32 |
| | 200 | 67 | 67 | 55 |
| 83-08 | 25 | 40 | 20 | 8 |
| | 50 | 57 | 30 | 28 |
| | 100 | 60 | 60 | 30 |
| | 200 | 70 | 77 | 48 |
| 83-09 | 25 | 47 | 20 | 22 |
| | 50 | 55 | 35 | 35 |
| | 100 | 62 | 65 | 38 |
| | 200 | 68 | 82 | 50 |
| 83-10 | 25 | 28 | 0 | 5 |
| | 50 | 48 | 0 | 10 |
| | 100 | 53 | 5 | 25 |
| | 200 | 62 | 35 | 40 |
| 83-11 | 25 | 35 | 0 | 5 |
| | 50 | 43 | 0 | 30 |
| | 100 | 50 | 0 | 35 |
| | 200 | 65 | 43 | 47 |
| 83-12 | 25 | 40 | 5 | 5 |
| | 50 | 55 | 18 | 35 |
| | 100 | 60 | 47 | 38 |
| | 200 | 70 | 62 | 48 |

Results of this test using acifluorfen as the exogenous chemical are summarized as follows:

At the low concentration of 0.05% used here, soybean lecithin containing 45% phospholipid (83-03) gave effectiveness similar to that obtained with the lecithin-based adjuvant LI-700 (83-06) widely used in the art.

Butyl stearate at 0.05% alone (83-05) and in combination with lecithin (83-02) enhanced effectiveness, particularly on ECHCF.

Fluorad FC-754, either alone (83-04) or in combination with lecithin (83-01) gave effectiveness on ABUTH and SIDSP superior to that obtained with the commercial standard.

Oleth-20 at the low concentration of 0.05% (83-09) gave effectiveness superior to that obtained with the commercial standard. Addition of 0.005% butyl stearate (83-07) or 0.01% methyl oleate (83-08) did not provide further enhancement.

Example 84

Spray compositions were prepared containing asulam and excipient ingredients. Compositions 84-01 to 84-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 11 days after planting ECHCF and 21 days after planting SIDSP. Evaluation of herbicidal inhibition was done 14 days after application.

Standards included technical asulam and Asulox, a commercial formulation of asulam from Rhône-Poulenc. Results, averaged for all replicates of each treatment, are shown in Table 84.

TABLE 84

| Spray composition | Asulam rate g a.i./ha | % Inhibition ABUTH | ECHCF | SIDSP |
|---|---|---|---|---|
| Asulam | 200 | 0 | 12 | 0 |
| (technical) | 400 | 17 | 27 | 5 |
| | 800 | 48 | 32 | 20 |
| | 1400 | 42 | 50 | 37 |
| Asulox | 200 | 3 | 5 | 0 |
| (commercial) | 400 | 27 | 30 | 20 |
| | 800 | 52 | 45 | 25 |
| | 1400 | 50 | 60 | 40 |
| 84-01 | 200 | 5 | 8 | 13 |
| | 400 | 23 | 45 | 22 |
| | 800 | 50 | 50 | 30 |
| | 1400 | 60 | 65 | 48 |
| 84-02 | 200 | 0 | 20 | 17 |
| | 400 | 33 | 40 | 20 |
| | 800 | 47 | 48 | 33 |
| | 1400 | 53 | 68 | 55 |
| 84-03 | 200 | 3 | 20 | 3 |
| | 400 | 28 | 52 | 7 |
| | 800 | 50 | 50 | 23 |
| | 1400 | 50 | 58 | 43 |
| 84-04 | 200 | 3 | 40 | 7 |
| | 400 | 35 | 45 | 18 |
| | 800 | 52 | 50 | 25 |
| | 1400 | 58 | 60 | 42 |
| 84-05 | 200 | 0 | 10 | 3 |
| | 400 | 23 | 30 | 18 |
| | 800 | 33 | 50 | 32 |
| | 1400 | 45 | 57 | 38 |
| 84-06 | 200 | 2 | 30 | 10 |
| | 400 | 8 | 47 | 17 |
| | 800 | 50 | 55 | 28 |
| | 1400 | 52 | 63 | 40 |
| 84-07 | 200 | 0 | 43 | 3 |
| | 400 | 22 | 48 | 17 |
| | 800 | 40 | 55 | 28 |
| | 1400 | 52 | 60 | 33 |
| 84-08 | 200 | 7 | 47 | 22 |
| | 400 | 20 | 48 | 22 |
| | 800 | 53 | 55 | 30 |
| | 1400 | 57 | 60 | 33 |
| 84-09 | 200 | 0 | 45 | 7 |
| | 400 | 25 | 50 | 7 |
| | 800 | 53 | 60 | 32 |
| | 1400 | 55 | 63 | 37 |
| 84-10 | 200 | 22 | 37 | 10 |
| | 400 | 27 | 45 | 10 |
| | 800 | 50 | 43 | 23 |
| | 1400 | 52 | 52 | 27 |

TABLE 84-continued

| Spray composition | Asulam rate g a.i./ha | % Inhibition ABUTH | ECHCF | SIDSP |
|---|---|---|---|---|
| 84-11 | 200 | 25 | 33 | 5 |
| | 400 | 15 | 37 | 13 |
| | 800 | 48 | 42 | 25 |
| | 1400 | 42 | 52 | 28 |
| 84-12 | 200 | 3 | 25 | 17 |
| | 400 | 13 | 42 | 18 |
| | 800 | 50 | 45 | 30 |
| | 1400 | 52 | 50 | 33 |

Results of this test using asulam as the exogenous chemical are summarized as follows:

At the low concentration of 0.05% used here, soybean lecithin containing 45% phospholipid (84-03) gave similar enhancement to that obtained with the lecithin-based adjuvant LI-700 (84-06) widely used in the art.

Butyl stearate alone at 0.05% (84-05) enhanced effectiveness on ECHCF.

The combination of lecithin and butyl stearate (84-02) gave greater enhancement of effectiveness than either excipient substance alone.

Fluorad FC-754, either alone (84-04) or in combination with lecithin (84-01) gave effectiveness equal to that obtained with the commercial standard.

Oleth-20 at the low concentration of 0.05% (84-09) gave, at low exogenous chemical rates, effectiveness on ECHCF superior to that obtained with the commercial standard. Addition of 0.005% butyl stearate (84-07) or 0.01% methyl oleate (84-08) did not provide further enhancement.

Example 85

Spray compositions were prepared containing dicamba sodium salt and excipient ingredients. Compositions 85-01 to 85-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 17 days after application.

Standards included technical dicamba sodium and Banvel, a commercial formulation of dicamba from Sandoz. Results, averaged for all replicates of each treatment, are shown in Table 85.

TABLE 85

| Spray composition | Dicamba rate g a.i./ha | % Inhibition ABUTH | ECHCF | SIDSP |
|---|---|---|---|---|
| Dicamba (technical) | 25 | 47 | 0 | 30 |
| | 50 | 63 | 0 | 40 |
| | 100 | 82 | 0 | 50 |
| | 200 | 93 | 5 | 58 |
| Banvel (commercial) | 25 | 47 | 0 | 35 |
| | 50 | 68 | 0 | 40 |
| | 100 | 91 | 0 | 53 |
| | 200 | 93 | 3 | 63 |
| 85-01 | 25 | 42 | 0 | 38 |
| | 50 | 67 | 0 | 48 |
| | 100 | 92 | 0 | 67 |
| | 200 | 93 | 3 | 73 |
| 85-02 | 25 | 43 | 0 | 43 |
| | 50 | 58 | 0 | 50 |
| | 100 | 85 | 0 | 62 |
| | 200 | 89 | 8 | 72 |
| 85-03 | 25 | 50 | 0 | 32 |
| | 50 | 65 | 0 | 45 |
| | 100 | 90 | 0 | 60 |
| | 200 | 94 | 13 | 68 |
| 85-04 | 25 | 43 | 0 | 35 |
| | 50 | 65 | 0 | 42 |
| | 100 | 94 | 0 | 53 |
| | 200 | 94 | 13 | 67 |
| 85-05 | 25 | 50 | 0 | 35 |
| | 50 | 68 | 0 | 40 |
| | 100 | 88 | 0 | 53 |
| | 200 | 92 | 15 | 60 |
| 85-06 | 25 | 40 | 0 | 40 |
| | 50 | 65 | 0 | 45 |
| | 100 | 88 | 0 | 52 |
| | 200 | 92 | 8 | 70 |
| 85-07 | 25 | 45 | 0 | 42 |
| | 50 | 57 | 0 | 45 |
| | 100 | 88 | 0 | 62 |
| | 200 | 88 | 20 | 68 |
| 85-08 | 25 | 40 | 0 | 38 |
| | 50 | 62 | 0 | 45 |
| | 100 | 97 | 18 | 62 |
| | 200 | 93 | 17 | 73 |
| 85-09 | 25 | 33 | 0 | 35 |
| | 50 | 60 | 0 | 45 |
| | 100 | 93 | 0 | 63 |
| | 200 | 96 | 15 | 73 |
| 85-10 | 25 | 35 | 0 | 30 |
| | 50 | 57 | 0 | 43 |
| | 100 | 90 | 0 | 50 |
| | 200 | 90 | 3 | 70 |
| 85-11 | 25 | 45 | 0 | 30 |
| | 50 | 53 | 0 | 42 |
| | 100 | 89 | 0 | 55 |
| | 200 | 92 | 0 | 73 |
| 85-12 | 25 | 38 | 0 | 37 |
| | 50 | 60 | 0 | 45 |
| | 100 | 96 | 0 | 52 |
| | 200 | 93 | 0 | 70 |

Results of this test using dicamba as the exogenous chemical are summarized as follows:

At the low concentration of 0.05% used here. soybean lecithin containing 45% phospholipid (85-03) gave similar enhancement of effectiveness to that obtained with the lecithin-based adjuvant LI-700 (85-06) widely used in the art.

Butyl stearate alone at 0.05% (85-05) provided slight enhancement of effectiveness.

The combination of lecithin and butyl stearate (85-02) gave greater enhancement of effectiveness on SIDSP than either of these two excipient substances alone.

Fluorad FC-754 (85-04) provided effectiveness similar to that obtained with the commercial standard. Further enhancement on SIDSP was obtained with the combination of Fluorad FC-754 and lecithin (85-01).

Oleth-20 at the low concentration of 0.05% (85-09) gave effectiveness on SIDSP superior to that obtained with the commercial standard. Addition of 0.005% butyl stearate (85-07) or 0.01% methyl oleate (85-08) did not provide significant further enhancement.

Example 86

Spray compositions were prepared containing metsulfuron-methyl and excipient ingredients. Compositions 86-01 to 86-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 14 days after application.

Standards included technical metsulfuron-methyl and Ally, a commercial formulation of metsulfuron from Du Pont. Results, averaged for all replicates of each treatment, are shown in Table 86.

TABLE 86

| Spray composition | Metsulfuron rate g a.i./ha | % Inhibition | | |
|---|---|---|---|---|
| | | ABUTH | ECHCF | SIDSP |
| Metsulfuron (technical) | 0.5 | 72 | 0 | 5 |
| | 1 | 90 | 0 | 23 |
| | 5 | 96 | 0 | 50 |
| | 10 | 97 | 30 | 55 |
| Ally (commercial) | 0.5 | 75 | 0 | 5 |
| | 1 | 85 | 0 | 22 |
| | 5 | 95 | 0 | 42 |
| | 10 | 97 | 25 | 53 |
| 86-01 | 0.5 | 95 | 0 | 47 |
| | 1 | 96 | 20 | 53 |
| | 5 | 97 | 25 | 62 |
| | 10 | 98 | 45 | 62 |
| 86-02 | 0.5 | 87 | 0 | 40 |
| | 1 | 90 | 10 | 55 |
| | 5 | 95 | 10 | 58 |
| | 10 | 96 | 40 | 63 |
| 86-03 | 0.5 | 87 | 0 | 27 |
| | 1 | 90 | 0 | 40 |
| | 5 | 96 | 10 | 57 |
| | 10 | 97 | 33 | 63 |
| 86-04 | 0.5 | 90 | 0 | 33 |
| | 1 | 95 | 10 | 50 |
| | 5 | 98 | 17 | 62 |
| | 10 | 99 | 28 | 58 |
| 86-05 | 0.5 | 85 | 0 | 27 |
| | 1 | 90 | 0 | 33 |
| | 5 | 95 | 0 | 47 |
| | 10 | 95 | 13 | 60 |
| 86-06 | 0.5 | 77 | 0 | 30 |
| | 1 | 89 | 10 | 47 |
| | 5 | 96 | 17 | 62 |
| | 10 | 98 | 33 | 60 |
| 86-07 | 0.5 | 94 | 0 | 55 |
| | 1 | 97 | 10 | 60 |
| | 5 | 98 | 43 | 60 |
| | 10 | 97 | 55 | 65 |
| 86-08 | 0.5 | 93 | 0 | 55 |
| | 1 | 96 | 5 | 58 |
| | 5 | 97 | 42 | 60 |
| | 10 | 97 | 50 | 60 |
| 86-09 | 0.5 | 93 | 0 | 55 |
| | 1 | 97 | 10 | 62 |
| | 5 | 98 | 55 | 62 |
| | 10 | 98 | 65 | 63 |
| 86-10 | 0.5 | 85 | 0 | 28 |
| | 1 | 82 | 0 | 30 |
| | 5 | 95 | 10 | 52 |
| | 10 | 96 | 17 | 57 |
| 86-11 | 0.5 | 73 | 0 | 25 |
| | 1 | 88 | 20 | 28 |
| | 5 | 94 | 25 | 53 |
| | 10 | 96 | 32 | 57 |
| 86-12 | 0.5 | 75 | 0 | 32 |
| | 1 | 85 | 20 | 37 |
| | 5 | 94 | 23 | 55 |
| | 10 | 96 | 25 | 57 |

Results of this test using metsulfuron as the exogenous chemical are summarized as follows:

At the low concentration of 0.05% used here, soybean lecithin containing 45% phospholipid (86-03) was a slightly more effective excipient than the lecithin-based adjuvant LI-700 (86-06) widely used in the art in improving performance on ABUTH at the lowest exogenous chemical rate tested.

Butyl stearate alone at 0.05% (86-05) enhanced effectiveness to a level superior to that obtained with the commercial standard.

The combination of lecithin and butyl stearate (86-02) gave greater enhancement of effectiveness than was obtained with either of these two excipient substances alone.

Fluorad FC-754, either alone (86-04) or in combination with lecithin (86-01) gave high effectiveness, superior to that obtained with the commercial standard.

Oleth-20 at the low concentration of 0.05% (86-09) gave high effectiveness, superior to that obtained with the commercial standard. Addition of 0.005% butyl stearate (86-07) or 0.01% methyl oleate (86-08) did not provide further enhancement.

Example 87

Spray compositions were prepared containing imazethapyr and excipient ingredients. Compositions 87-01 to 87-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Standards included technical imazethapyr and Pursuit, a commercial formulation of imazethapyr from American Cyanamid. Results, averaged for all replicates of each treatment, are shown in Table 87.

TABLE 87

| Spray composition | Imazethapyr rate g a.i./ha | % Inhibition ABUTH | ECHCF | SIDSP |
|---|---|---|---|---|
| Imazethapyr (technical) | 5 | 78 | 5 | 20 |
| | 10 | 83 | 20 | 30 |
| | 25 | 93 | 35 | 40 |
| | 50 | 94 | 53 | 50 |
| Pursuit (commercial) | 5 | 70 | 5 | 25 |
| | 10 | 73 | 33 | 30 |
| | 25 | 90 | 50 | 42 |
| | 50 | 93 | 62 | 57 |
| 87-01 | 5 | 70 | 45 | 35 |
| | 10 | 75 | 62 | 52 |
| | 25 | 92 | 63 | 57 |
| | 50 | 93 | 72 | 62 |
| 87-02 | 5 | 73 | 57 | 32 |
| | 10 | 75 | 67 | 43 |
| | 25 | 90 | 70 | 52 |
| | 50 | 92 | 72 | 57 |
| 87-03 | 5 | 70 | 42 | 27 |
| | 10 | 78 | 42 | 35 |
| | 25 | 90 | 53 | 45 |
| | 50 | 92 | 62 | 52 |
| 87-04 | 5 | 73 | 55 | 33 |
| | 10 | 77 | 68 | 45 |
| | 25 | 93 | 68 | 47 |
| | 50 | 94 | 68 | 60 |
| 87-05 | 5 | 73 | 47 | 32 |
| | 10 | 73 | 45 | 40 |
| | 25 | 90 | 62 | 47 |
| | 50 | 91 | 68 | 52 |
| 87-06 | 5 | 78 | 72 | 30 |
| | 10 | 83 | 70 | 35 |
| | 25 | 93 | 77 | 62 |
| | 50 | 94 | 78 | 58 |
| 87-07 | 5 | 82 | 75 | 38 |
| | 10 | 90 | 90 | 52 |
| | 25 | 93 | 93 | 53 |
| | 50 | 97 | 97 | 62 |
| 87-08 | 5 | 75 | 77 | 38 |
| | 10 | 90 | 92 | 50 |
| | 25 | 95 | 93 | 57 |
| | 50 | 97 | 99 | 63 |
| 87-09 | 5 | 78 | 80 | 40 |
| | 10 | 83 | 89 | 63 |
| | 25 | 93 | 93 | 62 |
| | 50 | 96 | 93 | 60 |
| 87-10 | 5 | 85 | 50 | 37 |
| | 10 | 77 | 50 | 45 |
| | 25 | 91 | 63 | 48 |
| | 50 | 93 | 75 | 57 |
| 87-11 | 5 | 75 | 38 | 43 |
| | 10 | 80 | 38 | 37 |
| | 25 | 92 | 62 | 45 |
| | 50 | 93 | 73 | 53 |
| 87-12 | 5 | 75 | 55 | 38 |
| | 10 | 83 | 60 | 43 |
| | 25 | 92 | 67 | 53 |
| | 50 | 93 | 77 | 55 |

Results of this test using imazethapyr as the exogenous chemical are summarized as follows:

At the low concentration of 0.05% used here, soybean lecithin containing 45% phospholipid (87-03) was a less effective excipient than the lecithin-based adjuvant LI-700 (87-06).

Butyl stearate alone at 0.05% (87-05) significantly enhanced effectiveness on ECHCF and slightly on SIDSP.

The combination of lecithin and butyl stearate (87-02) gave enhancement of effectiveness on ECHCF greater than that obtained with either of these two excipient substances alone.

Fluorad FC-754 (87-04) gave effectiveness on ECHCF superior to that obtained with the commercial standard. The combination of Fluorad FC-754 and lecithin (87-01) provided slight further enhancement of effectiveness on SIDSP.

Oleth-20 at the low concentration of 0.05% (87-09) gave extremely high effectiveness, greatly superior to that obtained with the commercial standard, especially on ECHCF. Addition of 0.005% butyl stearate (87-07) further enhanced performance of low exogenous chemical rates on ABUTH more effectively than addition of 0.01% methyl oleate (87-08).

Example 88

Spray compositions were prepared containing fluazifop-p-butyl salt and excipient ingredients. Compositions 88-01 to 88-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and broadleaf signalgrass (*Brachiaria platyphylla*, BRAPP) plants were grown and treated by the standard procedures given above. Applications of spray compositions were made 15 days after planting ABUTH, 15 days after planting ECHCF and 16 days after planting BRAPP. Evaluation of herbicidal inhibition was done 10 days after application.

Standards included technical fluazifop-p-butyl and Fusilade 5, a commercial formulation of fluazifop-p-butyl from Zeneca. Results, averaged for all replicates of each treatment, are shown in Table 88.

TABLE 88

| Spray composition | Fluazifop-p rate g a.i./ha | % Inhibition ABUTH | ECHCF | BRAPP |
|---|---|---|---|---|
| Fluazifop-p-butyl (technical) | 2 | 0 | 0 | 20 |
| | 5 | 0 | 3 | 35 |
| | 15 | 5 | 45 | 65 |
| | 30 | 5 | 57 | 78 |
| Fusilade 5 (commercial) | 2 | 0 | 0 | 27 |
| | 5 | 0 | 27 | 33 |
| | 15 | 5 | 52 | 78 |
| | 30 | 7 | 75 | 85 |
| 88-01 | 2 | 0 | 0 | 20 |
| | 5 | 2 | 27 | 30 |
| | 15 | 5 | 58 | 78 |
| | 30 | 10 | 87 | 83 |
| 88-02 | 2 | 0 | 7 | 25 |
| | 5 | 0 | 35 | 30 |
| | 15 | 2 | 58 | 75 |
| | 30 | 8 | 78 | 75 |
| 88-03 | 2 | 0 | 0 | 18 |
| | 5 | 0 | 8 | 27 |
| | 15 | 0 | 45 | 75 |
| | 30 | 0 | 55 | 75 |
| 88-04 | 2 | 0 | 20 | 32 |
| | 5 | 2 | 42 | 25 |
| | 15 | 2 | 55 | 72 |
| | 30 | 5 | 80 | 78 |
| 88-05 | 2 | 0 | 13 | 32 |
| | 5 | 2 | 42 | 32 |
| | 15 | 2 | 55 | 72 |
| | 30 | 7 | 58 | 73 |
| 88-06 | 2 | 2 | 17 | 23 |
| | 5 | 0 | 20 | 25 |
| | 15 | 0 | 50 | 75 |
| | 30 | 0 | 73 | 77 |
| 88-07 | 2 | 0 | 50 | 40 |
| | 5 | 0 | 52 | 60 |
| | 15 | 0 | 67 | 80 |
| | 30 | 0 | 92 | 85 |

TABLE 88-continued

| Spray composition | Fluazifop-p rate g a.i./ha | % Inhibition ABUTH | ECHCF | BRAPP |
|---|---|---|---|---|
| 88-08 | 2 | 0 | 43 | 35 |
|  | 5 | 0 | 55 | 37 |
|  | 15 | 7 | 88 | 82 |
|  | 30 | 3 | 96 | 85 |
| 88-09 | 2 | 0 | 47 | 18 |
|  | 5 | 0 | 50 | 35 |
|  | 15 | 0 | 80 | 80 |
|  | 30 | 3 | 93 | 85 |
| 88-10 | 2 | 0 | 23 | 10 |
|  | 5 | 0 | 37 | 42 |
|  | 15 | 5 | 55 | 75 |
|  | 30 | 10 | 58 | 80 |
| 88-11 | 2 | 0 | 7 | 10 |
|  | 5 | 0 | 30 | 28 |
|  | 15 | 0 | 50 | 62 |
|  | 30 | 12 | 53 | 68 |
| 88-12 | 2 | 0 | 5 | 20 |
|  | 5 | 0 | 7 | 35 |
|  | 15 | 5 | 48 | 68 |
|  | 30 | 12 | 60 | 77 |

Results of this test using fluazifop-p-butyl as the exogenous chemical are summarized as follows:

At the low concentration of 0.05% used here, soybean lecithin containing 45% phospholipid (88-03) was a less effective excipient on ECHCF than the lecithin-based adjuvant LI-700 (88-06).

Butyl stearate alone at 0.05% (88-05) and in combination with lecithin (88-02) enhanced effectiveness, especially on ECHCF.

Fluorad FC-754, either alone (88-04) or in combination with lecithin (88-01) gave effectiveness equal or superior to that obtained with the commercial standard.

Oleth-20 at the low concentration of 0.05% (88-09) gave extremely high effectiveness on ECHCF, superior to that obtained with the commercial standard. Addition of 0.005% butyl stearate (88-07) or 0.01% methyl oleate (88-08) did not provide significant further enhancement.

Example 89

Spray compositions were prepared containing alachlor and excipient ingredients. Compositions 89-01 to 89-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa* SIDSP) plants were grown and treated by the standard procedures given above. Applications of spray compositions were made 14 days after planting ABUTH, 8 days after planting ECHCF and 14 days after planting SIDSP. Evaluation of herbicidal inhibition was done 9 days after application.

Standards included technical alachlor and Lasso, a commercial formulation of alachlor from Monsanto Company. Results, averaged for all replicates of each treatment, are shown in Table 89.

TABLE 89

| Spray composition | Alachlor rate g a.i./ha | % Inhibition ABUTH | ECHCF | SIDSP |
|---|---|---|---|---|
| Alachlor (technical) | 500 | 0 | 0 | 0 |
|  | 1000 | 0 | 0 | 0 |
|  | 2000 | 0 | 0 | 0 |
|  | 4000 | 0 | 0 | 0 |
| Lasso (commercial) | 500 | 0 | 0 | 0 |
|  | 1000 | 0 | 5 | 13 |
|  | 2000 | 0 | 30 | 17 |
|  | 4000 | 15 | 43 | 65 |
| 89-01 | 500 | 0 | 0 | 0 |
|  | 1000 | 0 | 0 | 0 |
|  | 2000 | 0 | 0 | 0 |
|  | 4000 | 10 | 0 | 7 |
| 89-02 | 500 | 0 | 0 | 0 |
|  | 1000 | 0 | 0 | 0 |
|  | 2000 | 0 | 22 | 7 |
|  | 4000 | 12 | 47 | 12 |
| 89-03 | 500 | 0 | 0 | 0 |
|  | 1000 | 0 | 0 | 0 |
|  | 2000 | 0 | 0 | 0 |
|  | 4000 | 10 | 0 | 0 |
| 89-04 | 500 | 0 | 0 | 0 |
|  | 1000 | 0 | 0 | 0 |
|  | 2000 | 0 | 0 | 0 |
|  | 4000 | 5 | 0 | 15 |
| 89-05 | 500 | 0 | 0 | 0 |
|  | 1000 | 0 | 0 | 0 |
|  | 2000 | 0 | 0 | 0 |
|  | 4000 | 3 | 0 | 0 |
| 89-06 | 500 | 0 | 0 | 5 |
|  | 1000 | 0 | 0 | 0 |
|  | 2000 | 0 | 13 | 7 |
|  | 4000 | 0 | 37 | 12 |
| 89-07 | 500 | 0 | 0 | 0 |
|  | 1000 | 0 | 8 | 0 |
|  | 2000 | 0 | 28 | 15 |
|  | 4000 | 12 | 50 | 20 |
| 89-08 | 500 | 0 | 0 | 0 |
|  | 1000 | 0 | 8 | 0 |
|  | 2000 | 0 | 8 | 0 |
|  | 4000 | 5 | 20 | 5 |
| 89-09 | 500 | 0 | 0 | 0 |
|  | 1000 | 0 | 0 | 0 |
|  | 2000 | 0 | 3 | 0 |
|  | 4000 | 12 | 42 | 32 |
| 89-10 | 500 | 0 | 0 | 0 |
|  | 1000 | 0 | 0 | 0 |
|  | 2000 | 0 | 0 | 0 |
|  | 4000 | 0 | 0 | 0 |
| 89-11 | 500 | 0 | 0 | 0 |
|  | 1000 | 0 | 0 | 0 |
|  | 2000 | 0 | 0 | 0 |
|  | 4000 | 0 | 0 | 0 |
| 89-12 | 500 | 0 | 0 | 0 |
|  | 1000 | 0 | 0 | 0 |
|  | 2000 | 0 | 0 | 0 |
|  | 4000 | 0 | 0 | 0 |

None of the compositions tested enhanced post-emergence foliar-applied herbicidal effectiveness of alachlor in this test. Alachlor is not known as a foliar-applied herbicide.

Example 90

Spray compositions were prepared containing glufosinate ammonium salt and excipient ingredients. Compositions 90-01 to 90-12 were exactly like compositions 81-01 to 81-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida* spinosa, SIDSP) plants were grown and treated by the standard procedures given above. Applications of spray compositions were made 14 days after planting ABUTH, 10 days after planting ECHCF and 17 days after planting SIDSP. Evaluation of herbicidal inhibition was done 11 days after application.

Standards included technical glufosinate ammonium and Liberty, a commercial formulation of glufosinate from AgrEvo. Results, averaged for all replicates of each treatment, are shown in Table 90.

TABLE 90

| Spray composition | Glufosinate rate g a.i./ha | % Inhibition ABUTH | ECHCF | SIDSP |
|---|---|---|---|---|
| Glufosinate (technical) | 50 | 0 | 0 | 5 |
|  | 100 | 47 | 0 | 10 |
|  | 300 | 90 | 23 | 96 |
|  | 600 | 98 | 43 | 94 |
| Liberty (commercial) | 50 | 77 | 70 | 20 |
|  | 100 | 88 | 96 | 93 |
|  | 300 | 98 | 100 | 97 |
|  | 600 | 99 | 100 | 99 |
| 90-01 | 50 | 77 | 33 | 70 |
|  | 100 | 95 | 58 | 93 |
|  | 300 | 98 | 95 | 97 |
|  | 600 | 99 | 99 | 98 |
| 90-02 | 50 | 33 | 30 | 50 |
|  | 100 | 63 | 32 | 93 |
|  | 300 | 96 | 52 | 90 |
|  | 600 | 98 | 96 | 97 |
| 90-03 | 50 | 15 | 30 | 38 |
|  | 100 | 50 | 33 | 87 |
|  | 300 | 92 | 40 | 94 |
|  | 600 | 98 | 70 | 98 |
| 90-04 | 50 | 92 | 47 | 50 |
|  | 100 | 90 | 53 | 85 |
|  | 300 | 98 | 98 | 96 |
|  | 600 | 98 | 99 | 98 |
| 90-05 | 50 | 35 | 20 | 20 |
|  | 100 | 37 | 30 | 20 |
|  | 300 | 97 | 45 | 78 |
|  | 600 | 91 | 53 | 92 |
| 90-06 | 50 | 10 | 0 | 20 |
|  | 100 | 20 | 3 | 20 |
|  | 300 | 89 | 47 | 82 |
|  | 600 | 91 | 94 | 89 |
| 90-07 | 50 | 50 | 35 | 70 |
|  | 100 | 73 | 52 | 80 |
|  | 300 | 95 | 87 | 98 |
|  | 600 | 98 | 98 | 97 |
| 90-08 | 50 | 48 | 30 | 88 |
|  | 100 | 83 | 50 | 93 |
|  | 300 | 98 | 97 | 96 |
|  | 600 | 98 | 99 | 96 |
| 90-09 | 50 | 58 | 35 | 92 |
|  | 100 | 91 | 62 | 93 |
|  | 300 | 98 | 96 | 97 |
|  | 600 | 98 | 99 | 96 |
| 90-10 | 50 | 30 | 30 | 0 |
|  | 100 | 43 | 35 | 10 |
|  | 300 | 96 | 43 | 92 |
|  | 600 | 95 | 70 | 91 |
| 90-11 | 50 | 33 | 35 | 0 |
|  | 100 | 53 | 35 | 7 |
|  | 300 | 96 | 43 | 89 |
|  | 600 | 97 | 88 | 93 |
| 90-12 | 50 | 37 | 5 | 5 |
|  | 100 | 37 | 20 | 10 |
|  | 300 | 95 | 40 | 88 |
|  | 600 | 97 | 85 | 93 |

Results of this test using glufosinate as the exogenous chemical are summarized as follows:

At the low concentration of 0.05% used here, soybean lecithin containing 45% phospholipid (90-03) was a much more effective excipient than the lecithin-based adjuvant LI-700 (90-06) widely used in the art.

Butyl stearate alone at 0.05% (90-05) enhanced effectiveness on ECHCF.

The combination of lecithin and butyl stearate (90-02) gave greater enhancement of effectiveness than either of these two excipient substances alone.

Fluorad FC-754, either alone (90-04) or in combination with lecithin (90-01) gave extremely high effectiveness, similar to that obtained with the commercial standard.

Oleth-20 at the low concentration of 0.05% (90-09) gave extremely high effectiveness, superior on SIDSP to that obtained with the commercial standard. Addition of 0.005% butyl stearate (90-07) or 0.01% methyl oleate (90-08) did not provide further enhancement.

Example 91

Aqueous concentrate compositions were prepared containing glyphosate IPA salt and excipient ingredients as shown in Table 91a. Concentrate compositions 91-01 to 91-12 are aqueous solution concentrates containing colloidal particulates and were prepared by process (ix). Concentrate compositions 91-13 to 91-18 contained colloidal particulates but no surfactant.

The colloidal particulates of this example were in general too large to confer good storage stability to the compositions tested.

TABLE 91a

| Concentrate composition | Glyphosate g a.e./l | % w/w Surfactant | Silica | Type of surfactant | Type of silica |
|---|---|---|---|---|---|
| 91-01 | 488 | 3.0 | 0.8 | steareth-20 | Sident 9 |
| 91-02 | 488 | 3.0 | 0.8 | steareth-20 | Sipernat 22 |
| 91-03 | 488 | 3.0 | 0.8 | steareth-20 | Sipernat 22S |
| 91-04 | 488 | 3.0 | 0.8 | oleth-20 | Sident 9 |
| 91-05 | 488 | 3.0 | 0.8 | oleth-20 | Sipernat 22 |
| 91-06 | 488 | 3.0 | 0.8 | oleth-20 | Sipernat 22S |
| 91-07 | 488 | 3.0 | 1.5 | steareth-20 | Sident 9 |
| 91-08 | 488 | 3.0 | 1.5 | steareth-20 | Sipernat 22 |
| 91-09 | 488 | 3.0 | 1.5 | steareth-20 | Sipernat 22S |
| 91-10 | 488 | 3.0 | 1.5 | oleth-20 | Sident 9 |
| 91-11 | 488 | 3.0 | 1.5 | oleth-20 | Sipernat 22 |
| 91-12 | 488 | 3.0 | 1.5 | oleth-20 | Sipernat 22S |
| 91-13 | 488 |  | 0.8 | none | Sident 9 |
| 91-14 | 488 |  | 1.5 | none | Sipernat 22 |
| 91-15 | 488 |  | 0.8 | none | Sipernat 22S |
| 91-16 | 488 |  | 1.5 | none | Sident 9 |
| 91-17 | 488 |  | 0.8 | none | Sipernat 22 |
| 91-18 | 488 |  | 1.5 | none | Sipernat 22S |

Velvetleaf (Abutilon theophrasti, ABUTH) and Japanese millet (Echinochloa crus-galli, ECHCF) plants were grown and treated by the standard procedures given above. Applications of spray compositions were made 21 days after planting ABUTH and ECHCF, and evaluation of herbicidal inhibition was done 14 days after application.

Formulations B and J were applied as comparative treatments. Results, averaged for all replicates of each treatment, ar shown in Table 91b.

TABLE 91b

| Concentrate composition | Glyphosate rate g a.e./ha | % Inhibition ABUTH | ECHCF |
|---|---|---|---|
| Formulation B | 100 | 3 | 37 |
| | 200 | 10 | 57 |
| | 300 | 43 | 87 |
| | 400 | 57 | 88 |
| Formulation J | 100 | 33 | 80 |
| | 200 | 72 | 98 |
| | 300 | 96 | 99 |
| | 400 | 97 | 99 |
| 91-01 | 100 | 47 | 89 |
| | 200 | 78 | 97 |
| | 300 | 87 | 99 |
| | 400 | 98 | 99 |
| 91-02 | 100 | 37 | 83 |
| | 200 | 70 | 99 |
| | 300 | 90 | 99 |
| | 400 | 95 | 100 |
| 91-03 | 100 | 40 | 89 |
| | 200 | 70 | 99 |
| | 300 | 90 | 100 |
| | 400 | 95 | 100 |
| 91-04 | 100 | 37 | 94 |
| | 200 | 58 | 98 |
| | 300 | 87 | 99 |
| | 400 | 95 | 100 |
| 91-05 | 100 | 30 | 60 |
| | 200 | 73 | 95 |
| | 300 | 85 | 99 |
| | 400 | 97 | 99 |
| 91-06 | 100 | 33 | 67 |
| | 200 | 70 | 97 |
| | 300 | 78 | 99 |
| | 400 | 92 | 100 |
| 91-07 | 100 | 32 | 81 |
| | 200 | 60 | 99 |
| | 300 | 83 | 98 |
| | 400 | 88 | 100 |
| 91-08 | 100 | 40 | 63 |
| | 200 | 65 | 93 |
| | 300 | 90 | 99 |
| | 400 | 90 | 100 |
| 91-09 | 100 | 43 | 70 |
| | 200 | 55 | 98 |
| | 300 | 88 | 99 |
| | 400 | 94 | 100 |
| 91-10 | 100 | 33 | 91 |
| | 200 | 70 | 99 |
| | 300 | 83 | 99 |
| | 400 | 94 | 99 |
| 91-11 | 100 | 20 | 63 |
| | 200 | 70 | 97 |
| | 300 | 92 | 100 |
| | 400 | 94 | 100 |
| 91-12 | 100 | 48 | 67 |
| | 200 | 70 | 93 |
| | 300 | 88 | 98 |
| | 400 | 94 | 100 |
| 91-13 | 100 | 20 | 50 |
| | 200 | 60 | 83 |
| | 300 | 83 | 97 |
| | 400 | 94 | 99 |
| 91-14 | 100 | 43 | 43 |
| | 200 | 67 | 88 |
| | 300 | 83 | 97 |
| | 400 | 91 | 99 |
| 91-15 | 100 | 30 | 50 |
| | 200 | 67 | 73 |
| | 300 | 77 | 96 |
| | 400 | 97 | 96 |
| 91-16 | 100 | 43 | 43 |
| | 200 | 75 | 79 |
| | 300 | 87 | 94 |
| | 400 | 87 | 91 |
| 91-17 | 100 | 40 | 27 |
| | 200 | 68 | 53 |
| | 300 | 87 | 92 |
| | 400 | 93 | 98 |
| 91-18 | 100 | 47 | 10 |
| | 200 | 75 | 37 |
| | 300 | 83 | 63 |
| | 400 | 92 | 88 |

Many of the high-load (488 g a.e./l) glyphosate formulations of this Example exhibited herbicidal effectiveness equal to or greater than that obtained with commercial standard Formulation J, in spite of containing only 3% alkylether surfactant.

Example 92

Aqueous concentrate compositions were prepared containing glyphosate IPA salt and excipient ingredients as shown in Table 92a. Concentrate compositions 92-01 to 92-12 and 92-14 to 92-16 are oil-in-water emulsions and were prepared by process (vii). Concentrate composition 92-13 is an aqueous solution concentrate and was prepared by process (viii).

TABLE 92a

| Concentrate composition | Glyphosate g a.e./l | % w/w Oil | Surfactant | Type of oil | Type of surfactant |
|---|---|---|---|---|---|
| 92-01 | 163 | 0.5 | 5.0 | butyl stearate | steareth-30 |
| 92-02 | 163 | 0.5 | 5.0 | methyl stearate | steareth-30 |
| 92-03 | 163 | 0.5 | 5.0 | butyl stearate | Neodol 45-13 |
| 92-04 | 163 | 0.5 | 5.0 | methyl stearate | Neodol 45-13 |
| 92-05 | 163 | 0.5 | 5.0 | butyl stearate | ceteareth-15 |
| 92-06 | 163 | 0.5 | 5.0 | methyl stearate | ceteareth-15 |
| 92-07 | 163 | 0.5 | 5.0 | butyl stearate | laureth-23 |
| 92-08 | 163 | 0.5 | 5.0 | butyl stearate | oleth-20 |
| 92-09 | 163 | 0.5 | 5.0 | butyl stearate | steareth-20 |
| 92-10 | 163 | 0.5 | 5.0 | butyl stearate | ceteareth-27 |
| 92-11 | 163 | 0.3 | 5.0 | butyl stearate | ceteareth-27 |
| 92-12 | 163 | 0.3 | 2.5 | butyl stearate | ceteareth-27 |
| 92-13 | 163 | | 5.0 | none | ceteareth-27 |
| 92-14 | 163 | 0.5 | 5.0 | methyl stearate | ceteareth-27 |
| 92-15 | 163 | 0.5 | 5.0 | methyl stearate | steareth-20 |
| 92-16 | 163 | 0.5 | 5.0 | methyl stearate | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 92b.

TABLE 92b

| Concentrate composition | Glyphosate rate g a.e./ha | % Inhibition ABUTH | ECHCF |
|---|---|---|---|
| Formulation B | 100 | 45 | 57 |
|  | 200 | 35 | 53 |
|  | 300 | 50 | 57 |
|  | 400 | 38 | 33 |
| Formulation C | 100 | 70 | 98 |
|  | 200 | 90 | 99 |
|  | 300 | 97 | 100 |
|  | 400 | 100 | 100 |
| Formulation J | 100 | 72 | 88 |
|  | 200 | 93 | 99 |
|  | 300 | 97 | 99 |
|  | 400 | 98 | 99 |
| 92-01 | 100 | 83 | 97 |
|  | 200 | 97 | 100 |
|  | 300 | 99 | 100 |
|  | 400 | 100 | 100 |
| 92-02 | 100 | 80 | 99 |
|  | 200 | 96 | 100 |
|  | 300 | 99 | 100 |
|  | 400 | 99 | 100 |
| 92-03 | 100 | 73 | 98 |
|  | 200 | 92 | 100 |
|  | 300 | 98 | 99 |
|  | 400 | 99 | 100 |
| 92-04 | 100 | 73 | 98 |
|  | 200 | 87 | 99 |
|  | 300 | 97 | 99 |
|  | 400 | 99 | 100 |
| 92-05 | 100 | 80 | 98 |
|  | 200 | 87 | 100 |
|  | 300 | 98 | 100 |
|  | 400 | 100 | 100 |
| 92-06 | 100 | 78 | 97 |
|  | 200 | 95 | 98 |
|  | 300 | 98 | 100 |
|  | 400 | 99 | 100 |
| 92-07 | 100 | 78 | 98 |
|  | 200 | 88 | 100 |
|  | 300 | 96 | 100 |
|  | 400 | 98 | 100 |
| 92-08 | 100 | 75 | 98 |
|  | 200 | 93 | 99 |
|  | 300 | 97 | 99 |
|  | 400 | 100 | 99 |
| 92-09 | 100 | 83 | 93 |
|  | 200 | 95 | 100 |
|  | 300 | 98 | 100 |
|  | 400 | 100 | 100 |
| 92-10 | 100 | 80 | 97 |
|  | 200 | 95 | 98 |
|  | 300 | 98 | 99 |
|  | 400 | 100 | 100 |
| 92-11 | 100 | 80 | 97 |
|  | 200 | 93 | 99 |
|  | 300 | 98 | 100 |
|  | 400 | 100 | 99 |
| 92-12 | 100 | 77 | 93 |
|  | 200 | 88 | 100 |
|  | 300 | 99 | 100 |
|  | 400 | 99 | 100 |
| 92-13 | 100 | 80 | 73 |
|  | 200 | 95 | 95 |
|  | 300 | 99 | 100 |
|  | 400 | 100 | 100 |
| 92-14 | 100 | 77 | 94 |
|  | 200 | 92 | 99 |
|  | 300 | 98 | 100 |
|  | 400 | 100 | 99 |
| 92-15 | 100 | 78 | 92 |
|  | 200 | 94 | 99 |
|  | 300 | 98 | 100 |
|  | 400 | 99 | 100 |
| 92-16 | 100 | 77 | 93 |
|  | 200 | 90 | 98 |
|  | 300 | 98 | 99 |
|  | 400 | 99 | 100 |

Extremely high herbicidal effectiveness was provided by ceteareth-27 (composition 92-13); this was further enhanced by addition of a small amount of butyl stearate (92-10, 92-11) or methyl stearate (92-14). Compositions performing better than commercial standard Formulations C and J, at least on ABUTH, included those containing steareth-30, steareth-20 or ceteareth-27; in this test oleth-20 was not quite as effective as these saturated alkylethers.

Example 93

Aqueous concentrate compositions were prepared containing glyphosate IPA salt and excipient ingredients as shown in Table 93a. All are oil-in-water emulsions and were prepared by process (vii). Lecithin (45% phospholipid, Avanti) was first dispersed in using sonication.

TABLE 93a

| Concentrate composition | Glyphosate g a.e./l | Lecithin | Butyl stearate | Ethomeen T/25 | Ceteareth-20 | Ceteareth-27 |
|---|---|---|---|---|---|---|
| 93-01 | 220 | 0.75 | 0.75 | 1.5 | | |
| 93-02 | 220 | 0.75 | 0.75 | 1.5 | | |
| 93-03 | 220 | 0.75 | 0.75 | 3.0 | | |
| 93-04 | 220 | 0.75 | 7.50 | 1.5 | | |
| 93-05 | 220 | 0.75 | 7.50 | 3.0 | | |
| 93-06 | 220 | 3.75 | 3.75 | 3.0 | | |
| 93-07 | 220 | 1.50 | 1.50 | 3.0 | | |
| 93-08 | 220 | 1.50 | 1.50 | 1.5 | | |
| 93-09 | 220 | 3.75 | 3.75 | 1.5 | 1.5 | |
| 93-10 | 220 | 1.50 | 1.50 | 1.5 | 1.5 | |
| 93-11 | 220 | 3.75 | 7.50 | 1.5 | 1.5 | |
| 93-12 | 220 | 3.75 | 1.50 | 1.5 | 1.5 | |
| 93-13 | 220 | 0.75 | 3.75 | 1.5 | | 1.5 |
| 93-14 | 220 | 0.75 | 7.50 | 1.5 | | 1.5 |
| 93-15 | 220 | 0.75 | 3.75 | 3.0 | | 3.0 |
| 93-16 | 220 | 0.75 | 7.50 | 3.0 | | 3.0 |
| 93-17 | 220 | | 7.50 | 3.0 | | |
| 93-18 | 220 | 0.75 | 7.50 | | | 3.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 23 days after planting ABUTH and ECHCF, and evaluation of herbicidal inhibition was done 18 days after application.

Formulations B, C and J were applied as comparative treatments. Results, averaged for all replicates of each treatment, are shown in Table 92b.

TABLE 93b

| Concentrate composition | Glyphosate rate g a.e./ha | % Inhibition ABUTH | ECHCF |
|---|---|---|---|
| Formulation B | 100 | 12 | 62 |
|  | 200 | 5 | 55 |
|  | 300 | 23 | 63 |
|  | 400 | 43 | 78 |
| Formulation J | 100 | 27 | 82 |
|  | 200 | 62 | 98 |
|  | 300 | 88 | 95 |
|  | 400 | 96 | 99 |
| 93-01 | 100 | 13 | 79 |
|  | 200 | 68 | 95 |
|  | 300 | 82 | 99 |
|  | 400 | 95 | 91 |
| 93-02 | 100 | 27 | 82 |
|  | 200 | 60 | 97 |
|  | 300 | 81 | 95 |
|  | 400 | 87 | 99 |
| 93-03 | 100 | 37 | 77 |
|  | 200 | 62 | 96 |
|  | 300 | 78 | 98 |
|  | 400 | 89 | 90 |
| 93-04 | 100 | 37 | 84 |
|  | 200 | 57 | 95 |
|  | 300 | 84 | 99 |
|  | 400 | 89 | 100 |
| 93-05 | 100 | 33 | 77 |
|  | 200 | 65 | 100 |
|  | 300 | 78 | 97 |
|  | 400 | 88 | 97 |
| 93-06 | 100 | 43 | 78 |
|  | 200 | 62 | 95 |
|  | 300 | 87 | 97 |
|  | 400 | 95 | 96 |
| 93-07 | 100 | 48 | 78 |
|  | 200 | 80 | 91 |
|  | 300 | 90 | 99 |
|  | 400 | 76 | 93 |
| 93-08 | 100 | 48 | 83 |
|  | 200 | 67 | 89 |
|  | 300 | 86 | 96 |
|  | 400 | 93 | 97 |
| 93-09 | 100 | 62 | 84 |
|  | 200 | 82 | 98 |
|  | 300 | 85 | 99 |
|  | 400 | 91 | 97 |
| 93-10 | 100 | 63 | 80 |
|  | 200 | 75 | 96 |
|  | 300 | 85 | 99 |
|  | 400 | 99 | 99 |
| 93-11 | 100 | 42 | 75 |
|  | 200 | 78 | 98 |
|  | 300 | 92 | 99 |
|  | 400 | 93 | 100 |
| 93-12 | 100 | 52 | 80 |
|  | 200 | 73 | 93 |
|  | 300 | 86 | 99 |
|  | 400 | 97 | 97 |
| 93-13 | 100 | 55 | 83 |
|  | 200 | 75 | 97 |
|  | 300 | 97 | 99 |
|  | 400 | 92 | 99 |
| 93-14 | 100 | 52 | 87 |
|  | 200 | 73 | 95 |
|  | 300 | 91 | 97 |
|  | 400 | 87 | 98 |
| 93-15 | 100 | 57 | 83 |
|  | 200 | 92 | 96 |
|  | 300 | 98 | 100 |
|  | 400 | 100 | 98 |
| 93-16 | 100 | 79 | 88 |
|  | 200 | 87 | 97 |
|  | 300 | 99 | 99 |
|  | 400 | 97 | 94 |

TABLE 93b-continued

| Concentrate composition | Glyphosate rate g a.e./ha | % Inhibition ABUTH | ECHCF |
|---|---|---|---|
| 93-17 | 100 | 58 | 83 |
|  | 200 | 47 | 94 |
|  | 300 | 88 | 98 |
|  | 400 | 91 | 93 |
| 93-18 | 100 | 58 | 87 |
|  | 200 | 75 | 91 |
|  | 300 | 83 | 99 |
|  | 400 | 91 | 98 |

Outstanding herbicidal effectiveness was provided by composition 93-18, containing lecithin, ceteareth-27 and butyl stearate. Addition of 3% Ethomeen T/25 (93-16) further enhanced effectiveness. Slightly reduced effectiveness at the lowest glyphosate rate was observed on ABUTH when the butyl stearate concentration was cut in half (93-15).

Example 94

Aqueous concentrate compositions were prepared containing glyphosate IPA salt and excipient ingredients as shown in Table 94a. Concentrate compositions 94-01 to 94-04, 94-06, 94-08, 94-10 and 94-18 are oil-in-water emulsions and were prepared by process (vii). Concentrate compositions 94-05, 94-07 and 94-09 are aqueous solution concentrates and were prepared by process (viii). Concentrate compositions 94-11 to 94-17 contain colloidal particulates and were prepared by process (ix).

The compositions of this example all showed acceptable storage stability. The compositions shown as containing colloidal particulate were not storage-stable unless the colloidal particulate was included as shown.

TABLE 94a

| Concentrate composition | Glyphosate g a.e./l | % w/w Butyl stearate | Surfactant | Aerosil 380 | Type of surfactant |
|---|---|---|---|---|---|
| 94-01 | 163 | 0.5 | 5.0 |  | steareth-20 |
| 94-02 | 163 | 0.5 | 5.0 |  | ceteareth-27 |
| 94-03 | 163 | 0.5 | 5.0 |  | oleth-20 |
| 94-04 | 163 | 0.5 | 5.0 |  | ceteth-20 |
| 94-05 | 163 |  | 5.0 |  | ceteth-20 |
| 94-06 | 163 | 0.5 | 5.0 |  | Neodol 45-13 |
| 94-07 | 163 |  | 5.0 |  | Neodol 45-13 |
| 94-08 | 163 | 0.5 | 5.0 |  | ceteareth-15 |
| 94-09 | 163 |  | 5.0 |  | ceteareth-15 |
| 94-10 | 163 | 0.5 | 5.0 |  | steareth-30 |
| 94-11 | 360 | 1.0 | 10.0 | 1.25 | ceteth-20 |
| 94-12 | 360 | 1.0 | 10.0 | 1.25 | Neodol 45-13 |
| 94-13 | 360 | 1.0 | 10.0 | 1.25 | ceteareth-15 |
| 94-14 | 360 | 1.0 | 10.0 | 1.25 | steareth-30 |
| 94-15 | 360 | 1.0 | 10.0 | 1.25 | steareth-20 |
| 94-16 | 360 | 1.0 | 10.0 | 1.25 | oleth-20 |
| 94-17 | 360 | 1.0 | 10.0 | 1.25 | ceteareth-27 |
| 94-18 | 163 | 0.5 | 5.0 |  | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 22 days after planting ABUTH and ECHCF, and evaluation of herbicidal inhibition was done 18 days after application.

Formulations B, C and J were applied as comparative treatments. Results, averaged for all replicates of each treatment, are shown in Table 92b.

TABLE 94b

| Concentrate composition | Glyphosate rate g a.e./ha | % Inhibition ABUTH | % Inhibition ECHCF |
|---|---|---|---|
| Formulation B | 100 | 0 | 30 |
|  | 200 | 2 | 60 |
|  | 300 | 17 | 75 |
|  | 400 | 50 | 73 |
| Formulation J | 100 | 20 | 63 |
|  | 200 | 42 | 98 |
|  | 300 | 75 | 100 |
|  | 400 | 83 | 98 |
| 94-01 | 100 | 27 | 57 |
|  | 200 | 67 | 98 |
|  | 300 | 80 | 99 |
|  | 400 | 87 | 98 |
| 94-02 | 100 | 27 | 63 |
|  | 200 | 53 | 87 |
|  | 300 | 77 | 99 |
|  | 400 | 87 | 99 |
| 94-03 | 100 | 12 | 50 |
|  | 200 | 53 | 99 |
|  | 300 | 65 | 100 |
|  | 400 | 83 | 99 |
| 94-04 | 100 | 20 | 63 |
|  | 200 | 50 | 98 |
|  | 300 | 73 | 98 |
|  | 400 | 87 | 98 |
| 94-05 | 100 | 18 | 70 |
|  | 200 | 57 | 93 |
|  | 300 | 80 | 99 |
|  | 400 | 83 | 99 |
| 94-06 | 100 | 17 | 63 |
|  | 200 | 35 | 95 |
|  | 300 | 60 | 100 |
|  | 400 | 75 | 100 |
| 94-07 | 100 | 3 | 43 |
|  | 200 | 43 | 95 |
|  | 300 | 62 | 100 |
|  | 400 | 68 | 96 |
| 94-08 | 100 | 20 | 43 |
|  | 200 | 43 | 88 |
|  | 300 | 75 | 99 |
|  | 400 | 80 | 97 |
| 94-09 | 100 | 37 | 57 |
|  | 200 | 55 | 93 |
|  | 300 | 83 | 100 |
|  | 400 | 83 | 99 |
| 94-10 | 100 | 37 | 50 |
|  | 200 | 60 | 96 |
|  | 300 | 83 | 99 |
|  | 400 | 88 | 99 |
| 94-11 | 100 | 8 | 37 |
|  | 200 | 37 | 93 |
|  | 300 | 68 | 99 |
|  | 400 | 70 | 97 |
| 94-12 | 100 | 13 | 43 |
|  | 200 | 40 | 91 |
|  | 300 | 67 | 100 |
|  | 400 | 77 | 96 |
| 94-13 | 100 | 25 | 40 |
|  | 200 | 40 | 80 |
|  | 300 | 62 | 97 |
|  | 400 | 78 | 98 |
| 94-14 | 100 | 23 | 33 |
|  | 200 | 37 | 86 |
|  | 300 | 75 | 99 |
|  | 400 | 78 | 94 |
| 94-15 | 100 | 23 | 30 |
|  | 200 | 43 | 78 |
|  | 300 | 53 | 93 |
|  | 400 | 78 | 98 |

TABLE 94b-continued

| Concentrate composition | Glyphosate rate g a.e./ha | % Inhibition ABUTH | % Inhibition ECHCF |
|---|---|---|---|
| 94-16 | 100 | 23 | 37 |
|  | 200 | 37 | 95 |
|  | 300 | 63 | 97 |
|  | 400 | 78 | 95 |
| 94-18 | 100 | 18 | 50 |
|  | 200 | 45 | 88 |
|  | 300 | 75 | 69 |
|  | 400 | 73 | 93 |
| 94-19 | 100 | missing | missing |
|  | 200 | missing | missing |
|  | 300 | missing | missing |
|  | 400 | missing | missing |

Compositions exhibiting herbicidal effectiveness greater than that provided by commercial standard Formulation J included 94-01 (steareth-20 plus butyl stearate), 94-09 (ceteareth-15) and 94-10 (steareth-20 plus butyl stearate).

Example 95

Aqueous concentrate compositions were prepared containing glyphosate IPA salt and excipient ingredients as shown in Table 95a. All are oil-in-water emulsions and were prepared by process (vii).

TABLE 95a

| Concentrate composition | Glyphosate g a.e./l | Butyl stearate % w/w | Surfactant % w/w | Type of surfactant |
|---|---|---|---|---|
| 95-01 | 163 | 1.00 | 10.0 | laureth-23 |
| 95-02 | 163 | 0.50 | 5.0 | laureth-23 |
| 95-03 | 163 | 0.25 | 2.5 | laureth-23 |
| 95-04 | 163 | 1.00 | 10.0 | Neodol 1-9 |
| 95-05 | 163 | 0.50 | 5.0 | Neodol 1-9 |
| 95-06 | 163 | 0.25 | 2.5 | Neodol 1-9 |
| 95-07 | 163 | 1.00 | 10.0 | steareth-10 |
| 95-08 | 163 | 0.50 | 5.0 | steareth-10 |
| 95-09 | 163 | 0.25 | 2.5 | steareth-10 |
| 95-10 | 163 | 0.50 | 5.0 | steareth-20 |
| 95-11 | 163 | 0.25 | 2.5 | steareth-20 |
| 95-12 | 163 | 0.25 | 1.0 | steareth-20 |
| 95-13 | 163 | 0.50 | 5.0 | oleth-20 |
| 95-14 | 163 | 0.25 | 2.5 | oleth-20 |
| 95-15 | 163 | 0.25 | 1.0 | oleth-20 |
| 95-16 | 163 | 0.50 | 5.0 | ceteareth-27 |
| 95-17 | 163 | 0.25 | 2.5 | ceteareth-27 |
| 95-18 | 163 | 0.25 | 1.0 | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations B and J were applied as comparative treatments. Results, averaged for all replicates of each treatment, are shown in Table 95b.

TABLE 95b

| Concentrate composition | Glyphosate rate g a.e./ha | % Inhibition ABUTH | % Inhibition ECHCF |
|---|---|---|---|
| Formulation B | 100 | 0 | 42 |
| | 200 | 0 | 43 |
| | 300 | 23 | 50 |
| | 400 | 0 | 28 |
| Formulation J | 100 | 0 | 73 |
| | 200 | 57 | 85 |
| | 300 | 68 | 93 |
| | 400 | 87 | 94 |
| 95-01 | 100 | 18 | 75 |
| | 200 | 58 | 92 |
| | 300 | 85 | 90 |
| | 400 | 94 | 95 |
| 95-02 | 100 | 3 | 77 |
| | 200 | 47 | 90 |
| | 300 | 65 | 89 |
| | 400 | 87 | 95 |
| 95-03 | 100 | 13 | 80 |
| | 200 | 53 | 88 |
| | 300 | 72 | 98 |
| | 400 | 82 | 99 |
| 95-04 | 100 | 0 | 0 |
| | 200 | 53 | 88 |
| | 300 | 67 | 95 |
| | 400 | 83 | 95 |
| 95-05 | 100 | 2 | 60 |
| | 200 | 50 | 83 |
| | 300 | 70 | 93 |
| | 400 | 85 | 92 |
| 95-06 | 100 | 0 | 52 |
| | 200 | 55 | 83 |
| | 300 | 62 | 96 |
| | 400 | 77 | 98 |
| 95-07 | 100 | 8 | 70 |
| | 200 | 68 | 95 |
| | 300 | 91 | 99 |
| | 400 | 95 | 100 |
| 95-08 | 100 | 10 | 65 |
| | 200 | 67 | 99 |
| | 300 | 78 | 99 |
| | 400 | 93 | 100 |
| 95-09 | 100 | 5 | 80 |
| | 200 | 52 | 98 |
| | 300 | 75 | 100 |
| | 400 | 86 | 98 |
| 95-10 | 100 | 0 | 65 |
| | 200 | 62 | 84 |
| | 300 | 58 | 94 |
| | 400 | 75 | 100 |
| 95-11 | 100 | 5 | 83 |
| | 200 | 50 | 99 |
| | 300 | 63 | 97 |
| | 400 | 87 | 99 |
| 95-12 | 100 | 10 | 76 |
| | 200 | 60 | 96 |
| | 300 | 72 | 100 |
| | 400 | 100 | 100 |

TABLE 95b-continued

| Concentrate composition | Glyphosate rate g a.e./ha | % Inhibition ABUTH | % Inhibition ECHCF |
|---|---|---|---|
| 95-13 | 100 | 20 | 85 |
| | 200 | 67 | 100 |
| | 300 | 91 | 100 |
| | 400 | 96 | 98 |
| 95-14 | 100 | 23 | 68 |
| | 200 | 62 | 89 |
| | 300 | 80 | 100 |
| | 400 | 99 | 99 |
| 95-15 | 100 | 5 | 57 |
| | 200 | 55 | 93 |
| | 300 | 89 | 95 |
| | 400 | 90 | 98 |
| 95-16 | 100 | 30 | 68 |
| | 200 | 68 | 94 |
| | 300 | 83 | 98 |
| | 400 | 100 | 100 |
| 95-17 | 100 | 43 | 68 |
| | 200 | 62 | 99 |
| | 300 | 78 | 100 |
| | 400 | 100 | 99 |
| 95-18 | 100 | 25 | 52 |
| | 200 | 53 | 84 |
| | 300 | 85 | 94 |
| | 400 | 98 | 95 |

Compositions having a 1:3 or lower weight/weight ratio of surfactant to glyphosate a.e., yet outperforming commercial standard Formulation J at least on ABUTH in this test, included those containing just 1% alkylether surfactant (ratio about 1:15) together with 0.25% butyl stearate, where the alkylether surfactant was steareth-20 (95-12), oleth-20 (95-15) or ceteareth-27 (95-18).

Example 96

Aqueous concentrate compositions were prepared containing glyphosate IPA salt and excipient ingredients as shown in Table 96a. All are aqueous solution concentrates containing colloidal particulates and were prepared by process (ix).

The compositions of this example all showed acceptable storage stability. The compositions shown as containing colloidal particulate were not storage-stable unless the colloidal particulate was included as shown.

TABLE 96a

| Conc. comp. | Glyphosate g a.e./l | % w/w Surfactant | % w/w Aerosil | Other surfactant | Type of Aerosil | Other component |
|---|---|---|---|---|---|---|
| 96-01 | 488 | 3.0 | 1.5 | steareth-20 | MOX-80/380 (1:2) | |
| 96-02 | 488 | 4.5 | 1.5 | steareth-20 | 380 | |
| 96-03 | 488 | 4.5 | 1.5 | steareth-20 | MOX-80/380 (1:2) | |
| 96-04 | 488 | 4.5 | 1.5 | steareth-20 | MOX-80/MOX-170 (1:2) | |
| 96-05 | 488 | 6.0 | 1.5 | 4.12 steareth-20 | 380 | glycerin |
| 96-06 | 488 | 3.0 | 1.5 | steareth-20 | 380 | |
| 96-07 | 488 | 3.0 | 1.5 | 7.12 oleth-20 | 380 | propylene glycol |
| 96-08 | 488 | 3.0 | 1.5 | oleth-20 | MOX-80/380 (1:2) | |
| 96-09 | 488 | 4.5 | 1.5 | oleth-20 | 380 | |
| 96-10 | 488 | 4.5 | 1.5 | oleth-20 | MOX-80/380 (1:2) | |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations B and J were applied as comparative treatments. Results, averaged for all replicates of each treatment, are shown in Table 95b.

TABLE 96b

| Concentrate composition | Glyphosate rate g a.e./ha | % Inhibition ABUTH | % Inhibition ECHCF |
|---|---|---|---|
| Formulation B | 100 | 0 | 25 |
|  | 200 | 35 | 27 |
|  | 300 | 48 | 28 |
|  | 400 | 47 | 48 |
| Formulation J | 100 | 50 | 75 |
|  | 200 | 80 | 90 |
|  | 300 | 97 | 96 |
|  | 400 | 99 | 98 |
| 96-01 | 100 | 53 | 33 |
|  | 200 | 83 | 52 |
|  | 300 | 98 | 72 |
|  | 400 | 98 | 79 |
| 96-02 | 100 | 43 | 27 |
|  | 200 | 80 | 57 |
|  | 300 | 87 | 73 |
|  | 400 | 96 | 78 |
| 96-03 | 100 | 48 | 30 |
|  | 200 | 81 | 70 |
|  | 300 | 98 | 78 |
|  | 400 | 63 | 57 |
| 96-04 | 100 | 45 | 32 |
|  | 200 | 87 | 75 |
|  | 300 | 97 | 73 |
|  | 400 | 98 | 83 |
| 96-05 | 100 | 38 | 27 |
|  | 200 | 37 | 23 |
|  | 300 | 45 | 32 |
|  | 400 | 35 | 18 |

TABLE 96b-continued

| Concentrate composition | Glyphosate rate g a.e./ha | % Inhibition ABUTH | % Inhibition ECHCF |
|---|---|---|---|
| 96-06 | 100 | 42 | 40 |
|  | 200 | 78 | 52 |
|  | 300 | 91 | 72 |
|  | 400 | 96 | 80 |
| 96-07 | 100 | 37 | 43 |
|  | 200 | 48 | 32 |
|  | 300 | 73 | 58 |
|  | 400 | 55 | 28 |
| 96-08 | 100 | 43 | 37 |
|  | 200 | 68 | 57 |
|  | 300 | 84 | 62 |
|  | 400 | 89 | 82 |
| 96-09 | 100 | 37 | 32 |
|  | 200 | 83 | 67 |
|  | 300 | 94 | 82 |
|  | 400 | 63 | 48 |
| 96-10 | 100 | 32 | 40 |
|  | 200 | 75 | 68 |
|  | 300 | 90 | 88 |
|  | 400 | 65 | 63 |

Several high-load (488 g a.e./l) glyphosate compositions exhibited herbicidal effectiveness on ABUTH equal to commercial standard Formulation J, but none was equal to Formulation J on ECHCF in this test.

Example 97

Dry granular concentrate compositions were prepared containing glyphosate ammonium salt and excipient ingredients as shown in Table 97a. The preparation procedure was as follows. Ammoniun glyphosate powder was added to a blender. Excipient ingredients were slowly added, together with sufficient water to wet the powder and form a stiff dough. The blender was operated for sufficient time to thoroughly mix all ingredients. The dough was then transferred to extrusion apparatus and was extruded to form granules, which were finally dried in a fluid bed dryer.

TABLE 97a

| | % w/w | | | | | | |
|---|---|---|---|---|---|---|---|
| Conc. comp. | Glyphosate a.e. | Lecithin | Butyl stearate | Surfactant | Colloidal particulate | Type of surfactant | Type of colloidal particulate |
| 97-01 | 68.7 | | | 21.0 | | steareth-20 | |
| 97-02 | 66.0 | | 2.2 | 22.0 | | steareth-20 | |
| 97-03 | 66.1 | | | 24.0 | | oleth-20 | |
| 97-04 | 66.0 | | 2.2 | 22.0 | | oleth-20 | |
| 97-05 | 67.9 | 10.0 | 2.0 | 10.0 | | MON 0818 | |
| 97-06 | 59.2 | 10.0 | | 20.0 + 2.0 | | FC-754 + MON 0818 | |
| 97-07 | 68.0 | | | 21.0 | 0.8 | Flomo 1407 | Aerosil 90 |
| 97-08 | 68.0 | | | 21.0 | 0.8 | Flomo 1407 | Aluminum oxide C |
| 97-09 | 66.1 | | | 24.0 | | ceteth-20 | |
| 97-10 | 66.0 | | 2.2 | 22.0 | | ceteth-20 | |
| 97-11 | 71.2 | | | 16.1 | 2.0 | ceteth-20 | Aerosil 380 |
| 97-12 | 71.1 | | | 16.3 | 1.0 | ceteth-20 | Aerosil blend (*) |
| 97-13 | 71.2 | | | 16.1 | 2.0 | steareth-20 | Aerosil 380 |
| 97-14 | 71.2 | | | 16.1 | 1.0 | steareth-20 | Aerosil blend (*) |
| 97-15 | 68.0 | | | 20.0 | 1.9 | oleth-20 | Aerosil-380 |
| 97-16 | 70.8 | | | 16.6 | 1.0 | oleth-20 | Aerosil blend (*) |

(*) Aerosil MOX-80 + Aerosil MOX-170 (1:1)

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations J and K were applied as comparative treatments. Results, averaged for all replicates of each treatment, are shown in Table 97b.

TABLE 97b

| Concentrate composition | Glyphosate rate g a.e./ha | % Inhibition ABUTH | ECHCF |
|---|---|---|---|
| Formulation J | 100 | 52 | 80 |
|  | 200 | 90 | 96 |
|  | 300 | 96 | 100 |
|  | 400 | 97 | 99 |
| Formulation K | 100 | 33 | 70 |
|  | 200 | 67 | 93 |
|  | 300 | 83 | 99 |
|  | 400 | 93 | 100 |
| 97-01 | 100 | 47 | 60 |
|  | 200 | 87 | 98 |
|  | 300 | 97 | 98 |
|  | 400 | 100 | 98 |
| 97-02 | 100 | 47 | 63 |
|  | 200 | 80 | 94 |
|  | 300 | 90 | 99 |
|  | 400 | 98 | 100 |
| 97-03 | 100 | 62 | 62 |
|  | 200 | 83 | 93 |
|  | 300 | 97 | 96 |
|  | 400 | 97 | 100 |
| 97-04 | 100 | 47 | 57 |
|  | 200 | 78 | 94 |
|  | 300 | 87 | 100 |
|  | 400 | 98 | 100 |
| 97-05 | 100 | 25 | 53 |
|  | 200 | 60 | 88 |
|  | 300 | 80 | 97 |
|  | 400 | 83 | 98 |
| 97-06 | 100 | 35 | 37 |
|  | 200 | 65 | 62 |
|  | 300 | 83 | 83 |
|  | 400 | 90 | 95 |
| 97-07 | 100 | 63 | 55 |
|  | 200 | 72 | 97 |
|  | 300 | 83 | 100 |
|  | 400 | 94 | 100 |
| 97-08 | 100 | 30 | 65 |
|  | 200 | 72 | 94 |
|  | 300 | 87 | 100 |
|  | 400 | 92 | 99 |

TABLE 97b-continued

| Concentrate composition | Glyphosate rate g a.e./ha | % Inhibition ABUTH | ECHCF |
|---|---|---|---|
| 97-09 | 100 | 37 | 63 |
|  | 200 | 77 | 83 |
|  | 300 | 88 | 99 |
|  | 400 | 97 | 99 |
| 97-10 | 100 | 40 | 55 |
|  | 200 | 83 | 93 |
|  | 300 | 94 | 96 |
|  | 400 | 98 | 99 |
| 97-11 | 100 | 42 | 55 |
|  | 200 | 78 | 94 |
|  | 300 | 88 | 92 |
|  | 400 | 94 | 99 |
| 97-12 | 100 | 38 | 58 |
|  | 200 | 78 | 97 |
|  | 300 | 92 | 97 |
|  | 400 | 95 | 100 |
| 97-13 | 100 | 25 | 50 |
|  | 200 | 80 | 88 |
|  | 300 | 96 | 95 |
|  | 400 | 98 | 98 |
| 97-14 | 100 | 50 | 53 |
|  | 200 | 88 | 92 |
|  | 300 | 98 | 99 |
|  | 400 | 99 | 99 |
| 97-15 | 100 | 33 | 57 |
|  | 200 | 75 | 91 |
|  | 300 | 94 | 97 |
|  | 400 | 98 | 99 |
| 97-16 | 100 | 33 | 55 |
|  | 200 | 77 | 90 |
|  | 300 | 88 | 99 |
|  | 400 | 96 | 100 |

Several dry granular compositions of this Example outperformed commercial standard composition K, at least on ABUTH. They included 97-01 to 97-04 and 97-10 to 97-16, all containing an alkylether surfactant (steareth-20, oleth-20 or ceteth-20).

Example 98

Aqueous concentrate compositions were prepared containing glyphosate IPA salt and excipient ingredients as shown in Table 98a. All are oil-in-water emulsions and were prepared by process (vii). Soybean lecithin (45% phospholipid, Avanti) was first dispersed in water either by ultrasonication or by use of a microfluidizer as indicated in the column of Table 98a headed "Process".

TABLE 98a

| Conc. comp. | Glyphosate g a.e./l | Lecithin | Butyl stearate | Ethomeen T/25 | MON 0818 | Cetearetch-20 | Cetearetch-27 | Process (*) |
|---|---|---|---|---|---|---|---|---|
| 98-01 | 220 | 0.75 | 3.75 | 3.0 |  |  | 3.0 | B |
| 98-02 | 220 | 0.75 | 0.75 | 3.0 |  |  | 3.0 | B |
| 98-03 | 220 | 0.75 | 3.75 | 3.0 |  | 3.0 |  | B |
| 98-04 | 220 | 0.75 | 0.75 | 3.0 |  | 3.0 |  | B |
| 98-05 | 220 | 6.00 | 1.50 | 3.0 |  | 3.0 |  | B |
| 98-06 | 220 | 6.00 | 1.50 | 3.0 |  |  | 3.0 | B |
| 98-07 | 220 | 4.00 | 1.00 | 3.0 |  | 3.0 |  | B |
| 98-08 | 220 | 4.00 | 1.00 | 3.0 |  |  | 3.0 | B |
| 98-09 | 220 | 0.75 | 3.75 | 3.0 |  |  | 3.0 | A |
| 98-10 | 220 | 0.75 | 0.75 | 3.0 |  |  | 3.0 | A |
| 98-11 | 220 | 0.75 | 3.75 | 6.0 |  |  |  | B |
| 98-12 | 220 | 0.75 | 3.75 |  | 6.0 |  |  | B |

TABLE 98a-continued

| | | | % w/w | | | | | |
|---|---|---|---|---|---|---|---|---|
| Conc. comp. | Glyphosate g a.e./l | Lecithin | Butyl stearate | Ethomeen T/25 | MON 0818 | Ceteareth-20 | Ceteareth-27 | Process (*) |
| 98-13 | 345 | 6.00 | 1.50 | 4.5 | 4.5 | | | B |
| 98-14 | 345 | 6.00 | 1.50 | 6.0 | | | 3.0 | B |
| 98-15 | 345 | 6.00 | 1.50 | 6.0 | 6.0 | | | B |
| 98-16 | 345 | 0.50 | 7.50 | 12.0 | | | | B |
| 98-17 | 345 | 6.00 | 1.50 | 4.5 | 4.5 | | 3.0 | B |

(*) Process:
A Ultrasonicated
B Microfluidized, 3 cycles

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 15 days after application.

Formulations B and J were applied as comparative treatments. Results, averaged for all replicates of each treatment, are shown in Table 98b.

TABLE 98b

| | Glyphosate rate | % Inhibition | |
|---|---|---|---|
| Concentrate composition | g a.e./ha | ABUTH | ECHCF |
| Formulation B | 150 | 45 | 82 |
| | 250 | 55 | 71 |
| | 350 | 80 | 72 |
| | 450 | 88 | 77 |
| Formulation J | 150 | 55 | 83 |
| | 250 | 89 | 88 |
| | 350 | 97 | 93 |
| | 450 | 99 | 93 |
| | 550 | 99 | 87 |
| 98-01 | 150 | 92 | 83 |
| | 250 | 96 | 96 |
| | 350 | 99 | 96 |
| | 450 | 100 | 86 |
| 98-02 | 150 | 85 | 93 |
| | 250 | 97 | 78 |
| | 350 | 97 | 90 |
| | 450 | 99 | 90 |
| 98-03 | 150 | 87 | 85 |
| | 250 | 98 | 92 |
| | 350 | 99 | 95 |
| | 450 | 100 | 95 |
| 98-04 | 150 | 87 | 89 |
| | 250 | 97 | 92 |
| | 350 | 99 | 94 |
| | 450 | 99 | 91 |
| 98-05 | 150 | 87 | 77 |
| | 250 | 98 | 89 |
| | 350 | 99 | 93 |
| | 450 | 99 | 84 |
| 98-06 | 150 | 12 | 18 |
| | 250 | 96 | 73 |
| | 350 | 99 | 85 |
| | 450 | 99 | 84 |
| 98-07 | 150 | 82 | 89 |
| | 250 | 88 | 96 |
| | 350 | 96 | 98 |
| | 450 | 97 | 97 |
| 98-08 | 150 | 88 | 94 |
| | 250 | 95 | 90 |
| | 350 | 99 | 98 |
| | 450 | 99 | 98 |

TABLE 98b-continued

| | Glyphosate rate | % Inhibition | |
|---|---|---|---|
| Concentrate composition | g a.e./ha | ABUTH | ECHCF |
| 98-09 | 150 | 94 | 94 |
| | 250 | 95 | 100 |
| | 350 | 97 | 99 |
| | 450 | 99 | 98 |
| 98-10 | 150 | 94 | 94 |
| | 250 | 98 | 99 |
| | 350 | 99 | 97 |
| | 450 | 99 | 96 |
| 98-11 | 150 | 83 | 81 |
| | 250 | 94 | 88 |
| | 350 | 98 | 93 |
| | 450 | 99 | 99 |
| 98-12 | 150 | 68 | 79 |
| | 250 | 95 | 96 |
| | 350 | 98 | 100 |
| | 450 | 99 | 98 |
| 98-13 | 150 | 86 | 98 |
| | 250 | 95 | 98 |
| | 350 | 99 | 100 |
| | 450 | 100 | 98 |
| 98-14 | 150 | 85 | 98 |
| | 250 | 98 | 98 |
| | 350 | 99 | 98 |
| | 450 | 100 | 98 |
| 98-15 | 150 | 86 | 95 |
| | 250 | 97 | 97 |
| | 350 | 99 | 95 |
| | 450 | 100 | 96 |
| 98-16 | 150 | 93 | 94 |
| | 250 | 98 | 98 |
| | 350 | 99 | 98 |
| | 450 | 100 | 97 |
| 98-17 | 150 | 95 | 96 |
| | 250 | 98 | 100 |
| | 350 | 100 | 100 |
| | 450 | 100 | 98 |

Many compositions containing lecithin and butyl stearate outperformed commercial standard Formulation J in this test.

Example 99

Aqueous concentrate compositions were prepared containing glyphosate IPA salt and excipient ingredients as shown in Table 99a. Concentrate compositions 99-04 and 99-05 are aqueous solution concentrates and were prepared by process (viii). Concentrate compositions 99-06 to 99-13 are aqueous solution concentrates containing colloidal particulates and were prepared by process (ix). Concentrate compositions 99-01 to 99-03 contain colloidal particulate but no surfactant.

The compositions of this example containing colloidal particulate all showed acceptable storage stability. Of those containing steareth-20 but no colloidal particulate, composition 99-04 was acceptable storage-stable but composition 99-05 was not.

TABLE 99a

| Concentrate composition | Glyphosate g a.e./l | % w/w | | | Type of Aerosil |
|---|---|---|---|---|---|
| | | Steareth-20 | Oleth-20 | Aerosil | |
| 99-01 | 484 | | | 1.5 | MOX-80 |
| 99-02 | 484 | | | 1.5 | 380 |
| 99-03 | 484 | | | 1.5 | MOX-80/ MOX-170 (1:1) |
| 99-04 | 484 | 1.5 | | | none |
| 99-05 | 484 | 3.0 | | | none |
| 99-06 | 484 | 3.0 | | 1.5 | MOX-170 |
| 99-07 | 484 | 3.0 | | 1.5 | 380 |
| 99-08 | 484 | 3.0 | | 1.5 | MOX-80/ 380 (1:1) |
| 99-09 | 484 | 3.0 | | 1.5 | MOX-80/ MOX-170 (1:1) |
| 99-10 | 484 | | 3.0 | 1.5 | MOX-80 |
| 99-11 | 484 | | 3.0 | 1.5 | MOX-170 |
| 99-12 | 484 | | 3.0 | 1.5 | 380 |
| 99-13 | 484 | | 3.0 | 1.5 | MOX-80/ 380 (1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 19 days after application.

Formulations B and J were applied as comparative treatments. Results, averaged for all replicates of each treatment, are shown in Table 99b.

TABLE 99b

| Concentrate composition | Glyphosate rate g a.e./ha | % Inhibition | |
|---|---|---|---|
| | | ABUTH | ECHCF |
| Formulation B | 100 | 3 | 38 |
| | 200 | 28 | 63 |
| | 300 | 37 | 75 |
| | 400 | 55 | 78 |
| Formulation J | 100 | 23 | 73 |
| | 200 | 43 | 92 |
| | 300 | 67 | 96 |
| | 400 | 92 | 97 |
| 99-01 | 100 | 23 | 60 |
| | 200 | 40 | 77 |
| | 300 | 65 | 91 |
| | 400 | 75 | 92 |
| 99-02 | 100 | 18 | 50 |
| | 200 | 25 | 53 |
| | 300 | 33 | 75 |
| | 400 | 67 | 82 |
| 99-03 | 100 | 27 | 57 |
| | 200 | 35 | 72 |
| | 300 | 50 | 86 |
| | 400 | 70 | 93 |
| 99-04 | 100 | 42 | 67 |
| | 200 | 48 | 78 |
| | 300 | 78 | 82 |
| | 400 | 80 | 85 |
| 99-05 | 100 | 28 | 43 |
| | 200 | 45 | 77 |
| | 300 | 70 | 92 |
| | 400 | 80 | 95 |
| 99-06 | 100 | 42 | 57 |
| | 200 | 70 | 75 |
| | 300 | 89 | 87 |
| | 400 | 94 | 94 |
| 99-07 | 100 | 43 | 68 |
| | 200 | 62 | 90 |
| | 300 | 88 | 92 |
| | 400 | 97 | 92 |
| 99-08 | 100 | 53 | 57 |
| | 200 | 72 | 87 |
| | 300 | 88 | 94 |
| | 400 | 92 | 97 |
| 99-09 | 100 | 27 | 60 |
| | 200 | 62 | 75 |
| | 300 | 75 | 92 |
| | 400 | 83 | 90 |
| 99-10 | 100 | 47 | 43 |
| | 200 | 73 | 73 |
| | 300 | 82 | 88 |
| | 400 | 97 | 93 |
| 99-11 | 100 | 48 | 57 |
| | 200 | 63 | 75 |
| | 300 | 80 | 91 |
| | 400 | 89 | 98 |
| 99-12 | 100 | 30 | 40 |
| | 200 | 42 | 63 |
| | 300 | 68 | 75 |
| | 400 | 73 | 83 |
| 99-13 | 100 | 37 | 40 |
| | 200 | 57 | 75 |
| | 300 | 73 | 80 |
| | 400 | 78 | 94 |

Remarkably strong herbicidal effectiveness was provided by composition 99-05, in spite of its very low surfactant (stearth-20) to glyphosate a.e. ratio of about 1:13. Activity, at least on ABUTH, was further improved to a significant degree by inclusion in the composition of colloidal particulates such as Aerosil MOX-170 (99-06), Aerosil 380 (99-07), a blend of Aerosil MOX-80 and Aerosil 380 (99-08), and a blend of Aerosil MOX-80 and Aerosil MOX-170 (99-09).

Example 100

Aqueous and dry granular concentrate compositions were prepared as shown in Table 100a. Dry granular concentrate compositions 100-01 to 100-11 contain glyphosate ammonium salt, and were prepared by the process described in Example 97.

Aqueous concentrate compositions 100-12 to 100-16 contain glyphosate IPA salt and were prepared by process (v), using soybean lecithin (45% phospholipid, Avanti).

TABLE 100a

| Conc. comp. | Glyphosate g a.e./l | Glyphosate a.e. | Lecithin | Butyl stearate | Surfactant | Colloidal particulate | Type of surfactant | Type of colloidal particulate |
|---|---|---|---|---|---|---|---|---|
| 100-01 | | 68.7 | | | 21.0 | | steareth-20 | |
| 100-02 | | 66.1 | | | 24.0 | | oleth-20 | |
| 100-03 | | 67.9 | 10.0 | 2.0 | 10.0 | | MON 0818 | |
| 100-04 | | 59.2 | 10.0 | | 20.0 + 2.0 | | FC-754 + MON 0818 | |
| 100-05 | | 66.1 | | | 24.0 | | ceteth-20 | |
| 100-06 | | 71.2 | | | 16.1 | 2.0 | steareth-20 | Aerosil 380 |
| 100-07 | | 71.2 | | | 16.1 | 2.0 | steareth-20 | Aerosil blend |
| 100-08 | | 68.0 | | | 20.0 | 1.9 | oleth-20 | Aerosil 380 |
| 100-09 | | 63.5 | | | 25.0 | 2.0 | steareth-20 | Aerosil blend |
| 100-10 | | 67.9 | | | 20.0 | 2.0 | steareth-20 | Aerosil blend |
| 100-11 | | 72.2 | | | 15.0 | 2.0 | steareth-20 | Aerosil blend |
| 100-12 | 370 | | 4.7 | | 4.7 | | steareth-20 | |
| 100-13 | 350 | | 4.9 | | 4.9 | | ceteareth-27 | |
| 100-14 | 348 | | 5.0 | | 5.0 | | ceteareth-15 | |
| 100-15 | 348 | | 5.0 | | 5.0 | | oleth-20 | |
| 100-16 | 351 | | 4.4 | | 5.0 | | steareth-30 | |

Aerosil blend: Aerosil MOX-80 + Aerosil MOX-170 (1:1)

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations J and K were applied as comparative treatments. Results, averaged for all replicates of each treatment, are shown in Table 100b.

TABLE 100b

| Concentrate composition | Glyphosate rate g a.e./ha | % Inhibition ABUTH | % Inhibition ECHCF |
|---|---|---|---|
| Formulation J | 100 | 0 | 20 |
| | 200 | 28 | 57 |
| | 300 | 58 | 96 |
| | 400 | 73 | 99 |
| Formulation K | 100 | 22 | 13 |
| | 200 | 42 | 83 |
| | 300 | 48 | 91 |
| | 400 | 58 | 95 |
| 100-01 | 100 | 28 | 30 |
| | 200 | 48 | 80 |
| | 300 | 80 | 97 |
| | 400 | 85 | 99 |
| 100-02 | 100 | 43 | 52 |
| | 200 | 68 | 80 |
| | 300 | 72 | 88 |
| | 400 | 86 | 94 |
| 100-03 | 100 | 23 | 37 |
| | 200 | 50 | 83 |
| | 300 | 75 | 88 |
| | 400 | 85 | 96 |
| 100-04 | 100 | 50 | 45 |
| | 200 | 73 | 80 |
| | 300 | 85 | 92 |
| | 400 | 95 | 94 |
| 100-05 | 100 | 18 | 45 |
| | 200 | 65 | 83 |
| | 300 | 87 | 95 |
| | 400 | 94 | 86 |
| 100-06 | 100 | 47 | 50 |
| | 200 | 62 | 68 |
| | 300 | 82 | 94 |
| | 400 | 91 | 87 |
| 100-07 | 100 | 50 | 47 |
| | 200 | 60 | 78 |
| | 300 | 87 | 87 |
| | 400 | 93 | 93 |
| 100-08 | 100 | 30 | 55 |
| | 200 | 55 | 77 |
| | 300 | 82 | 85 |
| | 400 | 88 | 97 |
| 100-09 | 100 | 45 | 50 |
| | 200 | 57 | 78 |
| | 300 | 83 | 83 |
| | 400 | 84 | 89 |
| 100-10 | 100 | 42 | 50 |
| | 200 | 57 | 80 |
| | 300 | 73 | 91 |
| | 400 | 91 | 90 |
| 100-11 | 100 | 28 | 48 |
| | 200 | 50 | 75 |
| | 300 | 70 | 87 |
| | 400 | 82 | 89 |
| 100-12 | 100 | 20 | 40 |
| | 200 | 63 | 80 |
| | 300 | 67 | 96 |
| | 400 | 80 | 88 |
| 100-13 | 100 | 27 | 35 |
| | 200 | 50 | 85 |
| | 300 | 77 | 90 |
| | 400 | 84 | 86 |
| 100-14 | 100 | 27 | 25 |
| | 200 | 40 | 70 |
| | 300 | 68 | 94 |
| | 400 | 89 | 91 |
| 100-15 | 100 | 17 | 20 |
| | 200 | 47 | 82 |
| | 300 | 58 | 89 |
| | 400 | 91 | 95 |
| 100-16 | 100 | 22 | 20 |
| | 200 | 41 | 80 |
| | 300 | 84 | 89 |
| | 400 | 99 | 98 |

All compositions of the invention in this study exhibited greater herbicidal effectiveness on both ABUTH and ECHCF, in some cases by a very substantial margin, than commercial standard Formulation K.

Example 101

Aqueous concentrate compositions were prepared containing glyphosate IPA salt and excipient ingredients as shown in Table 101a. All contain colloidal particulates and were prepared by process (ix).

The compositions of this example all showed acceptable storage stability. The compositions shown as containing colloidal particulate were not storage-stable unless the colloidal particulate was included as shown.

TABLE 101a

| Conc. comp. | Glyphosate g a.e./l | Oil | Surfactant | Aerosil 380 | Type of oil | Type of surfactant |
|---|---|---|---|---|---|---|
| | | | % w/w | | | |
| 101-01 | 360 | 1.0 | 10.0 | 1.25 | butyl stearate | oleth-20 |
| 101-02 | 360 | 1.0 | 10.0 | 1.25 | stearylamine | oleth-20 |
| 101-03 | 360 | 1.0 | 10.0 | 1.25 | stearyl alcohol | oleth-20 |
| 101-04 | 360 | 1.0 | 10.0 | 1.25 | docosane | oleth-20 |
| 101-05 | 360 | | 10.0 | 1.25 | none | oleth-20 |
| 101-06 | 360 | 1.0 | 10.0 | 1.25 | butyl stearate | steareth-30 |
| 101-07 | 360 | 1.0 | 10.0 | 1.25 | stearylamine | steareth-30 |
| 101-08 | 360 | 1.0 | 10.0 | 1.25 | stearyl alcohol | steareth-30 |
| 101-09 | 360 | 1.0 | 10.0 | 1.25 | docosane | steareth-30 |
| 10l-10 | 360 | | 10.0 | 1.25 | none | steareth-30 |
| 101-11 | 360 | | 5.0 + 5.0 | 1.25 | none | oleth-20 + steareth-20 |
| 101-12 | 360 | | 5.0 + 5.0 | 1.25 | none | oleth-20 + steareth-30 |
| 101-13 | 360 | | 5.0 + 5.0 | 1.25 | none | oleth-20 + ceteareth-27 |
| 101-14 | 360 | | 5.0 + 5.0 | 1.25 | none | oleth-20 + ceteareth-15 |
| 101-15 | 360 | | 5.0 + 5.0 | 1.25 | none | steareth-30 + steareth-20 |
| 101-16 | 360 | | 5.0 + 5.0 | 1.25 | none | steareth-30 + ceteareth-27 |
| 101-17 | 360 | | 5.0 + 5.0 | 1.25 | none | steareth-30 + ceteareth-15 |
| 101-18 | 360 | | 10.0 | 1.25 | none | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 19 days after application.

Formulations B and J were applied as comparative treatments. Results, averaged for all replicates of each treatment, are shown in Table 101b.

TABLE 101b

| Concentrate composition | Glyphosate rate g a.e./ha | % Inhibition ABUTH | % Inhibition ECHCF |
|---|---|---|---|
| Formulation B | 100 | 0 | 60 |
| | 200 | 15 | 73 |
| | 300 | 33 | 88 |
| | 400 | 57 | 91 |
| Formulation J | 100 | 5 | 70 |
| | 200 | 37 | 92 |
| | 300 | 80 | 99 |
| | 400 | 77 | 96 |
| 100-01 | 100 | 13 | 88 |
| | 200 | 32 | 85 |
| | 300 | 48 | 98 |
| | 400 | 90 | 93 |
| 101-02 | 100 | 10 | 70 |
| | 200 | 45 | 98 |
| | 300 | 72 | 99 |
| | 400 | 80 | 98 |
| 101-03 | 100 | 3 | 77 |
| | 200 | 25 | 94 |
| | 300 | 47 | 98 |
| | 400 | 75 | 99 |
| 101-04 | 100 | 7 | 67 |
| | 200 | 23 | 94 |
| | 300 | 40 | 99 |
| | 400 | 7 | 47 |
| 101-05 | 100 | 7 | 76 |
| | 200 | 25 | 88 |
| | 300 | 45 | 96 |
| | 400 | 75 | 97 |
| 101-06 | 100 | 12 | 96 |
| | 200 | 30 | 97 |
| | 300 | 45 | 98 |
| | 400 | 15 | 60 |
| 101-07 | 100 | 8 | 83 |
| | 200 | 12 | 97 |
| | 300 | 35 | 94 |
| | 400 | 50 | 98 |
| 101-08 | 100 | 15 | 72 |
| | 200 | 30 | 88 |
| | 300 | 40 | 99 |
| | 400 | 0 | 33 |
| 101-09 | 100 | 5 | 73 |
| | 200 | 15 | 94 |
| | 300 | 47 | 99 |
| | 400 | 5 | 53 |
| 101-10 | 100 | 7 | 79 |
| | 200 | 15 | 95 |
| | 300 | 45 | 98 |
| | 400 | 62 | 99 |
| 101-11 | 100 | 5 | 84 |
| | 200 | 13 | 98 |
| | 300 | 30 | 98 |
| | 400 | 55 | 100 |
| 101-12 | 100 | 3 | 95 |
| | 200 | 17 | 99 |
| | 300 | 28 | 99 |
| | 400 | 67 | 100 |

TABLE 101b-continued

| Concentrate composition | Glyphosate rate g a.e./ha | % Inhibition ABUTH | ECHCF |
|---|---|---|---|
| 101-13 | 100 | 5 | 90 |
|  | 200 | 17 | 99 |
|  | 300 | 30 | 100 |
|  | 400 | 60 | 98 |
| 101-14 | 100 | 3 | 98 |
|  | 200 | 25 | 97 |
|  | 300 | 38 | 100 |
|  | 400 | 57 | 100 |
| 101-15 | 100 | 5 | 97 |
|  | 200 | 25 | 97 |
|  | 300 | 40 | 100 |
|  | 400 | 40 | 99 |
| 101-16 | 100 | 10 | 97 |
|  | 200 | 15 | 98 |
|  | 300 | 52 | 100 |
|  | 400 | 0 | 47 |
| 101-17 | 100 | 7 | 97 |
|  | 200 | 25 | 94 |
|  | 300 | 40 | 98 |
|  | 400 | 33 | 97 |
| 101-18 | 100 | 7 | 96 |
|  | 200 | 25 | 99 |
|  | 300 | 55 | 100 |
|  | 400 | 73 | 100 |

Percent inhibition data for the 400 g a.e./ha glyphosate rate in this test are unreliable and should be ignored. Neither oleth-20 (composition 101-05) nor steareth-20 (101-10) provided herbicidal effectiveness equal to Formulation J in this study, and no great or consistent further enhancement was obtained by adding butyl stearate.

Example 102

Aqueous concentrate compositions were prepared containing glyphosate IPA salt and excipient ingredients as shown in Table 102a. Concentrate compositions 102-01 to 102-03 are oil-in-water emulsions and were prepared by process (vii). Compositions 102-04 to 102-18 all contain colloidal particulates and were prepared by process (ix). Different mixing methods were employed in the final stage of preparation of these compositions, as indicated in the column of Table 102a headed "Process".

The compositions of this example all showed acceptable storage stability. The compositions shown as containing colloidal particulate were not storage-stable unless the colloidal particulate was included as shown.

TABLE 102a

| Concentrate composition | Gly-phosate g a.e./l | % w/w Butyl stearate | Sur-factant | Aerosil 380 | Type of surfactant | Proc-ess (*) |
|---|---|---|---|---|---|---|
| 102-01 | 163 | 0.5 | 5.0 |  | oleth-20 |  |
| 102-02 | 163 | 0.5 | 5.0 |  | steareth-20 |  |
| 102-03 | 163 | 0.5 | 5.0 |  | ceteareth-27 |  |
| 102-04 | 360 | 1.0 | 10.0 | 1.25 | ceteareth-15 | A |
| 102-05 | 360 | 1.0 | 10.0 | 1.25 | ceteth-20 | A |
| 102-06 | 360 | 1.0 | 10.0 | 1.25 | steareth-20 | A |
| 102-07 | 360 | 1.0 | 10.0 | 1.25 | oleth-20 | A |
| 102-08 | 360 | 1.0 | 10.0 | 1.25 | ceteareth-27 | A |
| 102-09 | 360 | 1.0 | 10.0 | 1.25 | steareth-30 | A |
| 102-10 | 360 |  | 10.0 | 1.25 | steareth-30 | A |
| 102-11 | 360 | 1.0 | 10.0 | 1.25 | oleth-20 | A |
| 102-12 | 360 | 1.0 | 10.0 | 1.25 | oleth-20 | B |
| 102-13 | 360 | 1.0 | 10.0 | 1.25 | oleth-20 | C |
| 102-14 | 360 | 1.0 | 10.0 | 1.25 | oleth-20 | D |
| 102-15 | 360 | 1.0 | 10.0 | 1.25 | oleth-20 | E |
| 102-16 | 360 | 1.0 | 10.0 | 1.25 | oleth-20 | F |
| 102-17 | 360 | 1.0 | 10.0 | 1.25 | oleth-20 | G |
| 102-18 | 360 | 1.0 | 10.0 | 1.25 | oleth-20 | A |

(*) Process:
A Silverson mixer, medium screen, 3 minutes at 7000 rpm
B Silverson mixer, coarse screen, 3 minutes at 7000 rpm
C Fann mixer, 50% output, 5 minutes
D Turrax mixer, 3 minutes at 8000 rpm
E Overhead stirrer, low speed
F Overhead stirrer, high speed
G Hand shaking, 3 minutes Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 19 days after application.

Formulations B and J were applied as comparative treatments. Results, averaged for all replicates of each treatment, are shown in Table 102b.

TABLE 102b

| Concentrate composition | Glyphosate rate g a.e./ha | % Inhibition ABUTH | ECHCF |
|---|---|---|---|
| Formulation B | 100 | 20 | 40 |
|  | 200 | 45 | 50 |
|  | 300 | 65 | 72 |
|  | 400 | 78 | 85 |
| Formulation J | 100 | 43 | 53 |
|  | 200 | 80 | 80 |
|  | 300 | 96 | 82 |
|  | 400 | 99 | 94 |
| 102-01 | 100 | 45 | 57 |
|  | 200 | 80 | 72 |
|  | 300 | 89 | 78 |
|  | 400 | 98 | 83 |
| 102-02 | 100 | 53 | 57 |
|  | 200 | 80 | 78 |
|  | 300 | 89 | 77 |
|  | 400 | 93 | 83 |
| 102-03 | 100 | 45 | 60 |
|  | 200 | 83 | 75 |
|  | 300 | 97 | 73 |
|  | 400 | 97 | 85 |
| 102-04 | 100 | 45 | 45 |
|  | 200 | 80 | 80 |
|  | 300 | 83 | 83 |
|  | 400 | 95 | 95 |
| 102-05 | 100 | 42 | 42 |
|  | 200 | 77 | 77 |
|  | 300 | 93 | 93 |
|  | 400 | 98 | 98 |
| 102-06 | 100 | 30 | 30 |
|  | 200 | 42 | 42 |
|  | 300 | 27 | 30 |
|  | 400 | 3 | 20 |

TABLE 102b-continued

| Concentrate composition | Glyphosate rate g a.e./ha | % Inhibition ABUTH | % Inhibition ECHCF |
|---|---|---|---|
| 102-07 | 100 | 40 | 40 |
|  | 200 | 77 | 75 |
|  | 300 | 90 | 93 |
|  | 400 | 97 | 86 |
| 102-08 | 100 | 43 | 50 |
|  | 200 | 80 | 80 |
|  | 300 | 92 | 93 |
|  | 400 | 96 | 98 |
| 102-09 | 100 | 0 | 2 |
|  | 200 | 82 | 75 |
|  | 300 | 83 | 96 |
|  | 400 | 90 | 88 |
| 102-10 | 100 | 57 | 60 |
|  | 200 | 80 | 70 |
|  | 300 | 88 | 88 |
|  | 400 | 95 | 93 |
| 102-11 | 100 | 35 | 47 |
|  | 200 | 72 | 75 |
|  | 300 | 80 | 75 |
|  | 400 | 85 | 77 |
| 102-12 | 100 | 47 | 47 |
|  | 200 | 72 | 77 |
|  | 300 | 80 | 90 |
|  | 400 | 86 | 78 |
| 102-13 | 100 | 55 | 50 |
|  | 200 | 75 | 83 |
|  | 300 | 78 | 92 |
|  | 400 | 91 | 92 |
| 102-14 | 100 | 52 | 50 |
|  | 200 | 75 | 78 |
|  | 300 | 83 | 88 |
|  | 400 | 99 | 92 |
| 102-15 | 100 | 47 | 47 |
|  | 200 | 70 | 73 |
|  | 300 | 87 | 87 |
|  | 400 | 75 | 63 |
| 102-16 | 100 | 43 | 40 |
|  | 200 | 78 | 75 |
|  | 300 | 88 | 88 |
|  | 400 | 87 | 91 |
| 102-17 | 100 | 43 | 43 |
|  | 200 | 67 | 88 |
|  | 300 | 80 | 75 |
|  | 400 | 92 | 83 |
| 102-18 | 100 | 27 | 40 |
|  | 200 | 63 | 57 |
|  | 300 | 82 | 73 |
|  | 400 | 87 | 70 |

Results obtained with composition 102-06 are out of line with other data in this Example and an error in formulation or application is suspected. Some differences in herbicidal effectiveness were evident when a composition containing 360 g a.e./l glyphosate, 1% butyl stearate, 10% oleth-20 and 1.25% Aerosil 380 was processed in different ways (102-11 to 102-17). However, as compositions 102-07 and 102-11 were identically processed yet differed in effectiveness, no firm conclusions can be drawn from this test.

Example 103

Aqueous concentrate compositions were prepared containing glyphosate IPA salt and excipient ingredients as shown in Table 103a. Concentrate compositions 103-01 to 103-09 are aqueous solution concentrates and were prepared by process (viii). Concentrate compositions 103-10 to 103-18 are aqueous solution concentrates containing colloidal particulates and were prepared by process (ix).

Compositions of this example containing 3% or 6% surfactant were not acceptably storage-stable except in the presence of colloidal particulate as shown.

TABLE 103a

| Composition no. | Glyphosate g a.e./l | % w/w Steareth-20 | % w/w Oleth-20 | % w/w Velvetex AB-45 | Aerosil | Type of Aerosil |
|---|---|---|---|---|---|---|
| 103-01 | 488 | 1.0 |  |  |  | none |
| 103-02 | 488 | 3.0 |  |  |  | none |
| 103-03 | 488 | 6.0 |  |  |  | none |
| 103-04 | 488 |  | 1.0 |  |  | none |
| 103-05 | 488 |  | 3.0 |  |  | none |
| 103-06 | 488 |  | 6.0 |  |  | none |
| 103-07 | 488 |  |  | 1.0 |  | none |
| 103-08 | 488 |  |  | 3.0 |  | none |
| 103-09 | 488 |  |  | 4.6 |  | none |
| 103-10 | 488 | 1.0 |  |  | 1.5 | MOX-80/MOX-170(1:1) |
| 103-11 | 488 | 3.0 |  |  | 1.5 | MOX-80/MOX-170(1:1) |
| 103-12 | 488 | 6.0 |  |  | 1.5 | MOX-80/MOX-170(1:1) |
| 103-13 | 488 |  | 1.0 |  | 1.5 | MOX-80/MOX-170(1:1) |
| 103-14 | 488 |  | 3.0 |  | 1.5 | MOX-80/MOX-170(1:1) |
| 103-15 | 488 |  | 6.0 |  | 1.5 | MOX-80/MOX-170(1:1) |
| 103-16 | 488 |  |  | 1.0 | 1.5 | MOX-80/MOX-170(1:1) |
| 103-17 | 488 |  |  | 3.0 | 1.5 | MOX-80/MOX-170(1:1) |
| 103-18 | 488 |  |  | 4.6 | 1.5 | MOX-80/MOX-170(1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 18 days after application.

Formulations B and J were applied as comparative treatments. Results, averaged for all replicates of each treatment, are shown in Table 103b.

TABLE 103b

| Concentrate composition | Glyphosate rate g a.e./ha | % Inhibition ABUTH | % Inhibition ECHCF |
|---|---|---|---|
| Formulation B | 100 | 10 | 40 |
|  | 200 | 38 | 67 |
|  | 300 | 70 | 80 |
|  | 400 | 86 | 92 |
| Formulation J | 100 | 43 | 58 |
|  | 200 | 65 | 82 |
|  | 300 | 91 | 94 |
|  | 400 | 100 | 95 |
| 103-01 | 100 | 23 | 60 |
|  | 200 | 40 | 65 |
|  | 300 | 73 | 87 |
|  | 400 | 80 | 92 |
| 103-02 | 100 | 38 | 67 |
|  | 200 | 77 | 82 |
|  | 300 | 95 | 83 |
|  | 400 | 99 | 93 |
| 103-03 | 100 | 33 | 67 |
|  | 200 | 78 | 73 |
|  | 300 | 90 | 94 |
|  | 400 | 100 | 96 |
| 103-04 | 100 | 23 | 63 |
|  | 200 | 48 | 81 |
|  | 300 | 68 | 87 |
|  | 400 | 72 | 88 |
| 103-05 | 100 | 30 | 63 |
|  | 200 | 63 | 80 |
|  | 300 | 78 | 89 |
|  | 400 | 95 | 93 |
| 103-06 | 100 | 25 | 85 |
|  | 200 | 68 | 93 |
|  | 300 | 77 | 93 |
|  | 400 | 99 | 95 |
| 103-07 | 100 | 13 | 60 |
|  | 200 | 42 | 80 |
|  | 300 | 57 | 95 |
|  | 400 | 92 | 96 |
| 103-08 | 100 | 20 | 73 |
|  | 200 | 43 | 92 |
|  | 300 | 83 | 93 |
|  | 400 | 72 | 96 |
| 103-09 | 100 | 30 | 73 |
|  | 200 | 50 | 94 |
|  | 300 | 65 | 96 |
|  | 400 | 75 | 98 |
| 103-10 | 100 | 10 | 65 |
|  | 200 | 53 | 88 |
|  | 300 | 72 | 94 |
|  | 400 | 83 | 95 |
| 103-11 | 100 | 15 | 50 |
|  | 200 | 57 | 77 |
|  | 300 | 82 | 95 |
|  | 400 | 92 | 97 |
| 103-12 | 100 | 30 | 70 |
|  | 200 | 68 | 98 |
|  | 300 | 78 | 97 |
|  | 400 | 96 | 98 |
| 103-13 | 100 | 15 | 77 |
|  | 200 | 43 | 93 |
|  | 300 | 68 | 95 |
|  | 400 | 77 | 99 |
| 103-14 | 100 | 10 | 73 |
|  | 200 | 40 | 93 |
|  | 300 | 68 | 98 |
|  | 400 | 78 | 98 |
| 103-15 | 100 | missing | missing |
|  | 200 | missing | missing |
|  | 300 | missing | missing |
|  | 400 | missing | missing |
| 103-16 | 100 | 0 | 60 |
|  | 200 | 30 | 93 |
|  | 300 | 40 | 99 |
|  | 400 | 50 | 99 |
| 103-17 | 100 | 2 | 83 |
|  | 200 | 43 | 99 |
|  | 300 | 67 | 100 |
|  | 400 | 67 | 100 |
| 103-18 | 100 | 5 | 95 |
|  | 200 | 37 | 100 |
|  | 300 | 60 | 100 |
|  | 400 | 78 | 100 |

In high-load (488 g a.e./l) glyphosate compositions, steareth-20 at 3% or 6% provided greater herbicidal effectiveness in this test than the same concentrations of oleth-20. Even at just 3%, steareth-20 (composition 103-02) gave effectiveness equal to commercial standard Formulation J. Addition of a blend of colloidal particulates to stabilize the composition (103-11) slightly reduced effectiveness in this study.

Example 104

Aqueous concentrate compositions were prepared containing glyphosate IPA salt and excipient ingredients as shown in Table 104a. Concentrate compositions 104-01 to 104-04 are aqueous solution concentrates and were prepared by process (viii). Concentrate compositions 104-08 to 104-18 are aqueous solution concentrates containing colloidal particulates and were prepared by process (ix). Concentrate compositions 104-05 to 104-07 contain colloidal particulate but no surfactant.

All compositions of this example except 104-01 to 104-03 were acceptably storage-stable.

TABLE 104a

| Concentrate composition | Glyphosate g a.e./l | % w/w | | | | Type of Aerosil |
|---|---|---|---|---|---|---|
| | | Steareth-20 | Steareth-100 | MON 0818 | Aerosil | |
| 104-01 | 488 | 3.0 | | | | |
| 104-02 | 488 | 4.5 | | | | |
| 104-03 | 488 | 6.0 | | | | |
| 104-04 | 488 | | | 3.0 | | |
| 104-05 | 488 | | | | 1.5 | 380 |
| 104-06 | 488 | | | | 1.5 | MOX-80/MOX-170(1:1) |
| 104-07 | 488 | | | | 3.0 | MOX-80/380(1:1) |
| 104-08 | 488 | | 1.5 | | | |
| 104-09 | 488 | 3.0 | | 3.0 | 1.5 | 380 |
| 104-10 | 488 | 4.5 | | 3.0 | 1.5 | 380 |
| 104-11 | 488 | 6.0 | | 3.0 | 1.5 | 380 |
| 104-12 | 488 | 3.0 | | 3.0 | 1.5 | MOX-80/MOX-170(1:1) |
| 104-13 | 488 | 4.5 | | 3.0 | 1.5 | MOX-80/MOX-170(1:1) |
| 104-14 | 488 | 6.0 | | 3.0 | 1.5 | MOX-80/MOX-170(1:1) |
| 104-15 | 488 | 3.0 | | 3.0 | 1.5 | MOX-80/380(1:1) |
| 104-16 | 488 | 4.5 | | 3.0 | 1.5 | MOX-80/380(1:1) |
| 104-17 | 488 | 6.0 | | 3.0 | 1.5 | MOX-80/380(1:1) |
| 104-18 | 488 | | 4.5 | 3.0 | 1.5 | MOX-80/MOX-170(1:1) |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 21 days after application.

Formulations B and J were applied as comparative treatments. Results, averaged for all replicates of each treatment, are shown in Table 104b.

TABLE 104b

| Concentrate composition | Glyphosate rate g a.e./ha | % Inhibition | |
|---|---|---|---|
| | | ABUTH | ECHCF |
| Formulation B | 100 | 2 | 23 |
| | 209 | 18 | 50 |
| | 300 | 42 | 67 |
| | 400 | 63 | 80 |
| Formulation J | 100 | 20 | 47 |
| | 200 | 40 | 86 |
| | 300 | 83 | 98 |
| | 400 | 93 | 98 |
| 104-01 | 100 | 10 | 75 |
| | 200 | 62 | 83 |
| | 300 | 80 | 96 |
| | 400 | 93 | 99 |
| 104-02 | 100 | 40 | 60 |
| | 200 | 77 | 92 |
| | 300 | 87 | 97 |
| | 400 | 93 | 99 |
| 104-03 | 100 | 23 | 40 |
| | 200 | 38 | 63 |
| | 300 | 78 | 91 |
| | 400 | 97 | 91 |
| 104-04 | 100 | 20 | 38 |
| | 200 | 23 | 77 |
| | 300 | 43 | 94 |
| | 400 | 73 | 94 |
| 104-05 | 100 | 7 | 30 |
| | 200 | 25 | 37 |
| | 300 | 42 | 60 |
| | 400 | 67 | 63 |
| 104-06 | 100 | 7 | 30 |
| | 200 | 20 | 53 |
| | 300 | 52 | 67 |
| | 400 | 83 | 67 |
| 104-07 | 100 | 5 | 35 |
| | 200 | 20 | 63 |
| | 300 | 57 | 80 |
| | 400 | 43 | 85 |
| 104-08 | 100 | 22 | 83 |
| | 200 | 47 | 99 |
| | 300 | 86 | 98 |
| | 400 | 78 | 100 |
| 104-09 | 100 | 12 | 45 |
| | 200 | 25 | 77 |
| | 300 | 40 | 83 |
| | 400 | 37 | 95 |
| 104-10 | 100 | 13 | 53 |
| | 200 | 73 | 99 |
| | 300 | 85 | 98 |
| | 400 | 99 | 99 |
| 104-11 | 100 | 25 | 50 |
| | 200 | 60 | 88 |
| | 300 | 93 | 99 |
| | 400 | 99 | 99 |
| 104-12 | 100 | 25 | 45 |
| | 200 | 57 | 88 |
| | 300 | 85 | 97 |
| | 400 | 100 | 94 |
| 104-13 | 100 | 30 | 52 |
| | 200 | 68 | 87 |
| | 300 | 93 | 99 |
| | 400 | 100 | 92 |
| 104-14 | 100 | 40 | 45 |
| | 200 | 73 | 88 |
| | 300 | 81 | 98 |
| | 400 | 100 | 99 |
| 104-15 | 100 | 8 | 57 |
| | 200 | 33 | 96 |
| | 300 | 81 | 99 |
| | 400 | 95 | 99 |
| 104-16 | 100 | 10 | 62 |
| | 200 | 48 | 83 |
| | 300 | 99 | 98 |
| | 400 | 100 | 100 |
| 104-17 | 100 | 27 | 58 |
| | 200 | 65 | 92 |
| | 300 | 75 | 98 |
| | 400 | 93 | 99 |

TABLE 104b-continued

| Concentrate composition | Glyphosate rate g a.e./ha | % Inhibition ABUTH | % Inhibition ECHCF |
|---|---|---|---|
| 104-18 | 100 | 5 | 40 |
|  | 200 | 33 | 87 |
|  | 300 | 55 | 98 |
|  | 400 | 75 | 98 |

Among stabilized high-load (488 g a.e./l) glyphosate compositions providing herbicidal effectiveness superior to commercial standard Formulation J, at least on ABUTH, were 104-10 and 104-11 (respectively 4.5% and 6% steareth-20+3% MON 0818+1.5% Aerosil 380), 104-13 (4.5% steareth-20+3% MON 0818+1.5% Aerosil MOX-80/MOX-170 blend) and 104-16 (4.5% steareth-20+3% MON 0818+1.5% Aerosil MOX-80/380 blend). The relatively poor performance of composition 104-04 and the good performance of composition 104-02 shows that the excellent results obtained with the stabilized compositions listed above are primarily attributable to the steareth-20 component.

Example 105

Aqueous concentrate compositions were prepared containing glyphosate IPA salt and excipient ingredients as shown in Table 105a. Concentrate compositions 105-01 to 105-09 are aqueous solution concentrates and were prepared by process (viii). Concentrate compositions 105-10 to 105-18 are aqueous solution concentrates containing colloidal particulates and were prepared by process (ix).

Compositions of this example containing 3% or 6% surfactant were not acceptably storage-stable except in the presence of colloidal particulate as shown.

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 22 days after application.

Formulations B and J were applied as comparative treatments. Results, averaged for all replicates of each treatment, are shown in Table 105b.

TABLE 105b

| Concentrate composition | Glyphosate rate g a.e./ha | % Inhibition ABUTH | % Inhibition ECHCF |
|---|---|---|---|
| Formulation B | 100 | 0 | 10 |
|  | 200 | 3 | 27 |
|  | 300 | 13 | 30 |
|  | 400 | 33 | 40 |
| Formulation J | 100 | 2 | 53 |
|  | 200 | 30 | 97 |
|  | 300 | 70 | 99 |
|  | 400 | 80 | 99 |
| 105-01 | 100 | 5 | 67 |
|  | 200 | 30 | 89 |
|  | 300 | 58 | 98 |
|  | 400 | 80 | 100 |
| 105-02 | 100 | 20 | 60 |
|  | 200 | 45 | 90 |
|  | 300 | 78 | 99 |
|  | 400 | 80 | 100 |
| 105-03 | 100 | 20 | 57 |
|  | 200 | 47 | 93 |
|  | 300 | 78 | 96 |
|  | 400 | 83 | 98 |
| 105-04 | 100 | 3 | 57 |
|  | 200 | 30 | 83 |
|  | 300 | 63 | 99 |
|  | 400 | 82 | 98 |

TABLE 105a

| Concentrate composition | Glyphosate g a.e./l | % w/w Steareth-20 | % w/w Oleth-20 | % w/w Velvetex AB-45 | % w/w Aerosil | Type of Aerosil |
|---|---|---|---|---|---|---|
| 105-01 | 488 | 1.5 |  |  |  | none |
| 105-02 | 488 | 3.0 |  |  |  | none |
| 105-03 | 488 | 6.0 |  |  |  | none |
| 105-04 | 488 |  | 1.5 |  |  | none |
| 105-05 | 488 |  | 3.0 |  |  | none |
| 105-06 | 488 |  | 6.0 |  |  | none |
| 105-07 | 488 |  |  | 1.5 |  | none |
| 105-08 | 488 |  |  | 3.0 |  | none |
| 105-09 | 488 |  |  | 4.5 |  | none |
| 105-10 | 488 | 1.5 |  |  | 1.5 | MOX-80/380(1:1) |
| 105-11 | 488 | 3.0 |  |  | 1.5 | MOX-80/380(1:1) |
| 105-12 | 488 | 6.0 |  |  | 1.5 | MOX-80/380(1:1) |
| 105-13 | 488 |  | 1.5 |  | 1.5 | MOX-80/380(1:1) |
| 105-14 | 488 |  | 3.0 |  | 1.5 | MOX-80/380(1:1) |
| 105-15 | 488 |  | 6.0 |  | 1.5 | MOX-80/380(1:1) |
| 105-16 | 488 |  |  | 1.5 | 1.5 | MOX-80/380(1:1) |
| 105-17 | 488 |  |  | 3.0 | 1.5 | MOX-80/380(1:1) |
| 105-18 | 488 |  |  | 4.5 | 1.5 | MOX-80/380(1:1) |

TABLE 105b-continued

| Concentrate composition | Glyphosate rate g a.e./ha | % Inhibition ABUTH | % Inhibition ECHCF |
|---|---|---|---|
| 105-05 | 100 | 5 | 53 |
|  | 200 | 27 | 83 |
|  | 300 | 47 | 98 |
|  | 400 | 77 | 100 |
| 105-06 | 100 | 5 | 40 |
|  | 200 | 23 | 70 |
|  | 300 | 47 | 92 |
|  | 400 | 77 | 99 |
| 105-07 | 100 | 3 | 53 |
|  | 200 | 30 | 85 |
|  | 300 | 60 | 94 |
|  | 400 | 72 | 97 |
| 105-08 | 100 | 3 | 50 |
|  | 200 | 22 | 88 |
|  | 300 | 53 | 97 |
|  | 400 | 80 | 100 |
| 105-09 | 100 | 0 | 40 |
|  | 200 | 20 | 83 |
|  | 300 | 40 | 99 |
|  | 400 | 67 | 99 |
| 105-10 | 100 | 0 | 40 |
|  | 200 | 27 | 60 |
|  | 300 | 47 | 83 |
|  | 400 | 78 | 94 |
| 105-11 | 100 | 5 | 47 |
|  | 200 | 25 | 77 |
|  | 300 | 57 | 96 |
|  | 400 | 87 | 97 |
| 105-12 | 100 | 15 | 43 |
|  | 200 | 52 | 88 |
|  | 300 | 87 | 98 |
|  | 400 | 87 | 98 |
| 105-13 | 100 | 0 | 40 |
|  | 200 | 17 | 70 |
|  | 300 | 35 | 83 |
|  | 400 | 53 | 88 |
| 105-14 | 100 | 0 | 33 |
|  | 200 | 18 | 67 |
|  | 300 | 28 | 90 |
|  | 400 | 62 | 98 |
| 105-15 | 100 | 2 | 33 |
|  | 200 | 25 | 70 |
|  | 300 | 53 | 85 |
|  | 400 | 72 | 97 |
| 105-16 | 100 | 0 | 30 |
|  | 200 | 17 | 50 |
|  | 300 | 27 | 67 |
|  | 400 | 72 | 87 |
| 105-17 | 100 | 0 | 0 |
|  | 200 | 7 | 63 |
|  | 300 | 32 | 88 |
|  | 400 | 47 | 90 |
| 105-18 | 100 | 0 | 5 |
|  | 200 | 12 | 60 |
|  | 300 | 25 | 83 |
|  | 400 | 45 | 97 |

Compositions containing steareth-20 generally performed better than counterparts containing oleth-20 in this study, both in the presence and in the absence of colloidal particulates.

Example 106

Aqueous concentrate compositions were prepared containing glyphosate IPA salt and excipient ingredients as shown in Table 106a. All contain colloidal particulates and were prepared by process (ix).

The compositions of this example all showed acceptable storage stability. The compositions shown as containing colloidal particulate were not storage-stable unless the colloidal particulate was included as shown.

TABLE 106a

| Concentrate composition | % w/w Glyphosate a.e. | Oil | Surfactant | Aerosil 380 | Type of oil | Type of surfactant |
|---|---|---|---|---|---|---|
| 106-01 | 31 | 1.0 | 10.0 | 1.25 | Butyl stearate | steareth-20 |
| 106-02 | 31 | 1.0 | 10.0 | 1.25 | Butyl stearate | oleth-20 |
| 106-03 | 31 | 1.0 | 10.0 | 1.25 | Butyl stearate | steareth-30 |
| 106-04 | 31 |  | 10.0 | 1.25 | none | steareth-30 |

Velvetleaf (*Abutilon theophrasti*, ABUTH) and Japanese millet (*Echinochloa crus-galli*, ECHCF) plants were grown and treated by the standard procedures given above. Treatments were applied at four different hours of the day. Applications of spray compositions were made 16 days after planting ABUTH and ECHCF, and evaluation of herbicidal inhibition was done 22 days after application.

Formulation J was applied as a comparative treatment. Results, averaged for all replicates of each treatment, are shown in Table 106b.

TABLE 106b

| Concentrate composition | Hour when applied | Glyphosate rate g a.e./ha | % Inhibition ABUTH | % Inhibition ECHCF |
|---|---|---|---|---|
| Formulation J | 1000 | 100 | 5 | 33 |
|  |  | 200 | 42 | 75 |
|  |  | 300 | 67 | 83 |
|  |  | 400 | 77 | 93 |
| 106-01 | 1000 | 100 | 7 | 33 |
|  |  | 200 | 40 | 70 |
|  |  | 300 | 50 | 82 |
|  |  | 400 | 78 | 91 |
| 106-02 | 1000 | 100 | 18 | 33 |
|  |  | 200 | 37 | 73 |
|  |  | 300 | 48 | 91 |
|  |  | 400 | 80 | 92 |
| 106-03 | 1000 | 100 | 30 | 33 |
|  |  | 200 | 40 | 75 |
|  |  | 300 | 82 | 85 |
|  |  | 400 | 83 | 80 |
| 106-04 | 1000 | 100 | 30 | 30 |
|  |  | 200 | 43 | 78 |
|  |  | 300 | 78 | 92 |
|  |  | 400 | 93 | 95 |
| Formulation J | 1200 | 100 | 5 | 38 |
|  |  | 200 | 35 | 87 |
|  |  | 300 | 53 | 96 |
|  |  | 400 | 88 | 99 |
| 106-01 | 1200 | 100 | 10 | 30 |
|  |  | 200 | 47 | 91 |
|  |  | 300 | 70 | 89 |
|  |  | 400 | 78 | 97 |
| 106-02 | 1200 | 100 | 5 | 37 |
|  |  | 200 | 40 | 75 |
|  |  | 300 | 48 | 87 |
|  |  | 400 | 70 | 94 |
| 106-03 | 1200 | 100 | 20 | 37 |
|  |  | 200 | 50 | 82 |
|  |  | 300 | 78 | 98 |
|  |  | 400 | 83 | 97 |
| 106-04 | 1200 | 100 | 33 | 33 |
|  |  | 200 | 45 | 93 |
|  |  | 300 | 75 | 98 |
|  |  | 400 | 95 | 100 |
| Formulation J | 1400 | 100 | 15 | 40 |
|  |  | 200 | 30 | 90 |
|  |  | 300 | 55 | 100 |
|  |  | 400 | 80 | 100 |
| 106-01 | 1400 | 100 | 17 | 40 |
|  |  | 200 | 45 | 70 |
|  |  | 300 | 75 | 97 |
|  |  | 400 | 80 | 98 |
| 106-02 | 1400 | 100 | 17 | 47 |
|  |  | 200 | 35 | 83 |
|  |  | 300 | 67 | 97 |
|  |  | 400 | 63 | 97 |
| 106-03 | 1400 | 100 | 30 | 40 |
|  |  | 200 | 63 | 80 |
|  |  | 300 | 77 | 97 |
|  |  | 400 | 78 | 100 |
| 106-04 | 1400 | 100 | 23 | 40 |
|  |  | 200 | 45 | 87 |
|  |  | 300 | 73 | 100 |
|  |  | 400 | 78 | 100 |

TABLE 106b-continued

| Concentrate composition | Hour when applied | Glyphosate rate g a.e./ha | % Inhibition ABUTH | % Inhibition ECHCF |
|---|---|---|---|---|
| Formulation J | 1600 | 100 | 10 | 37 |
|  |  | 200 | 32 | 83 |
|  |  | 300 | 52 | 97 |
|  |  | 400 | 75 | 98 |
| 106-01 | 1600 | 100 | 27 | 43 |
|  |  | 200 | 40 | 89 |
|  |  | 300 | 77 | 99 |
|  |  | 400 | 95 | 99 |
| 106-02 | 1600 | 100 | 20 | 53 |
|  |  | 200 | 40 | 95 |
|  |  | 300 | 53 | 98 |
|  |  | 400 | 80 | 98 |
| 106-03 | 1600 | 100 | 27 | 60 |
|  |  | 200 | 60 | 93 |
|  |  | 300 | 78 | 97 |
|  |  | 400 | 96 | 100 |
| 106-04 | 1600 | 100 | 15 | 37 |
|  |  | 200 | 43 | 83 |
|  |  | 300 | 67 | 97 |
|  |  | 400 | 78 | 96 |

Composition 106-03 illustrates the consistency of high-level performance obtainable with, in this case, steareth-30 at an approximately 1:3 weight/weight ratio to glyphosate a.e., together with a small amount of butyl stearate and Aerosil 380. An average of percent inhibition of ABUTH across all four glyphosate rates shows the following comparison of 106-03 with Formulation J. applied at four different hours of the day:

| Hour | Formulation J | Composition 106-03 |
|---|---|---|
| 1000 | 48 | 59 |
| 1200 | 45 | 58 |
| 1400 | 48 | 62 |
| 1600 | 42 | 65 |

Example 107

Aqueous concentrate compositions were prepared containing glyphosate IPA salt II and excipient ingredients as shown in Table 107a. Concentrate compositions 107-01 to 107-07 are aqueous solution concentrates and were prepared by process (viii). Concentrate compositions 107-08 to 107-18 are aqueous solution concentrates containing colloidal particulates and were prepared by process (ix).

Compositions 107-01 to 107-06 were not acceptably storage-stable. All other compositions showed acceptable storage stability.

TABLE 107a

| Concentrate composition | Glyphosate g a.e./l | % w/w Steareth-30 | Steareth-20 | Agrimul PG-2069 | Aerosil 380 |
|---|---|---|---|---|---|
| 107-01 | 488 | 3.00 |  |  |  |
| 107-02 | 488 | 4.50 |  |  |  |
| 107-03 | 488 | 6.00 |  |  |  |
| 107-04 | 488 |  | 3.00 |  |  |
| 107-05 | 488 |  | 4.50 |  |  |
| 107-06 | 488 |  | 6.00 |  |  |

TABLE 107a-continued

| Concentrate composition | Glyphosate g a.e./l | % w/w | | | |
|---|---|---|---|---|---|
| | | Steareth-30 | Steareth-20 | Agrimul PG-2069 | Aerosil 380 |
| 107-07 | 488 | | | 2.0 | |
| 107-08 | 488 | 3.00 | | | 1.5 |
| 107-09 | 488 | 4.50 | | | 1.5 |
| 107-10 | 488 | 6.00 | | | 1.5 |
| 107-11 | 488 | | 3.00 | | 1.5 |
| 107-12 | 488 | | 4.50 | | 1.5 |
| 107-13 | 488 | | 6.00 | | 1.5 |
| 107-14 | 488 | 1.50 | 1.50 | | 1.5 |
| 107-15 | 488 | 2.25 | 2.25 | | 1.5 |
| 107-16 | 488 | 3.00 | 3.00 | | 1.5 |
| 107-17 | 488 | 2.25 | 2.25 | 2.0 | 1.5 |
| 107-18 | 488 | 3.00 | 3.00 | 2.0 | 1.5 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 23 days after application.

Formulations B and J were applied as comparative treatments. Results, averaged for all replicates of each treatment, are shown in Table 107b.

TABLE 107b

| Concentrate composition | Glyphosate rate g a.e./ha | % Inhibition | |
|---|---|---|---|
| | | ABUTH | ECHCF |
| Formulation B | 100 | 2 | 20 |
| | 200 | 22 | 33 |
| | 300 | 35 | 67 |
| | 400 | 68 | 73 |
| Formulation J | 100 | 32 | 63 |
| | 200 | 78 | 90 |
| | 300 | 83 | 93 |
| | 400 | 92 | 97 |
| 107-01 | 100 | 38 | 57 |
| | 200 | 50 | 63 |
| | 300 | 62 | 80 |
| | 400 | 75 | 89 |
| 107-02 | 100 | 20 | 57 |
| | 200 | 63 | 70 |
| | 300 | 75 | 88 |
| | 400 | 80 | 96 |
| 107-03 | 100 | 47 | 53 |
| | 200 | 72 | 80 |
| | 300 | 87 | 96 |
| | 400 | 100 | 99 |
| 107-04 | 100 | 33 | 30 |
| | 200 | 48 | 60 |
| | 300 | 75 | 73 |
| | 400 | 90 | 83 |
| 107-05 | 100 | 10 | 30 |
| | 200 | 43 | 50 |
| | 300 | 68 | 82 |
| | 400 | 83 | 92 |
| 107-06 | 100 | 22 | 40 |
| | 200 | 43 | 50 |
| | 300 | 75 | 83 |
| | 400 | 83 | 87 |
| 107-07 | 100 | 10 | 37 |
| | 200 | 40 | 63 |
| | 300 | 78 | 86 |
| | 400 | 95 | 96 |
| 107-08 | 100 | 23 | 43 |
| | 200 | 68 | 63 |
| | 300 | 92 | 88 |
| | 400 | 98 | 93 |

TABLE 107b-continued

| Concentrate composition | Glyphosate rate g a.e./ha | % Inhibition | |
|---|---|---|---|
| | | ABUTH | ECHCF |
| 107-09 | 100 | 47 | 57 |
| | 200 | 78 | 70 |
| | 300 | 95 | 92 |
| | 400 | 100 | 96 |
| 107-10 | 100 | 37 | 57 |
| | 200 | 85 | 68 |
| | 300 | 92 | 85 |
| | 400 | 100 | 93 |
| 107-11 | 100 | 28 | 43 |
| | 200 | 63 | 73 |
| | 300 | 85 | 83 |
| | 400 | 95 | 96 |
| 107-12 | 100 | 40 | 53 |
| | 200 | 75 | 88 |
| | 300 | 90 | 92 |
| | 400 | 100 | 97 |
| 107-13 | 100 | 40 | 53 |
| | 200 | 75 | 75 |
| | 300 | 99 | 92 |
| | 400 | 100 | 98 |
| 107-14 | 100 | 30 | 43 |
| | 200 | 68 | 72 |
| | 300 | 83 | 82 |
| | 400 | 96 | 97 |
| 107-15 | 100 | 38 | 47 |
| | 200 | 77 | 72 |
| | 300 | 94 | 92 |
| | 400 | 100 | 96 |
| 107-16 | 100 | 33 | 43 |
| | 200 | 75 | 67 |
| | 300 | 92 | 88 |
| | 400 | 100 | 94 |
| 107-17 | 100 | 25 | 43 |
| | 200 | 68 | 82 |
| | 300 | 78 | 96 |
| | 400 | 99 | 96 |
| 107-18 | 100 | 13 | 37 |
| | 200 | 72 | 70 |
| | 300 | 87 | 80 |
| | 400 | 99 | 85 |

Several stabilized high-load (488 g a.e./l) glyphosate compositions of this Example provided herbicidal effectiveness equal or superior, at least on ABUTH, to that obtained with commercial standard Formulation J.

Example 108

Aqueous concentrate compositions were prepared containing glyphosate IPA salt and excipient ingredients as shown in Table 108a. Concentrate compositions 108-12 to 108-14 are aqueous solution concentrates and were prepared by process (viii). Concentrate compositions 108-01 to 108-11 and 108-15 to 108-17 are aqueous solution concentrates containing colloidal particulates and were prepared by process (ix).

TABLE 108a

| | | % w/w | | | | |
|---|---|---|---|---|---|---|
| Conc. comp. | Glyphosate g a.e./l | Steareth-20 | Ethomeen T/25 | Propylene glycol | Aerosil | Type of Aerosil |
| 108-01 | 488 | 3.0 | | | 0.8 | 380 |
| 108-02 | 488 | 6.0 | | | 1.5 | MOX-80/MOX-170(1:1) |
| 108-03 | 488 | 4.5 | | | 1.5 | 380 |
| 108-04 | 488 | 4.5 | 2.25 | 0.5 | 1.5 | MOX-80/380(1:2) |
| 108-05 | 488 | 4.5 | | 0.5 | 1.5 | MOX-80/380(1:2) |
| 108-06 | 488 | 6.0 | | 0.5 | 1.5 | MOX-80/380(1:2) |
| 108-07 | 488 | 3.0 | 1.50 | 0.5 | 1.5 | MOX-80/380(1:2) |
| 108-08 | 488 | 6.0 | 3.00 | 0.5 | 1.5 | MOX-80/380(1:2) |
| 108-09 | 488 | 3.0 | 1.50 | 0.5 | 1.5 | 380 |
| 108-10 | 488 | 4.5 | 2.25 | 0.5 | 1.5 | 380 |
| 108-11 | 488 | 6.0 | 3.00 | 0.5 | 1.5 | 380 |
| 108-12 | 488 | | 1.50 | 0.5 | | none |
| 108-13 | 488 | | 2.25 | 0.5 | | none |
| 108-14 | 488 | | 3.00 | 0.5 | | none |
| 108-15 | 488 | | 1.50 | 0.5 | 1.5 | MOX-80/380(1:2) |
| 108-16 | 488 | | 2.25 | 0.5 | 1.5 | MOX-80/380(1:2) |
| 108-17 | 488 | | 3.00 | 0.5 | 1.5 | MOX-80/380(1:2) |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 20 days after application.

Formulations B and J were applied as comparative treatments. Results, averaged for all replicates of each treatment, are shown in Table 108b.

TABLE 108b

| Concentrate composition | Glyphosate rate g a.e./ha | % Inhibition ABUTH | ECHCF |
|---|---|---|---|
| Formulation B | 100 | 0 | 3 |
| | 200 | 10 | 12 |
| | 300 | 43 | 22 |
| | 400 | 47 | 27 |
| Formulation J | 100 | 13 | 15 |
| | 200 | 25 | 22 |
| | 300 | 58 | 53 |
| | 400 | 68 | 82 |
| 108-01 | 100 | 30 | 20 |
| | 200 | 60 | 53 |
| | 300 | 73 | 88 |
| | 400 | 87 | 96 |
| 108-02 | 100 | 40 | 23 |
| | 200 | 63 | 55 |
| | 300 | 88 | 87 |
| | 400 | 93 | 93 |
| 108-03 | 100 | 42 | 20 |
| | 200 | 72 | 55 |
| | 300 | 82 | 83 |
| | 400 | 90 | 88 |
| 108-04 | 100 | 60 | 32 |
| | 200 | 70 | 57 |
| | 300 | 90 | 88 |
| | 400 | 90 | 93 |
| 108-05 | 100 | 47 | 32 |
| | 200 | 67 | 57 |
| | 300 | 88 | 85 |
| | 400 | 94 | 88 |
| 108-06 | 100 | 33 | 37 |
| | 200 | 68 | 67 |
| | 300 | 82 | 80 |
| | 400 | 90 | 88 |

TABLE 108b-continued

| Concentrate composition | Glyphosate rate g a.e./ha | % Inhibition ABUTH | ECHCF |
|---|---|---|---|
| 108-07 | 100 | 35 | 37 |
| | 200 | 67 | 70 |
| | 300 | 87 | 85 |
| | 400 | 97 | 93 |
| 108-08 | 100 | 32 | 35 |
| | 200 | 67 | 77 |
| | 300 | 85 | 92 |
| | 400 | 97 | 95 |
| 108-09 | 100 | 27 | 33 |
| | 200 | 57 | 67 |
| | 300 | 88 | 83 |
| | 400 | 93 | 95 |
| 108-10 | 100 | 13 | 33 |
| | 200 | 62 | 58 |
| | 300 | 80 | 80 |
| | 400 | 92 | 92 |
| 108-11 | 100 | 13 | 20 |
| | 200 | 60 | 57 |
| | 300 | 88 | 63 |
| | 400 | 93 | 82 |
| 108-12 | 100 | 10 | 27 |
| | 200 | 53 | 53 |
| | 300 | 70 | 67 |
| | 400 | 88 | 85 |
| 108-13 | 100 | 3 | 28 |
| | 200 | 50 | 57 |
| | 300 | 67 | 70 |
| | 400 | 90 | 82 |
| 108-14 | 100 | 3 | 28 |
| | 200 | 55 | 57 |
| | 300 | 70 | 83 |
| | 400 | 87 | 87 |
| 108-15 | 100 | 10 | 20 |
| | 200 | 58 | 43 |
| | 300 | 70 | 72 |
| | 400 | 83 | 85 |
| 108-16 | 100 | 12 | 22 |
| | 200 | 55 | 57 |
| | 300 | 73 | 77 |
| | 400 | 92 | 90 |
| 108-17 | 100 | 7 | 20 |
| | 200 | 53 | 55 |
| | 300 | 70 | 75 |
| | 400 | 85 | 88 |

Several stabilized high-load (488 g a.e./l) glyphosate compositions of this Example provided herbicidal effectiveness equal or superior, on both ABUTH and ECHCF, to that obtained with commercial standard Formulation J.

Example 109

Glyphosate-containing spray compositions were prepared by tank-mixing Formulation B with excipients as shown in Table 109.

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 22 days after application. Results, averaged for all replicates of each treatment, are shown in Table 109.

TABLE 109

| Glyphosate composition | Glyphosate rate g a.e./ha | Additive | Ratio add./a.e. | % Inhibition ABUTH | ECHCF |
|---|---|---|---|---|---|
| Formulation B | 150 | none | | 18 | 25 |
| | 250 | | | 73 | 58 |
| | 350 | | | 80 | 82 |
| Formulation J | 150 | none | | 47 | 90 |
| | 250 | | | 77 | 93 |
| | 350 | | | 95 | 94 |
| Formulation B | 150 | steareth-10 | 1:0.3 | 53 | 88 |
| | 250 | | | 83 | 94 |
| | 350 | | | 98 | 98 |
| Formulation B | 150 | steareth-10 | 1:1 | 48 | 73 |
| | 250 | | | 67 | 97 |
| | 350 | | | 93 | 99 |
| Formulation B | 150 | steareth-10 | 1:1.5 | 52 | 60 |
| | 250 | | | 65 | 95 |
| | 350 | | | 86 | 99 |
| Formulation B | 150 | steareth-10 | 1:3 | 48 | 73 |
| | 250 | | | 65 | 83 |
| | 350 | | | 80 | 98 |
| Formulation B | 150 | steareth-10 | 1:6 | 50 | 81 |
| | 250 | | | 60 | 87 |
| | 350 | | | 85 | 97 |
| Formulation B | 150 | steareth-20 | 1:0.3 | 76 | 92 |
| | 250 | | | 100 | 93 |
| | 350 | | | 100 | 99 |
| Formulation B | 150 | steareth-20 | 1:1 | 65 | 75 |
| | 250 | | | 94 | 96 |
| | 350 | | | 99 | 99 |
| Formulation B | 150 | steareth-20 | 1:1.5 | 52 | 95 |
| | 250 | | | 84 | 92 |
| | 350 | | | 98 | 98 |
| Formulation B | 150 | steareth-20 | 1:3 | 53 | 82 |
| | 250 | | | 82 | 100 |
| | 350 | | | 98 | 93 |
| Formulation B | 150 | steareth-20 | 1:6 | 47 | 62 |
| | 250 | | | 63 | 93 |
| | 350 | | | 92 | 97 |
| Formulation B | 150 | steareth-30 | 1:0.3 | 63 | 88 |
| | 250 | | | 97 | 100 |
| | 350 | | | 100 | 100 |
| Formulation B | 150 | steareth-30 | 1:1 | 53 | 72 |
| | 250 | | | 88 | 96 |
| | 350 | | | 97 | 97 |
| Formulation B | 150 | steareth-30 | 1:1.5 | 50 | 79 |
| | 250 | | | 81 | 89 |
| | 350 | | | 96 | 100 |
| Formulation B | 150 | steareth-30 | 1:3 | 50 | 67 |
| | 250 | | | 78 | 88 |
| | 350 | | | 97 | 91 |
| Formulation B | 150 | steareth-30 | 1:6 | 47 | 58 |
| | 250 | | | 75 | 99 |
| | 350 | | | 89 | 99 |
| Formulation B | 150 | ceteareth-30 | 1:0.3 | 55 | 86 |
| | 250 | | | 89 | 91 |
| | 350 | | | 99 | 100 |
| Formulation B | 150 | ceteareth-30 | 1:1 | 50 | 86 |
| | 250 | | | 85 | 95 |
| | 350 | | | 97 | 100 |
| Formulation B | 150 | ceteareth-30 | 1:1.5 | 43 | 75 |
| | 250 | | | 80 | 100 |
| | 350 | | | 88 | 98 |

TABLE 109-continued

| Glyphosate composition | Glyphosate rate g a.e./ha | Additive | Ratio add./a.e. | % Inhibition ABUTH | % Inhibition ECHCF |
|---|---|---|---|---|---|
| Formulation B | 150 | ceteareth-30 | 1:3 | 33 | 73 |
| | 250 | | | 60 | 92 |
| | 350 | | | 94 | 100 |
| Formulation B | 150 | ceteareth-30 | 1:6 | 37 | 73 |
| | 250 | | | 53 | 89 |
| | 350 | | | 88 | 100 |
| Formulation B | 150 | Ethomeen T/25 | 1:0.3 | 67 | 90 |
| | 250 | | | 92 | 99 |
| | 350 | | | 100 | 100 |
| Formulation B | 150 | Ethomeen T/25 | 1:1 | 58 | 94 |
| | 250 | | | 83 | 96 |
| | 350 | | | 93 | 98 |
| Formulation B | 150 | Ethomeen T/25 | 1:1.5 | 50 | 73 |
| | 250 | | | 86 | 100 |
| | 350 | | | 99 | 100 |
| Formulation B | 150 | Ethomeen T/25 | 1:3 | 45 | 83 |
| | 250 | | | 89 | 95 |
| | 350 | | | 100 | 100 |
| Formulation B | 150 | Ethomeen T/25 | 1:6 | 35 | 82 |
| | 250 | | | 73 | 98 |
| | 350 | | | 88 | 98 |

Steareth-20, steareth-30 and ceteareth-30 were more effective additives for Formulation B than steareth-10 in this study.

Example 110

Aqueous spray compositions were prepared containing glyphosate IPA salt and excipient ingredients as shown in Table 110a. Process (iii) was followed for spray compositions 110-01 to 110-22 and 110-26 to 110-72, using soybean lecithin (45% phospholipid, Avanti). Process (i) was followed for spray compositions 110-23 to 110-25.

TABLE 110a

| Spray compositions | Lecithin (% w/w) | Butyl stearate (% w/w) | MON 0818 (% w/w) |
|---|---|---|---|
| 110-01 | 0.10 | 0.10 | |
| 110-02 | 0.10 | 0.08 | |
| 110-03 | 0.10 | 0.05 | |
| 110-04 | 0.10 | 0.03 | |
| 110-05 | 0.10 | 0.01 | |
| 110-06 | 0.08 | 0.10 | |
| 110-07 | 0.05 | 0.10 | |
| 110-08 | 003 | 0.10 | |
| 110-09 | 0.01 | 0.10 | |
| 110-10 | 0.08 | 0.01 | |
| 110-11 | 0.05 | 0.01 | |
| 110-12 | 0.03 | 0.01 | |
| 110-13 | 0.01 | 0.01 | |
| 110-14 | 0.01 | 0.03 | |
| 110-15 | 0.01 | 0.05 | |
| 110-16 | 0.01 | 0.08 | |
| 110-17 | 0.03 | 0.03 | |
| 110-18 | 0.05 | 0.05 | |
| 110-19 | 0.08 | 0.08 | |
| 110-20 | 0.08 | 0.03 | |
| 110-21 | 0.03 | 0.08 | |
| 110-22 | 0.05 | | |
| 110-23 | | 0.05 | |
| 110-24 | | | 0.09 |
| 110-25 | | | 0.03 |
| 110-26 | 0.09 | 0.02 | 0.09 |
| 110-27 | 0.09 | 0.02 | 0.05 |
| 110-28 | 0.01 | 0.01 | 0.01 |
| 110-29 | 0.01 | 0.01 | 0.03 |
| 110-30 | 0.01 | 0.01 | 0.05 |
| 110-31 | 0.01 | 0.01 | 0.08 |
| 110-32 | 0.01 | 0.01 | 0.10 |
| 110-33 | 0.01 | 0.05 | 0.01 |
| 110-34 | 0.01 | 0.05 | 0.03 |
| 110-35 | 0.01 | 0.05 | 0.05 |
| 110-36 | 0.01 | 0.05 | 0.08 |
| 110-37 | 0.01 | 0.05 | 0.10 |
| 110-38 | 0.01 | 0.10 | 0.01 |
| 110-39 | 0.01 | 0.10 | 0.03 |
| 110-40 | 0.01 | 0.10 | 0.05 |
| 110-41 | 0.01 | 0.10 | 0.08 |
| 110-42 | 0.01 | 0.10 | 0.10 |
| 110-43 | 0.05 | 0.01 | 0.01 |
| 110-44 | 0.05 | 0.01 | 0.03 |
| 110-45 | 0.05 | 0.01 | 0.05 |
| 110-46 | 0.05 | 0.01 | 0.08 |
| 110-47 | 0.05 | 0.01 | 0.10 |
| 110-48 | 0.05 | 0.05 | 0.01 |
| 110-49 | 0.05 | 0.05 | 0.03 |
| 110-50 | 0.05 | 0.05 | 0.05 |
| 110-51 | 0.05 | 0.05 | 0.08 |
| 110-52 | 0.05 | 0.05 | 0.10 |
| 110-53 | 0.05 | 0.10 | 0.01 |
| 110-54 | 0.05 | 0.10 | 0.03 |
| 110-55 | 0.05 | 0.10 | 0.05 |
| 110-56 | 0.05 | 0.10 | 0.08 |
| 110-57 | 0.05 | 0.10 | 0.10 |
| 110-58 | 0.10 | 0.01 | 0.01 |
| 110-59 | 0.10 | 0.01 | 0.03 |
| 110-60 | 0.10 | 0.01 | 0.05 |
| 110-61 | 0.10 | 0.01 | 0.08 |
| 110-62 | 0.10 | 0.01 | 0.10 |
| 110-63 | 0.10 | 0.05 | 0.01 |
| 110-64 | 0.10 | 0.05 | 0.03 |
| 110-65 | 0.10 | 0.05 | 0.05 |
| 110-66 | 0.10 | 0.05 | 0.08 |
| 110-67 | 0.10 | 0.05 | 0.10 |
| 110-68 | 0.10 | 0.10 | 0.01 |
| 110-69 | 0.10 | 0.10 | 0.03 |
| 110-70 | 0.10 | 0.10 | 0.05 |

TABLE 110a-continued

| Spray compositions | Lecithin | Butyl stearate | MON 0818 |
|---|---|---|---|
| | | % w/w | |
| 110-71 | 0.10 | 0.10 | 0.08 |
| 110-72 | 0.10 | 0.10 | 0.10 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulations C and J were applied as comparative treatments. Results, averaged for all replicates of each treatment, are shown in Table 110b.

TABLE 110b

| Spray composition | Glyphosate rate g a.e./ha | % Inhibition ABUTH | ECHCF |
|---|---|---|---|
| Formulation C | 280 | 71 | 73 |
| Formulation J | 280 | 65 | 77 |
| 110-01 | 280 | 60 | 49 |
| 110-02 | 280 | 46 | 47 |
| 110-03 | 280 | 34 | 48 |
| 110-04 | 280 | 33 | 35 |
| 110-05 | 280 | 50 | 33 |
| 110-06 | 280 | 49 | 52 |
| 110-07 | 280 | 39 | 42 |
| 110-08 | 280 | 48 | 38 |
| 110-09 | 280 | 51 | 42 |
| 110-10 | 280 | 37 | 30 |
| 110-11 | 280 | 48 | 30 |
| 110-12 | 280 | 56 | 34 |
| 110-13 | 280 | 41 | 45 |
| 110-14 | 280 | 52 | 56 |
| 110-15 | 280 | 38 | 40 |
| 110-16 | 280 | 53 | 33 |
| 110-17 | 280 | 45 | 40 |
| 110-18 | 280 | 52 | 38 |
| 110-19 | 280 | 37 | 34 |
| 110-20 | 280 | 36 | 28 |
| 110-21 | 280 | 40 | 38 |
| 110-22 | 280 | 44 | 47 |
| 110-23 | 280 | 60 | 42 |
| 110-24 | 280 | 92 | 76 |
| 110-25 | 280 | 87 | 69 |
| 110-26 | 280 | 89 | 88 |
| 110-27 | 280 | 79 | 80 |
| 110-28 | 280 | 74 | 73 |
| 110-29 | 280 | 91 | 76 |
| 110-30 | 280 | 94 | 92 |
| 110-31 | 280 | 87 | 81 |
| 110-32 | 280 | 93 | 77 |
| 110-33 | 280 | 88 | 73 |
| 110-34 | 280 | 92 | 85 |
| 110-35 | 280 | 90 | 82 |
| 110-36 | 280 | 92 | 77 |
| 110-37 | 280 | 87 | 77 |
| 110-38 | 280 | 88 | 77 |
| 110-39 | 280 | 84 | 74 |
| 110-40 | 280 | 87 | 68 |
| 110-41 | 280 | 93 | 76 |
| 110-42 | 280 | 94 | 78 |
| 110-43 | 280 | 80 | 59 |
| 110-44 | 280 | 69 | 54 |
| 110-45 | 280 | 88 | 74 |
| 110-46 | 280 | 94 | 79 |
| 110-47 | 280 | 95 | 79 |
| 110-48 | 280 | 71 | 63 |
| 110-49 | 280 | 81 | 72 |
| 110-50 | 280 | 81 | 79 |
| 110-51 | 280 | 79 | 85 |
| 110-52 | 280 | 98 | 69 |
| 110-53 | 280 | 69 | 70 |
| 110-54 | 280 | 74 | 69 |
| 110-55 | 280 | 84 | 78 |
| 110-56 | 280 | 86 | 68 |
| 110-57 | 280 | 98 | 82 |
| 110-58 | 280 | 71 | 69 |
| 110-59 | 280 | 95 | 79 |
| 110-60 | 280 | 92 | 70 |
| 110-61 | 280 | 93 | 70 |
| 110-62 | 280 | 98 | 80 |
| 110-63 | 280 | 81 | 74 |
| 110-64 | 280 | 84 | 73 |
| 110-65 | 280 | 89 | 70 |
| 110-66 | 280 | 91 | 65 |
| 110-67 | 280 | 94 | 81 |
| 110-68 | 280 | 87 | 81 |
| 110-69 | 280 | 72 | 79 |
| 110-70 | 280 | 87 | 76 |
| 110-71 | 280 | 94 | 71 |
| 110-72 | 280 | 97 | 73 |

Compositions outperforming commercial standard Formulations C and J on both ABUTH and ECHCF in this test included 110-26, 110-27, 110-30, 110-34, 110-35, 110-51 and 110-57, all containing lecithin, butyl stearate and MON 0818.

Example 111

Aqueous concentrate compositions were prepared containing glyphosate IPA salt and excipient ingredients as shown in Table 111a. Concentrate compositions 111-01 to 111-06 were prepared by process (x), using soybean lecithin (45% phospholipid, Avanti). Composition 111-07 was prepared by process (viii).

TABLE 111a

| Concentrate composition | Glyphosate g a.e./l | Lecithin | Butyl stearate | Ethomeen T/25 |
|---|---|---|---|---|
| | | % w/w | | |
| 111-01 | 200 | 6.0 | 2 | 6.0 |
| 111-02 | 200 | | 3 | 6.0 |
| 111-03 | 200 | | 1.5 | 9.0 |
| 111-04 | 200 | | 3 | 9.0 |
| 111-05 | 200 | 6.0 | 1.5 | 9.0 |
| 111-06 | 200 | 6.0 | 1.5 | 3.0 |
| 111-07 | 200 | | | 9.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulations B and J were applied as comparative treatments. Results, averaged for all replicates of each treatment, are shown in Table 111b.

TABLE 111b

| Concentrate composition | Glyphosate rate g a.e./ha | % Inhibition ABUTH | ECHCF |
|---|---|---|---|
| Formulation B | 150 | 29 | 22 |
|  | 250 | 41 | 29 |
|  | 350 | 53 | 32 |
|  | 450 | 68 | 35 |
| Formulation J | 150 | 43 | 32 |
|  | 250 | 76 | 43 |
|  | 350 | 86 | 47 |
|  | 450 | 94 | 66 |
| 111-01 | 150 | 67 | 33 |
|  | 250 | 85 | 40 |
|  | 350 | 96 | 71 |
|  | 450 | 97 | 59 |
| 111-02 | 150 | 65 | 36 |
|  | 250 | 81 | 52 |
|  | 350 | 97 | 68 |
|  | 450 | 98 | 62 |
| 111-03 | 150 | 67 | 40 |
|  | 250 | 85 | 77 |
|  | 350 | 94 | 77 |
|  | 450 | 97 | 63 |
| 111-04 | 150 | 69 | 38 |
|  | 250 | 86 | 58 |
|  | 350 | 93 | 84 |
|  | 450 | 98 | 62 |
| 111-05 | 150 | 73 | 40 |
|  | 250 | 83 | 53 |
|  | 350 | 93 | 75 |
|  | 450 | 96 | 61 |
| 111-06 | 150 | 45 | 30 |
|  | 250 | 71 | 38 |
|  | 350 | 91 | 45 |
|  | 450 | 89 | 39 |
| 111-07 | 150 | 59 | 39 |
|  | 250 | 83 | 44 |
|  | 350 | 95 | 63 |
|  | 450 | 95 | 70 |

Data for the 450 g a.e./ha glyphosate rate in this study are unreliable. Application error is suspected. The high levels of Ethomeen T/25 included in compositions of this Example tends to obscure the effects of lecithin and butyl stearate, but composition 111-05, for example, showed outstanding effectiveness.

Example 112

Aqueous concentrate compositions were prepared containing glyphosate IPA salt and excipient ingredients as shown in Table 112a. Process (vii) was followed for concentrate composition 112-08 and process (x) for concentrate compositions 112-01 to 112-07 and 112-09, using soybean lecithin (45% phospholipid, Avanti).

TABLE 112a

| Concentrate composition | Glyphosate g a.e./l | % w/w Lecithin | Butyl stearate | MON 0818 |
|---|---|---|---|---|
| 112-01 | 220 | 4.0 |  | 6.0 |
| 112-02 | 220 | 4.0 | 0.5 | 6.0 |
| 112-03 | 220 | 4.0 | 1.0 | 6.0 |
| 112-04 | 220 | 4.0 | 2.0 | 6.0 |
| 112-05 | 220 | 2.0 | 0.5 | 2.0 |
| 112-06 | 220 | 2.0 | 0.5 | 4.0 |
| 112-07 | 220 | 2.0 | 0.5 | 6.0 |
| 112-08 | 220 |  | 0.5 | 6.0 |
| 112-09 | 220 | 6.0 | 1.5 | 6.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and C were applied as comparative treatments. Results, averaged for all replicates of each treatment, are shown in Table 112b.

TABLE 112b

| Concentrate composition | Glyphosate rate g a.e./ha | % Inhibition ABUTH | ECHCF |
|---|---|---|---|
| Formulation B | 150 | 40 | 59 |
|  | 250 | 68 | 61 |
|  | 350 | 90 | 91 |
|  | 450 | 93 | 94 |
| Formulation C | 150 | 74 | 78 |
|  | 250 | 93 | 90 |
|  | 350 | 97 | 96 |
|  | 450 | 100 | 94 |
| 112-01 | 150 | 79 | 85 |
|  | 250 | 93 | 98 |
|  | 350 | 96 | 97 |
|  | 450 | 97 | 95 |
| 112-02 | 150 | 71 | 87 |
|  | 250 | 93 | 96 |
|  | 350 | 96 | 94 |
|  | 450 | 98 | 94 |
| 112-03 | 150 | 87 | 99 |
|  | 250 | 94 | 100 |
|  | 350 | 99 | 97 |
|  | 450 | 97 | 94 |
| 112-04 | 150 | 89 | 100 |
|  | 250 | 94 | 99 |
|  | 350 | 97 | 98 |
|  | 450 | 98 | 95 |
| 112-05 | 150 | 73 | 100 |
|  | 250 | 90 | 100 |
|  | 350 | 95 | 98 |
|  | 450 | 96 | 94 |
| 112-06 | 150 | 80 | 99 |
|  | 250 | 94 | 96 |
|  | 350 | 95 | 100 |
|  | 450 | 99 | 98 |
| 112-07 | 150 | 88 | 83 |
|  | 250 | 94 | 92 |
|  | 350 | 96 | 92 |
|  | 450 | 100 | 90 |
| 112-08 | 150 | 81 | 91 |
|  | 250 | 92 | 96 |
|  | 350 | 97 | 89 |
|  | 450 | 99 | 92 |
| 112-09 | 150 | 90 | 96 |
|  | 250 | 93 | 93 |
|  | 350 | 95 | 95 |
|  | 450 | 94 | 98 |

Herbicidal effectiveness overall was very high under the conditions of this study but a tendency can be discerned in compositions 112-01 to 112-04 for performance to improve as butyl stearate concentration was increased from zero to 2%.

Example 113

Aqueous spray compositions were prepared containing various tetraalkylammonium salts of glyphosate and excipient ingredients as shown in Table 113a. Process (iii) was followed for spray compositions 113-02 to 113-04, 113-06 to 113-08, 113-10 to 113-12 and 113-14 to 113-16, using soybean lecithin (45% phospholipid, Avanti). Compositions 113-01, 113-05, 113-09 and 113-13 are simple solutions of the tetraalkylammonium salts of glyphosate in water.

TABLE 113a

| Spray composition | % w/w Lecithin | Glyphosate salt |
|---|---|---|
| 113-01 |  | (Me)$_4$N |
| 113-02 | 0.10 | (Me)$_4$N |
| 113-03 | 0.05 | (Me)$_4$N |
| 113-04 | 0.02 | (Me)$_4$N |
| 113-05 |  | (Et)$_4$N |
| 113-06 | 0.10 | (Et)$_4$N |
| 113-07 | 0.05 | (Et)$_4$N |
| 113-08 | 0.02 | (Et)$_4$N |
| 113-09 |  | (Pr)$_4$N |
| 113-10 | 0.10 | (Pr)$_4$N |
| 113-11 | 0.05 | (Pr)$_4$N |
| 113-12 | 0.02 | (Pr)$_4$N |
| 113-13 |  | (Bu)$_4$N |
| 113-14 | 0.10 | (Bu)$_4$N |
| 113-15 | 0.05 | (Bu)$_4$N |
| 113-16 | 0.02 | (Bu)$_4$N |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 20 days after planting ECHCF, and evaluation of herbicidal inhibition was done 16 days after application.

Formulations B, C and J were applied as comparative treatments. In addition, Formulations B and C were tank-mixed with a pre-dispersed lecithin composition prepared from soybean lecithin (45% phosphplipid, Avanti). Results, averaged for all replicates of each treatment, are shown in Table 113b.

TABLE 113b

| Spray composition | Glyphosate rate g a.e./ha | % Inhibition ABUTH | % Inhibition ECHCF |
|---|---|---|---|
| Formulation B | 200 | 23 | 34 |
|  | 400 | 43 | 38 |
|  | 600 | 69 | 54 |
|  | 800 | 75 | 41 |
| Formulation B + lecithin 0.1% w/v | 200 | 7 | 15 |
|  | 400 | 31 | 36 |
|  | 600 | 58 | 37 |
| Formulation B + lecithin 0.05% w/v | 200 | 10 | 17 |
|  | 400 | 34 | 40 |
|  | 600 | 61 | 47 |
| Formulation B + lecithin 0.025% w/v | 200 | 11 | 17 |
|  | 400 | 27 | 39 |
|  | 600 | 63 | 39 |
| Formulation C | 200 | 38 | 62 |
|  | 400 | 90 | 91 |
|  | 600 | 96 | 100 |
|  | 800 | 100 | 99 |
| Formulation C + lecithin 0.1% w/v | 200 | 36 | 55 |
|  | 400 | 81 | 93 |
|  | 600 | 100 | 95 |
| Formulation C + lecithin 0.05% w/v | 200 | 35 | 53 |
|  | 400 | 79 | 90 |
|  | 600 | 91 | 99 |
| Formulation C + lecithin 0.025% w/v | 200 | 32 | 55 |
|  | 400 | 77 | 88 |
|  | 600 | 96 | 100 |
| Formulation J | 200 | 40 | 34 |
|  | 400 | 83 | 78 |
|  | 600 | 87 | 96 |
|  | 800 | 100 | 95 |
| 113-01 | 200 | 27 | 34 |
|  | 400 | 74 | 52 |
|  | 600 | 84 | 46 |
| 113-02 | 200 | 39 | 37 |
|  | 400 | 73 | 64 |
|  | 600 | 89 | 68 |
| 113-03 | 200 | 24 | 35 |
|  | 400 | 73 | 59 |
|  | 600 | 88 | 75 |
| 113-04 | 200 | 29 | 43 |
|  | 400 | 71 | 59 |
|  | 600 | 82 | 90 |
| 113-05 | 200 | 51 | 43 |
|  | 400 | 79 | 48 |
|  | 600 | 98 | 49 |
| 113-06 | 200 | 58 | 47 |
|  | 400 | 84 | 81 |
|  | 600 | 86 | 97 |
| 113-07 | 200 | 69 | 41 |
|  | 400 | 83 | 84 |
|  | 600 | 90 | 94 |
| 113-08 | 200 | 55 | 48 |
|  | 400 | 79 | 79 |
|  | 600 | 93 | 92 |
| 113-09 | 200 | 73 | 60 |
|  | 400 | 96 | 58 |
|  | 600 | 98 | 73 |
| 113-10 | 200 | 69 | 75 |
|  | 400 | 94 | 94 |
|  | 600 | 99 | 91 |
| 113-11 | 200 | 72 | 62 |
|  | 400 | 94 | 98 |
|  | 600 | 100 | 99 |
| 113-12 | 200 | 76 | 65 |
|  | 400 | 97 | 79 |
|  | 600 | 100 | 100 |
| 113-13 | 200 | 85 | 64 |
|  | 400 | 97 | 58 |
|  | 600 | 99 | 65 |
| 113-14 | 200 | 83 | 87 |
|  | 400 | 99 | 84 |
|  | 600 | 99 | 98 |
| 113-15 | 200 | 87 | 66 |
|  | 400 | 94 | 96 |
|  | 600 | 100 | 100 |
| 113-16 | 200 | 91 | 87 |
|  | 400 | 97 | 91 |
|  | 600 | 100 | 94 |

Addition of lecithin to composition B (glyphosate IPA salt) did not provide significant enhancement of herbicidal effectiveness. However, when lecithin was added to tetraalkylammonium salts of glyphosate, significant improvements were obtained. In some cases adding a very low amount of lecithin (0.02%) gave better results than adding a larger amount (0.1%). Outstanding effectiveness, for example, was obtained with composition 113-16, containing the tetrabutylanmonium salt of glyphosate and 0.02% lecithin.

Example 114

Aqueous concentrate compositions were prepared containing glyphosate IPA salt and excipient ingredients as shown in Table 114a. Process (v) was followed for all concentrate compositions, using soybean lecithin (45% phospholipid, Avanti).

TABLE 114a

| Concentrate composition | Glyphosate g a.e./l | % w/w Lecithin | Benzalkonium Cl |
|---|---|---|---|
| 114-01 | 363 | 8.1 | 5.4 |
| 114-02 | 363 | 8.1 | 4.1 |
| 114-03 | 363 | 8.1 | 3.0 |
| 114-04 | 363 | 8.1 | 2.1 |
| 114-05 | 372 | 8.3 | 2.5 |
| 114-06 | 363 | 6.8 | 4.0 |
| 114-07 | 362 | 6.8 | 2.9 |
| 114-08 | 355 | 3.5 | 10.0 |
| 114-09 | 354 | 3.0 | 13.3 |
| 114-10 | 352 | 2.5 | 16.7 |
| 114-11 | 352 | 2.0 | 20.0 |
| 114-12 | 295 | 5.0 | 10.0 |
| 114-13 | 295 | 4.5 | 13.3 |
| 114-14 | 294 | 4.0 | 16.7 |
| 114-15 | 294 | 3.5 | 20.0 |
| 114-16 | 292 | 3.0 | 23.3 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 18 days after application.

Formulations B and J were applied as comparative treatments. Results, averaged for all replicates of each treatment, are shown in Table 114b.

TABLE 114b

| Concentrate composition | Glyphosate rate g a.e./ha | % Inhibition ABUTH | ECHCF |
|---|---|---|---|
| Formulation B | 150 | 52 | 27 |
|  | 250 | 72 | 40 |
|  | 350 | 87 | 60 |
|  | 450 | 88 | 77 |
| Formulation J | 150 | 82 | 90 |
|  | 250 | 92 | 99 |
|  | 350 | 99 | 99 |
|  | 450 | 100 | 100 |
| 114-01 | 150 | 78 | 97 |
|  | 250 | 87 | 99 |
|  | 350 | 98 | 99 |
|  | 450 | 99 | 100 |
| 114-02 | 150 | 68 | 83 |
|  | 250 | 73 | 99 |
|  | 350 | 96 | 99 |
|  | 450 | 98 | 99 |
| 114-03 | 150 | 65 | 53 |
|  | 250 | 77 | 92 |
|  | 350 | 93 | 99 |
|  | 450 | 98 | 100 |
| 114-04 | 150 | 62 | 76 |
|  | 250 | 83 | 88 |
|  | 350 | 96 | 98 |
|  | 450 | 95 | 99 |
| 114-05 | 150 | 68 | 57 |
|  | 250 | 90 | 88 |
|  | 350 | 95 | 98 |
|  | 450 | 98 | 99 |
| 114-06 | 150 | 72 | 57 |
|  | 250 | 83 | 98 |
|  | 350 | 93 | 98 |
|  | 450 | 98 | 100 |
| 114-07 | 150 | 77 | 69 |
|  | 250 | 85 | 85 |
|  | 350 | 97 | 98 |
|  | 450 | 98 | 99 |

TABLE 114b-continued

| Concentrate composition | Glyphosate rate g a.e./ha | % Inhibition ABUTH | ECHCF |
|---|---|---|---|
| 114-08 | 150 | 80 | 85 |
|  | 250 | 93 | 99 |
|  | 350 | 99 | 100 |
|  | 450 | 100 | 100 |
| 114-09 | 150 | 88 | 88 |
|  | 250 | 95 | 99 |
|  | 350 | 100 | 99 |
|  | 450 | 100 | 100 |
| 114-10 | 150 | 99 | 97 |
|  | 250 | 97 | 100 |
|  | 350 | 100 | 100 |
|  | 450 | 99 | 99 |
| 114-11 | 150 | 98 | 92 |
|  | 250 | 98 | 97 |
|  | 350 | 99 | 99 |
|  | 450 | 100 | 100 |
| 114-12 | 150 | 83 | 92 |
|  | 250 | 95 | 99 |
|  | 350 | 98 | 99 |
|  | 450 | 99 | 99 |
| 114-13 | 150 | 91 | 95 |
|  | 250 | 94 | 97 |
|  | 350 | 99 | 100 |
|  | 450 | 99 | 100 |
| 114-14 | 150 | 93 | 96 |
|  | 250 | 90 | 97 |
|  | 350 | 98 | 99 |
|  | 450 | 99 | 98 |
| 114-15 | 150 | 90 | 97 |
|  | 250 | 99 | 97 |
|  | 350 | 100 | 100 |
|  | 450 | 99 | 99 |
| 114-16 | 150 | 92 | 94 |
|  | 250 | 98 | 100 |
|  | 350 | 99 | 100 |
|  | 450 | 100 | 99 |

Overall herbicidal effectiveness in this study was extremely high and enhancements over commercial standard Formulation J are therefore difficult to discern. However, particularly outstanding performance was obtained with compositions 114-10, 114-11 and 114-13 to 114-16 containing lecithin and benzalkonium chloride.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. An in vitro assay method for selecting an exogenous chemical composition having enhanced biological effectiveness when applied to plants, comprising the steps of:

(1) providing a glass microscope slide coated with a thin, uniform layer of wax, such that the wax layer on the slide exhibits a dark field when illuminated by transmitted polarized light and examined through a microscope, (2) preparing a sample of an aqueous solution or dispersion of an exogenous chemical composition, diluted or concentrated if necessary such that the concentration of exogenous chemical is about 15% to about 20% by weight of the composition, (3) positioning the slide on a stage of a microscope that transmits polarized light through the slide, (4) placing a drop of the sample on the wax layer to form an assay slide, (5) maintaining the assay slide at approximately ambient temperature for a period of about 5 to about 20 minutes, (6) determining at the end of said period whether when transmitting polarized light the locus of the drop on the assay slide displays birefringence, and (7) selecting for biological evaluation a composition wherein birefringence is displayed.

2. An in vitro assay method for selecting a composition of an excipient substance providing enhanced biological effectiveness of an exogenous chemical when applied therewith to plants, comprising the steps of:

(1) providing a glass microscope slide coated with a thin, uniform layer of wax, such that the wax layer on the slide exhibits a dark field when illuminated by transmitted polarized light and examined through a microscope, (2) preparing a sample of an aqueous solution or dispersion of a composition of an excipient substance, diluted or concentrated if necessary such that the concentration of excipient substance is about 5% to about 7% by weight of the composition, (3) positioning the slide on a stage of a microscope that transmits polarized light through the slide, (4) placing a drop of the sample on the wax layer to form an assay slide, (5) maintaining the assay slide at approximately ambient temperature for a period of about 5 to about 20 minutes, (6) determining at the end of said period whether when transmitting polarized light the locus of the drop on the assay slide displays birefringence, and (7) selecting for biological evaluation a composition wherein birefringence is displayed.

* * * * *